US012152073B2

(12) United States Patent
Loew et al.

(10) Patent No.: US 12,152,073 B2
(45) Date of Patent: Nov. 26, 2024

(54) MULTIFUNCTIONAL MOLECULES THAT BIND TO CALRETICULIN AND USES THEREOF

(71) Applicant: MARENGO THERAPEUTICS, INC., Cambridge, MA (US)

(72) Inventors: Andreas Loew, Boston, MA (US); Ilaria Lamberto, Arlington, MA (US); John Leonard Herrmann, Winchester, MA (US); Brian Edward Vash, Cambridge, MA (US)

(73) Assignee: MARENGO THERAPEUTICS, INC., Cambridge, MA (US)

( * ) Notice: Subject to any disclaimer, the term of this patent is extended or adjusted under 35 U.S.C. 154(b) by 1107 days.

(21) Appl. No.: 16/980,730

(22) PCT Filed: Mar. 14, 2019

(86) PCT No.: PCT/US2019/022282
§ 371 (c)(1),
(2) Date: Sep. 14, 2020

(87) PCT Pub. No.: WO2019/178362
PCT Pub. Date: Sep. 19, 2019

(65) Prior Publication Data
US 2021/0238280 A1 Aug. 5, 2021

Related U.S. Application Data

(60) Provisional application No. 62/642,647, filed on Mar. 14, 2018.

(51) Int. Cl.
*C07K 16/28* (2006.01)

(52) U.S. Cl.
CPC .... *C07K 16/2803* (2013.01); *C07K 2317/565* (2013.01); *C07K 2317/567* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | |
|---|---|---|
| 861,745 A | 7/1907 | Maxwell |
| 4,433,059 A | 2/1984 | Chang et al. |
| 4,439,196 A | 3/1984 | Higuchi |
| 4,444,878 A | 4/1984 | Paulus |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,676,980 A | 6/1987 | Segal et al. |
| 4,737,456 A | 4/1988 | Weng et al. |
| 4,790,824 A | 12/1988 | Morrow et al. |
| 4,816,567 A | 3/1989 | Cabilly et al. |
| 4,941,880 A | 7/1990 | Burns |
| 5,057,423 A | 10/1991 | Hiserodt et al. |
| 5,064,413 A | 11/1991 | McKinnon et al. |
| 5,116,615 A | 5/1992 | Gokcen et al. |
| 5,208,020 A | 5/1993 | Chari et al. |
| 5,223,409 A | 6/1993 | Ladner et al. |
| 5,225,539 A | 7/1993 | Winter |
| 5,273,743 A | 12/1993 | Ahlem et al. |
| 5,312,335 A | 5/1994 | McKinnon et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,416,016 A | 5/1995 | Low et al. |
| 5,416,064 A | 5/1995 | Chari et al. |
| 5,500,362 A | 3/1996 | Robinson et al. |
| 5,534,254 A | 7/1996 | Huston et al. |
| 5,571,894 A | 11/1996 | Wels et al. |
| 5,582,996 A | 12/1996 | Curtis |
| 5,585,089 A | 12/1996 | Queen et al. |
| 5,587,458 A | 12/1996 | King et al. |
| 5,591,828 A | 1/1997 | Bosslet et al. |

(Continued)

FOREIGN PATENT DOCUMENTS

| | | |
|---|---|---|
| AU | 2001278662 B2 | 9/2006 |
| CN | 101802010 A | 8/2010 |

(Continued)

OTHER PUBLICATIONS

Lloyd et al (Protein Engineering, Design & Selection, 22:159-168, 2009).*
Edwards et al (J Mol Biol, 14;334(1):103-118, 2003).*
Gussow et al (Methods in Enzymology. 1991; 203: 99-121).*
Winkler et al (J. Imm., 265:4505-4514, 2000).*
Hongyan, et al., "Fc Engineering for Developing Therapeutic Bispecific Antibodies and Novel Scaffolds" Frontiers In Immunology, (2017) vol. 8.
International Search Report and Written Opinion for PCT Application No. PCT/US2019/022282 issued Jul. 1, 2019.
International Search Report and Written Opinion for PCT Application No. PCT/US2019/012900 dated Jul. 5, 2019.
PCT/US2020/019324 International Preliminary Report on Patentability dated Aug. 10, 2021.
PCT/US2020/019324 International Search Report and Written Opinion dated Jun. 10, 2020.

(Continued)

*Primary Examiner* — Brad Duffy
(74) *Attorney, Agent, or Firm* — Wilson Sonsini Goodrich & Rosati

(57) ABSTRACT

Multifunctional molecules that include i) an antigen binding domain that binds to a calreticulin mutant protein; and one, two or all of: (ii) an immune cell engager (e.g., chosen from an NK cell engager, a T cell engager, a B cell engager, a dendritic cell engager, or a macrophage cell engager); (iii) a cytokine molecule or a modulator of a cytokine molecule; and/or (iv) a stromal modifying moiety are disclosed. Additionally disclosed are nucleic acids encoding the same, methods of producing the aforesaid molecules, and methods of treating a cancer using the aforesaid molecules.

20 Claims, 6 Drawing Sheets

Specification includes a Sequence Listing.

(56) References Cited

U.S. PATENT DOCUMENTS

| | | |
|---|---|---|
| 5,624,821 A | 4/1997 | Winter et al. |
| 5,626,561 A | 5/1997 | Butler et al. |
| 5,635,483 A | 6/1997 | Pettit et al. |
| 5,635,602 A | 6/1997 | Cantor et al. |
| 5,637,481 A | 6/1997 | Ledbetter et al. |
| 5,641,870 A | 6/1997 | Rinderknecht et al. |
| 5,648,237 A | 7/1997 | Carter |
| 5,648,260 A | 7/1997 | Winter et al. |
| 5,693,761 A | 12/1997 | Queen et al. |
| 5,693,762 A | 12/1997 | Queen et al. |
| 5,712,374 A | 1/1998 | Kuntsmann et al. |
| 5,714,586 A | 2/1998 | Kunstmann et al. |
| 5,731,116 A | 3/1998 | Matsuo et al. |
| 5,731,168 A | 3/1998 | Carter et al. |
| 5,739,116 A | 4/1998 | Hamann et al. |
| 5,750,373 A | 5/1998 | Garrard et al. |
| 5,767,285 A | 6/1998 | Hamann et al. |
| 5,770,429 A | 6/1998 | Lonberg et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,787,900 A | 8/1998 | Butler et al. |
| 5,789,199 A | 8/1998 | Joly et al. |
| 5,811,097 A | 9/1998 | Allison et al. |
| 5,821,337 A | 10/1998 | Carter et al. |
| 5,831,012 A | 11/1998 | Nilsson et al. |
| 5,837,242 A | 11/1998 | Holliger et al. |
| 5,837,821 A | 11/1998 | Wu |
| 5,840,523 A | 11/1998 | Simmons et al. |
| 5,843,069 A | 12/1998 | Butler et al. |
| 5,844,094 A | 12/1998 | Hudson et al. |
| 5,849,500 A | 12/1998 | Breitling et al. |
| 5,861,155 A | 1/1999 | Lin |
| 5,864,019 A | 1/1999 | King et al. |
| 5,869,046 A | 2/1999 | Presta et al. |
| 5,869,620 A | 2/1999 | Whitlow et al. |
| 5,877,296 A | 3/1999 | Hamann et al. |
| 5,902,745 A | 5/1999 | Butler et al. |
| 5,910,573 A | 6/1999 | Plueckthun et al. |
| 5,913,998 A | 6/1999 | Butler et al. |
| 5,932,448 A | 8/1999 | Tso et al. |
| 5,959,083 A | 9/1999 | Bosslet et al. |
| 5,959,177 A | 9/1999 | Hein et al. |
| 5,980,889 A | 11/1999 | Butler et al. |
| 5,989,830 A | 11/1999 | Davis et al. |
| 6,005,079 A | 12/1999 | Casterman et al. |
| 6,040,498 A | 3/2000 | Stomp et al. |
| 6,075,181 A | 6/2000 | Kucherlapati et al. |
| 6,120,766 A | 9/2000 | Hale et al. |
| 6,150,584 A | 11/2000 | Kucherlapati et al. |
| 6,171,586 B1 | 1/2001 | Lam et al. |
| 6,172,197 B1 | 1/2001 | McCafferty et al. |
| 6,194,551 B1 | 2/2001 | Idusogie et al. |
| 6,239,259 B1 | 5/2001 | Davis et al. |
| 6,248,516 B1 | 6/2001 | Winter et al. |
| 6,267,958 B1 | 7/2001 | Andya et al. |
| 6,291,158 B1 | 9/2001 | Winter et al. |
| 6,294,353 B1 | 9/2001 | Pack et al. |
| 6,333,396 B1 | 12/2001 | Filpula et al. |
| 6,352,694 B1 | 3/2002 | June et al. |
| 6,417,429 B1 | 7/2002 | Hein et al. |
| 6,420,548 B1 | 7/2002 | Vezina et al. |
| 6,476,198 B1 | 11/2002 | Kang |
| 6,511,663 B1 | 1/2003 | King et al. |
| 6,534,055 B1 | 3/2003 | June et al. |
| 6,582,915 B1 | 6/2003 | Griffiths et al. |
| 6,593,081 B1 | 7/2003 | Griffiths et al. |
| 6,602,684 B1 | 8/2003 | Umana et al. |
| 6,630,579 B2 | 10/2003 | Chari et al. |
| 6,632,427 B1 | 10/2003 | Finiels et al. |
| 6,670,453 B2 | 12/2003 | Frenken et al. |
| 6,696,245 B2 | 2/2004 | Winter et al. |
| 6,703,199 B1 | 3/2004 | Koide |
| 6,737,056 B1 | 5/2004 | Presta |
| 6,743,896 B2 | 6/2004 | Filpula et al. |
| 6,756,523 B1 | 6/2004 | Kahn et al. |
| 6,765,087 B1 | 7/2004 | Casterman et al. |
| 6,809,185 B1 | 10/2004 | Schoonjans et al. |
| 6,818,418 B1 | 11/2004 | Lipovsek et al. |
| 6,833,441 B2 | 12/2004 | Wang et al. |
| 6,838,254 B1 | 1/2005 | Hamers et al. |
| 6,905,680 B2 | 6/2005 | June et al. |
| 6,979,546 B2 | 12/2005 | Moretta et al. |
| 6,982,321 B2 | 1/2006 | Winter |
| 7,041,870 B2 | 5/2006 | Tomizuka et al. |
| 7,083,785 B2 | 8/2006 | Browning et al. |
| 7,087,409 B2 | 8/2006 | Barbas, III et al. |
| 7,105,149 B1 | 9/2006 | Dalla-Favera |
| 7,125,978 B1 | 10/2006 | Vezina et al. |
| 7,129,330 B1 | 10/2006 | Little et al. |
| 7,183,076 B2 | 2/2007 | Arathoon et al. |
| 7,186,804 B2 | 3/2007 | Gillies et al. |
| 7,189,826 B2 | 3/2007 | Rodman |
| 7,250,297 B1 | 7/2007 | Beste et al. |
| 7,276,241 B2 | 10/2007 | Schneider et al. |
| 7,332,581 B2 | 2/2008 | Presta |
| 7,361,360 B2 | 4/2008 | Kitabwalla et al. |
| 7,371,826 B2 | 5/2008 | Presta |
| 7,402,314 B2 | 7/2008 | Sherman |
| 7,431,380 B1 | 10/2008 | Buresh |
| 7,476,724 B2 | 1/2009 | Dennis et al. |
| 7,498,298 B2 | 3/2009 | Doronina et al. |
| 7,501,121 B2 | 3/2009 | Tchistiakova et al. |
| 7,517,966 B2 | 4/2009 | Moretta et al. |
| 7,521,056 B2 | 4/2009 | Chang et al. |
| 7,521,541 B2 | 4/2009 | Eigenbrot et al. |
| 7,527,787 B2 | 5/2009 | Chang et al. |
| 7,527,791 B2 | 5/2009 | Adams et al. |
| 7,534,866 B2 | 5/2009 | Chang et al. |
| 7,601,803 B1 | 10/2009 | Fiedler et al. |
| 7,612,181 B2 | 11/2009 | Wu et al. |
| 7,642,228 B2 | 1/2010 | Carter et al. |
| 7,741,446 B2 | 6/2010 | Pardridge et al. |
| 7,750,128 B2 | 7/2010 | Gegg et al. |
| 7,767,429 B2 | 8/2010 | Bookbinder et al. |
| 7,799,902 B2 | 9/2010 | Browning et al. |
| 7,803,376 B2 | 9/2010 | Velardi et al. |
| 7,855,275 B2 | 12/2010 | Eigenbrot et al. |
| 7,858,759 B2 | 12/2010 | Brandt et al. |
| 7,906,118 B2 | 3/2011 | Chang et al. |
| 7,919,257 B2 | 4/2011 | Hoogenboom et al. |
| 7,943,743 B2 | 5/2011 | Korman et al. |
| 7,999,077 B2 | 8/2011 | Pastan et al. |
| 8,003,774 B2 | 8/2011 | Stavenhagen et al. |
| 8,008,449 B2 | 8/2011 | Korman et al. |
| 8,012,465 B2 | 9/2011 | Elias et al. |
| 8,034,326 B2 | 10/2011 | Hjorth et al. |
| 8,202,517 B2 | 6/2012 | Bookbinder et al. |
| 8,216,805 B2 | 7/2012 | Carter et al. |
| 8,299,220 B2 | 10/2012 | Dalla-Favera |
| 8,354,509 B2 | 1/2013 | Carven et al. |
| 8,362,213 B2 | 1/2013 | Elkins et al. |
| 8,450,470 B2 | 5/2013 | Bookbinder et al. |
| 8,466,260 B2 | 6/2013 | Elkins et al. |
| 8,552,156 B2 | 10/2013 | Takayanagi et al. |
| 8,580,252 B2 | 11/2013 | Bookbinder et al. |
| 8,586,713 B2 | 11/2013 | Davis et al. |
| 8,592,562 B2 | 11/2013 | Kannan et al. |
| 8,609,089 B2 | 12/2013 | Langermann et al. |
| 8,617,559 B2 | 12/2013 | Elkins et al. |
| 8,658,135 B2 | 2/2014 | O'Connor-McCourt et al. |
| 8,703,132 B2 | 4/2014 | Imhof-Jung et al. |
| 8,772,246 B2 | 7/2014 | Bookbinder et al. |
| 8,790,895 B2 | 7/2014 | Fiedler et al. |
| 8,821,883 B2 | 9/2014 | Ambrose et al. |
| 8,846,042 B2 | 9/2014 | Zhou |
| 8,871,912 B2 | 10/2014 | Davis et al. |
| 8,920,776 B2 | 12/2014 | Gaiger et al. |
| 8,945,571 B2 | 2/2015 | Mössner et al. |
| 8,993,524 B2 | 3/2015 | Bedi et al. |
| 9,000,130 B2 | 4/2015 | Bhakta et al. |
| 9,034,324 B2 | 5/2015 | Kalled et al. |
| 9,056,905 B2 | 6/2015 | Olson et al. |

(56) References Cited

U.S. PATENT DOCUMENTS

| | | |
|---|---|---|
| 9,145,588 B2 | 9/2015 | Throsby et al. |
| 9,200,060 B2 | 12/2015 | Kannan et al. |
| 9,243,058 B2 | 1/2016 | Armitage et al. |
| 9,309,311 B2 | 4/2016 | Gurney et al. |
| 9,340,621 B2 | 5/2016 | Kufer et al. |
| 9,358,286 B2 | 6/2016 | De Kruif et al. |
| 9,359,437 B2 | 6/2016 | Davis et al. |
| 9,382,323 B2 | 7/2016 | Brinkmann et al. |
| 9,387,237 B2 | 7/2016 | Kalled et al. |
| 9,447,159 B2 | 9/2016 | Ast et al. |
| 9,447,185 B2 | 9/2016 | Romagne et al. |
| 9,545,086 B2 | 1/2017 | Mackay et al. |
| 9,593,376 B2 | 3/2017 | Zitvogel et al. |
| 9,663,577 B2 | 5/2017 | Pierres et al. |
| 9,676,863 B2 | 6/2017 | Lo |
| 10,610,571 B2 | 4/2020 | Ptacin et al. |
| 10,676,516 B2 | 6/2020 | Viney et al. |
| 10,730,942 B2 | 8/2020 | Pule et al. |
| 2002/0004587 A1 | 1/2002 | Miller et al. |
| 2002/0076406 A1 | 6/2002 | Leung |
| 2002/0103345 A1 | 8/2002 | Zhu |
| 2002/0164328 A1 | 11/2002 | Shinkawa et al. |
| 2003/0115614 A1 | 6/2003 | Kanda et al. |
| 2003/0130496 A1 | 7/2003 | Winter et al. |
| 2003/0157108 A1 | 8/2003 | Presta |
| 2003/0175884 A1 | 9/2003 | Umana et al. |
| 2003/0207346 A1 | 11/2003 | Arathoon et al. |
| 2003/0211078 A1 | 11/2003 | Heavner |
| 2004/0009530 A1 | 1/2004 | Wilson et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0175756 A1 | 9/2004 | Kolkman et al. |
| 2004/0219643 A1 | 11/2004 | Winter et al. |
| 2004/0220388 A1 | 11/2004 | Mertens et al. |
| 2004/0241817 A1 | 12/2004 | Umana et al. |
| 2004/0242847 A1 | 12/2004 | Fukushima et al. |
| 2005/0003403 A1 | 1/2005 | Rossi et al. |
| 2005/0004352 A1 | 1/2005 | Kontermann et al. |
| 2005/0014934 A1 | 1/2005 | Hinton et al. |
| 2005/0048512 A1 | 3/2005 | Kolkman et al. |
| 2005/0053973 A1 | 3/2005 | Kolkman et al. |
| 2005/0069552 A1 | 3/2005 | Bleck et al. |
| 2005/0079170 A1 | 4/2005 | Le Gall et al. |
| 2005/0090648 A1 | 4/2005 | Tsurushita et al. |
| 2005/0100543 A1 | 5/2005 | Hansen et al. |
| 2005/0119455 A1 | 6/2005 | Fuh et al. |
| 2005/0123546 A1 | 6/2005 | Umana et al. |
| 2005/0136049 A1 | 6/2005 | Ledbetter et al. |
| 2005/0136051 A1 | 6/2005 | Scallon |
| 2005/0163782 A1 | 7/2005 | Glaser et al. |
| 2005/0260186 A1 | 11/2005 | Bookbinder et al. |
| 2005/0266000 A1 | 12/2005 | Bond et al. |
| 2005/0266425 A1 | 12/2005 | Zauderer et al. |
| 2006/0008844 A1 | 1/2006 | Stemmer et al. |
| 2006/0025576 A1 | 2/2006 | Miller et al. |
| 2006/0083747 A1 | 4/2006 | Winter et al. |
| 2006/0104968 A1 | 5/2006 | Bookbinder et al. |
| 2006/0120960 A1 | 6/2006 | Deyev et al. |
| 2006/0141581 A1 | 6/2006 | Gillies et al. |
| 2006/0204493 A1 | 9/2006 | Huang et al. |
| 2006/0263367 A1 | 11/2006 | Fey et al. |
| 2007/0004909 A1 | 1/2007 | Johnson et al. |
| 2007/0036783 A1 | 2/2007 | Humeau et al. |
| 2007/0061900 A1 | 3/2007 | Murphy et al. |
| 2007/0087381 A1 | 4/2007 | Kojima |
| 2007/0117126 A1 | 5/2007 | Sidhu et al. |
| 2007/0128150 A1 | 6/2007 | Norman |
| 2007/0141049 A1 | 6/2007 | Bredehorst et al. |
| 2007/0154901 A1 | 7/2007 | Thogersen et al. |
| 2007/0160598 A1 | 7/2007 | Dennis et al. |
| 2007/0178106 A1 | 8/2007 | Romagne |
| 2007/0184052 A1 | 8/2007 | Lin et al. |
| 2007/0231322 A1 | 10/2007 | Romagne et al. |
| 2007/0237764 A1 | 10/2007 | Birtalan et al. |
| 2007/0274985 A1 | 11/2007 | Dubel et al. |
| 2007/0292936 A1 | 12/2007 | Barthelemy et al. |
| 2008/0050370 A1 | 2/2008 | Glaser et al. |
| 2008/0063717 A1 | 3/2008 | Romagne et al. |
| 2008/0069820 A1 | 3/2008 | Fuh et al. |
| 2008/0152645 A1 | 6/2008 | Pardridge et al. |
| 2008/0171855 A1 | 7/2008 | Rossi et al. |
| 2008/0241884 A1 | 10/2008 | Shitara et al. |
| 2008/0247944 A1 | 10/2008 | Graziano et al. |
| 2008/0254512 A1 | 10/2008 | Capon |
| 2008/0260738 A1 | 10/2008 | Moore et al. |
| 2008/0299137 A1 | 12/2008 | Svendsen et al. |
| 2009/0002360 A1 | 1/2009 | Chen et al. |
| 2009/0010843 A1 | 1/2009 | Spee et al. |
| 2009/0130106 A1 | 5/2009 | Christopherson et al. |
| 2009/0148905 A1 | 6/2009 | Ashman et al. |
| 2009/0155275 A1 | 6/2009 | Wu et al. |
| 2009/0162359 A1 | 6/2009 | Klein et al. |
| 2009/0162360 A1 | 6/2009 | Klein et al. |
| 2009/0175851 A1 | 7/2009 | Klein et al. |
| 2009/0175867 A1 | 7/2009 | Thompson et al. |
| 2009/0214533 A1 | 8/2009 | Clynes |
| 2009/0232811 A1 | 9/2009 | Klein et al. |
| 2009/0234105 A1 | 9/2009 | Gervay-Hague et al. |
| 2009/0263392 A1 | 10/2009 | Igawa et al. |
| 2009/0274649 A1 | 11/2009 | Qu et al. |
| 2009/0324538 A1 | 12/2009 | Wong et al. |
| 2010/0015133 A1 | 1/2010 | Igawa et al. |
| 2010/0028330 A1 | 2/2010 | Collins et al. |
| 2010/0047169 A1 | 2/2010 | Mandelboim et al. |
| 2010/0168393 A1 | 7/2010 | Clube et al. |
| 2010/0260704 A1 | 10/2010 | Berenguer et al. |
| 2010/0316645 A1 | 12/2010 | Imhof-Jung et al. |
| 2011/0014659 A1 | 1/2011 | Balazs et al. |
| 2011/0054151 A1 | 3/2011 | Lazar et al. |
| 2011/0091372 A1 | 4/2011 | Ghayur et al. |
| 2011/0150892 A1 | 6/2011 | Thudium et al. |
| 2011/0177073 A1 | 7/2011 | Van Berkel et al. |
| 2011/0177093 A1 | 7/2011 | Kalled et al. |
| 2011/0250170 A1 | 10/2011 | Pedretti et al. |
| 2011/0287056 A1 | 11/2011 | Gu et al. |
| 2011/0293613 A1 | 12/2011 | Brinkmann et al. |
| 2012/0039906 A1 | 2/2012 | Olive |
| 2012/0114649 A1 | 5/2012 | Langermann et al. |
| 2012/0149876 A1 | 6/2012 | Von Kreudenstein et al. |
| 2012/0184716 A1 | 7/2012 | Fischer et al. |
| 2012/0201746 A1 | 8/2012 | Liu et al. |
| 2012/0213768 A1 | 8/2012 | Oh et al. |
| 2012/0294857 A1 | 11/2012 | Sentman et al. |
| 2013/0017200 A1 | 1/2013 | Scheer et al. |
| 2013/0022601 A1 | 1/2013 | Brinkmann et al. |
| 2013/0078249 A1 | 3/2013 | Ast et al. |
| 2013/0129723 A1 | 5/2013 | Blankenship et al. |
| 2013/0165638 A1 | 6/2013 | Hsu et al. |
| 2013/0178605 A1 | 7/2013 | Blein et al. |
| 2013/0195849 A1 | 8/2013 | Spreter Von Kreudenstein et al. |
| 2013/0243775 A1 | 9/2013 | Papadopoulos et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0303396 A1 | 11/2013 | Igawa et al. |
| 2013/0317200 A1 | 11/2013 | Elson et al. |
| 2014/0037621 A1 | 2/2014 | Tsurushita et al. |
| 2014/0044728 A1 | 2/2014 | Takayanagi et al. |
| 2014/0051833 A1 | 2/2014 | Fischer et al. |
| 2014/0051835 A1 | 2/2014 | Dixit et al. |
| 2014/0072528 A1 | 3/2014 | Gerdes et al. |
| 2014/0072581 A1 | 3/2014 | Dixit et al. |
| 2014/0079689 A1 | 3/2014 | Elliott et al. |
| 2014/0099254 A1 | 4/2014 | Chang et al. |
| 2014/0154254 A1 | 6/2014 | Kannan et al. |
| 2014/0199294 A1 | 7/2014 | Mimoto et al. |
| 2014/0200331 A1 | 7/2014 | Corper et al. |
| 2014/0242075 A1 | 8/2014 | Parren et al. |
| 2014/0242077 A1 | 8/2014 | Choi et al. |
| 2014/0308285 A1 | 10/2014 | Yan et al. |
| 2014/0322212 A1 | 10/2014 | Brogdon et al. |

(56) References Cited

U.S. PATENT DOCUMENTS

| | | |
|---|---|---|
| 2014/0322221 A1 | 10/2014 | Miller et al. |
| 2014/0348839 A1 | 11/2014 | Chowdhury et al. |
| 2014/0363426 A1 | 12/2014 | Moore et al. |
| 2014/0377269 A1 | 12/2014 | Mabry et al. |
| 2015/0017187 A1 | 1/2015 | Thanos et al. |
| 2015/0018529 A1 | 1/2015 | Humphreys et al. |
| 2015/0056199 A1 | 2/2015 | Kumar et al. |
| 2015/0098900 A1 | 4/2015 | Ebens et al. |
| 2015/0133638 A1 | 5/2015 | Wranik et al. |
| 2015/0166661 A1 | 6/2015 | Chen et al. |
| 2015/0166670 A1 | 6/2015 | Castoldi et al. |
| 2015/0175707 A1 | 6/2015 | De Jong et al. |
| 2015/0203591 A1 | 7/2015 | Yancopoulos et al. |
| 2015/0211001 A1 | 7/2015 | Ohrn et al. |
| 2015/0218260 A1 | 8/2015 | Klein et al. |
| 2015/0232560 A1 | 8/2015 | Heindl et al. |
| 2015/0315296 A1 | 11/2015 | Schaefer et al. |
| 2015/0337049 A1 | 11/2015 | Labrijn et al. |
| 2015/0344570 A1 | 12/2015 | Igawa et al. |
| 2015/0353636 A1 | 12/2015 | Parren et al. |
| 2015/0368351 A1 | 12/2015 | Vu et al. |
| 2015/0368352 A1 | 12/2015 | Liu |
| 2015/0376287 A1 | 12/2015 | Vu et al. |
| 2016/0015749 A1 | 1/2016 | Gottschalk et al. |
| 2016/0039947 A1 | 2/2016 | Demarest et al. |
| 2016/0075785 A1 | 3/2016 | Ast et al. |
| 2016/0102135 A1 | 4/2016 | Escobar-Cabrera |
| 2016/0114057 A1 | 4/2016 | Dixit et al. |
| 2016/0130347 A1 | 5/2016 | Bruenker et al. |
| 2016/0131654 A1 | 5/2016 | Berenson et al. |
| 2016/0145340 A1 | 5/2016 | Borges et al. |
| 2016/0176973 A1 | 6/2016 | Kufer et al. |
| 2016/0194389 A1 | 7/2016 | Regula et al. |
| 2016/0229915 A1 | 8/2016 | Igawa et al. |
| 2016/0244523 A1 | 8/2016 | Blank et al. |
| 2016/0257763 A1 | 9/2016 | Von Kreudenstein et al. |
| 2016/0264685 A1 | 9/2016 | Fouque et al. |
| 2016/0297885 A1 | 10/2016 | Kuo et al. |
| 2016/0311915 A1 | 10/2016 | Pulé et al. |
| 2016/0368985 A1 | 12/2016 | Hotzel et al. |
| 2016/0368988 A1 | 12/2016 | Bakker et al. |
| 2017/0022284 A1 | 1/2017 | Timmer et al. |
| 2017/0035905 A1 | 2/2017 | Abrams et al. |
| 2017/0037128 A1 | 2/2017 | Little et al. |
| 2017/0051068 A1 | 2/2017 | Pillarisetti et al. |
| 2017/0066827 A1 | 3/2017 | Pulé et al. |
| 2017/0151281 A1 | 6/2017 | Wagner et al. |
| 2017/0204176 A1 | 7/2017 | Bonvini et al. |
| 2017/0269092 A1 | 9/2017 | Kralovics |
| 2017/0298445 A1 | 10/2017 | Ogg |
| 2017/0334998 A1 | 11/2017 | Pulé et al. |
| 2017/0368169 A1 | 12/2017 | Loew et al. |
| 2018/0153938 A1 | 6/2018 | Keating et al. |
| 2018/0256716 A1 | 9/2018 | Schendel et al. |
| 2019/0062448 A1 | 2/2019 | Soros et al. |
| 2019/0315883 A1 | 10/2019 | Ast et al. |
| 2019/0322763 A1 | 10/2019 | Ast et al. |
| 2020/0109195 A1 | 4/2020 | Watkins et al. |
| 2020/0140549 A1 | 5/2020 | Cordoba et al. |
| 2020/0172591 A1 | 6/2020 | Hosse et al. |
| 2020/0200756 A1 | 6/2020 | Pulé et al. |
| 2020/0230208 A1 | 7/2020 | Wang et al. |
| 2020/0299349 A1 | 9/2020 | Garcia et al. |
| 2020/0306301 A1 | 10/2020 | Andresen et al. |
| 2020/0308242 A1 | 10/2020 | Lowe et al. |
| 2020/0317787 A1 | 10/2020 | Li et al. |
| 2020/0332003 A1 | 10/2020 | Britanova et al. |
| 2021/0024631 A1 | 1/2021 | Kley et al. |
| 2021/0221863 A1 | 7/2021 | Kang et al. |
| 2021/0277119 A1 | 9/2021 | Tan et al. |
| 2022/0064297 A1 | 3/2022 | Tan et al. |
| 2022/0112286 A1 | 4/2022 | Britanova et al. |

FOREIGN PATENT DOCUMENTS

| | | |
|---|---|---|
| CN | 104203981 A | 12/2014 |
| EP | 0125023 A1 | 11/1984 |
| EP | 0171496 A2 | 2/1986 |
| EP | 0173494 A2 | 3/1986 |
| EP | 0184187 A2 | 6/1986 |
| EP | 0346087 A2 | 12/1989 |
| EP | 0368684 A1 | 5/1990 |
| EP | 0388151 A1 | 9/1990 |
| EP | 0404097 A2 | 12/1990 |
| EP | 0519596 A1 | 12/1992 |
| EP | 0616640 A1 | 9/1994 |
| EP | 0425235 B1 | 9/1996 |
| EP | 0403156 B1 | 9/1997 |
| EP | 1176195 A1 | 1/2002 |
| EP | 1301605 B1 | 11/2005 |
| EP | 1870459 A1 | 12/2007 |
| EP | 2581113 A1 | 4/2013 |
| EP | 1846020 B1 | 8/2013 |
| EP | 2699259 A1 | 2/2014 |
| EP | 2467165 B1 | 1/2015 |
| EP | 2847231 A1 | 3/2015 |
| EP | 2982694 A1 | 2/2016 |
| EP | 3023437 A1 | 5/2016 |
| EP | 3029068 A1 | 6/2016 |
| EP | 3055329 A1 | 8/2016 |
| EP | 3137500 A1 | 3/2017 |
| EP | 3059246 B1 | 7/2018 |
| EP | 2723380 B1 | 8/2019 |
| EP | 3294768 B1 | 8/2019 |
| EP | 3590967 A1 | 1/2020 |
| EP | 3626739 A1 | 3/2020 |
| EP | 3642228 A1 | 4/2020 |
| EP | 3189132 B1 | 6/2020 |
| GB | 2188638 A | 10/1987 |
| WO | WO-8500817 A1 | 2/1985 |
| WO | WO-8601533 A1 | 3/1986 |
| WO | WO-8702671 A1 | 5/1987 |
| WO | WO-9002809 A1 | 3/1990 |
| WO | WO-9100906 A1 | 1/1991 |
| WO | WO-9103493 A1 | 3/1991 |
| WO | WO-9110741 A1 | 7/1991 |
| WO | WO-9117271 A1 | 11/1991 |
| WO | WO-9201047 A1 | 1/1992 |
| WO | WO-9203917 A1 | 3/1992 |
| WO | WO-9203918 A1 | 3/1992 |
| WO | WO-9209690 A2 | 6/1992 |
| WO | WO-9215679 A1 | 9/1992 |
| WO | WO-9218619 A1 | 10/1992 |
| WO | WO-9220791 A1 | 11/1992 |
| WO | WO-9301161 A1 | 1/1993 |
| WO | WO-9301288 A1 | 1/1993 |
| WO | WO-9308829 A1 | 5/1993 |
| WO | WO-9311161 A1 | 6/1993 |
| WO | WO-9311236 A1 | 6/1993 |
| WO | WO-9323537 A1 | 11/1993 |
| WO | WO-9404678 A1 | 3/1994 |
| WO | WO-9405801 A1 | 3/1994 |
| WO | WO-9409131 A1 | 4/1994 |
| WO | WO-9411026 A2 | 5/1994 |
| WO | WO-9412625 A2 | 6/1994 |
| WO | WO-9425591 A1 | 11/1994 |
| WO | WO-9429351 A2 | 12/1994 |
| WO | WO-9509917 A1 | 4/1995 |
| WO | WO-9516038 A2 | 6/1995 |
| WO | WO-9637621 A2 | 11/1996 |
| WO | WO-9730087 A1 | 8/1997 |
| WO | WO-9856915 A2 | 12/1998 |
| WO | WO-9858964 A1 | 12/1998 |
| WO | WO-9904820 A2 | 2/1999 |
| WO | WO-9916873 A1 | 4/1999 |
| WO | WO-9922764 A1 | 5/1999 |
| WO | WO-9945110 A1 | 9/1999 |
| WO | WO-9951642 A1 | 10/1999 |
| WO | WO-9964460 A1 | 12/1999 |
| WO | WO-0006605 A2 | 2/2000 |
| WO | WO-0034784 A1 | 6/2000 |
| WO | WO-0060070 A1 | 10/2000 |

(56) References Cited

FOREIGN PATENT DOCUMENTS

| | | |
|---|---|---|
| WO | WO-0061739 A1 | 10/2000 |
| WO | WO-0104144 A2 | 1/2001 |
| WO | WO-0129246 A1 | 4/2001 |
| WO | WO-0164942 A1 | 9/2001 |
| WO | WO-0231140 A1 | 4/2002 |
| WO | WO-02070647 A2 | 9/2002 |
| WO | WO-02072635 A2 | 9/2002 |
| WO | WO-03002609 A2 | 1/2003 |
| WO | WO-03011878 A2 | 2/2003 |
| WO | WO-03014161 A2 | 2/2003 |
| WO | WO-03056914 A1 | 7/2003 |
| WO | WO-03084570 A1 | 10/2003 |
| WO | WO-03085107 A1 | 10/2003 |
| WO | WO-03085119 A1 | 10/2003 |
| WO | WO-2004003019 A2 | 1/2004 |
| WO | WO-2004024927 A1 | 3/2004 |
| WO | WO-2004033685 A1 | 4/2004 |
| WO | WO-2004056312 A2 | 7/2004 |
| WO | WO-2004056392 A1 | 7/2004 |
| WO | WO-2004056873 A1 | 7/2004 |
| WO | WO-2004057002 A2 | 7/2004 |
| WO | WO-2004058821 A2 | 7/2004 |
| WO | WO-2004065540 A2 | 8/2004 |
| WO | WO-2004081026 A2 | 9/2004 |
| WO | WO-2004081051 A1 | 9/2004 |
| WO | WO-2004101790 A1 | 11/2004 |
| WO | WO-2004106368 A1 | 12/2004 |
| WO | WO-2005035572 A2 | 4/2005 |
| WO | WO-2005035586 A1 | 4/2005 |
| WO | WO-2005035778 A1 | 4/2005 |
| WO | WO-2005053742 A1 | 6/2005 |
| WO | WO-2005100402 A1 | 10/2005 |
| WO | WO-2006000830 A2 | 1/2006 |
| WO | WO-2006020258 A2 | 2/2006 |
| WO | WO-2006029879 A2 | 3/2006 |
| WO | WO-2006044908 A2 | 4/2006 |
| WO | WO-2006079372 A1 | 8/2006 |
| WO | WO-2006106905 A1 | 10/2006 |
| WO | WO-2006121168 A1 | 11/2006 |
| WO | WO-2006135886 A2 | 12/2006 |
| WO | WO-2007005874 A2 | 1/2007 |
| WO | WO-2007044887 A2 | 4/2007 |
| WO | WO-2007059782 A1 | 5/2007 |
| WO | WO-2007095338 A2 | 8/2007 |
| WO | WO-2007110205 A2 | 10/2007 |
| WO | WO-2007137760 A2 | 12/2007 |
| WO | WO-2008017859 A2 | 2/2008 |
| WO | WO-2008077546 A1 | 7/2008 |
| WO | WO-2008119353 A1 | 10/2008 |
| WO | WO-2009021754 A2 | 2/2009 |
| WO | WO-2009068630 A1 | 6/2009 |
| WO | WO-2009089004 A1 | 7/2009 |
| WO | WO-2009101611 A1 | 8/2009 |
| WO | WO-2009103538 A1 | 8/2009 |
| WO | WO-2009114335 A2 | 9/2009 |
| WO | WO-2010019570 A2 | 2/2010 |
| WO | WO-2010027797 A1 | 3/2010 |
| WO | WO-2010027827 A2 | 3/2010 |
| WO | WO-2010077634 A1 | 7/2010 |
| WO | WO-2010129304 A2 | 11/2010 |
| WO | WO-2011066342 A2 | 6/2011 |
| WO | WO-2011131746 A2 | 10/2011 |
| WO | WO-2011155607 A1 | 12/2011 |
| WO | WO-2012088309 A1 | 6/2012 |
| WO | WO-2012107417 A1 | 8/2012 |
| WO | WO-2012131555 A2 | 10/2012 |
| WO | WO-2012138475 A1 | 10/2012 |
| WO | WO-2012143498 A1 | 10/2012 |
| WO | WO-2013019615 A2 | 2/2013 |
| WO | WO-2013060867 A2 | 5/2013 |
| WO | WO-2013079174 A1 | 6/2013 |
| WO | WO-2013103912 A1 | 7/2013 |
| WO | WO-2013170168 A1 | 11/2013 |
| WO | WO-2014008218 A1 | 1/2014 |
| WO | WO-2014100823 A1 | 6/2014 |
| WO | WO-2015052230 A1 | 4/2015 |
| WO | WO-2015107015 A1 | 7/2015 |
| WO | WO-2015107025 A1 | 7/2015 |
| WO | WO-2015107026 A1 | 7/2015 |
| WO | WO-2015121383 A1 | 8/2015 |
| WO | WO-2015127158 A1 | 8/2015 |
| WO | WO-2015132598 A1 | 9/2015 |
| WO | WO-2015164815 A1 | 10/2015 |
| WO | WO-2015166073 A1 | 11/2015 |
| WO | WO-2015181805 A1 | 12/2015 |
| WO | WO-2015197582 A1 | 12/2015 |
| WO | WO-2015197593 A1 | 12/2015 |
| WO | WO-2015197598 A2 | 12/2015 |
| WO | WO-2016016299 A1 | 2/2016 |
| WO | WO-2016019969 A1 | 2/2016 |
| WO | WO-2016026943 A1 | 2/2016 |
| WO | WO-2016033555 A1 | 3/2016 |
| WO | WO-2016071376 A2 | 5/2016 |
| WO | WO-2016071377 A1 | 5/2016 |
| WO | WO-2016079081 A1 | 5/2016 |
| WO | WO-2016087416 A1 | 6/2016 |
| WO | WO-2016087514 A1 | 6/2016 |
| WO | WO-2016087650 A1 | 6/2016 |
| WO | WO-2016090327 A2 | 6/2016 |
| WO | WO-2016110468 A1 | 7/2016 |
| WO | WO-2016110584 A1 | 7/2016 |
| WO | WO-2016115274 A1 | 7/2016 |
| WO | WO-2016118641 A1 | 7/2016 |
| WO | WO-2016168149 A1 | 10/2016 |
| WO | WO-2016180969 A1 | 11/2016 |
| WO | WO-2016193301 A1 | 12/2016 |
| WO | WO-2017021450 A1 | 2/2017 |
| WO | WO-2017037634 A1 | 3/2017 |
| WO | WO-2017055391 A1 | 4/2017 |
| WO | WO-2017059551 A1 | 4/2017 |
| WO | WO-2017062604 A1 | 4/2017 |
| WO | WO-2017077382 A1 | 5/2017 |
| WO | WO-2017165464 A1 | 9/2017 |
| WO | WO-2017167919 A1 | 10/2017 |
| WO | WO-2017180913 A2 | 10/2017 |
| WO | WO-2018057955 A1 | 3/2018 |
| WO | WO-2018098365 A2 | 5/2018 |
| WO | WO-2018144777 A2 | 8/2018 |
| WO | WO-2018201047 A1 | 11/2018 |
| WO | WO-2018224844 A1 | 12/2018 |
| WO | WO-2018237192 A1 | 12/2018 |
| WO | WO-2019005641 A1 | 1/2019 |
| WO | WO-2019040700 A1 | 2/2019 |
| WO | WO-2019086865 A1 | 5/2019 |
| WO | WO-2019101695 A1 | 5/2019 |
| WO | WO-2019132738 A1 | 7/2019 |
| WO | WO-2019139987 A1 | 7/2019 |
| WO | WO-2019158764 A1 | 8/2019 |
| WO | WO-2019178362 A1 | 9/2019 |
| WO | WO-2019178364 A2 | 9/2019 |
| WO | WO-2019191519 A1 | 10/2019 |
| WO | WO-2019231920 A1 | 12/2019 |
| WO | WO-2020005819 A1 | 1/2020 |
| WO | WO-2020010250 A2 | 1/2020 |
| WO | WO-2020018708 A1 | 1/2020 |
| WO | WO-2020025928 A1 | 2/2020 |
| WO | WO-2020057646 A1 | 3/2020 |
| WO | WO-2020082048 A1 | 4/2020 |
| WO | WO-2020084290 A1 | 4/2020 |
| WO | WO-2020086758 A1 | 4/2020 |
| WO | WO-2020088459 A1 | 5/2020 |
| WO | WO-2020089644 A1 | 5/2020 |
| WO | WO-2020091635 A2 | 5/2020 |
| WO | WO-2020106708 A1 | 5/2020 |
| WO | WO-2020139171 A1 | 7/2020 |
| WO | WO-2020139175 A1 | 7/2020 |
| WO | WO-2020142672 A2 | 7/2020 |
| WO | WO-2020172571 A1 | 8/2020 |
| WO | WO-2020172596 A1 | 8/2020 |
| WO | WO-2020172598 A1 | 8/2020 |
| WO | WO-2020172601 A1 | 8/2020 |
| WO | WO-2020183245 A2 | 9/2020 |
| WO | WO-2021097325 | 5/2021 |

(56) References Cited

FOREIGN PATENT DOCUMENTS

| WO | WO-2021138474 A2 | 7/2021 |
|----|------------------|--------|
| WO | WO-2021217085 A1 | 10/2021 |
| WO | WO-2022046920 A2 | 3/2022 |

OTHER PUBLICATIONS

Stein, et al., "A new monoclonal antibody (CAL2) detects Calreticulin mutations in formalin-fixed and paraffin-embedded bone marrow biopsies," Leukemia, Jul. 23, 2015, vol. 30, No. 1, pp. 131-135.

Ten Hacken, et al., "Calreticulin as a novel B-cell receptor antigen in chronic lymphocytic leukemia," Haematologica, Oct. 31, 2017, vol. 102, No. 10, pp. e394-e396.

Vannucchi, et al., "Calreticulin mutation-specific immunostaining in myeloproliferative neoplasms: pathogenetic insight and diagnostic value" Leukemia (2014) 28, p. 1811-1818.

Vyas et al.: Natural ligands and antibody-based fusion proteins: harnessing the immune system against cancer. Trends Mol Med. 20(2):72-82 (2014).

Adachi, Osamu, et al., Targeted Disruption of the MyD88 Gene Results in Loss of IL-1- and IL-8-Mediated Function. Immunity 9(1):143-150 (1998).

Agata et al. Expression of the PD-1 antigen on the surface of stimulated mouse T and B lymphocytes. Int. Immunol 8:765-75 (1996).

Aggen, David, et al., Single-chain VαVβ T-cell Receptors Function Without Mispairing With Endogenous TCR Chains. Gene therapy 19(4):365-374 (2012).

Agostinis, Patrizia, et al., Photodynamic Therapy of Cancer: An Update. CA: A Cancer Journal for Clinicians 61(4):250-281 (2011).

Aigner et al.: An effective tumor vaccine optimized for costimulation via bispecific and trispecific fusion proteins. Int J Oncol. 32(4):777-789 (2008).

Akers, Michael J, et al., Formulation development of protein dosage forms. Pharm Biotechnol 14:47-127 (2002).

Akiyama et al.: TNFalpha induces rapid activation and nuclear translocation of telomerase in human lymphocytes. Biochem Biophys Res Commun. 316(2):528-532 (2004).

Ala-Aho, Risto, et al., Collagenases in Cancer. Biochimie 87(3-4):273-286 (2005).

Al-Aghbar, M.A. et al., "High-affinity ligands can trigger T cell receptor signaling without CD45 segregation," Frontiers in Immunology, 2018;9(713):1-18.

Ali et al.: Modulation of human natural killer cytotoxicity by influenza virus and its subunit protein. Immunology 52(4):687-695 (1984).

Al-Lazikani, B. et al., "Standard Conformations for Canonical Structures of Immunoglobulins", J. Mol. Biol., 1997, vol. 273, pp. 927-948.

Almagro et al. Humanization of antibodies. Front Biosci 13:1619-1633 (2008).

Altschul, Stephen F, et al., Basic Local Alignment Search Tool. Journal of Molecular Biology 215(3):403-410 (1990).

Amarante-Mendes GP, Griffith TS. Therapeutic applications of TRAIL receptor agonists in cancer and beyond. Pharmacol Ther. Nov. 2015;155:117-31. Epub Sep. 5, 2015.

Arai, R. et al., "Design of the linkers which effectively separate domains of a bifunctional fusion protein", Protein Engineering, 2001, vol. 14, No. 8, pp. 529-532.

Arenas-Ramirez et al.: Interleukin-2: Biology, Design and Application. Trends in Immunology 36(12):763-777 (2015).

Arnon, T.I. et al., "Recognition of viral hemagglutinins by NKp44 but not by NKp30", Eur J. Immunol., 2001, vol. 31, No. 9, pp. 2680-2689.

Aslan, J.E. et al., "S6K1 and mTOR regulate Rac1-driven platelet activation and aggregation", Blood, 2011, vol. 118, No. 11, pp. 3129-3136.

Aversa, Ilenia, et al., Molecular T-Cell Repertoire Analysis as Source of Prognostic and Predictive Biomarkers for Checkpoint blockade Immunotherapy. International Journal of Molecular Sciences 21(7):2378, 1-19 (2020).

Baca et al.: Antibody humanization using monovalent phage display. J Biol Chem 272(16):10678-10684 (1997).

Banerjee, Hridesh, et al., 33rd Annual Meeting & Pre-Conference Programs of the Society for Immunotherapy of Cancer (SITC). Journal for Immunotherapy of Cancer 6(1):1-192 (2018).

Barbas, Carlos, et al., Assembly of Combinatorial Antibody Libraries on Phage Surfaces: The Gene III Site. Proceedings of the National Academy of Sciences of the United States of America 88(18):7978-7982 (1991).

Batzer et al. Enhanced evolutionary PCR using oligonucleotides with inosine at the 3'-terminus Nucleic Acids Research 19(18):5081 (1991).

Beidler, C B, et al., Cloning and High Level Expression of a Chimeric Antibody With Specificity for Human Carcinoembryonic Antigen. Journal of Immunology 141(11):4053-4060 (1988).

Berge, Ten, et al., Selective Expansion of a Peripheral Blood Cd8+ Memory T Cell Subset Expressing Both Granzyme B and L-selectin During Primary Viral Infection in Renal Allograft Recipients. Transplantation Proceedings 30(8):3975-3977 (1998).

Better, M. et al., "*Escherichia coli* Secretion of an Active Chimeric Antibody Fragment", Science, 1988, vol. 240, No. 4855, pp. 1041-1043.

Beun, G. et al., "T cell Retargeting Using Bispecific Monoclonal Antibodies in a Rat Colon Carcinoma Model", The Journal of Immunology, 1993, vol. 150, No. 6, pp. 2305-2315.

Bierer, B E, et al., Cyclosporin a and Fk506: Molecular Mechanisms of Immunosuppression and Probes for Transplantation Biology. Current Opinion in Immunology 5(5):763-773 (1993).

Bird, R.E. et al., Single-Chain Antigen-binding Proteins, Science, vol. 242, 4877 (1988):423-426.

Blank et al., Interaction of PD-L1 on Tumor Cells with PD-1 on Tumor-Specific T cells as a Mechanism of Immune Evasion: Implications for Tumor Immunotherapy. Cancer Immunol Immunother 54:307-314 (2005) (Published Online on Dec. 15, 2004).

Bloeman et al. Adhesion molecules: a new target for immunoliposome-mediated drug delivery. FEBS Lett. 357:140 (1995).

Bluemel, C. et al., "Epitope distance to the target cell membrane and antigen size determine the potency of T cell-mediated lysis by BiTE antibodies specific for a large melanoma surface antigen", Cancer Immunology, Immunotherapy, 2010, vol. 59, No. 8, pp. 1197-1209.

Boerner et al. Production of antigen-specific human monoclonal antibodies from in vitro-primed human splenocytes. J Immunol. 147(1):86-95 (Jul. 1, 1991).

Bolt, S. et al., "The generation of a humanized, non-mitogenic CD3 monoclonal antibody which retains in vitro immunosuppressive properties," Eur. J. Immunol., 1993;23:403-411.

Borrebaeck, C. Antibody engineering. Oxford University Press, 1995.

Breman, E. et al., "Overcoming target driven fratricide for T Cell Therapy," Frontiers in Immunology, 2018;9(2940):1-11.

Brennan et al. Preparation of bispecific antibodies by chemical recombination of monoclonal immunoglobulin G1 fragments. Science 229:81-83, 1985.

Briscoe et al. Delivery of superoxide dismutase to pulmonary epithelium via pH-sensitive liposomes. Am. J. Physiol. 1233:134 (1995).

Brodeur et al.: In: Monoclonal Antibody Production Techniques and Applications. New York: Marcel Dekker:51-63 (1987).

Bruggemann, M. et al., Designer Mice: The Production of Human Antibody Repertoires in Transgenic Animals, Terhorst C. Malavasi F, Albertini A (eds): Generation of Antibodies by Cell and Gene Immortalization, Year Immunol, 1993, vol. 7, pp. 33-40.

Bruggemann, M. et al., "Human antibody production in transgenic mice: expression from 100kb of the human IgH locus", Eur J. Immunol, 1991, vol. 21, pp. 1323-1326.

Buchwald et al. Long-term, continuous intravenous heparin administration by an implantable infusion pump in ambulatory patients with recurrent venous thrombosis. Surgery 88:507-516 (1980).

(56) References Cited

OTHER PUBLICATIONS

Cadwell, R. C. et al., "Randomization of Genes by PCR Mutagenesis", PCR Methods Appl., 1992, vol. 2, No. 1, pp. 28-33.
Cain, Chris, et al., Crossing over to Bispecificity. SciBX 4(28):1-3 (2011).
Carter et al.: Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Cazzola, Mario, et al., From Janus kinase 2 to calreticulin: the clinically relevant genomic landscape of myeloproliferative neoplasms. Blood 123(24):3714-3719 (2014).
Chang et al.: A therapeutic T cell receptor mimic antibody targets tumor-associated PRAME peptide/HLA-I antigens. J Clin Invest. 127(7):2705-2718 (2017).
Chao, G. et al., "Isolating and engineering human antibodies using yeast surface display", Nature Protocols, 2006, vol. 1, No. 2, pp. 755-768.
Chari et al.: Immunoconjugates containing novel maytansinoids: promising anticancer drugs. Cancer Res. 52(1):127-131 (1992).
Charlton. Chapter 14: Expression and Isolation of Recombinant Antibody Fragments in E. coli. Methods in Molecular Biology 248:245-254 (2003).
Chaudry, et al. EpCAM an immunotherapeutic target for gastrointestinal malignancy: current experience and future challenges. Br J Cancer. Apr. 10, 2007;96(7):1013-9. Epub Feb. 27, 2007.
Chen et al.: Chromosome X-encoded cancer/testis antigens show distinctive expression patterns in developing gonads and in testicular seminoma. Hum Reprod. 26(12):3232-3243 doi:10.1093/humrep/der330 (2011).
Chen et al.: Selection And Analysis Of An Optimized Anti-VEGF Antibody: Crystal Structure Of An Affinity-matured Fab In Complex With Antigen. Journal of Molecular Biology 293(4):865-881 (1999).
Chen et al.: The nuclear localization sequences of the BRCA1 protein interact with the importin-alpha subunit of the nuclear transport signal receptor. J Biol Chem. 271(51):32863-32868 (1996).
Chiang, E. et al., "Abstract 3527: Potent anti-tumor activity of AbGn-100, an anti-CD326 x anti-TCR bispecific antibody to CD326-expressing solid tumors," Cancer Res., 2012;72(8_supplement):3527.
Chichili, V.P.R. et al., "Linkers in the structural biology of protein-protein interactions," Protein Science, 2013;22:153-167.
Chinese Patent Application No. 201780028089.4 2nd Office Action dated Apr. 18, 2022.
Chothia, C. et al., "Canonical Structures for the Hypervariable Regions of Immunoglobulins", J. Mol. Biol, 1987, vol. 196, pp. 901-917.
Chothia et al., Structural repertoire of the human VH segments. J Mol Biol 227:799-817 (1992).
Chowdhury. Engineering hot spots for affinity enhancement of antibodies. Methods Mol. Biol. 207:179-196 (2008).
Ciccone, E. et al., "A monoclonal antibody specific for a common determinant of the human T cell receptor gamma/delta directly activates CD3+WT31-lymphocytes to express their functional program(s)," J Exp Med., 1988;168(1):1-11.
Clackson, T. et al., Making antibody fragments using phage display libraries, Nature, 1991, vol. 352, pp. 624-628.
Clynes et al. Fc receptors are required in passive and active immunity to melanoma. PNAS USA 95(2):652-656 (1998).
Colcher, David, et al., Single-Chain Antibodies in Pancreatic Cancer. Annals of the New York Academy of Sciences 880:263-280 (1999).
Coloma, J. et al., "Design and production of novel tetravalent bispecific antibodies", Nature Biotech, 1997, vol. 15, pp. 159-163.
Costa-Mattioli, Mauro, et al., RAPping Production of type I Interferon in pDCs through mTOR. Nature Immunology 9(10):1097-1099 (2008).
Cragg et al. Antibody specificity controls in vivo effector mechanisms of anti-CD20 reagents. Blood 103(7):2738-2743 (2004).
Cragg et al.: Complement-mediated lysis by anti-CD20 mAb correlates with segregation into lipid rafts. Blood 101(3):1045-1052 (2003).
Cui, et al., "T cell receptor B-chain repertoire analysis of tumor-infiltrating lymphocytes in pancreatic cancer" Cancer Science (2018) 60-71.
Cunningham and Wells, High-resolution epitope mapping of hGH-receptor interactions by alanine-scanning mutagenesis. Science, 244(4908):1081-1085, 1989.
Dall'Acqua, et al.: Antibody humanization by framework shuffling. Methods. 36(1):43-60 (2005).
Dao, Tao, et al., Targeting the Intracellular Wt1 Oncogene Product With a Therapeutic Human Antibody. Science Translational Medicine 5(176):176ra33, 1-22 (2013).
Davis, J. et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection, 2010, vol. 23, No. 4, pp. 195-202.
Dela Cruz et al.: Anti-HER2/neu IgG3-(IL-2) and anti-HER2/neu IgG3-(GM-CSF) promote HER2/neu processing and presentation by dendritic cells: Implications in immunotherapy and vaccination strategies. Molecular Immunology 43(6):667-676 (2006).
Dickopf, S. et a., "Formal and geometries matter: Structure-based design defines the functionality of bispecific antibodies", Computational and Structural Biotechnology Journal, 2020, vol. 18, pp. 1221-1227.
Dimasi et al. Development of a trispecific antibody designed to simultaneously and efficiently target three different antigens on tumor cells. Mol Pharm 12(9):3490-3501 (2015).
Dimasi, Nazzareno, et al., The design and characterization of oligospecific antibodies for simultaneous targeting of multiple disease mediators. Journal of molecular biology 393(3):672-692 (2009).
Dong et al., B7-H1 Pathway and its Role in the Evasion of Tumor Immunity. J Mol Med 81:281-287 (Apr. 30, 2003).
Doyle, Sean, et al., IRF3 Mediates a TLR3/TLR4-Specific Antiviral Gene Program. Immunity 17(3):251-263 (2002).
Dubowchik, Gene M, et al., Doxorubicin immunoconjugates containing bivalent, lysosomally-cleavable dipeptide linkages. Bioorganic & medicinal chemistry letters 12(11):1529-32 (2002).
Duhen et al., Co-expression of $CD_{39}$ and $CD_{103}$ identifies tumor-reactive CD8 T cells in human solid tumors. Nat Commun. 9(1):2724, pp. 1-13 (2018).
Duncan et al. The binding site for C1q on IgG. Nature 332(6166):738-40 (1988).
During, M J, et al., Controlled Release of Dopamine From a Polymeric Brain Implant: in Vivo Characterization. American Neurological Association 25(4):351-356 (1989).
El Achi, H. et al., "CD123 as a Biomarker in Hematolymphoid Malignancies: Principles of Detection and Targeted Therapies," Cancers, 2020;12(11):3087.
European Patent Application No. 17 718 441.3 Office Action dated Jan. 24, 2022.
European Search Report issued in EP20736073, dated Aug. 2, 2022.
Falini et al.: Cytoplasmic nucleophosmin in acute myelogenous leukemia with a normal karyotype. N Engl J Med. 352(3):254-266 doi: 10.1056/NEJMoa041974 (2005).
Farrar et al.: The Molecular Cell Biology Of Interferon-gamma And Its Receptor. Annu Rev Immunol 11:571-611 (1993).
Fellouse, et al. Synthetic antibodies from a four-amino-acid code: a dominant role for tyrosine in antigen recognition. Proc Natl Acad Sci U S A. Aug. 24, 2004;101(34):12467-72. Epub Aug. 11, 2004.
Fernandez-Malave, Edgar, et al., An Natural Anti-T-Cell Receptor Monoclonal Antibody Protects Against Experimental Autoimmune Encephalomyelitis. Journal of Neuroimmunology 234(1-2):63-70 (2011).
Flatman et al., Process analytics for purification of monoclonal antibodies. J. Chromatogr. B 848:79-87 (2007).
Fontana, et al., Probing the partly folded states of proteins by limited proteolysis. Folding & design 2(2):R17-26 (1997).

(56) References Cited

OTHER PUBLICATIONS

Freeman et al. Engagement of the PD-1 immunoinhibitory receptor by a novel B7 family member leads to negative regulation of lymphocyte activation. J Exp Med 192:1027-1034 (2000).
Frost, Gregory, et al., A Microtiter-Based Assay for Hyaluronidase Activity Not Requiring Specialized Reagents. Analytical Biochemistry 251(2):263-269 (1997).
Fuchs, P. et al., "Targeting Recombinant Antibodies to the surface of *Escherichia coli*: Fusion to the Peptidoglycan associated Lipoprotein", Nat Biotechnol 1991, vol. 9, No. 12, pp. 1369-1372.
Funayama et al.: Embryonic axis induction by the armadillo repeat domain of beta-catenin: evidence for intracellular signaling. J Cell Biol. 128(5):959-968 (1995).
Gao et al.: Alg14 recruits Alg13 to the cytoplasmic face of the endoplasmic reticulum to form a novel bipartite UDP-N-acetylglucosamine transferase required for the second step of N-linked glycosylation. J Biol Chem. 280(43):36254-36262 doi: 10.1074/jbc.M507569200 (2005).
Garland, R.J., et al., "The use of Teflon cell culture bags to expand functionally active CD8+ cytotoxic T lymphocytes", Journal of Immunological Methods, 1999, vol. 227, pp. 53-63.
Garrard, L. et al., "FAB Assembly and Enrichment in a Monovalent Phage Display System", *Nat Biotechnol*, 1991, vol. 9, pp. 1373-1377.
Garrity, David, et al., The Activating NKG2D Receptor Assembles in the Membrane With Two Signaling Dimers Into a Hexameric Structure. Proceedings of the National Academy of Sciences of the United States of America 102(21):7641-7646 (2005).
Gazzano-Santoro, H. et al., A non-radioactive complement-dependent cytotoxicity assay for anti-CD20 monoclonal antibody, Journal of Immunol. Methods, vol. 202, (1996):163-171.
GB Exam Report for GB2109794.4 dated Jun. 21, 2020.
Gerngross. Advances in the production of human therapeutic proteins in yeasts and filamentous fungi. Nat Biotech 22:1409-1414 (2004).
Gillies, S.D. et al., "Bi-functional cytokine fusion proteins for gene therapy and antibody-targeted treatment of cancer," Cancer Immunol Immunotherapy, 2002;51:449-460.
Gjerstorff et al.: GAGE cancer-germline antigens are recruited to the nuclear envelope by germ cell-less (GCL). PLoS One 7(9):e45819:1-12 doi:10.1371/journal.pone.0045819 (2012).
Goel, M. et a., "Plasticity within the Antigen-Combining site may manifest as molecular mimicry in the humoral immune response," J Immunology, 2004; 173(12):7358-7367.
Gohal, G. et al., "T-cell receptor phenotype pattern in atopic children using commercial fluorescently labeled antibodies against 21 human class-specific v segments for the tcrß chain (vβ) of peripheral blood: a cross sectional study," Allergy Asthma Clin Immunol., 2016;12:10.
Gokden et al.: Diagnostic utility of renal cell carcinoma marker in cytopathology. Appl Immunohistochem Mol Morphol. Abstract Only. 11(2):116-119 doi:10.1097/00129039-200306000-00004 (2003).
Gordon, E.D. et al., "Alternative splicing of interleukin-33 and type 2 inflammation in asthma," PNAS, 2016;113(31):8765-8770.
Graham et al. Characteristics of a human cell line transformed by DNA from human adenovirus type 5. J. Gen Virol. 36:59-74 (1977).
Gram, H. et al., In vitro selection and affinity maturation of antibodies from a naïve combinatorial immunoglobulin library, PNAS, 1992, vol. 89, pp. 3576-3580.
Green, Edward, et al., TCR Validation Toward Gene Therapy for Cancer. Methods in Enzymology 629(21):419-441 (2019).
Green, L.L. et al., "Antigen-specific human monoclonal antibodies from mice engineered with human Ig heavy and light chain YACS", Nature Genet, 1994, vol. 7, pp. 13-21.
Griffiths, A.D. et al., "Human anti-self antibodies with high specificity from phage display libraries", The EMBO Journal, 1993, vol. 12, No. 2, pp. 725-734.
Gruber et al., Efficient tumor cell lysis mediated by a bispecific single chain antibody expressed in *Escherichia coli*. J. Immunol. 152: 5368 (1994).
Gulley, J.L. et al., "New drugs on the horizon," Eur J Cancer, 2022;174(S1):S5.
Gupta, S. et al., "T cell activation via the T cell receptor: a comparison between WT31 (defining alpha/beta TcR)-induced and anti-CD3-induced activation of human T lymphocytes," Cell Immunol., 1991;132(1):26-44.
Haanen, J. et al., "Selective Expansion of Cross-reactive CD8+ Memory T Cells by Viral Variants", J. Exp. Med., 1999, vol. 190, No. 9, pp. 1319-1328.
Halin, C. et al., "Synergistic Therapeutic Effects of a Tumor Targeting Antibody Fragment, Fused to Interleukin 12 and to Tumor Necrosis Factor a1," Cancer Research, 2003;63:3202-3210.
Hall, MacLean, et al., Expansion of Tumor-Infiltrating Lymphocytes (TIL) from Human Pancreatic Tumors. Journal for Immuno Therapy of Cancer 4:61, 1-12 (2016).
Hamers-Casterman et al. Naturally occurring antibodies devoid of light chains. Nature 363(6428):446-8 (1993).
Hamid, O. et al., "Safety and Tumor Responses with Lambrolizumab (Anti-PD-1) in Melanoma", The New England Journal of Medicine, 2013, vol. 369, No. 2, pp. 134-144.
Hamming et al. Crystal Structure of Interleukin-21 Receptor (IL-21R) Bound to IL-21 Reveals That Sugar Chain Interacting with WSXWS Motif Is Integral Part of IL-21R. The Journal of Biological Chemistry 287(12):9454-9460 (2012).
Hawkins, R. et al., "Selection of phage antibodies by binding affinity. Mimicking affinity maturation", J. Mol. Biol., 1992, vol. 226, No. 3, pp. 889-896.
Hay, B. et al., "Bacteriophage cloning and *Escherichia coli* expression of a human IgM Fab" Hum Antibodies Hybridomas, 1992, vol. 3, No. 2, pp. 81-85.
Henderson, D J, et al., Comparison of the Effects of FK-506, Cyclosporin A and Rapamycin on IL-2 Production. Immunology 73(3):316-321 (1991).
Herskovitz, O. et al., "NKp44 receptor mediates interaction of the envelope glycoproteins from the West-Nile and dengue viruses with Natural Killer cells," The Journal of Immunology, 2009;183(4):2610-2621.
Hinman, et al. Preparation and characterization of monoclonal antibody conjugates of the calicheamicins: a novel and potent family of antitumor antibiotics. Cancer Res. Jul. 15, 1993;53(14):3336-3342.
Hirai et al.: Nucleolar scaffold protein, WDR46, determines the granular compartmental localization of nucleolin and DDX21. Genes Cells 18(9):780-797 (2013).
Hiyama, K, et al., Action of Chondroitinases. I. The Mode of Action of Two Chondroitinase-AC Preparations of Different Origin. Journal of Biochemistry 80(6):1201-1207 (1976).
Hiyama, K, et al., Crystallization and Some Properties of Chondroitinase from Arthrobacter Aurescens. The Journal of Biological Chemistry 250(5):1824-1828 (1975).
Hollinger, Philipp, et al., "Diabodies": small bivalent and bispecific antibody fragments. Proceedings of the National Academy of Sciences of the United States of America 90:6444-6448 (1993).
Hollinger, Philipp, et al., Engineered Antibody Fragments and the Rise of Single Domains. Nature Biotechnology 23(9):1126-1136 (2005).
Hombach, A.A. et al., "Antibody-IL2 Fusion Proteins for Tumor Targeting," Antibody Engineering, 2012:611-626.
Hoogenboom, et al. By-passing immunisation. Human antibodies from synthetic repertoires of germline VH gene segments rearranged in vitro. J Mol Biol. Sep. 20, 1992;227(2):381-8.
Hoogenboom et al.: Overview of antibody phage-display technology and its applications. In: Methods in Molecular Biology. 178:1-37 (2001).
Hoogenboom, H.R. et al., "Multi-subunit proteins on the surface of filamentous phage: methodologies for displaying antibody (Fab) heavy and light chains", Nuc Acid Res, 1991, vol. 19, No. 15, pp. 4133-4137.
Howard, M A, et al., Intracerebral Drug Delivery in Rats with Lesion-induced Memory Deficits. Journal of Neurosurgery 71(1):105-112 (1989).
Hudson et al.: Engineered Antibodies. Nature Medicine 9(1):129-134 (2003).

(56) References Cited

OTHER PUBLICATIONS

Hudspeth et al.: Natural cytotoxicity receptors: broader expression patterns and functions in innate and adaptive immune cells. Frontiers in Immunology 4(69):1-15 (2013).
Hunig, T. et al., "A monoclonal antibody to a constant determinant of the rat t cell antigen receptor that induces t cell activation", J. Exp. Med., 1989, vol. 169, pp. 73-86.
Huse, W. et al., "Generation of a large combinatorial library of the immunoglobulin repertoire in phage lambda" Science, 1989, vol. 246, No. 4935, pp. 1275-1281.
Huston, James, et al., Protein Engineering Of Antibody Binding Sites: Recovery Of Specific Activity In An Anti-digoxin Single-chain Fv Analogue Produced In *Escherichia coli*. Proceedings of the National Academy of Sciences of the United States of America 85(16):5879-5883 (1988).
Idusogie et al.: Mapping of the C1q binding site on rituxan, a chimeric antibody with a human IgG1 Fc. J Immunol. 164(8):4178-84 (2000).
Imai-Nishiya H. et al., Double knockdown of α1,6-fucosyltransferase (FUT8) and GDP-mannose 4,6-dehydratase (GMD) in antibody-producing cells: a new strategy for generating fully non-fucosylated therapeutic antibodies with enhanced ADCC. BMC Biotechnology 7(84):1-13 (2007).
International Preliminary Report on Patentability issued in PCT/US2017/023483, dated Sep. 25, 2018.
International Preliminary Report on Patentability issued in PCT/US2019/040592, dated Jan. 5, 2021.
International Preliminary Report on Patentability issued in PCT/US2020/012162, dated Jun. 16, 2021.
International Preliminary Report on Patentability issued in PCT/US2020/019291, dated Aug. 10, 2021.
International Preliminary Report on Patentability issued in PCT/US2020/019319, dated Aug. 10, 2021.
International Preliminary Report on Patentability issued in PCT/US2020/019321, dated Aug. 10, 2021.
International Preliminary Report on Patentability issued in PCT/US2020/060557 dated May 17, 2022.
International Preliminary Report on Patentability issued in PCT/US/2020/067543, dated Jul. 5, 2022.
International Preliminary Report on Patentability issued in PCT/US2021/022408, dated Sep. 20, 2022.
International Preliminary Report on Patentability issued in PCT/US2021/028970, dated Oct. 25, 2022.
International Search Report and Written Opinion issued in PCT/US2017/023483, mailed Aug. 29, 2017.
International Search Report and Written Opinion issued in PCT/US2019/040592, mailed Jan. 9, 2020.
International Search Report and Written Opinion issued in PCT/US2020/012162 mailed Jun. 26, 2020.
International Search Report and Written Opinion issued in PCT/US2020/019291, mailed Jun. 15, 2020.
International Search Report and Written Opinion issued in PCT/US2020/019319, mailed Jun. 26, 2020.
International Search Report and Written Opinion issued in PCT/US2020/019321, mailed Aug. 10, 2020.
International Search Report and Written Opinion issued in PCT/US2020/060557, mailed Mar. 30, 2021.
International Search Report and Written Opinion issued in PCT/US2020/067543, mailed Jul. 7, 2021.
International Search Report and Written Opinion issued in PCT/US2021/022408, mailed Aug. 31, 2021.
International Search Report and Written Opinion issued in PCT/US2021/028970 mailed Oct. 4, 2021.
International Search Report and Written Opinion issued in PCT/US2021/047571, dated Feb. 14, 2022.
International Search Report and Written Opinion issued in PCT/US2022/023922, mailed Oct. 17, 2022.
Islam, D, et al., Changes in the Peripheral Blood T-Cell Receptor V Beta Repertoire in Vivo and in Vitro During Shigellosis. Infection and Immunity 64(4):1391-1399 (1996).
Jameson, Stephen C., "T cell receptor antagonism in vivo, at last", Proc. Natl. Acad. Sci., 1998, vol. 95, pp. 14001-14002.
Jeffrey, Scott C, et al., Dipeptide-based highly potent doxorubicin antibody conjugates. Bioorganic & medicinal chemistry letters 16(2):358-62 (2006).
Jiang, B. et al., "A novel peptide isolated from a phage display peptide library with trastuzumab can mimic antigen epitope of HER-2*," The Journal of Biological Chemistry, 2005;280(6):4656-4662.
Jiang et al.: Nuclear expression of CDK4 correlates with disease progression and poor prognosis in human nasopharyngeal carcinoma. Histopathology 64(5):722-730 doi:10.1111/his.12319 (2013).
Johnsson et al. Comparison of methods for immobilization to carboxymethyl dextran sensor surfaces by analysis of the specific activity of monoclonal antibodies. J. Mol. Recognit. 8:125-131 (1995).
Johnsson et al. Immobilization of proteins to a carboxymethyldextran-modified gold surface for biospecific interaction analysis in surface plasmon resonance sensors. Anal Biochem. 198(2):268-277 (1991).
Jones et al., Replacing The Complementarity-determining Regions In A Human Antibody With Those From A Mouse. Nature 321(6069):522-525 (1986).
Jonsson et al. Introducing a biosensor based technology for real-time biospecific interaction analysis. Ann Biol Clin 51:19-26 (1993).
Jonsson et al. Real-time biospecific interaction analysis using surface plasmon resonance and a sensor chip technology. Biotechniques 11:620-627 (1991).
Ju et al.: Structure-function analysis of human interleukin-2. Identification of amino acid residues required for biological activity. The Journal of Biological Chemistry 262(12):5723-5731 (1987).
Kabat et al.: Sequences of Proteins of Immunological Interest. NIH Pub. No. 91-3242. Public Health Service, National Institutes of Health. 1:647-669 (1991).
Kam, Nadine Wong Shi et al. "Carbon nanotubes as multifunctional biological transporters and near-infrared agents for selective cancer cell destruction." Proceedings of the National Academy of Sciences of the United States of America vol. 102,33 (2005): 11600-5. doi:10.1073/pnas.0502680102.
Kanagawa, et al., "In Vivo T Cell Tumor Therapy With Monoclonal Antibody Directed to the VB chain of T Cell Antigen Receptor" J. Exp. Med., vol. 170, (1989) p. 1513-1519.
Kanagawa, O, et al., The T Cell Receptor VB6 Domain Imparts Reactivity to the Mls-1a Antigen. Cellular Immunology 119(2):412-426 (1989).
Kanda et al. Comparison of cell lines for stable production of fucose-negative antibodies with enhanced ADCC. Biotechnol. Bioeng. 94(4):680-688 (2006).
Karlin, Samuel, et al., Applications and Statistics for Multiple High-scoring Segments in Molecular Sequences. Proceedings of the National Academy of Sciences of the United States of America 90(12):5873-5877 (1993).
Kashmiri et al.: SDR grafting—a new approach to antibody humanization, Methods vol. 36, No. 1, pp. 25-34 (2005).
Kato et al.: The structure and binding mode of interleukin-18. Nature Structural Biology 10(11):366-971 (2003).
Kato, Y. et al., "Molecular analysis of the pathophysiological binding of the platelet aggregation-inducing factor podoplanin to the C-type lectin-like receptor CLEC-2", Cancer Sci, Jan. 2008, vol. 99, No. 1, pp. 54-61.
Kawaguchi, M, et al., Differential Activation Through the TCR-CD3 Complex Affects the Requirement for Costimulation of Human T Cells. Human immunology 43(2):136-148 (1995).
Keinanen, K. et al., "Biosynthetic lipid-tagging of antibodies", FEBS Lett., vol. 346, pp. 123, pp. 123-126.
Kellner et al.: Enhancing natural killer cell-mediated lysis of lymphoma cells by combining therapeutic antibodies with CD20-specific immunoligands engaging NKG2D or NKp30. Oncoimmunology 5(1) e1058459 [1-12] (2016).
Kerkela, E, et al., Expression of Human Macrophage Metalloelastase (MMP-12) by Tumor Cells in Skin Cancer. Journal of Investigative Dermatology 114(6):1113-1119 (2000).

(56) References Cited

OTHER PUBLICATIONS

Kiefer, J.D. et al., "Immunocytokines and bispecific antibodies: two complementary strategies for the selective activation of immune cells at the tumor site," Immunol Rev., 2016;270(1):178-192.
Killion, J.J et al., Systemic targeting of liposome-encapsulated immunomodulators to macrophages for treatment of cancer metastasis, Immunomethods, vol. 4, (1994):273-279.
Kim, E.J. et al., "Interleukin-2 fusion protein with anti-CD3 single-chain Fv (sFv) selectively protects T cells from dexamethasone-induced apoptosis," Vaccine, 2002;20:608-615.
King, H.D. et al., Monoclonal antibody conjugates of doxorubicin prepared with branched peptide linkers: inhibition of aggregation by methaxytriethyleneglycol chains, J Med Chem, vol. 45, (2002): 4336-4343.
Kirkin, et al. Melanoma-associated antigens recognized by cytotoxic T lymphocytes. APMIS. Jul. 1998; 106(7):665-79.
Kitaura, K. et al., "A new high-throughput sequencing method for determining diversity and similarity of T cell receptor (TCR) α and β repertoires and identifying potential new invariant TCR α chains," BMC Immunology, 2016, vol. 17, No. 38, pp. 1-16.
Klampfl, T. et al., "Somatic Mutations of Calreticulin in Myeloproliferative Neoplasms", N Engl J Med., 2013, vol. 369, No. 25, pp. 2379-2390.
Klein, Christian, et al., Progress in Overcoming the Chain Association Issue in Bispecific Heterodimeric IgG Antibodies. mAbs 4(6):653-663 (2012).
Klimka et al.: Human anti-CD30 recombinant antibodies by guided phage antibody selection using cell panning. British Journal of Cancer. 83(2):252-260 (2000).
Koch et al.: Activating natural cytotoxicity receptors of natural killer cells in cancer and infection. Trends Immunol. 34(4):182-191 doi:10.1016/j.it.2013.01.003 (2013).
Konishi et al., B7-H1 Expression On Non-Small Cell Lung Cancer Cells And Its Relationship With Tumor-Infiltrating Lymphocytes And Their PD-1 Expression. Clinical Cancer Research 10:5094-5100 (Aug. 1, 2004).
Kostelny et al. Formation of a bispecific antibody by the use of leucine zippers. J. Immunol. 148(5):1547-1553 (1992).
Kozbor et al.: A human hybrid myeloma for production of human monoclonal antibodies. J Immunol. 133(6):3001-3005 (1984).
Kratz, F, et al., Prodrugs of anthracyclines in cancer chemotherapy. Current Medicinal Chemistry 13(5):477-523 (2006).
Kunkel, Thomas A., "Rapid and efficient site-specific mutagenesis without phenotypic selection", Proc Natl Acad Sci, 1985, vol. 82, No. 2, pp. 488-492.
Kushner et al.: Aberrant expression of cyclin A and cyclin B1 proteins in oral carcinoma. J Oral Pathol Med. 28(2):77-81 (1999).
Labrijn, Aran, et al., Controlled Fab-arm Exchange for the Generation of Stable Bispecific IgG1. Nature Protocols 9(10):2450-2463 (2014).
Labrijn, Aran, et al., Efficient Generation of Stable Bispecific IgG1 by Controlled Fab-arm Exchange. Proceedings of the National Academy of Sciences of the United States of America 110(13):5145-5150 (2013).
Lain et al.: Accumulating active p53 in the nucleus by inhibition of nuclear export: a novel strategy to promote the p53 tumor suppressor function. Exp Cell Res. 253(2):315-324 (1999).
Langer, Robert, et al., Chemical and Physical Structure of Polymers as Carriers for Controlled Release of Bioactive Agents: A Review. Journal of Macromolecular Science—Reviews in Macromolecular Chemistry and Physics 23(1):61-126 (1983).
Langer, Robert, et al., Medical Applications of Controlled Release. 2:115-138 (1984).
Langer, Robert, New Methods of Drug Delivery. Science 249(4976):1527-1533 (1990).
Lanier, L.L. et al., "Distinct epitopes on the t cell antigen receptor of HPB-ALL tumor cells identified by monoclonal antibodies," 1986; 137(7):2286-2292.
Latchman et al. PD-L2 is a second ligand for PD-1 and inhibits T cell activation. Nat Immunol 2:261-268 (2001).
Leclercq, G. et al., "Dissecting the mechanism of cytokine release induced by T-cell engagers highlights the contribution of neutrophils," Oncoimmunology, 2022;11(1):e2039432.
Lee, C. M. et al., "Selection of human antibody fragments by phage display", Nat Protoc., 2007, vol. 2, No. 11, pp. 3001-3008.
Lee, et al. Bivalent antibody phage display mimics natural immunoglobulin. J Immunol Methods. Jan. 2004;284(1-2):119-132.
Lee, et al. High-affinity human antibodies from phage-displayed synthetic Fab libraries with a single framework scaffold. J Mol Biol. Jul. 23, 2004;340(5):1073-1093.
Lee, K.D. et al., "Construction and characterization of a novel fusion protein consisting of anti-CD3 antibody fused to recombinant interleukin-2," Oncology Reports, 2006;15:1211-1216.
Leonard, E.K. et al., "Engineered cytokine/antibody fusion proteins improve delivery of IL-2 to pro-inflammatory cells and promote antitumor activity," bioRxiv, 2023:1-36.
Leong et al.: Optimized expression and specific activity of IL-12 by directed molecular evolution. Proc. Natl. Acad. Sci. USA; 100(3): 1163-1168 (2003).
Leutkens et al.: Functional autoantibodies against SSX-2 and NY-ESO-1 in multiple myeloma patients after allogeneic stem cell transplantation. Cancer Immunol Immunother. 63(11):1151-1162 (2014).
Levy, R J, et al., Inhibition of Calcification of Bioprosthetic Heart Valves by Local Controlled-Release Diphosphonate. Science 228(4696):190-192 (1985).
Li, B. et al., "Landscape of tumor-infiltrating T cell repertoire of human cancers," Nature Genetics, 2016, vol. 48, No. 7, pp. 725-735.
Li, et al. Human antibodies for immunotherapy development generated via a human B cell hybridoma technology. Proc Natl Acad Sci U S A. Mar. 7, 2006;103(10):3557-62. Epub Feb. 27, 2006.
Li et al.: Optimization of humanized IgGs in glycoengineered Pichia pastoris. Nat Biotechnol. 24(2):210-215 (2006).
Li, F. et al., "T cell receptor B-chain-targeting chimeric antigen receptor T cells against T cell malignancies," Nature Communications, 2022;13:4334.
Li, Hanchen, et al., Tumor Microenvironment: The Role of the Tumor Stroma in Cancer. Journal of Cellular Biochemistry 101(4):805-815 (2007).
Li, Peng, et al., Design and Synthesis of Paclitaxel Conjugated with an ErbB2-recognizing Peptide, EC-1. Biopolymers 87(4):225-230 (2007).
Liddy et al.: Monoclonal TCR-redirected tumor cell killing. Nat Med. 18(6):980-987 doi:10.1038/nm.2764 (2012).
Lifely, M.R, et al., Glycosylation and biological activity of CAMPATH-1H expressed in different cell lines and grown under different culture conditions. Glycobiology 5(8):813-22 (1995).
Liu, Alvin, et al., Chimeric Mouse-human IgG1 Antibody that can Mediate Lysis of Cancer Cells. Proceedings of the National Academy of Sciences of the United States of America 84(10):3439-3443 (1987).
Liu, Alvin, et al., Production of a Mouse-human Chimeric Monoclonal Antibody to CD20 With Potent Fc-dependent Biologic Activity. Journal of Immunology 139(10):3521-3526 (1987).
Liu, Der-Zen, et al., Synthesis of 2'-paclitaxel Methyl 2-glucopyranosyl Succinate for Specific Targeted Delivery to Cancer Cells. Bioorganic & Medicinal Chemistry Letters 17(3):617-620 (2007).
Liu, D.V. et al., "Engineered Interleukin-2 Antagonists for the Inhibition of Regulatory T Cells," J. Immunother., 2009;32(9):887-894.
Liu, J, et al., Calcineurin is a Common Target of Cyclophilin—Cyclosporin A and FKBP-FK506 Complexes. Cell 66(4):807-815 (1991).
Liu, K. et al., "CD123 and its potential clinical application in leukemias," Life Sciences, 2015;122:59-64.
Lobuglio, Albert, et al., Phase I Clinical Trial of CO17-1A Monoclonal Antibody. Hybridomia 5(1):S117-S123 (1986).
Lode, et al. Targeted therapy with a novel enediyene antibiotic calicheamicin theta(I)1 effectively suppresses growth and dissemination of liver metastases in a syngeneic model of murine neuroblastoma. Cancer Res. Jul. 15, 1998;58(14):2925-2928.
Lonberg et al., Human antibodies from transgenic animals. Nature Biotechnology 23(9):1117-1125 (2005).

(56) References Cited

OTHER PUBLICATIONS

Lonberg, Nils, et al., Antigen-Specific Human Antibodies From Mice Comprising Four Distinct Genetic Modifications. Nature 368(6474):856-859 (1994).
Lonberg, Nils, Fully human antibodies from transgenic mouse and phage display platforms. Current opinion in immunology 20(4):450-459 (2008).
Luo, S. et al., "Worldwide genetic variation of the IGHV and TRBV immune receptor gene families in humans" (2019) Life Sciences Alliance, vol. 2, No. 2, p. 1-9.
Lustgarten, J. et al., "Redirecting Effector T Cells through their IL-2 receptors," J Immunology, 1999;162:359-365.
Maciocia, P. M. et al., "Targeting the T cell receptor β-chain constant region for immunotherapy of T cell malignancies", Nature Medicine, 2017, vol. 23, No. 12, pp. 1416-1423.
Mackay, C.R. et al., "Gamma/delta T cells express a unique surface molecule appearing late during thymic development," Eur J Immunol., 1989;19(8):1477-1483.
Macor, P. et al., "Bispecific antibodies targeting tumor-associated antigens and neutralizing complement regulators increase the efficacy of antibody-based immunotherapy in mice", Leukemia, 2015, vol. 29, pp. 406-414.
Mandelboim, O. et al., "Recognition of hemagglutinins on virus-infected cells by NKp46 activates lysis by human NK cells", Nature, 2001, vol. 409, No. 6823, pp. 1055-1060.
Mao et al.: Inhibition of human natural killer cell activity by influenza virions and hemagglutinin. Journal of Virology 84(9):4148-4157 (2010).
Marks, et al. Selection of human antibodies from phage display libraries. In: Methods in Molecular Biology. Lo B., ed. Totowa, N.J.:Human Press. 2003; 248:161-176.
Marks, J.D. et al., Selection of Human antibodies from phage display libraries, J. Mol. Biol., vol. 222, (1992): 581-597.
Martens, Tobias, et al., A Novel One-Armed Anti-c-Met Antibody Inhibits Glioblastoma Growth In Vivo. Clinical Cancer Research 12(20 Pt 1):6144-6152 (2006).
Martin, A. et al., "Chapter 3: Protein Sequence and Structure Analysis of Antibody Variable Domains", In: Antibody Engineering Lab Manual (Ed: Duebel, S. and Kontermann, R., Springer-Verlag, Heidelberg), 2010, vol. 2, pp. 33-51.
Martin, F. et al., "The affinity-selection of a minibody polypeptide inhibitor of human interleukin-6", EMBO J., 1994, vol. 13, No. 22, pp. 5303-5309.
Mccafferty, et al. Phage antibodies: filamentous phage displaying antibody variable domains. Nature. Dec. 6, 1990;348(6301):552-4.
Mcconnell, Stephen, et al., Tendamistat as a Scaffold for Conformationally Constrained Phage Peptide Libraries. Journal of Molecular Biology 250(4):460-470 (1995).
McElroy et al.: Structural and Biophysical Studies of the Human IL-7/IL-7R alpha Complex. Structure 17(1):54-65 (2009).
Mclellan, Jason, et al., Structure of HIV-1 gp120 V1/V2 Domain with Broadly Neutralizign Antibody PG9. Nature 480(7377):336-343 (2011).
Merchant, A.M. et al., "An efficient route to human bispecific IgG," Nature Biotechnology, 1998;16(7):677-681.
Meschendoerfer, W. et al., "SPR-based assays enable the full functional analysis of bispecific molecules," Journal of Pharmaceutical and Biomedical Analysis, 2017, vol. 5, No. 132, pp. 141-147.
Meyers, E. et al., "Optimal alignments in linear space", Cabios, 1988, vol. 4, No. 1, pp. 11-17.
Michelacci, YM, et al., A Comparative Study Between a Chondroitinase B and a Chondroitinase AC From Flavobacterium Heparinum: Isolation of a Chondroitinase AC-Susceptible Dodecasaccharide From Chondroitin Sulphate B. The Biochemical Journal 151(1):121-129 (1975).
Michelacci, Yara, et al., Isolation and Partial Characterization of an Induced Chondroitinase B from Flavobacterium Heparinum. Biochemical and Biophysical Research Communications 56(4):973-980 (1974).

Miller et al.: Trispecific Killer Engagers (TriKEs) that contain IL-15 to make NK cells antigen specific and to sustain their persistence and expansion. Blood 126(23):232-232 (2015).
Milone, Michael, et al., Chimeric Receptors Containing CD137 Signal Transduction Domains Mediate Enhanced Survival of T Cells and Increased Antileukemic Efficacy in Vivo. Molecular Therapy 17(8):1453-1464 (2009).
Milstein et al.: Hybrid hybridomas and their use in immunohistochemistry. Nature 305(5934):537-540 (1983).
Mitra, S. et al., "Interleukin-2 Activity can be Fine-Tuned with Engineering Receptor Signaling Clamps," Immunity, 2015;42(5):826-838.
Modak et al.: Disialoganglioside GD2 and a novel tumor antigen: potential targets for immunotherapy of desmoplastic small round cell tumor. Med Pediatr Oncol. 39(6):547-551 (2002).
Moore, Gregory, et al., A Novel Bispecific Antibody Format Enables Simultaneous Bivalent and Monovalent Co-engagement of Distinct Target Antigens. mAbs 3(6):546-557 (2011).
Morel et al.: Processing of some antigens by the standard proteasome but not by the immunoproteasome results in poor presentation by dendritic cells. Immunity. 12(1):107-117 doi:10.1016/s1074-7613(00)80163-6 (2000).
Morris, Glenn E, et al., Epitope Mapping Protocols. Methods in Molecular Biology 66: (1996).
Morrison, Sherie, et al., Chimeric Human Antibody Molecules: Mouse Antigen-binding Domains With Human Constant Region Domains. Proceedings of the National Academy of Sciences of the United States of America 81(21):6851-6855 (1984).
Morrison, Sherie, Transfectomas Provide Novel Chimeric Antibodies. Science 229(4719):1202-1207 (1985).
Murer, P. et al., "Antibody-cytokine fusion proteins: A novel class of biopharmaceuticals for the therapy of cancer and of chronic inflammation", New Biotechnology, 2019, vol. 52, pp. 42-53.
Murzin, A G, et al., SCOP: A Structural Classification of Proteins Database for the Investigation of Sequences and Structures. Journal of Molecular Biology 247(4):536-540 (1995).
Nagarajan et al.: Ligand binding and phagocytosis by CD16 (Fc gamma receptor III) isoforms. Phagocytic signaling by associated zeta and gamma subunits in Chinese hamster ovary cells. Journal of Biological Chemistry J Biol Chem. 270(43):25762-25770 (1995).
Nagy, Attila, et al., Stability of cytotoxic luteinizing hormone-releasing hormone conjugate (AN-152) containing doxorubicin 14-O-hemiglutarate in mouse and human serum in vitro: Implications for the design of preclinical studies. Biological Sciences 97(2): 829-834 (2000).
Naing, et al., "Strategies for improving the management of immune-related adverse events" Journal for Immuno Therapy of Cancer, (2020) p. 1-9.
Nandi et al.: CD28-mediated costimulation is necessary for optimal proliferation of murine NK cells. J Immunol. 152(7):3361-3369 (1994).
Nangalia, J. et al., "Somatic CALR Mutations in Myeloproliferative Neoplasms with Nonmutated JAK2", N Engl J Med., 2013, vol. 369, No. 25, pp. 2391-2405.
Natsume et al. Engineered Antibodies of IgG1/IgG3 Mixed Isotype With Enhanced Cytotoxic Activities. Cancer Res 68(10):3863-72 (2008).
Newman et al.: Combining Early Heat Shock Protein Vaccination with Directed IL-2 Leads to Effective Anti-Tumor Immunity in Autologous Hematopoietic Cell Transplantation Recipients. Blood118(21):998-998 (2011).
Niederberger, N. et al., "Thymocyte stimulation by anti-TCR-b, but not by anti-TCR-a, leads to induction of developmental transcription program," Journal of Leukoeyte Biology, 2005;77(5):830-841.
Nishimura, Yushi, et al., Recombinant Human-Mouse Chimeric Monoclonal Antibody Specific for Common Acute Lymphocytic Leukemia Antigen. Cancer Research 47(4):999-1005 (1987).
No Author "PE anti-human TCR VB23 Antibody" (2012).
No Author "PE anti-mouse TCR VB6 Antibody" (2012).
Nolo, R. et al., "Targeting p. selection blocks neuroblastoma growth", Oncotarget, 2017, vol. 8, No. 49, pp. 86657-86670.

(56) References Cited

OTHER PUBLICATIONS

Novellino et al.: A listing of human tumor antigens recognized by T cells: Mar. 2004 update. Cancer Immunol Immunother. 54(3):187-207 doi:10.1007/s00262-004-0560-6 (2005).

Oh, Julyun, et al., Single Variable Domains From the T Cell Receptor B Chain Function as Mono- and Bifunctional CARs and TCRs. Scientific Reports 9(1):17291, 1-12 (2019).

Ohtsuka et al.: An Alternative Approach To Deoxyoligonucleotides As Hybridization Probes By Insertion Of Deoxyinosine At Ambiguous Codon Positions. Journal of Biological Chemistry 260(5):2605-2608 (1985).

Oi, Vernon, et al., Chimeric Antibodies. BioTechniques 4(3):214-221 (1986).

Okazaki et al.: Fucose depletion from human IgG1 oligosaccharide enhances binding enthalpy and association rate between IgG1 and FcgammaRIIIa. J Mol Biol. 336(5):1239-49 (Mar. 5, 2004).

Ortiz-Sanchez, Elizabeth, et al., Antibody-Cytokine Fusion Proteins: Applications in Cancer Therapy. Expert Opinion on Biological Therapy 8(5):609-632 (2008).

Osbourn et al.: From rodent reagents to human therapeutics using antibody guided selection. Methods 36(1):61-68 (2005).

Osol et al., eds. Remington's Pharmaceutical Sciences. Easton, PA USA. Mack Publishing Company. 16th edition (1980).

Owais et al. Chloroquine encapsulated in malaria-infected erythrocyte-specific antibody-bearing liposomes effectively controls chloroquine-resistant Plasmodium berghei infections in mice. Antimicrob. Agents Chemother. 39:180-184 (1995).

Padlan, et al.: A possible procedure for reducing the immunogenicity of antibody variable domains while preserving their ligand-binding properties. Mol Immunol 28(4-5):489-498 (1991).

Page, David, et al., Deep Sequencing of T-cell Receptor DNA as a Biomarker of Clonally Expanded TILs in Breast Cancer after Immunotherapy. Cancer Immunology Research 4(10):835-844 (2016).

Pardoll, D.M., "The blockade of immune checkpoints in cancer immunotherapy", Nat Rev Cancer, 2012, Vo. 12, pp. 252-264.

Park, Y.P. et al., "Complex Regulation of human NKG2D-DAP10 cell surface expression: opposing roles of the γc cytokines and TGF-β1", Blood, 2011, vol. 118, No. 11, pp. 3019-3027.

Pasche, N. et al., "Immunocytokines: a novel class of potent armed antibodies," Drug Discovery Today, 2012;17(11):583-590.

Paul, S. et al., "TCR beta chain-directed bispecific antibodies for the treatment of T-cell cancers," Science Translational Medicine, 2021, pp. 1-21.

Payne, J. et al., "Two Monoclonal Rat Antibodies with Specificity for the ß-Chain Variable Region Vβ6 of the Murine T-Cell Receptor", Proc. Natl. Acad. Sci., 1988, vol. 85, pp. 7695-7698.

PCT/US2017/023483 International Search Report and Written Opinion dated Aug. 29, 2017.

PCT/US2018/029951 International Preliminary Report on Patentability dated Oct. 29, 2019.

PCT/US2018/029951 International Search Report and Written Opinion dated Mar. 7, 2018.

PCT/US2019/022284 International Preliminary Report on Patentability dated Sep. 15, 2020.

PCT/US2019/022284 International Search Report and Written Opinion dated Sep. 10, 2019.

Pearson, W R, et al., Improved Tools for Biological Sequence Comparison. Proceedings of the National Academy of Sciences of the United States of America 85(8):2444-2448 (1988).

Pejchal, Robert, et al., A Potent and Broad Neutralizing Antibody Recognizes and Penetrates the HIV Glycan Shield. Science 334(6059):1097-1103 (2011).

Petkova, S.B. et al., Enhanced half-life of genetically engineered human IgG1 antibodies in a humanized FcRn mouse model: potential application in humorally mediated autoimmune disease, International Immunology, vol. 18, 12(2006): 1759-1769.

Pettit et al.: Structure-function studies of interleukin 15 using site-specific mutagenesis, polyethylene glycol conjugation, and homology modeling. J Biol Chem. 272(4):2312-2318 (1997).

Pilch, H, et al., Improved Assessment of T-Cell Receptor (TCR) VB Repertoire in Clinical Specimens: Combination of TCR-CDR3 Spectratyping with Flow Cytometry-Based TCR VB Frequency Analysis. Clinical and Diagnostic Laboratory Immunology 9(2):257-266 (2002).

Pluckthun, Antibodies from *Escherichia coli*. The Pharmacology of Monoclonal Antibodies 113(11):269-315 (1994).

Posnett, D.N. et al., "Inherited polymorphism of the human T-cell antigen receptor detected by a monoclonal antibody," PNAS, 1986;83:7888-7892.

Presta et al.: Humanization of an antibody directed against IgE. J Immunol 151:2623-2632 (1993).

Presta, et al. Humanization of an anti-vascular endothelial growth factor monoclonal antibody for the therapy of solid tumors and other disorders. Cancer Res. Oct. 15, 1997;57(20):4593-9.

Presta, Leonard, Antibody Engineering. Current Opinion in Structural Biology 2(4):593-596 (1992).

Provenzano et al.: Enzymatic targeting of the stroma ablates physical barriers to treatment of pancreatic ductal adenocarcinoma. Cancer Cell. 21(3):418-429 doi:10.1016/j.ccr.2012.01.007 (2012).

Qi, et al., "Potent and selective antitumor activity of a T cell-engaging bispecific antibody targeting a membrane-proximal epitope of ROR1," PNAS, 2018;115(24):E5467-E5476.

Queen et al., A humanized antibody that binds to the interleukin 2 receptor. PNAS USA 86:10029-10033 (1989).

Rabia, L. et al., "Understanding and overcoming trade-offs between antibody affinity, specificity, stability and solubility," Biochemical Engineering Journal, 2018;137:365-374.

Rakoff-Nahoum, Seth, et al., Toll-like Receptors and Cancer. Nature Reviews Cancer 9(1):57-63 (2009).

Ranade. Drug delivery systems. 1. site-specific drug delivery using liposomes as carriers. J. Clin. Pharmacol. 29:685 (1989).

Rath, et al., "Engineering Strategies to Enhance TCR-Based Adoptive T Cell Therapy" (2020) Cells, 9, 1485, p. 1-34.

Reiter, Yoram, et al., Antibody Engineering of Recombinant Fv Immunotoxins for Improved Targeting of Cancer: Disulfide-stabilized Fv Immunotoxins. Clin Cancer Res 2(2):245-252 (1996).

Ridgway, John, et al., Knobs-Into-Holes Engineering of Antibody CH3 Domains for Heavy Chain Heterodimerization. Protein Engineering 9(7):617-621 (1996).

Riechmann, L, et al., Reshaping Human Antibodies for Therapy. Nature 332(6162):323-327 (1988).

Riemer, A.B. et al., "Matching of trastuzumab (Herceptin) epitope mimics onto the surface of Her-2/neu—a new method of epitope definition," Molecular Immunology, 2005;42:1121-1124.

Ring et al.: Mechanistic and structural insight into the functional dichotomy between interleukin-2 and interleukin-15. Nat Immunol. 13(12):1187-1195 (2012).

Ripka et al.: Two Chinese hamster ovary glycosylation mutants affected in the conversion of GDP-mannose to GDP-fucose. Arch Biochem Biophys. 249(2):533-545 (Sep. 1986).

Roda-Navarro, P. et al., "Understanding the Spatial Topology of Artificial Immunology Synapses Assembled in T Cell-Redirecting Strategies: A Major Issue in Cancer Immunotherapy", Frontiers in Cell and Developmental Biology, 2020, vol. 7, No. 370.

Rohena-Rivera et al.: IL-15 regulates migration, invasion, angiogenesis and genes associated with lipid metabolism and inflammation in prostate cancer. PloS one 12(4):e0172786:1-27 (2017).

Rosenberg, Steven, et al., Use of Tumor-Infiltrating Lymphocytes and Interleukin-2 in the Immunotherapy of Patients with Metastatic Melanoma. The New England Journal of Medicine 319(25):1676-1680 (1988).

Rosok et al.: A Combinatorial Library Strategy for the Rapid Humanization of Anticarcinoma BR96 Fab. J Biol Chem 271:22611-22618 (1996).

Rossolini et al.: Use Of Deoxyinosine-containing Primers Vs Degenerate Primers For Polymerase Chain Reaction Based On Ambiguous Sequence Information. Molecular and Cellular Probes 8(2):91-98 (1994).

Rudikoff et al.: Single Amino Acid Substitution Altering Antigen-binding Specificity. PNAS USA 79(6):1979-1983 (1982).

(56) References Cited

OTHER PUBLICATIONS

Ruggiero, Eliana, et al., High-resolution Analysis of the Human T-Cell Receptor Repertoire. Nature Communication 6:8081, 1-7 (2014).

Salameire, et al., "Accurate detection of the tumor clone in peripheral T-cell lymphoma biopsies by flow cytometric analysis of TCR-V B repertoire" Modern Pathology (2012) 25, p. 1246-1257.

Saleh, Mansoor, et al., A Phase II Trial of Murine Monoclonal Antibody 17-1A and Interferon-gamma: Clinical and Immunological Data. Cancer Immunology, Immunotherapy 32(3):185-190 (1990).

Sanchez-Ruiz, J M, et al., Differential scanning calorimetry of the irreversible thermal denaturation of thermolysin. Biochemistry 27(5):1648-1652 (1988).

Sano, Y. et al., "Properties of Blocking and Non-blocking Monoclonal Antibodies Specific for Human Macrophage Galactose-type C-type Lectin (MGL/ClecSF10A/CD301)," J. Biochem., 2007;127-136.

Sastry, Konduru, et al., Targeting Hepatitis B virus-infected cells with a T-Cell Receptor-like Antibody. Journal of Virology 85(5):1935-1942 (2011).

Saudek et al. A preliminary trial of the programmable implantable medication system for insulin delivery. N. Engl. J. Med. 321(9):574-579 (1989).

Saunders, Kevin, Conceptual Approaches to Modulating Antibody Effector Functions and Circulation Half-Life. Frontiers in Immunology 10:1296, 1-20 (2019).

Schachter, H, et al., Biosynthetic controls that determine the branching and microheterogeneity of protein-bound oligosaccharides. Biochem Cell Biol 64(3):163-181 (1986).

Scheid et al., Sequence and Structural Convergence of Broad and Potent HIV Antibodies that Mimic CD4 Binding, Science 333(6049):1633-1637 (2011).

Schleinitz, N. et al., "Natural killer cells in human autoimmune diseases," Immunology, 2010;131(4):451-458.

Schliemann et al.: Targeting interleukin-2 to the bone marrow stroma for therapy of acute myeloid leukemia relapsing after allogeneic hematopoietic stem cell transplantation. Cancer immunology research 3(5 ):547-556 (2015).

Schmittnaegel, Martina, et al., Activation of Cytomegalovirus-Specific CD8+ T-cell response by Antibody-Mediated peptide-major Histocompatibility class I Complexes. OncoImmunology 5(1):e1052930, 1-3 (2015).

Schreier, H. et al., "Targeting of Liposomes to Cells Expressing CD4 Using Glycosylphosphatidylinositol-anchored gp120 Influence of Liposome Composition on Intracellular Trafficking", J. Biol. Chem., 1994, vol. 269, No. 12, pp. 9090-9098.

Scodeller, Pablo, Hyaluronidase and Other Extracellular Matrix Degrading Enzymes for Cancer Therapy: New Uses and Nano-Formulations, Journal of Carcinogenesis & Mutagenesis 5(4):1-5 (2014).

Sefton, Michael, Implantable Pumps. Critical Reviews in Biomedical Engineering 14(3):201-240 (1987).

Seidel, U. et al., "Natural killer cell mediated antibody-dependent cellular cytotoxicity in tumor immunotherapy with therapeutic antibodies", frontiers in Immunology, 2013, vol. 4, No. 76, pp. 1-8.

Sekine, T. et al., "A feasible method for expansion of peripheral blood lymphocytes by culture with immobilized anti-CD3 monoclonal antibody and interleukin-2 for use in adoptive immunotherapy of cancer patients," Biomed & Pharmacother, 1993;47:73-78.

Sen, S. et al., "Expression of epithelial cell adhesion molecule (EpCAM) in oral squamous cell carcinoma," Histopathology, 2015:6:897-904. Abstract only.

Sergeeva, Anna, et al., An Anti-PR1/HLA-A2 T-cell Receptor-like Antibody Mediates Complement-Dependent Cytotoxicity Against Acute Myeloid Leukemia Progenitor Cells. Blood 117(16):4262-4272 (2011).

Shaw, Denise, et al., Mouse/Human Chimeric Antibodies to a Tumor-Associated Antigen: Biologic Activity of the Four Human IgG Subclasses. Journal of the National Cancer Institute 80(19):1553-1559 (1988).

Shi, M. et al., "A recombinant anti-erbB2, scFv-Fc-IL-2 fusion protein retains antigen specificity and cytokine function," Biotechnology letters, 2003;25:815-819.

Shields et al.: High Resolution Mapping of the Binding Site on Human IgG1 for FcγRI, FcγRII, FcγRIII, and FcRn and Design of IgG1 Variants with Improved Binding to the FcγR. J Biol Chem 276(9):6591-6604 (2001).

Shimabukuro-Vornhagen, Alexander, et al., Cytokine Release Syndrome. Journal for Immuno Therapy of Cancer 6(56):1-14 (2018).

Shitaoka, Kiyomi, et al., Identification of Tumoricidal TCRs from Tumor-Infiltrating Lymphocytes by Single-Cell Analysis. Cancer Immunology Research 6(4):378-388 (2018).

Shpilberg, O, et al., Subcutaneous Administration of Rituximab (MabThera) and Trastuzumab (Herceptin) using Hyaluronidase. British Journal of Cancer 109(6):1556-1561 (2013).

Sidhu, et al. Phage-displayed antibody libraries of synthetic heavy chain complementarity determining regions. J Mol Biol. Apr. 23, 2004;338(2):299-310.

Sims et al. A humanized CD18 antibody can block function without cell destruction. J Immunol. 151:2296-2308 (1993).

Skegro, D. et al., "Immunoglobulin domain interface exchange as a platform technology for the generation of Fc heterodimers and bispecific antibodies," J Biol Chem, 2017, vol. 292, No. 23, pp. 9745-9759.

Song et al. CD27 costimulation augments the survival and antitumor activity of redirected human T cells in vivo. Blood 119(3):696-706 (2012).

Spiess, C. et al., "Alternative molecular formats and therapeutic applications for bispecific antibodies", Molecular Immunology, 2015, vol. 67, pp. 95-106.

Stauber, D.J. et al., "Crystal structure of the IL-2 signaling complex: Paradigm for a heterotrimeric cytokine receptor," PNAS, 2006; 103(8):2788-2793.

Stauber et al.: Nuclear and cytoplasmic survivin: molecular mechanism, prognostic, and therapeutic potential. Cancer Res. 67(13):5999-6002 (2007).

Stivala, Alex, et al., Automatic Generation of Protein Structure Cartoons With Pro-origami. Bioinformatics 27(23):3315-3316 (2011).

Streltsov, Victor A, et al., Structure of a shark IgNAR antibody variable domain and modeling of an early-developmental isotype. Protein Science 14(11):2901-2909 (2005).

Sun, Lee, et al., Chimeric Antibody With Human Constant Regions and Mouse Variable Regions Directed Against Carcinoma-Associated Antigen 17-1A. Proceedings of the National Academy of Sciences of the United States of America 84(1):214-218 (1987).

Suzuki, Sakaru, et al., Formation of Three Types of Disulfated Disaccharides from Chondroitin Sulfates by Chondroitinase Digestion. The Journal of Biological Chemistry 243(7):1543-1550 (1968).

Swencki-Underwood, B. et al., "Engineering human IL-18 with increased bioactivity and bioavailability," Cytokine, 2006, vol. 34, pp. 114-124.

Tang, et al., "Anti-TCR Antibody Treatment Activates a Novel Population of Nonintestinal CD8aa+TCRaB+ Regulatory T Cells and Prevents Experimental Autoimmune Encephalomyelitis" The Journal of Immunology , 178(10), 6043-6050 (2007).

Tang, Yong, et al., Regulation of antibody-dependent cellular cytotoxicity by IgG intrinsic and apparent affinity for target antigen. J Immunol 179(5):2815-2823 (2007).

Tassev, D V, et al., Retargeting NK92 Cells using an HLA-A2-Restricted, EBNA3C-Specific Chimeric Antigen Receptor. Cancer Gene Ther 19(2):84-100 (2012).

Thorpe, Philip, Vascular Targeting Agents as Cancer Therapeutics. Clinical Cancer Research 10(2):415-427 (2004).

Tomlinson, Ian, et al., The Repertoire of Human Germline VH Sequences Reveals About Fifty Groups of VH Segments With Different Hypervariable Loops. Journal of Molecular Biology 227(3):776-798 (1992).

Tomonari, K. et al., "Epitope-specific binding of CD8 regulates activation of T cells and induction of cytotoxicity," International Immunology, 1990;2(12):1189-1194.

Torgov, Michael Y, et al., Generation of an intensely potent anthracycline by a monoclonal antibody-beta-galactosidase conjugate. Bioconjugate Chem 16(3):717-721 (2005).

(56) References Cited

OTHER PUBLICATIONS

Tramontano et al.: The making of the minibody: an engineered beta-protein for the display of conformationally constrained peptides. J. Mol. Recognition. 7:9-24 (1994).
Traunecker et al., Bispecific Single Chain Molecules (Janusins) Target Cytotoxic Lymphocytes On HIV Infected Cells. The EMBO Journal 10(12):3655-3659 (1991).
Trenevska et al.: Therapeutic Antibodies against Intracellular Tumor Antigens. Front Immunol. 8:1001 doi:10.3389/fimmu.2017.01001 [1-12] (2017).
Tsytsikov, V.N. et al., "Identification and Characterization of Two Alternative Splice Variants of Human Interleukin-2*" The Journal of Biological Chemistry, 1996;71(38):23055-23060.
Tuaillon, Nadine, et al., Human Immunoglobulin Heavy-Chain Minilocus Recombination in Transgenic Mice: Gene-Segment Use in Mu and Gamma Transcripts. Proceedings of the National Academy of Sciences of the United States of America 90(8):3720-3724 (1993).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Umezawa et al. Liposome targeting to mouse brain: mannose as a recognition marker. Biochem. Biophys. Res. Commun. 153:1038 (1988).
U.S. Appl. No. 17/529,017 Non-Final Office Action dated Apr. 27, 2022.
Vallera et al.: Heterodimeric bispecific single-chain variable-fragment antibodies against EpCAM and CD16 induce effective antibody-dependent cellular cytotoxicity against human carcinoma cells. Cancer Biother Radiopharm. 28(4):274-282 doi:10.1089/cbr.2012.1329 (2013).
Van Dijk et al. Human antibodies as next generation therapeutics. Curr Opin Chem Biol. 5(4):368-74 (Aug. 2001).
Van Mierlo, C P, et al., Protein folding and stability investigated by fluorescence, circular dichroism (CD), and nuclear magnetic resonance (NMR) spectroscopy: the flavodoxin story. Journal of Biotechnology 79(3):281-298 (2000).
Verhoeyen, M. et al., "Reshaping Human Antibodies: Grafting an Antilysozyme Activity", Science, 1988, vol. 239, pp. 1534-1536.
Verma, Bhavna, et al., TCR Mimic Monoclonal Antibody Targets a Specific Peptide/HLA Class I Complex and Significantly Impedes Tumor Growth In Vivo Using Breast Cancer Models. J Immunol 184(4):2156-2165 (2010).
Verwilghen, J. et al., "Differences in the stimulating capacity of immobilized anti-CD3 monoclonal antibodies: variable dependence on interleukin-1 as a helper signal for T-cell activation," Immunology. 1991;72:269-276.
Vitetta et al. Redesigning nature's poisons to create anti-tumor reagents. Science 238(4830):1098-1104 (1987).
Vollmers, et al. Death by stress: natural IgM-induced apoptosis. Methods Find Exp Clin Pharmacol. Apr. 2005;27(3):185-91.
Vollmers et al.: The "early birds": natural IgM antibodies and immune surveillance. Histol Histopathol. 20(3):927-937 (2005).
Vonderheid, Eric, et al., Evidence for Restricted Vβ Usage in the Leukemic Phase of Cutaneous T Cell Lymphoma. The Journal of Investigative Dermatology 124(3):650-661 (2005).
Wadia, P. et al., "Impaired lymphocyte responses and their restoration in oral cancer patients expressing distinct TCR variable region," Cancer Investigation, 2008;26:471-480.
Wagner, E.K. et al., "Engineering therapeutics antibodies to combat infectious disease," Current Opinion in Chemical Engineering, 2018:19;131-141.
Walker, Laura M, et al., Broad and Potent Neutralizing Antibodies from an African Donor Reveal a New HIV-1 Vaccine Target. Science 326(5950):285-289 (2009).
Walker, Laura M, et al., Broad Neutralization Coverage of HIV by Multiple Highly Potent Antibodies. Nature 477(7365):1-13 (2011).
Wan, Y.Y. et al., "'Yin-Yang' functions of TGF-b and tregs in immune regulation," Immunol Rev., 2007;220:199-213.

Wang, Chun-Yan, et al., αβ T-Cell Receptor Bias in Disease and Therapy (Review). International Journal of Oncology 48(6):2247-2256 (2016).
Wang et al.: Cloning genes encoding MHC class II-restricted antigens: mutated CDC27 as a tumor antigen. Science 284(5418):1351-1354 doi:10.1126/science.284.5418.1351 (1999).
Wang et al.: RNA interference targeting CML66, a novel tumor antigen, inhibits proliferation, invasion and metastasis of Hela cells. Cancer Lett. 269(1):127-138 (2008).
Wang, H. et al., "Preparation and functional identification of a monoclonal antibody against the recombinant soluble human NKp30 receptor," Internal Immunopharmacology, 2011;11(11):1732-1739.
Warren, H.S. et al., "Evidence that the cellular ligand for the Human NK Cell Activation Receptor NKp30 is not a Heparan Sulfate Glycosaminoglycan," The Journal of Immunology, 2005;175(1):207-212.
Watanabe, M, et al., Interleukin-21 can efficiently restore impaired antibody-dependent cell-mediated cytotoxicity in patients with oesophageal squamous cell carcinoma. British Journal of Cancer 102(3):520-529 (2010).
Wei, Shan, et al., Identification of a Novel Human T-cell Receptor Vβ Subfamily by Genomic Cloning. Human Immunology 41(3):201-206 (1994).
Weidle, U. et al., "The Intriguing Options of Multispecific Antibody Formats for Treatment of Cancer", Cancer Genomics & Proteomics, 2013, vol. 1, pp. 1-18.
Weidle, U.H. et al., "Tumor-Antigen-Binding Bispecific Antibodies for Cancer Treatment", Seminars in Oncology, 2014, vol. 41, No. 5, pp. 653-660.
Willemsen, R A, et al., Grafting primary human T lymphocytes with cancer-specific chimeric single chain and two chain TCR. Gene Therapy 7(16):1369-1377 (2000).
Williemsen, R A, et al., A Phage Display Selected Fab Fragment with MHC Class I-Restricted Specificity for MAGE-A1 allows for Retargeting of Primary Human T Lymphocytes. Gene Therapy 8(21):1601-1608 (2001).
Winter et al.: Making antibodies by phage display technology. Annu Rev Immunol. 12:433-55 (1994).
Wood, Clive, et al., The Synthesis and in Vivo Assembly of Functional Antibodies in Yeast. Nature 314(6010):446-449 (1985).
Wright et al. Effect of glycosylation on antibody function: implications for genetic engineering. Tibtech 15:26-32 (1997).
Wu, M.R. et al., "B7H6-Specific Bispecific T Cell Engagers Lead to Tumor Elimination and Host Antitumor Immunity", The Journal of Immunology, 2015, vol. 194, No. 11, pp. 5305-5311.
Wurzer et al.: Nuclear Ras: unexpected subcellular distribution of oncogenic forms.J Cell Biochem Suppl. Suppl 36:1-11 doi:10.1002/jcb.1070 (2001).
Xiao, Y.F. et al., "Peptide-based treatment: A promising cancer therapy", Journal of Immunology Research, 2015, pp. 1-14.
Xiaoying, C. et al., "Fusion protein linkers: Property, design and functionality", Advanced Drug Delivery Reviews, 2012, vol. 65, No. 10, pp. 1357-1369.
Xu, Xiao-Jun, et al., Cytokine Release Syndrome in Cancer Immunotherapy with Chimeric Antigen Receptor Engineered T Cells. Cancer Letters 343(2):172-178 (2014).
Yamagata, Tatsuya, et al., Purification and Properties of Bacterial Chondroitinases and Chondrosulfatases. The Journal of Biological Chemistry 243(7):1523-1535 (1968).
Yamane-Ohnuki, et al. Establishment of FUT8 knockout Chinese hamster ovary cells: An ideal host cell line for producing completely defucosylated antibodies with enhanced antibody-dependent cellular cytotoxicity. Biotech. Bioeng. 87:614-622 (2004).
Yassai, Maryam, et al., A Clonotype Nomenclature for T Cell Receptors. Immunogenetics 61(7):493-502 (2009).
Yazaki and Wu, "Expression of Recombinant Antibodies in Mammalian Cell Lines", Methods in Molecular Biology, vol. 248, pp. 255-268, 2003.
Yoon et al.: Charged residues dominate a unique interlocking topography in the heterodimeric cytokine interleukin-12. The EMBO J. 19(14):3530-3541 (2000).

(56) References Cited

OTHER PUBLICATIONS

Yoon, S.T. et al., "Both high and low avidity antibodies to the T cell receptor can have agonist or antagonist activity," Immunity, 1994;1(7):563-569.

Zhang, T. et al., "Cancer Immunotherapy Using a Bispecific NK Receptor Fusion Protein that Engages both T Cells and Tumor Cells", Cancer Research, 2011, vol. 71, No. 6, pp. 2066-2076.

Zhang, Tong, et al., Transgenic TCR expression: comparison of single chain with full-length receptor constructs for T-cell function. Cancer Gene Therapy 11(7):487-496 (2004).

\* cited by examiner

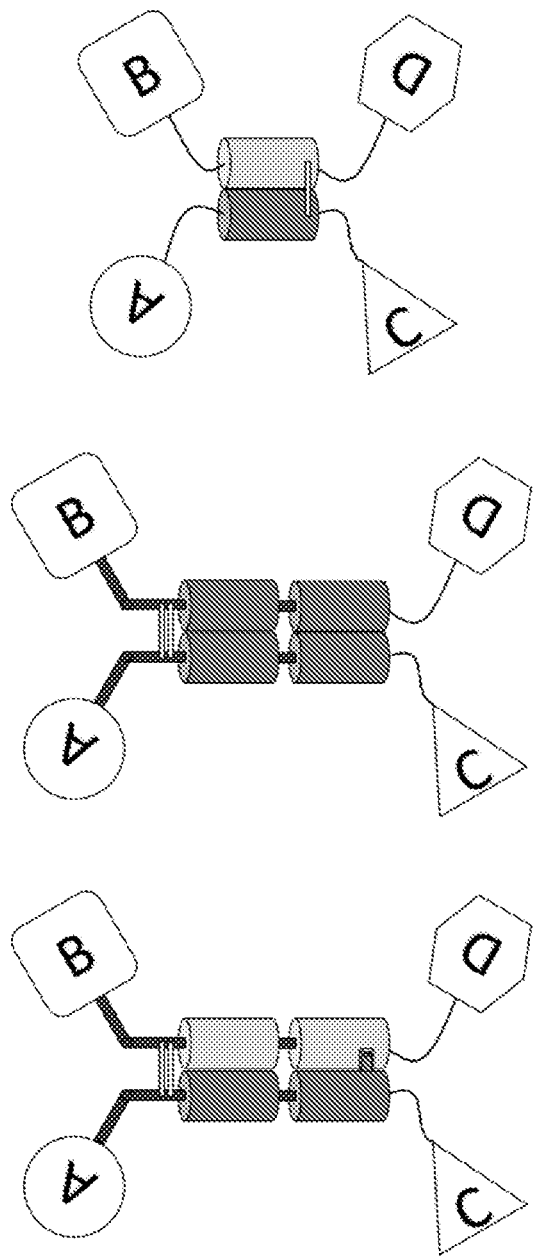

SEQUENCE LISTING

<160> NUMBER OF SEQ ID NOS: 400

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17
<211> LENGTH: 114
<212> TYPE: PRT
<213> ORGANISM: Homo sapiens

<400> SEQUENCE: 17

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 18
<211> LENGTH: 77
<212> TYPE: PRT
<213> ORGANISM: Homo sapiens

<400> SEQUENCE: 18

```
Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
        35                  40                  45

Tyr Ser Leu Tyr Ser Arg Glu Arg Tyr Ile Cys Asn Ser Gly Phe Lys
    50                  55                  60

Arg Lys Ala Gly Thr Ser Ser Leu Thr Glu Cys Val Leu
65                  70                  75
```

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Ser Gly Gly Ser Gly Gly Gly Ser Gly Gly Ser Gly Gly Gly
1               5                   10                  15

Gly Ser Leu Gln
            20

<210> SEQ ID NO 20
<211> LENGTH: 133
<212> TYPE: PRT
<213> ORGANISM: Homo sapiens

<400> SEQUENCE: 20

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 21
<211> LENGTH: 157
<212> TYPE: PRT
<213> ORGANISM: Homo sapiens

<400> SEQUENCE: 21

Tyr Phe Gly Lys Leu Glu Ser Lys Leu Ser Val Ile Arg Asn Leu Asn
1               5                   10                  15

Asp Gln Val Leu Phe Ile Asp Gln Gly Asn Arg Pro Leu Phe Glu Asp
                20                  25                  30

Met Thr Asp Ser Asp Cys Arg Asp Asn Ala Pro Arg Thr Ile Phe Ile
            35                  40                  45

Ile Ser Met Tyr Lys Asp Ser Gln Pro Arg Gly Met Ala Val Thr Ile
        50                  55                  60

Ser Val Lys Cys Glu Lys Ile Ser Thr Leu Ser Cys Glu Asn Lys Ile
65                  70                  75                  80

Ile Ser Phe Lys Glu Met Asn Pro Pro Asp Asn Ile Lys Asp Thr Lys
                85                  90                  95

Ser Asp Ile Ile Phe Phe Gln Arg Ser Val Pro Gly His Asp Asn Lys
            100                 105                 110

Met Gln Phe Glu Ser Ser Tyr Glu Gly Tyr Phe Leu Ala Cys Glu
        115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155

<210> SEQ ID NO 22
<211> LENGTH: 133
<212> TYPE: PRT
<213> ORGANISM: Homo sapiens

<400> SEQUENCE: 22

```
Gln Gly Gln Asp Arg His Met Ile Arg Met Arg Gln Leu Ile Asp Ile
1               5                   10                  15

Val Asp Gln Leu Lys Asn Tyr Val Asn Asp Leu Val Pro Glu Phe Leu
            20                  25                  30

Pro Ala Pro Glu Asp Val Glu Thr Asn Cys Glu Trp Ser Ala Phe Ser
        35                  40                  45

Cys Phe Gln Lys Ala Gln Leu Lys Ser Ala Asn Thr Gly Asn Asn Glu
    50                  55                  60

Arg Ile Ile Asn Val Ser Ile Lys Lys Leu Lys Arg Lys Pro Pro Ser
65                  70                  75                  80

Thr Asn Ala Gly Arg Arg Gln Lys His Arg Leu Thr Cys Pro Ser Cys
                85                  90                  95

Asp Ser Tyr Glu Lys Lys Pro Pro Lys Glu Phe Leu Glu Arg Phe Lys
            100                 105                 110

Ser Leu Leu Gln Lys Met Ile His Gln His Leu Ser Ser Arg Thr His
        115                 120                 125

Gly Ser Glu Asp Ser
    130
```

<210> SEQ ID NO 23
<211> LENGTH: 138
<212> TYPE: PRT
<213> ORGANISM: Homo sapiens

<400> SEQUENCE: 23

```
Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
            20                  25                  30

Leu Lys Asn Trp Lys Glu Glu Ser Asp Arg Lys Ile Met Gln Ser Gln
        35                  40                  45

Ile Val Ser Phe Tyr Phe Lys Leu Phe Lys Asn Phe Lys Asp Asp Gln
    50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
            100                 105                 110

Leu Ile Gln Val Met Ala Glu Leu Ser Pro Ala Ala Lys Thr Gly Lys
        115                 120                 125

Arg Lys Arg Ser Gln Met Leu Phe Arg Gly
    130                 135
```

<210> SEQ ID NO 24
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Asp Leu Lys Val Glu Met Met Ala Gly Gly Thr Gln Ile Thr Pro Leu
1               5                   10                  15

Asn Asp Asn Val Thr Ile Phe Cys Asn Ile Phe Tyr Ser Gln Pro Leu
            20                  25                  30

Asn Ile Thr Ser Met Gly Ile Thr Trp Phe Trp Lys Ser Leu Thr Phe
        35                  40                  45

Asp Lys Glu Val Lys Val Phe Glu Phe Phe Gly Asp His Gln Glu Ala
    50                  55                  60

Phe Arg Pro Gly Ala Ile Val Ser Pro Trp Arg Leu Lys Ser Gly Asp
65                  70                  75                  80

Ala Ser Leu Arg Leu Pro Gly Ile Gln Leu Glu Ala Gly Glu Tyr
                85                  90                  95

Arg Cys Glu Val Val Val Thr Pro Leu Lys Ala Gln Gly Thr Val Gln
                100                 105                 110

Leu Glu Val Val Ala Ser Pro Ala Ser Arg Leu Leu Leu Asp Gln Val
            115                 120                 125

Gly Met Lys Glu Asn Glu Asp Lys Tyr Met Cys Glu Ser Ser Gly Phe
        130                 135                 140

Tyr Pro Glu Ala Ile Asn Ile Thr Trp Glu Lys Gln Thr Gln Lys Phe
145                 150                 155                 160

Pro His Pro Ile Glu Ile Ser Glu Asp Val Ile Thr Gly Pro Thr Ile
                165                 170                 175

Lys Asn Met Asp Gly Thr Phe Asn Val Thr Ser Cys Leu Lys Leu Asn
            180                 185                 190

Ser Ser Gln Glu Asp Pro Gly Thr Val Tyr Gln Cys Val Val Arg His
        195                 200                 205

Ala Ser Leu His Thr Pro Leu Arg Ser Asn Phe Thr Leu Thr Ala Ala
    210                 215                 220

Arg His Ser Leu Ser Glu Thr Glu Lys Thr Asp Asn Phe Ser
225                 230                 235
```

<210> SEQ ID NO 25
<211> LENGTH: 284
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Pro His Ser Leu Arg Tyr Asn Leu Thr Val Leu Ser Trp Asp Gly
1               5                   10                  15

Ser Val Gln Ser Gly Phe Leu Thr Glu Val His Leu Asp Gly Gln Pro
            20                  25                  30

Phe Leu Arg Cys Asp Arg Gln Lys Cys Arg Ala Lys Pro Gln Gly Gln
        35                  40                  45

Trp Ala Glu Asp Val Leu Gly Asn Lys Thr Trp Asp Arg Glu Thr Arg
    50                  55                  60

Asp Leu Thr Gly Asn Gly Lys Asp Leu Arg Met Thr Leu Ala His Ile
65                  70                  75                  80

Lys Asp Gln Lys Glu Gly Leu His Ser Leu Gln Glu Ile Arg Val Cys
                85                  90                  95

Glu Ile His Glu Asp Asn Ser Thr Arg Ser Ser Gln His Phe Tyr Tyr
                100                 105                 110
```

```
Asp Gly Glu Leu Phe Leu Ser Gln Asn Leu Glu Thr Lys Glu Trp Thr
            115                 120                 125

Met Pro Gln Ser Ser Arg Ala Gln Thr Leu Ala Met Asn Val Arg Asn
    130                 135                 140

Phe Leu Lys Glu Asp Ala Met Lys Thr Lys Thr His Tyr His Ala Met
145                 150                 155                 160

His Ala Asp Cys Leu Gln Glu Leu Arg Arg Tyr Leu Lys Ser Gly Val
                165                 170                 175

Val Leu Arg Arg Thr Val Pro Pro Met Val Asn Val Thr Arg Ser Glu
            180                 185                 190

Ala Ser Glu Gly Asn Ile Thr Val Thr Cys Arg Ala Ser Gly Phe Tyr
            195                 200                 205

Pro Trp Asn Ile Thr Leu Ser Trp Arg Gln Asp Gly Val Ser Leu Ser
210                 215                 220

His Asp Thr Gln Gln Trp Gly Asp Val Leu Pro Asp Gly Asn Gly Thr
225                 230                 235                 240

Tyr Gln Thr Trp Val Ala Thr Arg Ile Cys Gln Gly Glu Glu Gln Arg
                245                 250                 255

Phe Thr Cys Tyr Met Glu His Ser Gly Asn His Ser Thr His Pro Val
                260                 265                 270

Pro Ser Gly Lys Val Leu Val Leu Gln Ser His Trp
            275                 280
```

```
<210> SEQ ID NO 26
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ala Glu Pro His Ser Leu Arg Tyr Asn Leu Met Val Leu Ser Gln Asp
1               5                   10                  15

Glu Ser Val Gln Ser Gly Phe Leu Ala Glu Gly His Leu Asp Gly Gln
            20                  25                  30

Pro Phe Leu Arg Tyr Asp Arg Gln Lys Arg Arg Ala Lys Pro Gln Gly
        35                  40                  45

Gln Trp Ala Glu Asp Val Leu Gly Ala Lys Thr Trp Asp Thr Glu Thr
    50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asp Gly Glu Leu Phe Leu Ser Gln Asn Leu Glu Thr Gln Glu Ser
        115                 120                 125

Thr Val Pro Gln Ser Ser Arg Ala Gln Thr Leu Ala Met Asn Val Thr
    130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg Arg Thr Val Pro Pro Met Val Asn Val Thr Cys Ser
            180                 185                 190
```

```
Glu Val Ser Glu Gly Asn Ile Thr Val Thr Cys Arg Ala Ser Ser Phe
            195                 200                 205

Tyr Pro Arg Asn Ile Thr Leu Thr Trp Arg Gln Asp Gly Val Ser Leu
        210                 215                 220

Ser His Asn Thr Gln Gln Trp Gly Asp Val Leu Pro Asp Gly Asn Gly
225                 230                 235                 240

Thr Tyr Gln Thr Trp Val Ala Thr Arg Ile Arg Gln Gly Glu Glu Gln
            245                 250                 255

Arg Phe Thr Cys Tyr Met Glu His Ser Gly Asn His Gly Thr His Pro
        260                 265                 270

Val Pro Ser Gly Lys Val Leu Val Leu Gln Ser Gln Arg Thr Asp
            275                 280                 285
```

<210> SEQ ID NO 27
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
Gly Trp Val Asp Thr His Cys Leu Cys Tyr Asp Phe Ile Ile Thr Pro
1               5                   10                  15

Lys Ser Arg Pro Glu Pro Gln Trp Cys Glu Val Gln Gly Leu Val Asp
            20                  25                  30

Glu Arg Pro Phe Leu His Tyr Asp Cys Val Asn His Lys Ala Lys Ala
        35                  40                  45

Phe Ala Ser Leu Gly Lys Lys Val Asn Val Thr Lys Thr Trp Glu Glu
    50                  55                  60

Gln Thr Glu Thr Leu Arg Asp Val Val Asp Phe Leu Lys Gly Gln Leu
65                  70                  75                  80

Leu Asp Ile Gln Val Glu Asn Leu Ile Pro Ile Glu Pro Leu Thr Leu
                85                  90                  95

Gln Ala Arg Met Ser Cys Glu His Glu Ala His Gly His Gly Arg Gly
            100                 105                 110

Ser Trp Gln Phe Leu Phe Asn Gly Gln Lys Phe Leu Leu Phe Asp Ser
        115                 120                 125

Asn Asn Arg Lys Trp Thr Ala Leu His Pro Gly Ala Lys Lys Met Thr
130                 135                 140

Glu Lys Trp Glu Lys Asn Arg Asp Val Thr Met Phe Phe Gln Lys Ile
145                 150                 155                 160

Ser Leu Gly Asp Cys Lys Met Trp Leu Glu Glu Phe Leu Met Tyr Trp
                165                 170                 175

Glu Gln Met Leu Asp Pro Thr Lys Pro Pro Ser Leu Ala Pro Gly
            180                 185                 190
```

<210> SEQ ID NO 28
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

```
Gln Asp Val Arg Val Gln Val Leu Pro Glu Val Arg Gly Gln Leu Gly
1               5                   10                  15
```

Gly Thr Val Glu Leu Pro Cys His Leu Leu Pro Pro Val Pro Gly Leu
            20                  25                  30

Tyr Ile Ser Leu Val Thr Trp Gln Arg Pro Asp Ala Pro Ala Asn His
         35                  40                  45

Gln Asn Val Ala Ala Phe His Pro Lys Met Gly Pro Ser Phe Pro Ser
 50                  55                  60

Pro Lys Pro Gly Ser Glu Arg Leu Ser Phe Val Ser Ala Lys Gln Ser
 65                  70                  75                  80

Thr Gly Gln Asp Thr Glu Ala Glu Leu Gln Asp Ala Thr Leu Ala Leu
             85                  90                  95

His Gly Leu Thr Val Glu Asp Glu Gly Asn Tyr Thr Cys Glu Phe Ala
            100                 105                 110

Thr Phe Pro Lys Gly Ser Val Arg Gly Met Thr Trp Leu Arg Val Ile
            115                 120                 125

Ala Lys Pro Lys Asn Gln Ala Glu Ala Gln Lys Val Thr Phe Ser Gln
130                 135                 140

Asp Pro Thr Thr Val Ala Leu Cys Ile Ser Lys Glu Gly Arg Pro Pro
145                 150                 155                 160

Ala Arg Ile Ser Trp Leu Ser Ser Leu Asp Trp Glu Ala Lys Glu Thr
            165                 170                 175

Gln Val Ser Gly Thr Leu Ala Gly Thr Val Thr Val Thr Ser Arg Phe
            180                 185                 190

Thr Leu Val Pro Ser Gly Arg Ala Asp Gly Val Thr Val Thr Cys Lys
            195                 200                 205

Val Glu His Glu Ser Phe Glu Glu Pro Ala Leu Ile Pro Val Thr Leu
            210                 215                 220

Ser Val Arg Tyr Pro Pro Glu Val Ser Ile Ser Gly Tyr Asp Asp Asn
225                 230                 235                 240

Trp Tyr Leu Gly Arg Thr Asp Ala Thr Leu Ser Cys Asp Val Arg Ser
            245                 250                 255

Asn Pro Glu Pro Thr Gly Tyr Asp Trp Ser Thr Thr Ser Gly Thr Phe
            260                 265                 270

Pro Thr Ser Ala Val Ala Gln Gly Ser Gln Leu Val Ile His Ala Val
            275                 280                 285

Asp Ser Leu Phe Asn Thr Thr Phe Val Cys Thr Val Thr Asn Ala Val
            290                 295                 300

Gly Met Gly Arg Ala Glu Gln Val Ile Phe Val Arg Glu Thr Pro Asn
305                 310                 315                 320

Thr Ala Gly Ala Gly Ala Thr Gly Gly
            325

<210> SEQ ID NO 29
<211> LENGTH: 323
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Trp Pro Pro Pro Gly Thr Gly Asp Val Val Gln Ala Pro Thr Gln
1               5                   10                  15

Val Pro Gly Phe Leu Gly Asp Ser Val Thr Leu Pro Cys Tyr Leu Gln
            20                  25                  30

Val Pro Asn Met Glu Val Thr His Val Ser Gln Leu Thr Trp Ala Arg

```
              35                  40                  45
His Gly Glu Ser Gly Ser Met Ala Val Phe His Gln Thr Gln Gly Pro
 50                  55                  60

Ser Tyr Ser Glu Ser Lys Arg Leu Glu Phe Val Ala Ala Arg Leu Gly
 65                  70                  75                  80

Ala Glu Leu Arg Asn Ala Ser Leu Arg Met Phe Gly Leu Arg Val Glu
                 85                  90                  95

Asp Glu Gly Asn Tyr Thr Cys Leu Phe Val Thr Phe Pro Gln Gly Ser
                100                 105                 110

Arg Ser Val Asp Ile Trp Leu Arg Val Leu Ala Lys Pro Gln Asn Thr
            115                 120                 125

Ala Glu Val Gln Lys Val Gln Leu Thr Gly Glu Pro Val Pro Met Ala
        130                 135                 140

Arg Cys Val Ser Thr Gly Gly Arg Pro Pro Ala Gln Ile Thr Trp His
145                 150                 155                 160

Ser Asp Leu Gly Gly Met Pro Asn Thr Ser Gln Val Pro Gly Phe Leu
                165                 170                 175

Ser Gly Thr Val Thr Val Thr Ser Leu Trp Ile Leu Val Pro Ser Ser
            180                 185                 190

Gln Val Asp Gly Lys Asn Val Thr Cys Lys Val Glu His Glu Ser Phe
        195                 200                 205

Glu Lys Pro Gln Leu Leu Thr Val Asn Leu Thr Val Tyr Tyr Pro Pro
210                 215                 220

Glu Val Ser Ile Ser Gly Tyr Asp Asn Asn Trp Tyr Leu Gly Gln Asn
225                 230                 235                 240

Glu Ala Thr Leu Thr Cys Asp Ala Arg Ser Asn Pro Glu Pro Thr Gly
                245                 250                 255

Tyr Asn Trp Ser Thr Thr Met Gly Pro Leu Pro Pro Phe Ala Val Ala
            260                 265                 270

Gln Gly Ala Gln Leu Leu Ile Arg Pro Val Asp Lys Pro Ile Asn Thr
        275                 280                 285

Thr Leu Ile Cys Asn Val Thr Asn Ala Leu Gly Ala Arg Gln Ala Glu
290                 295                 300

Leu Thr Val Gln Val Lys Glu Gly Pro Pro Ser Glu His Ser Gly Ile
305                 310                 315                 320

Ser Arg Asn

<210> SEQ ID NO 30
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Asn Leu Phe Thr Lys Asp Val Thr Val Ile Glu Gly Glu Val Ala
  1               5                  10                  15

Thr Ile Ser Cys Gln Val Asn Lys Ser Asp Ser Val Ile Gln Leu
                 20                  25                  30

Leu Asn Pro Asn Arg Gln Thr Ile Tyr Phe Arg Asp Phe Arg Pro Leu
             35                  40                  45

Lys Asp Ser Arg Phe Gln Leu Leu Asn Phe Ser Ser Ser Glu Leu Lys
         50                  55                  60

Val Ser Leu Thr Asn Val Ser Ile Ser Asp Glu Gly Arg Tyr Phe Cys
```

```
            65                  70                  75                  80
    Gln Leu Tyr Thr Asp Pro Pro Gln Glu Ser Tyr Thr Thr Ile Thr Val
                        85                  90                  95

Leu Val Pro Pro Arg Asn Leu Met Ile Asp Ile Gln Lys Asp Thr Ala
                    100                 105                 110

Val Glu Gly Glu Ile Glu Val Asn Cys Thr Ala Met Ala Ser Lys
                115                 120                 125

Pro Ala Thr Thr Ile Arg Trp Phe Lys Gly Asn Thr Glu Leu Lys Gly
            130                 135                 140

Lys Ser Glu Val Glu Glu Trp Ser Asp Met Tyr Thr Val Thr Ser Gln
    145                 150                 155                 160

Leu Met Leu Lys Val His Lys Glu Asp Asp Gly Val Pro Val Ile Cys
                    165                 170                 175

Gln Val Glu His Pro Ala Val Thr Gly Asn Leu Gln Thr Gln Arg Tyr
                180                 185                 190

Leu Glu Val Gln Tyr Lys Pro Gln Val His Ile Gln Met Thr Tyr Pro
            195                 200                 205

Leu Gln Gly Leu Thr Arg Glu Gly Asp Ala Leu Glu Leu Thr Cys Glu
        210                 215                 220

Ala Ile Gly Lys Pro Gln Pro Val Met Val Thr Trp Val Arg Val Asp
    225                 230                 235                 240

Asp Glu Met Pro Gln His Ala Val Leu Ser Gly Pro Asn Leu Phe Ile
                    245                 250                 255

Asn Asn Leu Asn Lys Thr Asp Asn Gly Thr Tyr Arg Cys Glu Ala Ser
                260                 265                 270

Asn Ile Val Gly Lys Ala His Ser Asp Tyr Met Leu Tyr Val Tyr Asp
            275                 280                 285

Pro Pro Thr Thr Ile Pro Pro Thr Thr Thr Thr Thr Thr Thr Thr Thr
        290                 295                 300

Thr Thr Thr Thr Thr Ile Leu Thr Ile Ile Thr Asp Ser Arg Ala Gly
    305                 310                 315                 320

Glu Glu Gly Ser Ile Arg Ala Val Asp His
                    325                 330

<210> SEQ ID NO 31
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Arg Phe Ala Gln Ala Gln Gln Leu Pro Leu Glu Ser Leu Gly
    1               5                   10                  15

Trp Asp Val Ala Glu Leu Gln Leu Asn His Thr Gly Pro Gln Gln Asp
                    20                  25                  30

Pro Arg Leu Tyr Trp Gln Gly Pro Ala Leu Gly Arg Ser Phe Leu
                35                  40                  45

His Gly Pro Glu Leu Asp Lys Gly Gln Leu Arg Ile His Arg Asp Gly
        50                  55                  60

Ile Tyr Met Val His Ile Gln Val Thr Leu Ala Ile Cys Ser Ser Thr
    65                  70                  75                  80

Thr Ala Ser Arg His His Pro Thr Thr Leu Ala Val Gly Ile Cys Ser
                    85                  90                  95
```

```
Pro Ala Ser Arg Ser Ile Ser Leu Leu Arg Leu Ser Phe His Gln Gly
                100                 105                 110

Cys Thr Ile Ala Ser Gln Arg Leu Thr Pro Leu Ala Arg Gly Asp Thr
            115                 120                 125

Leu Cys Thr Asn Leu Thr Gly Thr Leu Leu Pro Ser Arg Asn Thr Asp
130                 135                 140

Glu Thr Phe Phe Gly Val Gln Trp Val Arg Pro
145                 150                 155

<210> SEQ ID NO 32
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Trp Thr Tyr His Tyr Ser Glu Lys Pro Met Asn Trp Gln Arg Ala Arg
1               5                   10                  15

Arg Phe Cys Arg Asp Asn Tyr Thr Asp Leu Val Ala Ile Gln Asn Lys
            20                  25                  30

Ala Glu Ile Glu Tyr Leu Glu Lys Thr Leu Pro Phe Ser Arg Ser Tyr
        35                  40                  45

Tyr Trp Ile Gly Ile Arg Lys Ile Gly Gly Ile Trp Thr Trp Val Gly
    50                  55                  60

Thr Asn Lys Ser Leu Thr Glu Glu Ala Glu Asn Trp Gly Asp Gly Glu
65                  70                  75                  80

Pro Asn Asn Lys Lys Asn Lys Glu Asp Cys Val Glu Ile Tyr Ile Lys
                85                  90                  95

Arg Asn Lys Asp Ala Gly Lys Trp Asn Asp Asp Ala Cys His Lys Leu
            100                 105                 110

Lys Ala Ala Leu Cys Tyr Thr Ala Ser Cys Gln Pro Trp Ser Cys Ser
        115                 120                 125

Gly His Gly Glu Cys Val Glu Ile Ile Asn Asn Tyr Thr Cys Asn Cys
    130                 135                 140

Asp Val Gly Tyr Tyr Gly Pro Gln Cys Gln Phe Val Ile Gln Cys Glu
145                 150                 155                 160

Pro Leu Glu Ala Pro Glu Leu Gly Thr Met Asp Cys Thr His Pro Leu
                165                 170                 175

Gly Asn Phe Ser Phe Ser Ser Gln Cys Ala Phe Ser Cys Ser Glu Gly
            180                 185                 190

Thr Asn Leu Thr Gly Ile Glu Glu Thr Thr Cys Gly Pro Phe Gly Asn
        195                 200                 205

Trp Ser Ser Pro Glu Pro Thr Cys Gln Val Ile Gln Cys Glu Pro Leu
    210                 215                 220

Ser Ala Pro Asp Leu Gly Ile Met Asn Cys Ser His Pro Leu Ala Ser
225                 230                 235                 240

Phe Ser Phe Thr Ser Ala Cys Thr Phe Ile Cys Ser Glu Gly Thr Glu
                245                 250                 255

Leu Ile Gly Lys Lys Lys Thr Ile Cys Glu Ser Ser Gly Ile Trp Ser
            260                 265                 270

Asn Pro Ser Pro Ile Cys Gln Lys Leu Asp Lys Ser Phe Ser Met Ile
        275                 280                 285

Lys Glu Gly Asp Tyr Asn
    290
```

<210> SEQ ID NO 33
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Arg Tyr Leu Gln Val Ser Gln Gln Leu Gln Gln Thr Asn Arg Val Leu
1               5                   10                  15

Glu Val Thr Asn Ser Ser Leu Arg Gln Gln Leu Arg Leu Lys Ile Thr
                20                  25                  30

Gln Leu Gly Gln Ser Ala Glu Asp Leu Gln Gly Ser Arg Arg Glu Leu
            35                  40                  45

Ala Gln Ser Gln Glu Ala Leu Gln Val Glu Gln Arg Ala His Gln Ala
        50                  55                  60

Ala Glu Gly Gln Leu Gln Ala Cys Gln Ala Asp Arg Gln Lys Thr Lys
65                  70                  75                  80

Glu Thr Leu Gln Ser Glu Glu Gln Gln Arg Arg Ala Leu Glu Gln Lys
                85                  90                  95

Leu Ser Asn Met Glu Asn Arg Leu Lys Pro Phe Phe Thr Cys Gly Ser
                100                 105                 110

Ala Asp Thr Cys Cys Pro Ser Gly Trp Ile Met His Gln Lys Ser Cys
            115                 120                 125

Phe Tyr Ile Ser Leu Thr Ser Lys Asn Trp Gln Glu Ser Gln Lys Gln
    130                 135                 140

Cys Glu Thr Leu Ser Ser Lys Leu Ala Thr Phe Ser Glu Ile Tyr Pro
145                 150                 155                 160

Gln Ser His Ser Tyr Tyr Phe Leu Asn Ser Leu Leu Pro Asn Gly Gly
                165                 170                 175

Ser Gly Asn Ser Tyr Trp Thr Gly Leu Ser Ser Asn Lys Asp Trp Lys
            180                 185                 190

Leu Thr Asp Asp Thr Gln Arg Thr Arg Thr Tyr Ala Gln Ser Ser Lys
        195                 200                 205

Cys Asn Lys Val His Lys Thr Trp Ser Trp Trp Thr Leu Glu Ser Glu
    210                 215                 220

Ser Cys Arg Ser Ser Leu Pro Tyr Ile Cys Glu Met Thr Ala Phe Arg
225                 230                 235                 240

Phe Pro Asp

<210> SEQ ID NO 34
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Lys Leu Thr Arg Asp Ser Gln Ser Leu Cys Pro Tyr Asp Trp Ile Gly
1               5                   10                  15

Phe Gln Asn Lys Cys Tyr Tyr Phe Ser Lys Glu Glu Gly Asp Trp Asn
                20                  25                  30

Ser Ser Lys Tyr Asn Cys Ser Thr Gln His Ala Asp Leu Thr Ile Ile
            35                  40                  45

Asp Asn Ile Glu Glu Met Asn Phe Leu Arg Arg Tyr Lys Cys Ser Ser
 50                  55                  60

Asp His Trp Ile Gly Leu Lys Met Ala Lys Asn Arg Thr Gly Gln Trp
 65                  70                  75                  80

Val Asp Gly Ala Thr Phe Thr Lys Ser Phe Gly Met Arg Gly Ser Glu
                 85                  90                  95

Gly Cys Ala Tyr Leu Ser Asp Asp Gly Ala Ala Thr Ala Arg Cys Tyr
                100                 105                 110

Thr Glu Arg Lys Trp Ile Cys Arg Lys Arg Ile His
            115                 120

<210> SEQ ID NO 35
<211> LENGTH: 194
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Gly His Leu Val His Met Thr Val Val Ser Gly Ser Asn Val Thr
 1               5                  10                  15

Leu Asn Ile Ser Glu Ser Leu Pro Glu Asn Tyr Lys Gln Leu Thr Trp
                 20                  25                  30

Phe Tyr Thr Phe Asp Gln Lys Ile Val Glu Trp Asp Ser Arg Lys Ser
             35                  40                  45

Lys Tyr Phe Glu Ser Lys Phe Lys Gly Arg Val Arg Leu Asp Pro Gln
 50                  55                  60

Ser Gly Ala Leu Tyr Ile Ser Lys Val Gln Lys Glu Asp Asn Ser Thr
 65                  70                  75                  80

Tyr Ile Met Arg Val Leu Lys Lys Thr Gly Asn Glu Gln Glu Trp Lys
                 85                  90                  95

Ile Lys Leu Gln Val Leu Asp Pro Val Pro Lys Pro Val Ile Lys Ile
                100                 105                 110

Glu Lys Ile Glu Asp Met Asp Asp Asn Cys Tyr Leu Lys Leu Ser Cys
            115                 120                 125

Val Ile Pro Gly Glu Ser Val Asn Tyr Thr Trp Tyr Gly Asp Lys Arg
130                 135                 140

Pro Phe Pro Lys Glu Leu Gln Asn Ser Val Leu Glu Thr Thr Leu Met
145                 150                 155                 160

Pro His Asn Tyr Ser Arg Cys Tyr Thr Cys Gln Val Ser Asn Ser Val
                165                 170                 175

Ser Ser Lys Asn Gly Thr Val Cys Leu Ser Pro Pro Cys Thr Leu Ala
                180                 185                 190

Arg Ser

<210> SEQ ID NO 36
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Ser His Arg Tyr Pro Arg Ile Gln Ser Ile Lys Val Gln Phe
 1               5                  10                  15

Thr Glu Tyr Lys Lys Glu Lys Gly Phe Ile Leu Thr Ser Gln Lys Glu

```
                    20                  25                  30
Asp Glu Ile Met Lys Val Gln Asn Asn Ser Val Ile Ile Asn Cys Asp
            35                  40                  45

Gly Phe Tyr Leu Ile Ser Leu Lys Gly Tyr Phe Ser Gln Glu Val Asn
        50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130
```

<210> SEQ ID NO 37
<211> LENGTH: 149
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

```
Met Gln Lys Gly Asp Gln Asn Pro Gln Ile Ala Ala His Val Ile Ser
1               5                   10                  15

Glu Ala Ser Ser Lys Thr Thr Ser Val Leu Gln Trp Ala Glu Lys Gly
            20                  25                  30

Tyr Tyr Thr Met Ser Asn Asn Leu Val Thr Leu Glu Asn Gly Lys Gln
        35                  40                  45

Leu Thr Val Lys Arg Gln Gly Leu Tyr Tyr Ile Tyr Ala Gln Val Thr
    50                  55                  60

Phe Cys Ser Asn Arg Glu Ala Ser Ser Gln Ala Pro Phe Ile Ala Ser
65                  70                  75                  80

Leu Cys Leu Lys Ser Pro Gly Arg Phe Glu Arg Ile Leu Leu Arg Ala
                85                  90                  95

Ala Asn Thr His Ser Ser Ala Lys Pro Cys Gly Gln Gln Ser Ile His
            100                 105                 110

Leu Gly Gly Val Phe Glu Leu Gln Pro Gly Ala Ser Val Phe Val Asn
        115                 120                 125

Val Thr Asp Pro Ser Gln Val Ser His Gly Thr Gly Phe Thr Ser Phe
    130                 135                 140

Gly Leu Leu Lys Leu
145
```

<210> SEQ ID NO 38
<211> LENGTH: 205
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
```

```
                    20                  25                  30
Ala Gly Leu Leu Asp Leu Arg Gln Gly Met Phe Ala Gln Leu Val Ala
                35                  40                  45
Gln Asn Val Leu Leu Ile Asp Gly Pro Leu Ser Trp Tyr Ser Asp Pro
            50                  55                  60
Gly Leu Ala Gly Val Ser Leu Thr Gly Gly Leu Ser Tyr Lys Glu Asp
65                  70                  75                  80
Thr Lys Glu Leu Val Val Ala Lys Ala Gly Val Tyr Tyr Val Phe Phe
                85                  90                  95
Gln Leu Glu Leu Arg Arg Val Val Ala Gly Glu Gly Ser Gly Ser Val
                100                 105                 110
Ser Leu Ala Leu His Leu Gln Pro Leu Arg Ser Ala Ala Gly Ala Ala
                115                 120                 125
Ala Leu Ala Leu Thr Val Asp Leu Pro Pro Ala Ser Ser Glu Ala Arg
            130                 135                 140
Asn Ser Ala Phe Gly Phe Gln Gly Arg Leu Leu His Leu Ser Ala Gly
145                 150                 155                 160
Gln Arg Leu Gly Val His Leu His Thr Glu Ala Arg Ala Arg His Ala
                165                 170                 175
Trp Gln Leu Thr Gln Gly Ala Thr Val Leu Gly Leu Phe Arg Val Thr
                180                 185                 190
Pro Glu Ile Pro Ala Gly Leu Pro Ser Pro Arg Ser Glu
                195                 200                 205

<210> SEQ ID NO 39
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Asn Phe Arg Ala Pro Pro Val Ile Pro Asn Val Pro Phe Leu Trp
1               5                   10                  15
Ala Trp Asn Ala Pro Ser Glu Phe Cys Leu Gly Lys Phe Asp Glu Pro
                20                  25                  30
Leu Asp Met Ser Leu Phe Ser Phe Ile Gly Ser Pro Arg Ile Asn Ala
            35                  40                  45
Thr Gly Gln Gly Val Thr Ile Phe Tyr Val Asp Arg Leu Gly Tyr Tyr
        50                  55                  60
Pro Tyr Ile Asp Ser Ile Thr Gly Val Thr Val Asn Gly Gly Ile Pro
65                  70                  75                  80
Gln Lys Ile Ser Leu Gln Asp His Leu Asp Lys Ala Lys Lys Asp Ile
                85                  90                  95
Thr Phe Tyr Met Pro Val Asp Asn Leu Gly Met Ala Val Ile Asp Trp
                100                 105                 110
Glu Glu Trp Arg Pro Thr Trp Ala Arg Asn Trp Lys Pro Lys Asp Val
                115                 120                 125
Tyr Lys Asn Arg Ser Ile Glu Leu Val Gln Gln Asn Val Gln Leu
            130                 135                 140
Ser Leu Thr Glu Ala Thr Glu Lys Ala Lys Gln Glu Phe Glu Lys Ala
145                 150                 155                 160
Gly Lys Asp Phe Leu Val Glu Thr Ile Lys Leu Gly Lys Leu Leu Arg
                165                 170                 175
```

```
Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400

Ser Cys Tyr Ser Thr Leu Ser Cys Lys Glu Lys Ala Asp Val Lys Asp
                405                 410                 415

Thr Asp Ala Val Asp Val Cys Ile Ala Asp Gly Val Cys Ile Asp Ala
            420                 425                 430

Phe Leu Lys Pro Pro Met Glu Thr Glu Glu Pro Gln Ile Phe Tyr Asn
        435                 440                 445

Ala Ser Pro Ser Thr Leu Ser
    450                 455

<210> SEQ ID NO 40

<400> SEQUENCE: 40

000

<210> SEQ ID NO 41

<400> SEQUENCE: 41

000

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42
```

```
Gly Gly Gly Gly Ser
1               5

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Gly Gly Ser Gly Gly Gly Gly Ser
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly Gly Ser Gly Gly Gly Gly Ser Gly Gly Gly Gly Ser
1               5                   10                  15

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Val Pro Ser Gly Pro Gly Gly Gly Gly Ser Gly Gly Gly Gly
1               5                   10                  15

Ser

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50
```

000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61
<211> LENGTH: 455
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 61

```
Leu Asn Phe Arg Ala Pro Pro Val Ile Pro Asn Val Pro Phe Leu Trp
1               5                   10                  15

Ala Trp Asn Ala Pro Ser Glu Phe Cys Leu Gly Lys Phe Asp Glu Pro
            20                  25                  30

Leu Asp Met Ser Leu Phe Ser Phe Ile Gly Ser Pro Arg Ile Asn Ala
        35                  40                  45

Thr Gly Gln Gly Val Thr Ile Phe Tyr Val Asp Arg Leu Gly Tyr Tyr
    50                  55                  60

Pro Tyr Ile Asp Ser Ile Thr Gly Val Thr Val Asn Gly Gly Ile Pro
65                  70                  75                  80

Gln Lys Ile Ser Leu Gln Asp His Leu Asp Lys Ala Lys Lys Asp Ile
                85                  90                  95

Thr Phe Tyr Met Pro Val Asp Asn Leu Gly Met Ala Val Ile Asp Trp
            100                 105                 110

Glu Glu Trp Arg Pro Thr Trp Ala Arg Asn Trp Lys Pro Lys Asp Val
        115                 120                 125

Tyr Lys Asn Arg Ser Ile Glu Leu Val Gln Gln Asn Val Gln Leu
    130                 135                 140

Ser Leu Thr Glu Ala Thr Glu Lys Ala Lys Gln Glu Phe Glu Lys Ala
145                 150                 155                 160

Gly Lys Asp Phe Leu Val Glu Thr Ile Lys Leu Gly Lys Leu Leu Arg
                165                 170                 175

Pro Asn His Leu Trp Gly Tyr Tyr Leu Phe Pro Asp Cys Tyr Asn His
            180                 185                 190

His Tyr Lys Lys Pro Gly Tyr Asn Gly Ser Cys Phe Asn Val Glu Ile
        195                 200                 205

Lys Arg Asn Asp Asp Leu Ser Trp Leu Trp Asn Glu Ser Thr Ala Leu
    210                 215                 220

Tyr Pro Ser Ile Tyr Leu Asn Thr Gln Gln Ser Pro Val Ala Ala Thr
225                 230                 235                 240

Leu Tyr Val Arg Asn Arg Val Arg Glu Ala Ile Arg Val Ser Lys Ile
                245                 250                 255

Pro Asp Ala Lys Ser Pro Leu Pro Val Phe Ala Tyr Thr Arg Ile Val
            260                 265                 270

Phe Thr Asp Gln Val Leu Lys Phe Leu Ser Gln Asp Glu Leu Val Tyr
        275                 280                 285

Thr Phe Gly Glu Thr Val Ala Leu Gly Ala Ser Gly Ile Val Ile Trp
    290                 295                 300

Gly Thr Leu Ser Ile Met Arg Ser Met Lys Ser Cys Leu Leu Leu Asp
305                 310                 315                 320

Asn Tyr Met Glu Thr Ile Leu Asn Pro Tyr Ile Ile Asn Val Thr Leu
                325                 330                 335

Ala Ala Lys Met Cys Ser Gln Val Leu Cys Gln Glu Gln Gly Val Cys
            340                 345                 350

Ile Arg Lys Asn Trp Asn Ser Ser Asp Tyr Leu His Leu Asn Pro Asp
        355                 360                 365

Asn Phe Ala Ile Gln Leu Glu Lys Gly Gly Lys Phe Thr Val Arg Gly
    370                 375                 380

Lys Pro Thr Leu Glu Asp Leu Glu Gln Phe Ser Glu Lys Phe Tyr Cys
385                 390                 395                 400
```

-continued

```
Ser Cys Tyr Ser Thr Leu Ser Cys Lys Glu Lys Ala Asp Val Lys Asp
            405                 410                 415

Thr Asp Ala Val Asp Val Cys Ile Ala Asp Gly Val Cys Ile Asp Ala
        420                 425                 430

Phe Leu Lys Pro Pro Met Glu Thr Glu Glu Pro Gln Ile Phe Tyr Asn
    435                 440                 445

Ala Ser Pro Ser Thr Leu Ser
    450                 455

<210> SEQ ID NO 62
<211> LENGTH: 413
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Phe Arg Gly Pro Leu Leu Pro Asn Arg Pro Phe Thr Thr Val Trp Asn
1               5                   10                  15

Ala Asn Thr Gln Trp Cys Leu Glu Arg His Gly Val Asp Val Asp Val
            20                  25                  30

Ser Val Phe Asp Val Val Ala Asn Pro Gly Gln Thr Phe Arg Gly Pro
        35                  40                  45

Asp Met Thr Ile Phe Tyr Ser Ser Gln Gly Thr Tyr Pro Tyr Tyr Thr
    50                  55                  60

Pro Thr Gly Glu Pro Val Phe Gly Gly Leu Pro Gln Asn Ala Ser Leu
65                  70                  75                  80

Ile Ala His Leu Ala Arg Thr Phe Gln Asp Ile Leu Ala Ala Ile Pro
                85                  90                  95

Ala Pro Asp Phe Ser Gly Leu Ala Val Ile Asp Trp Glu Ala Trp Arg
            100                 105                 110

Pro Arg Trp Ala Phe Asn Trp Asp Thr Lys Asp Ile Tyr Arg Gln Arg
        115                 120                 125

Ser Arg Ala Leu Val Gln Ala Gln His Pro Asp Trp Pro Ala Pro Gln
    130                 135                 140

Val Glu Ala Val Ala Gln Asp Gln Phe Gln Gly Ala Ala Arg Ala Trp
145                 150                 155                 160

Met Ala Gly Thr Leu Gln Leu Gly Arg Ala Leu Arg Pro Arg Gly Leu
                165                 170                 175

Trp Gly Phe Tyr Gly Phe Pro Asp Cys Tyr Asn Tyr Asp Phe Leu Ser
            180                 185                 190

Pro Asn Tyr Thr Gly Gln Cys Pro Ser Gly Ile Arg Ala Gln Asn Asp
        195                 200                 205

Gln Leu Gly Trp Leu Trp Gly Gln Ser Arg Ala Leu Tyr Pro Ser Ile
    210                 215                 220

Tyr Met Pro Ala Val Leu Glu Gly Thr Gly Lys Ser Gln Met Tyr Val
225                 230                 235                 240

Gln His Arg Val Ala Glu Ala Phe Arg Val Ala Val Ala Ala Gly Asp
                245                 250                 255

Pro Asn Leu Pro Val Leu Pro Tyr Val Gln Ile Phe Tyr Asp Thr Thr
            260                 265                 270

Asn His Phe Leu Pro Leu Asp Glu Leu Glu His Ser Leu Gly Glu Ser
        275                 280                 285

Ala Ala Gln Gly Ala Ala Gly Val Val Leu Trp Val Ser Trp Glu Asn
```

```
                     290                 295                 300

Thr Arg Thr Lys Glu Ser Cys Gln Ala Ile Lys Glu Tyr Met Asp Thr
305                 310                 315                 320

Thr Leu Gly Pro Phe Ile Leu Asn Val Thr Ser Gly Ala Leu Leu Cys
                325                 330                 335

Ser Gln Ala Leu Cys Ser Gly His Gly Arg Cys Val Arg Arg Thr Ser
            340                 345                 350

His Pro Lys Ala Leu Leu Leu Asn Pro Ala Ser Phe Ser Ile Gln
        355                 360                 365

Leu Thr Pro Gly Gly Pro Leu Ser Leu Arg Gly Ala Leu Ser Leu
    370                 375                 380

Glu Asp Gln Ala Gln Met Ala Val Glu Phe Lys Cys Arg Cys Tyr Pro
385                 390                 395                 400

Gly Trp Gln Ala Pro Trp Cys Glu Arg Lys Ser Met Trp
                405                 410

<210> SEQ ID NO 63
<211> LENGTH: 551
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Tyr Asn Phe Phe Pro Arg Lys Pro Lys Trp Asp Lys Asn Gln Ile Thr
1               5                   10                  15

Tyr Arg Ile Ile Gly Tyr Thr Pro Asp Leu Asp Pro Glu Thr Val Asp
            20                  25                  30

Asp Ala Phe Ala Arg Ala Phe Gln Val Trp Ser Asp Val Thr Pro Leu
        35                  40                  45

Arg Phe Ser Arg Ile His Asp Gly Glu Ala Asp Ile Met Ile Asn Phe
    50                  55                  60

Gly Arg Trp Glu His Gly Asp Gly Tyr Pro Phe Asp Gly Lys Asp Gly
65                  70                  75                  80

Leu Leu Ala His Ala Phe Ala Pro Gly Thr Gly Val Gly Gly Asp Ser
                85                  90                  95

His Phe Asp Asp Asp Glu Leu Trp Thr Leu Gly Glu Gly Gln Val Val
            100                 105                 110

Arg Val Lys Tyr Gly Asn Ala Asp Gly Glu Tyr Cys Lys Phe Pro Phe
        115                 120                 125

Leu Phe Asn Gly Lys Glu Tyr Asn Ser Cys Thr Asp Thr Gly Arg Ser
    130                 135                 140

Asp Gly Phe Leu Trp Cys Ser Thr Thr Tyr Asn Phe Glu Lys Asp Gly
145                 150                 155                 160

Lys Tyr Gly Phe Cys Pro His Glu Ala Leu Phe Thr Met Gly Gly Asn
                165                 170                 175

Ala Glu Gly Gln Pro Cys Lys Phe Pro Phe Arg Phe Gln Gly Thr Ser
            180                 185                 190

Tyr Asp Ser Cys Thr Thr Glu Gly Arg Thr Asp Gly Tyr Arg Trp Cys
        195                 200                 205

Gly Thr Thr Glu Asp Tyr Asp Arg Asp Lys Lys Tyr Gly Phe Cys Pro
    210                 215                 220

Glu Thr Ala Met Ser Thr Val Gly Gly Asn Ser Glu Gly Ala Pro Cys
225                 230                 235                 240
```

```
Val Phe Pro Phe Thr Phe Leu Gly Asn Lys Tyr Glu Ser Cys Thr Ser
                245                 250                 255

Ala Gly Arg Ser Asp Gly Lys Met Trp Cys Ala Thr Thr Ala Asn Tyr
            260                 265                 270

Asp Asp Asp Arg Lys Trp Gly Phe Cys Pro Asp Gln Gly Tyr Ser Leu
            275                 280                 285

Phe Leu Val Ala Ala His Glu Phe Gly His Ala Met Gly Leu Glu His
            290                 295                 300

Ser Gln Asp Pro Gly Ala Leu Met Ala Pro Ile Tyr Thr Tyr Thr Lys
305                 310                 315                 320

Asn Phe Arg Leu Ser Gln Asp Ile Lys Gly Ile Gln Glu Leu Tyr
                325                 330                 335

Gly Ala Ser Pro Asp Ile Asp Leu Gly Thr Gly Pro Thr Pro Thr Leu
            340                 345                 350

Gly Pro Val Thr Pro Glu Ile Cys Lys Gln Asp Ile Val Phe Asp Gly
            355                 360                 365

Ile Ala Gln Ile Arg Gly Glu Ile Phe Phe Lys Asp Arg Phe Ile
            370                 375                 380

Trp Arg Thr Val Thr Pro Arg Asp Lys Pro Met Gly Pro Leu Leu Val
385                 390                 395                 400

Ala Thr Phe Trp Pro Glu Leu Pro Glu Lys Ile Asp Ala Val Tyr Glu
                405                 410                 415

Ala Pro Gln Glu Glu Lys Ala Val Phe Phe Ala Gly Asn Glu Tyr Trp
            420                 425                 430

Ile Tyr Ser Ala Ser Thr Leu Glu Arg Gly Tyr Pro Lys Pro Leu Thr
            435                 440                 445

Ser Leu Gly Leu Pro Pro Asp Val Gln Arg Val Asp Ala Ala Phe Asn
450                 455                 460

Trp Ser Lys Asn Lys Lys Thr Tyr Ile Phe Ala Gly Asp Lys Phe Trp
465                 470                 475                 480

Arg Tyr Asn Glu Val Lys Lys Lys Met Asp Pro Gly Phe Pro Lys Leu
                485                 490                 495

Ile Ala Asp Ala Trp Asn Ala Ile Pro Asp Asn Leu Asp Ala Val Val
            500                 505                 510

Asp Leu Gln Gly Gly Gly His Ser Tyr Phe Phe Lys Gly Ala Tyr Tyr
            515                 520                 525

Leu Lys Leu Glu Asn Gln Ser Leu Lys Ser Val Lys Phe Gly Ser Ile
            530                 535                 540

Lys Ser Asp Trp Leu Gly Cys
545                 550

<210> SEQ ID NO 64

<400> SEQUENCE: 64

000

<210> SEQ ID NO 65

<400> SEQUENCE: 65

000

<210> SEQ ID NO 66

<400> SEQUENCE: 66
```

```
<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Glu Ala Ala Ala Lys Glu Ala Ala Lys Ala Ala Ala
1               5                   10

<210> SEQ ID NO 76
<211> LENGTH: 19
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 76

Ala Glu Ala Ala Ala Lys Glu Ala Ala Lys Glu Ala Ala Lys
1               5                   10                  15

Ala Ala Ala

<210> SEQ ID NO 77
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Glu Ala Ala Ala Lys Glu Ala Ala Lys Glu Ala Ala Lys
1               5                   10                  15

Glu Ala Ala Ala Lys Ala Ala Ala
                20

<210> SEQ ID NO 78
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Glu Ala Ala Ala Lys Glu Ala Ala Lys Glu Ala Ala Lys
1               5                   10                  15

Glu Ala Ala Ala Lys Glu Ala Ala Ala Lys Ala Ala Ala
                20                  25

<210> SEQ ID NO 79

<400> SEQUENCE: 79

000

<210> SEQ ID NO 80
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Glu
<220> FEATURE:
<221> NAME/KEY: MOD_RES
<222> LOCATION: (5)..(5)
<223> OTHER INFORMATION: Any amino acid except Glu
<220> FEATURE:
<221> NAME/KEY: MOD_RES
<222> LOCATION: (9)..(9)
<223> OTHER INFORMATION: Any amino acid except Pro
<220> FEATURE:
<221> NAME/KEY: MOD_RES
<222> LOCATION: (11)..(11)
<223> OTHER INFORMATION: Any amino acid except Leu
<220> FEATURE:
<221> NAME/KEY: MOD_RES
<222> LOCATION: (12)..(12)
<223> OTHER INFORMATION: Any amino acid except Val
<220> FEATURE:

```
<221> NAME/KEY: MOD_RES
<222> LOCATION: (14)..(14)
<223> OTHER INFORMATION: Any amino acid except Thr
<220> FEATURE:
<221> NAME/KEY: MOD_RES
<222> LOCATION: (20)..(20)
<223> OTHER INFORMATION: Any amino acid except Ile

<400> SEQUENCE: 80

Xaa Val Gln Leu Xaa Gln Ser Gly Xaa Glu Xaa Xaa Lys Xaa Gly Ala
1               5                   10                  15

Ser Val Lys Xaa Ser Cys Lys Ala Ser Gly
            20                  25

<210> SEQ ID NO 81
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid except Lys
<220> FEATURE:
<221> NAME/KEY: MOD_RES
<222> LOCATION: (5)..(5)
<223> OTHER INFORMATION: Any amino acid except Ser
<220> FEATURE:
<221> NAME/KEY: MOD_RES
<222> LOCATION: (6)..(6)
<223> OTHER INFORMATION: Any amino acid except His
<220> FEATURE:
<221> NAME/KEY: MOD_RES
<222> LOCATION: (8)..(8)
<223> OTHER INFORMATION: Any amino acid except Lys
<220> FEATURE:
<221> NAME/KEY: MOD_RES
<222> LOCATION: (9)..(9)
<223> OTHER INFORMATION: Any amino acid except Ser
<220> FEATURE:
<221> NAME/KEY: MOD_RES
<222> LOCATION: (11)..(11)
<223> OTHER INFORMATION: Any amino acid except Glu
<220> FEATURE:
<221> NAME/KEY: MOD_RES
<222> LOCATION: (13)..(13)
<223> OTHER INFORMATION: Any amino acid except Ile

<400> SEQUENCE: 81

Trp Val Xaa Gln Xaa Xaa Gly Xaa Xaa Leu Xaa Trp Xaa Gly
1               5                   10

<210> SEQ ID NO 82
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Any amino acid except Lys
<220> FEATURE:
<221> NAME/KEY: MOD_RES
<222> LOCATION: (2)..(2)
<223> OTHER INFORMATION: Any amino acid except Ala
<220> FEATURE:
<221> NAME/KEY: MOD_RES
<222> LOCATION: (4)..(4)
<223> OTHER INFORMATION: Any amino acid except Phe
<220> FEATURE:
```

```
<221> NAME/KEY: MOD_RES
<222> LOCATION: (10)..(10)
<223> OTHER INFORMATION: Any amino acid except Ser
<220> FEATURE:
<221> NAME/KEY: MOD_RES
<222> LOCATION: (15)..(15)
<223> OTHER INFORMATION: Any amino acid except Met
<220> FEATURE:
<221> NAME/KEY: MOD_RES
<222> LOCATION: (16)..(16)
<223> OTHER INFORMATION: Any amino acid except Gln
<220> FEATURE:
<221> NAME/KEY: MOD_RES
<222> LOCATION: (17)..(17)
<223> OTHER INFORMATION: Any amino acid except Phe
<220> FEATURE:
<221> NAME/KEY: MOD_RES
<222> LOCATION: (18)..(18)
<223> OTHER INFORMATION: Any amino acid except Asn
<220> FEATURE:
<221> NAME/KEY: MOD_RES
<222> LOCATION: (21)..(21)
<223> OTHER INFORMATION: Any amino acid except Thr
<220> FEATURE:
<221> NAME/KEY: MOD_RES
<222> LOCATION: (23)..(23)
<223> OTHER INFORMATION: Any amino acid except Gly
<220> FEATURE:
<221> NAME/KEY: MOD_RES
<222> LOCATION: (25)..(25)
<223> OTHER INFORMATION: Any amino acid except Ser
<220> FEATURE:
<221> NAME/KEY: MOD_RES
<222> LOCATION: (27)..(27)
<223> OTHER INFORMATION: Any amino acid except Val

<400> SEQUENCE: 82

Xaa Xaa Thr Xaa Thr Val Asp Thr Ser Xaa Ser Thr Ala Tyr Xaa Xaa
1               5                   10                  15

Xaa Xaa Ser Leu Xaa Ser Xaa Asp Xaa Ala Xaa Tyr Tyr Cys Ala
            20                  25                  30

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any amino acid except Ser

<400> SEQUENCE: 83

Trp Gly Gln Gly Thr Xaa Val Thr Val Ser Ser
1               5                   10

<210> SEQ ID NO 84
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid except Asp
<220> FEATURE:
<221> NAME/KEY: MOD_RES
<222> LOCATION: (3)..(3)
<223> OTHER INFORMATION: Any amino acid except Gln
<220> FEATURE:
```

```
<221> NAME/KEY: MOD_RES
<222> LOCATION: (5)..(5)
<223> OTHER INFORMATION: Any amino acid except Gln
<220> FEATURE:
<221> NAME/KEY: MOD_RES
<222> LOCATION: (10)..(10)
<223> OTHER INFORMATION: Any amino acid except Gly
<220> FEATURE:
<221> NAME/KEY: MOD_RES
<222> LOCATION: (14)..(14)
<223> OTHER INFORMATION: Any amino acid except Asn
<220> FEATURE:
<221> NAME/KEY: MOD_RES
<222> LOCATION: (15)..(15)
<223> OTHER INFORMATION: Any amino acid except Ser
<220> FEATURE:
<221> NAME/KEY: MOD_RES
<222> LOCATION: (16)..(16)
<223> OTHER INFORMATION: Any amino acid except Gln
<220> FEATURE:
<221> NAME/KEY: MOD_RES
<222> LOCATION: (17)..(17)
<223> OTHER INFORMATION: Any amino acid except Ser
<220> FEATURE:
<221> NAME/KEY: MOD_RES
<222> LOCATION: (19)..(19)
<223> OTHER INFORMATION: Any amino acid except Ser
<220> FEATURE:
<221> NAME/KEY: MOD_RES
<222> LOCATION: (25)..(25)
<223> OTHER INFORMATION: Any amino acid except Thr

<400> SEQUENCE: 84

Xaa Val Xaa Leu Xaa Glu Ser Gly Pro Xaa Leu Val Lys Xaa Xaa Xaa
1               5                   10                  15

Xaa Leu Xaa Leu Thr Cys Thr Val Xaa Gly
            20                  25

<210> SEQ ID NO 85
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid except Phe
<220> FEATURE:
<221> NAME/KEY: MOD_RES
<222> LOCATION: (8)..(8)
<223> OTHER INFORMATION: Any amino acid except Asn
<220> FEATURE:
<221> NAME/KEY: MOD_RES
<222> LOCATION: (9)..(9)
<223> OTHER INFORMATION: Any amino acid except Lys
<220> FEATURE:
<221> NAME/KEY: MOD_RES
<222> LOCATION: (13)..(13)
<223> OTHER INFORMATION: Any amino acid except Met
<220> FEATURE:
<221> NAME/KEY: MOD_RES
<222> LOCATION: (14)..(14)
<223> OTHER INFORMATION: Any amino acid except Gly

<400> SEQUENCE: 85

Trp Ile Arg Gln Xaa Pro Gly Xaa Xaa Leu Glu Trp Xaa Xaa
1               5                   10

<210> SEQ ID NO 86
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Any amino acid except Ile
<220> FEATURE:
<221> NAME/KEY: MOD_RES
<222> LOCATION: (6)..(6)
<223> OTHER INFORMATION: Any amino acid except Arg
<220> FEATURE:
<221> NAME/KEY: MOD_RES
<222> LOCATION: (11)..(11)
<223> OTHER INFORMATION: Any amino acid except Asn
<220> FEATURE:
<221> NAME/KEY: MOD_RES
<222> LOCATION: (13)..(13)
<223> OTHER INFORMATION: Any amino acid except Phe
<220> FEATURE:
<221> NAME/KEY: MOD_RES
<222> LOCATION: (14)..(14)
<223> OTHER INFORMATION: Any amino acid except Phe
<220> FEATURE:
<221> NAME/KEY: MOD_RES
<222> LOCATION: (16)..(16)
<223> OTHER INFORMATION: Any amino acid except Gln
<220> FEATURE:
<221> NAME/KEY: MOD_RES
<222> LOCATION: (17)..(17)
<223> OTHER INFORMATION: Any amino acid except Leu
<220> FEATURE:
<221> NAME/KEY: MOD_RES
<222> LOCATION: (18)..(18)
<223> OTHER INFORMATION: Any amino acid except Asn
<220> FEATURE:
<221> NAME/KEY: MOD_RES
<222> LOCATION: (19)..(19)
<223> OTHER INFORMATION: Any amino acid except Ser
<220> FEATURE:
<221> NAME/KEY: MOD_RES
<222> LOCATION: (20)..(20)
<223> OTHER INFORMATION: Any amino acid except Val
<220> FEATURE:
<221> NAME/KEY: MOD_RES
<222> LOCATION: (21)..(21)
<223> OTHER INFORMATION: Any amino acid except Thr
<220> FEATURE:
<221> NAME/KEY: MOD_RES
<222> LOCATION: (23)..(23)
<223> OTHER INFORMATION: Any amino acid except Glu

<400> SEQUENCE: 86

Arg Xaa Ser Ile Thr Xaa Asp Thr Ser Lys Xaa Gln Xaa Xaa Leu Xaa
1               5                   10                  15

Xaa Xaa Xaa Xaa Xaa Pro Xaa Asp Thr Ala Thr Tyr Tyr Cys Ala Arg
            20                  25                  30

<210> SEQ ID NO 87
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid except Thr
<220> FEATURE:
<221> NAME/KEY: MOD_RES
<222> LOCATION: (10)..(10)
<223> OTHER INFORMATION: Any amino acid except Thr
<220> FEATURE:
<221> NAME/KEY: MOD_RES
<222> LOCATION: (12)..(12)
```

```
<223> OTHER INFORMATION: Any amino acid except Ser
<220> FEATURE:
<221> NAME/KEY: MOD_RES
<222> LOCATION: (15)..(15)
<223> OTHER INFORMATION: Any amino acid except Ile

<400> SEQUENCE: 87

Asp Val Val Met Thr Gln Xaa Pro Leu Xaa Leu Xaa Val Thr Xaa Gly
1               5                   10                  15

Gln Pro Ala Ser Ile Ser Cys
            20

<210> SEQ ID NO 88
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid except Leu
<220> FEATURE:
<221> NAME/KEY: MOD_RES
<222> LOCATION: (11)..(11)
<223> OTHER INFORMATION: Any amino acid except Lys

<400> SEQUENCE: 88

Trp Leu Xaa Gln Arg Pro Gly Gln Ser Pro Xaa Arg Leu Ile Tyr
1               5                   10                  15

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Any amino acid except Thr
<220> FEATURE:
<221> NAME/KEY: MOD_RES
<222> LOCATION: (27)..(27)
<223> OTHER INFORMATION: Any amino acid except Leu

<400> SEQUENCE: 89

Gly Val Pro Asp Arg Phe Xaa Gly Ser Gly Ser Gly Thr Asp Phe Thr
1               5                   10                  15

Leu Lys Ile Ser Arg Val Glu Ala Glu Asp Xaa Gly Val Tyr His Cys
            20                  25                  30

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid except Leu

<400> SEQUENCE: 90

Phe Gly Gly Gly Thr Lys Xaa Glu Ile Lys
1               5                   10
```

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Glu Leu Gly Trp Met
        35                  40                  45

Gly Tyr Ile Ser Cys Tyr Asn Gly Ala Ser Ser Tyr Asn Gln Lys Phe
    50                  55                  60

Lys Gly Arg Val Thr Met Thr Val Asp Thr Ser Ile Ser Thr Ala Tyr
65                  70                  75                  80

Thr Glu Leu Ser Ser Leu Arg Ser Glu Asp Thr Ala Thr Tyr Tyr Cys
                85                  90                  95

Ala Ser Ser Met Asp Tyr Trp Gly Gln Gly Thr Leu Val Thr Val Ser
            100                 105                 110

Ser

<210> SEQ ID NO 102
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Thr Leu Lys Glu Ser Gly Pro Val Leu Val Lys Pro Thr Glu
1               5                   10                  15

Thr Leu Thr Leu Thr Cys Thr Val Ser Gly Tyr Ser Ile Thr Ser Asp
            20                  25                  30

Tyr Ala Trp Asn Trp Ile Arg Gln Pro Pro Gly Lys Ala Leu Glu Trp
        35                  40                  45

Leu Ala Tyr Ile Ser Tyr Ser Gly Ser Thr Ser Tyr Asn Pro Ser Leu
    50                  55                  60

Lys Ser Arg Leu Ser Ile Thr Lys Asp Thr Ser Lys Ser Gln Val Val
65                  70                  75                  80

Leu Thr Met Thr Asn Met Asp Pro Val Asp Thr Ala Thr Tyr Tyr Cys
                85                  90                  95

Ala Arg Asp Pro Pro Tyr Tyr Gly Ser Trp Gly Gln Gly Thr Thr
            100                 105                 110

Val Thr Val Ser Ser
        115

<210> SEQ ID NO 103
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

```
Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Trp Gln Gly
                85                  90                  95

Thr His Phe Pro Tyr Thr Phe Gly Gly Gly Thr Lys Val Glu Ile Lys
                100                 105                 110
```

<210> SEQ ID NO 104
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Glu Val Gln Leu Glu Gln Ser Gly Pro Glu Leu Val Lys Thr Gly Ala
1               5                   10                  15

Ser Val Lys Ile Ser Cys Lys Ala Ser Gly Tyr Ser Phe Thr Gly Tyr
                20                  25                  30

Tyr Ile His Trp Val Lys Gln Ser His Gly Lys Ser Leu Glu Trp Ile
                35                  40                  45

Gly Tyr Ile Ser Cys Tyr Asn Gly Ala Ser Ser Tyr Asn Gln Lys Phe
                50                  55                  60

Lys Gly Lys Ala Thr Phe Thr Val Asp Thr Ser Ser Ser Thr Ala Tyr
65                  70                  75                  80

Met Gln Phe Asn Ser Leu Thr Ser Gly Asp Ser Ala Val Tyr Tyr Cys
                85                  90                  95

Ala Ser Ser Met Asp Tyr Trp Gly Gln Gly Thr Ser Val Thr Val Ser
                100                 105                 110

Ser
```

<210> SEQ ID NO 105
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

```
Asp Val Gln Leu Gln Glu Ser Gly Pro Gly Leu Val Lys Asn Ser Gln
1               5                   10                  15

Ser Leu Ser Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
                35                  40                  45

Met Gly Tyr Ile Ser Tyr Ser Gly Ser Thr Ser Tyr Asn Pro Ser Leu
                50                  55                  60

Lys Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys
                85                  90                  95

Ala Arg Asp Pro Pro Tyr Tyr Gly Ser Asn Gly Thr Trp Gly Gln
                100                 105                 110
```

```
Gly Thr Ser Val Thr Val Ser Ser
        115                 120
```

<210> SEQ ID NO 106
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr His Cys Trp Gln Gly
                85                  90                  95

Thr His Phe Pro Tyr Thr Phe Gly Gly Gly Thr Lys Leu Glu Ile Lys
            100                 105                 110
```

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

```
Tyr Ser Phe Thr Gly Tyr Tyr Ile His
1               5
```

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

```
Tyr Ile Ser Cys Tyr Asn Gly Ala Ser Ser Tyr Asn Gln Lys Phe Lys
1               5                   10                  15

Gly
```

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
Ser Ser Met Asp Tyr
1               5
```

<210> SEQ ID NO 110
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Tyr Ser Ile Thr Ser Asp Tyr Ala Trp Asn
1               5                   10

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Tyr Ile Ser Tyr Ser Gly Ser Thr Ser Tyr Asn Pro Ser Leu Lys Ser
1               5                   10                  15

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Pro Pro Tyr Tyr Tyr Gly Ser
1               5

<210> SEQ ID NO 113
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Ser Ser Gln Ser Leu Leu Asp Ser Asp Gly Lys Thr Tyr Leu Asn
1               5                   10                  15

<210> SEQ ID NO 114
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Leu Val Ser Lys Leu Asp Ser
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Trp Gln Gly Thr His Phe Pro Tyr Thr
1               5

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asp Pro Pro Tyr Tyr Tyr Gly Ser Asn Gly Thr
1               5                   10

<210> SEQ ID NO 117
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 118
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Trp Val Arg Gln Ala Pro Gly Gln Glu Leu Gly Trp Met Gly
1               5                   10

<210> SEQ ID NO 119
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Arg Val Thr Met Thr Val Asp Thr Ser Ile Ser Thr Ala Tyr Thr Glu
1               5                   10                  15

Leu Ser Ser Leu Arg Ser Glu Asp Thr Ala Thr Tyr Tyr Cys Ala
            20                  25                  30

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Trp Gly Gln Gly Thr Leu Val Thr Val Ser Ser

<210> SEQ ID NO 121
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Val Thr Leu Lys Glu Ser Gly Pro Val Leu Val Lys Pro Thr Glu
1               5                   10                  15

Thr Leu Thr Leu Thr Cys Thr Val Ser Gly
            20                  25

<210> SEQ ID NO 122
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Trp Ile Arg Gln Pro Pro Gly Lys Ala Leu Glu Trp Leu Ala
1               5                   10

<210> SEQ ID NO 123
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Arg Leu Ser Ile Thr Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Trp Gly Gln Gly Thr Thr Val Thr Val Ser Ser
1               5                   10

<210> SEQ ID NO 125
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Glu Val Gln Leu Glu Gln Ser Gly Pro Glu Leu Val Lys Thr Gly Ala
1               5                   10                  15

Ser Val Lys Ile Ser Cys Lys Ala Ser Gly

```
                  20                  25

<210> SEQ ID NO 126
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Trp Val Lys Gln Ser His Gly Lys Ser Leu Glu Trp Ile Gly
1               5                   10

<210> SEQ ID NO 127
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Lys Ala Thr Phe Thr Val Asp Thr Ser Ser Thr Ala Tyr Met Gln
1               5                   10                  15

Phe Asn Ser Leu Thr Ser Gly Asp Ser Ala Val Tyr Tyr Cys Ala
                20                  25                  30

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Trp Gly Gln Gly Thr Ser Val Thr Val Ser Ser
1               5                   10

<210> SEQ ID NO 129
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asp Val Gln Leu Gln Glu Ser Gly Pro Gly Leu Val Lys Asn Ser Gln
1               5                   10                  15

Ser Leu Ser Leu Thr Cys Thr Val Thr Gly
                20                  25

<210> SEQ ID NO 130
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Trp Ile Arg Gln Phe Pro Gly Asn Lys Leu Glu Trp Met Gly
1               5                   10
```

```
<210> SEQ ID NO 131
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Arg Ile Ser Ile Thr Arg Asp Thr Ser Lys Asn Gln Phe Phe Leu Gln
1               5                   10                  15

Leu Asn Ser Val Thr Pro Glu Asp Thr Ala Thr Tyr Tyr Cys Ala Arg
            20                  25                  30

<210> SEQ ID NO 132
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Trp Leu Gln Gln Arg Pro Gly Gln Ser Pro Arg Arg Leu Ile Tyr
1               5                   10                  15

<210> SEQ ID NO 134
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr His Cys
            20                  25                  30

<210> SEQ ID NO 135
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Phe Gly Gly Gly Thr Lys Val Glu Ile Lys
1               5                   10
```

```
<210> SEQ ID NO 136
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Asp Val Val Met Thr Gln Thr Pro Leu Thr Leu Ser Val Thr Ile Gly
1               5                   10                  15

Gln Pro Ala Ser Ile Ser Cys
            20

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Leu Leu Gln Arg Pro Gly Gln Ser Pro Lys Arg Leu Ile Tyr
1               5                   10                  15

<210> SEQ ID NO 138
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gly Val Pro Asp Arg Phe Thr Gly Ser Gly Ser Gly Thr Asp Phe Thr
1               5                   10                  15

Leu Lys Ile Ser Arg Val Glu Ala Glu Asp Leu Gly Val Tyr His Cys
            20                  25                  30

<210> SEQ ID NO 139
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Phe Gly Gly Gly Thr Lys Leu Glu Ile Lys
1               5                   10

<210> SEQ ID NO 140
<211> LENGTH: 400
<212> TYPE: PRT
<213> ORGANISM: Homo sapiens

<400> SEQUENCE: 140

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
```

```
                50                  55                  60
Glu Pro Phe Ser Asn Lys Gly Gln Thr Leu Val Val Gln Phe Thr Val
 65                  70                  75                  80

Lys His Glu Gln Asn Ile Asp Cys Gly Gly Tyr Val Lys Leu Phe
                 85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
                115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
                180                 185                 190

Asp Pro Asp Ala Ser Lys Pro Glu Asp Trp Asp Glu Arg Ala Lys Ile
                195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
                275                 280                 285

Tyr Ala Tyr Asp Asn Phe Gly Val Leu Gly Leu Asp Leu Trp Gln Val
                290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Gln Arg Leu Lys Glu
                340                 345                 350

Glu Glu Glu Asp Lys Lys Arg Lys Glu Glu Glu Glu Ala Glu Asp Lys
                355                 360                 365

Glu Asp Asp Glu Asp Lys Asp Glu Asp Glu Asp Glu Glu Asp Lys
                370                 375                 380

Glu Glu Asp Glu Glu Asp Val Pro Gly Gln Ala Lys Asp Glu Leu
385                 390                 395                 400

<210> SEQ ID NO 141
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Arg Arg Lys Met Ser Pro Ala Arg Pro Arg Thr Ser Cys Arg Glu Ala
 1               5                  10                  15
```

```
Cys Leu Gln Gly Trp Thr Glu Ala
            20

<210> SEQ ID NO 142
<211> LENGTH: 45
<212> TYPE: PRT
<213> ORGANISM: Homo sapiens

<400> SEQUENCE: 142

Thr Arg Arg Met Met Arg Thr Lys Met Arg Met Arg Arg Met Arg
1               5                   10                  15

Thr Arg Arg Lys Met Arg Arg Lys Met Ser Pro Ala Arg Pro Arg Thr
            20                  25                  30

Ser Cys Arg Glu Ala Cys Leu Gln Gly Trp Thr Glu Ala
            35                  40                  45

<210> SEQ ID NO 143
<211> LENGTH: 46
<212> TYPE: PRT
<213> ORGANISM: Homo sapiens

<400> SEQUENCE: 143

Asn Cys Arg Arg Met Met Arg Thr Lys Met Arg Met Arg Arg Met Arg
1               5                   10                  15

Arg Thr Arg Arg Lys Met Arg Arg Lys Met Ser Pro Ala Arg Pro Arg
            20                  25                  30

Thr Ser Cys Arg Glu Ala Cys Leu Gln Gly Trp Thr Glu Ala
            35                  40                  45

<210> SEQ ID NO 144
<211> LENGTH: 47
<212> TYPE: PRT
<213> ORGANISM: Homo sapiens

<400> SEQUENCE: 144

Gln Arg Thr Arg Arg Met Met Arg Thr Lys Met Arg Met Arg Arg Met
1               5                   10                  15

Arg Arg Thr Arg Arg Lys Met Arg Arg Lys Met Ser Pro Ala Arg Pro
            20                  25                  30

Arg Thr Ser Cys Arg Glu Ala Cys Leu Gln Gly Trp Thr Glu Ala
            35                  40                  45

<210> SEQ ID NO 145
<211> LENGTH: 50
<212> TYPE: PRT
<213> ORGANISM: Homo sapiens

<400> SEQUENCE: 145

Arg Arg Arg Gln Arg Thr Arg Arg Met Met Arg Thr Lys Met Arg Met
1               5                   10                  15

Arg Arg Met Arg Arg Thr Arg Arg Lys Met Arg Arg Lys Met Ser Pro
            20                  25                  30

Ala Arg Pro Arg Thr Ser Cys Arg Glu Ala Cys Leu Gln Gly Trp Thr
            35                  40                  45

Glu Ala
    50

<210> SEQ ID NO 146
<211> LENGTH: 48
<212> TYPE: PRT
<213> ORGANISM: Homo sapiens
```

<400> SEQUENCE: 146

Gly Gln Arg Thr Arg Arg Met Met Arg Thr Lys Met Arg Met Arg Arg
1               5                   10                  15

Met Arg Arg Thr Arg Arg Lys Met Arg Arg Lys Met Ser Pro Ala Arg
                20                  25                  30

Pro Arg Thr Ser Cys Arg Glu Ala Cys Leu Gln Gly Trp Thr Glu Ala
                35                  40                  45

<210> SEQ ID NO 147
<211> LENGTH: 49
<212> TYPE: PRT
<213> ORGANISM: Homo sapiens

<400> SEQUENCE: 147

Arg Arg Gln Arg Thr Arg Met Met Arg Thr Lys Met Arg Met Arg
1               5                   10                  15

Arg Met Arg Arg Thr Arg Arg Lys Met Arg Arg Lys Met Ser Pro Ala
                20                  25                  30

Arg Pro Arg Thr Ser Cys Arg Glu Ala Cys Leu Gln Gly Trp Thr Glu
                35                  40                  45

Ala

<210> SEQ ID NO 148
<211> LENGTH: 44
<212> TYPE: PRT
<213> ORGANISM: Homo sapiens

<400> SEQUENCE: 148

Arg Arg Met Met Arg Thr Lys Met Arg Met Arg Arg Met Arg Arg Thr
1               5                   10                  15

Arg Arg Lys Met Arg Arg Lys Met Ser Pro Ala Arg Pro Arg Thr Ser
                20                  25                  30

Cys Arg Glu Ala Cys Leu Gln Gly Trp Thr Glu Ala
                35                  40

<210> SEQ ID NO 149
<211> LENGTH: 48
<212> TYPE: PRT
<213> ORGANISM: Homo sapiens

<400> SEQUENCE: 149

Arg Gln Arg Thr Arg Arg Met Met Arg Thr Lys Met Arg Met Arg Arg
1               5                   10                  15

Met Arg Arg Thr Arg Arg Lys Met Arg Arg Lys Met Ser Pro Ala Arg
                20                  25                  30

Pro Arg Thr Ser Cys Arg Glu Ala Cys Leu Gln Gly Trp Thr Glu Ala
                35                  40                  45

<210> SEQ ID NO 150
<211> LENGTH: 46
<212> TYPE: PRT
<213> ORGANISM: Homo sapiens

<400> SEQUENCE: 150

Met Cys Arg Arg Met Met Arg Thr Lys Met Arg Met Arg Arg Met Arg
1               5                   10                  15

Arg Thr Arg Arg Lys Met Arg Arg Lys Met Ser Pro Ala Arg Pro Arg
                20                  25                  30

```
Thr Ser Cys Arg Glu Ala Cys Leu Gln Gly Trp Thr Glu Ala
        35                  40                  45

<210> SEQ ID NO 151
<211> LENGTH: 50
<212> TYPE: PRT
<213> ORGANISM: Homo sapiens

<400> SEQUENCE: 151

Asp Gln Arg Gln Arg Thr Arg Arg Met Met Arg Thr Lys Met Arg Met
1               5                   10                  15

Arg Arg Met Arg Arg Thr Arg Arg Lys Met Arg Lys Met Ser Pro
            20                  25                  30

Ala Arg Pro Arg Thr Ser Cys Arg Glu Ala Cys Leu Gln Gly Trp Thr
        35                  40                  45

Glu Ala
    50

<210> SEQ ID NO 152
<211> LENGTH: 51
<212> TYPE: PRT
<213> ORGANISM: Homo sapiens

<400> SEQUENCE: 152

Arg Arg Arg Arg Gln Arg Thr Arg Arg Met Met Arg Thr Lys Met Arg
1               5                   10                  15

Met Arg Arg Met Arg Arg Thr Arg Arg Lys Met Arg Lys Met Ser
            20                  25                  30

Pro Ala Arg Pro Arg Thr Ser Cys Arg Glu Ala Cys Leu Gln Gly Trp
        35                  40                  45

Thr Glu Ala
    50

<210> SEQ ID NO 153
<211> LENGTH: 51
<212> TYPE: PRT
<213> ORGANISM: Homo sapiens

<400> SEQUENCE: 153

Gln Arg Arg Arg Gln Arg Thr Arg Arg Met Met Arg Thr Lys Met Arg
1               5                   10                  15

Met Arg Arg Met Arg Arg Thr Arg Arg Lys Met Arg Lys Met Ser
            20                  25                  30

Pro Ala Arg Pro Arg Thr Ser Cys Arg Glu Ala Cys Leu Gln Gly Trp
        35                  40                  45

Thr Glu Ala
    50

<210> SEQ ID NO 154
<211> LENGTH: 50
<212> TYPE: PRT
<213> ORGANISM: Homo sapiens

<400> SEQUENCE: 154

Arg Arg Arg Glu Arg Thr Arg Arg Met Met Arg Thr Lys Met Arg Met
1               5                   10                  15

Arg Arg Met Arg Arg Thr Arg Arg Lys Met Arg Lys Met Ser Pro
            20                  25                  30

Ala Arg Pro Arg Thr Ser Cys Arg Glu Ala Cys Leu Gln Gly Trp Thr
        35                  40                  45
```

Glu Ala
    50

<210> SEQ ID NO 155
<211> LENGTH: 50
<212> TYPE: PRT
<213> ORGANISM: Homo sapiens

<400> SEQUENCE: 155

Gln Arg Arg Gln Arg Thr Arg Arg Met Met Arg Thr Lys Met Arg Met
1               5                   10                  15

Arg Arg Met Arg Arg Thr Arg Arg Lys Met Arg Lys Met Ser Pro
            20                  25                  30

Ala Arg Pro Arg Thr Ser Cys Arg Glu Ala Cys Leu Gln Gly Trp Thr
        35                  40                  45

Glu Ala
    50

<210> SEQ ID NO 156
<211> LENGTH: 49
<212> TYPE: PRT
<213> ORGANISM: Homo sapiens

<400> SEQUENCE: 156

Arg Arg Gln Trp Thr Arg Arg Met Met Arg Thr Lys Met Arg Met Arg
1               5                   10                  15

Arg Met Arg Arg Thr Arg Arg Lys Met Arg Arg Lys Met Ser Pro Ala
            20                  25                  30

Arg Pro Arg Thr Ser Cys Arg Glu Ala Cys Leu Gln Gly Trp Thr Glu
        35                  40                  45

Ala

<210> SEQ ID NO 157
<211> LENGTH: 43
<212> TYPE: PRT
<213> ORGANISM: Homo sapiens

<400> SEQUENCE: 157

Arg Met Met Arg Thr Lys Met Arg Met Arg Arg Met Arg Arg Thr Arg
1               5                   10                  15

Arg Lys Met Arg Arg Lys Met Ser Pro Ala Arg Pro Arg Thr Ser Cys
            20                  25                  30

Arg Glu Ala Cys Leu Gln Gly Trp Thr Glu Ala
        35                  40

<210> SEQ ID NO 158
<211> LENGTH: 50
<212> TYPE: PRT
<213> ORGANISM: Homo sapiens

<400> SEQUENCE: 158

Gly Arg Arg Gln Arg Thr Arg Arg Met Met Arg Thr Lys Met Arg Met
1               5                   10                  15

Arg Arg Met Arg Arg Thr Arg Arg Lys Met Arg Arg Lys Met Ser Pro
            20                  25                  30

Ala Arg Pro Arg Thr Ser Cys Arg Glu Ala Cys Leu Gln Gly Trp Thr
        35                  40                  45

Glu Ala
    50

<210> SEQ ID NO 159
<211> LENGTH: 49
<212> TYPE: PRT
<213> ORGANISM: Homo sapiens

<400> SEQUENCE: 159

Ala Phe Lys Arg Thr Arg Arg Met Met Arg Thr Lys Met Arg Met Arg
1               5                   10                  15

Arg Met Arg Arg Thr Arg Arg Lys Met Arg Arg Lys Met Ser Pro Ala
            20                  25                  30

Arg Pro Arg Thr Ser Cys Arg Glu Ala Cys Leu Gln Gly Trp Thr Glu
        35                  40                  45

Ala

<210> SEQ ID NO 160
<211> LENGTH: 54
<212> TYPE: PRT
<213> ORGANISM: Homo sapiens

<400> SEQUENCE: 160

Asn Ala Lys Arg Arg Arg Gln Arg Thr Arg Arg Met Met Arg Thr
1               5                   10                  15

Lys Met Arg Met Arg Arg Met Arg Arg Thr Arg Arg Lys Met Arg Arg
            20                  25                  30

Lys Met Ser Pro Ala Arg Pro Arg Thr Ser Cys Arg Glu Ala Cys Leu
        35                  40                  45

Gln Gly Trp Thr Glu Ala
    50

<210> SEQ ID NO 161
<211> LENGTH: 53
<212> TYPE: PRT
<213> ORGANISM: Homo sapiens

<400> SEQUENCE: 161

Cys Val Arg Arg Arg Arg Gln Arg Thr Arg Arg Met Met Arg Thr Lys
1               5                   10                  15

Met Arg Met Arg Arg Met Arg Arg Thr Arg Arg Lys Met Arg Arg Lys
            20                  25                  30

Met Ser Pro Ala Arg Pro Arg Thr Ser Cys Arg Glu Ala Cys Leu Gln
        35                  40                  45

Gly Trp Thr Glu Ala
    50

<210> SEQ ID NO 162
<211> LENGTH: 55
<212> TYPE: PRT
<213> ORGANISM: Homo sapiens

<400> SEQUENCE: 162

Cys Phe Ala Lys Arg Arg Arg Gln Arg Thr Arg Arg Met Met Arg
1               5                   10                  15

Thr Lys Met Arg Met Arg Arg Met Arg Arg Thr Arg Arg Lys Met Arg
            20                  25                  30

Arg Lys Met Ser Pro Ala Arg Pro Arg Thr Ser Cys Arg Glu Ala Cys
        35                  40                  45

Leu Gln Gly Trp Thr Glu Ala
    50                  55

<210> SEQ ID NO 163
<211> LENGTH: 49
<212> TYPE: PRT
<213> ORGANISM: Homo sapiens

<400> SEQUENCE: 163

Pro Pro Leu Cys Leu Arg Arg Met Met Arg Thr Lys Met Arg Met Arg
1               5                   10                  15

Arg Met Arg Arg Thr Arg Arg Lys Met Arg Arg Lys Met Ser Pro Ala
                20                  25                  30

Arg Pro Arg Thr Ser Cys Arg Glu Ala Cys Leu Gln Gly Trp Thr Glu
            35                  40                  45

Ala

<210> SEQ ID NO 164
<211> LENGTH: 48
<212> TYPE: PRT
<213> ORGANISM: Homo sapiens

<400> SEQUENCE: 164

Asp His Pro Cys Arg Arg Met Met Arg Thr Lys Met Arg Met Arg Arg
1               5                   10                  15

Met Arg Arg Thr Arg Arg Lys Met Arg Arg Lys Met Ser Pro Ala Arg
                20                  25                  30

Pro Arg Thr Ser Cys Arg Glu Ala Cys Leu Gln Gly Trp Thr Glu Ala
            35                  40                  45

<210> SEQ ID NO 165
<211> LENGTH: 47
<212> TYPE: PRT
<213> ORGANISM: Homo sapiens

<400> SEQUENCE: 165

Gly Asn Cys Arg Arg Met Met Arg Thr Lys Met Arg Met Arg Arg Met
1               5                   10                  15

Arg Arg Thr Arg Arg Lys Met Arg Arg Lys Met Ser Pro Ala Arg Pro
                20                  25                  30

Arg Thr Ser Cys Arg Glu Ala Cys Leu Gln Gly Trp Thr Glu Ala
            35                  40                  45

<210> SEQ ID NO 166
<211> LENGTH: 45
<212> TYPE: PRT
<213> ORGANISM: Homo sapiens

<400> SEQUENCE: 166

Cys Arg Arg Met Met Arg Thr Lys Met Arg Met Arg Arg Met Arg Arg
1               5                   10                  15

Thr Arg Arg Lys Met Arg Arg Lys Met Ser Pro Ala Arg Pro Arg Thr
                20                  25                  30

Ser Cys Arg Glu Ala Cys Leu Gln Gly Trp Thr Glu Ala
            35                  40                  45

<210> SEQ ID NO 167
<211> LENGTH: 46
<212> TYPE: PRT
<213> ORGANISM: Homo sapiens

<400> SEQUENCE: 167

```
Thr Cys Arg Arg Met Met Arg Thr Lys Met Arg Met Arg Met Arg
1               5                   10                  15

Arg Thr Arg Lys Met Arg Arg Lys Met Ser Pro Ala Arg Pro Arg
            20                  25                  30

Thr Ser Cys Arg Glu Ala Cys Leu Gln Gly Trp Thr Glu Ala
        35                  40                  45

<210> SEQ ID NO 168
<211> LENGTH: 46
<212> TYPE: PRT
<213> ORGANISM: Homo sapiens

<400> SEQUENCE: 168

Ile Cys Arg Arg Met Met Arg Thr Lys Met Arg Met Arg Met Arg
1               5                   10                  15

Arg Thr Arg Lys Met Arg Arg Lys Met Ser Pro Ala Arg Pro Arg
            20                  25                  30

Thr Ser Cys Arg Glu Ala Cys Leu Gln Gly Trp Thr Glu Ala
        35                  40                  45

<210> SEQ ID NO 169
<211> LENGTH: 394
<212> TYPE: PRT
<213> ORGANISM: Homo sapiens

<400> SEQUENCE: 169

Glu Pro Ala Val Tyr Phe Lys Glu Gln Phe Leu Asp Gly Asp Gly
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Lys Pro Glu His
    210                 215                 220

Ile Pro Asp Pro Asp Ala Lys Lys Pro Glu Asp Trp Asp Glu Glu Met
225                 230                 235                 240
```

```
Asp Gly Glu Trp Glu Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Thr Arg Arg
            340                 345                 350

Met Met Arg Thr Lys Met Arg Met Arg Met Arg Thr Arg Arg
            355                 360                 365

Lys Met Arg Arg Lys Met Ser Pro Ala Arg Pro Arg Thr Ser Cys Arg
            370                 375                 380

Glu Ala Cys Leu Gln Gly Trp Thr Glu Ala
385                 390
```

<210> SEQ ID NO 170
<211> LENGTH: 413
<212> TYPE: PRT
<213> ORGANISM: Homo sapiens

<400> SEQUENCE: 170

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
210                 215                 220
```

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
            245                 250                 255

Glu Trp Lys Pro Arg Gln Ile Asp Asn Pro Asp Tyr Lys Gly Thr Trp
        260                 265                 270

Ile His Pro Glu Ile Asp Asn Pro Glu Tyr Ser Pro Asp Pro Ser Ile
    275                 280                 285

Tyr Ala Tyr Asp Asn Phe Gly Val Leu Gly Leu Asp Leu Trp Gln Val
290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
            325                 330                 335

Glu Lys Gln Met Lys Asp Lys Gln Asp Glu Glu Gln Arg Leu Lys Glu
        340                 345                 350

Glu Glu Glu Asp Lys Lys Arg Lys Glu Glu Glu Glu Ala Glu Asp Asn
    355                 360                 365

Cys Arg Arg Met Met Arg Thr Lys Met Arg Met Arg Arg Met Arg Arg
370                 375                 380

Thr Arg Arg Lys Met Arg Arg Lys Met Ser Pro Ala Arg Pro Arg Thr
385                 390                 395                 400

Ser Cys Arg Glu Ala Cys Leu Gln Gly Trp Thr Glu Ala
            405                 410

<210> SEQ ID NO 171
<211> LENGTH: 396
<212> TYPE: PRT
<213> ORGANISM: Homo sapiens

<400> SEQUENCE: 171

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys

```
                    180                 185                 190
Asp Pro Asp Ala Ser Lys Pro Glu Asp Trp Asp Glu Arg Ala Lys Ile
                195                 200                 205

Asp Asp Pro Thr Asp Ser Lys Pro Glu Asp Trp Asp Lys Pro Glu His
            210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
                275                 280                 285

Tyr Ala Tyr Asp Asn Phe Gly Val Leu Gly Leu Asp Leu Trp Gln Val
                290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Arg Gln Arg Thr
                340                 345                 350

Arg Arg Met Met Arg Thr Lys Met Arg Met Arg Met Arg Arg Thr
                355                 360                 365

Arg Arg Lys Met Arg Arg Lys Met Ser Pro Ala Arg Pro Arg Thr Ser
                370                 375                 380

Cys Arg Glu Ala Cys Leu Gln Gly Trp Thr Glu Ala
385                 390                 395

<210> SEQ ID NO 172
<211> LENGTH: 400
<212> TYPE: PRT
<213> ORGANISM: Homo sapiens

<400> SEQUENCE: 172

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
        50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160
```

Pro Asp Asn Thr Tyr Glu Val Lys Ile Asp Asn Ser Gln Val Ser
            165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
            210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                    245                 250                 255

Glu Trp Lys Pro Arg Gln Ile Asp Asn Pro Asp Tyr Lys Gly Thr Trp
                    260                 265                 270

Ile His Pro Glu Ile Asp Asn Pro Glu Tyr Ser Pro Asp Pro Ser Ile
                    275                 280                 285

Tyr Ala Tyr Asp Asn Phe Gly Val Leu Gly Leu Asp Leu Trp Gln Val
                    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                    325                 330                 335

Glu Lys Gln Met Lys Asp Lys Gln Asp Glu Glu Gln Arg Leu Arg Arg
                    340                 345                 350

Arg Gln Arg Thr Arg Arg Met Met Arg Thr Lys Met Arg Met Arg Arg
                    355                 360                 365

Met Arg Arg Thr Arg Arg Lys Met Arg Arg Lys Met Ser Pro Ala Arg
                    370                 375                 380

Pro Arg Thr Ser Cys Arg Glu Ala Cys Leu Gln Gly Trp Thr Glu Ala
385                 390                 395                 400

<210> SEQ ID NO 173
<211> LENGTH: 394
<212> TYPE: PRT
<213> ORGANISM: Homo sapiens

<400> SEQUENCE: 173

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                    20                  25                  30

Val Leu Ser Ser Gly Lys Phe Tyr Gly Asp Glu Glu Lys Asp Lys Gly
                35                  40                  45

Leu Gln Thr Ser Gln Asp Ala Arg Phe Tyr Ala Leu Ser Ala Ser Phe
            50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                    85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
        130                 135                 140

```
Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Gly Gln Arg Thr Arg Arg
            340                 345                 350

Met Met Arg Thr Lys Met Arg Met Arg Met Arg Thr Arg Arg
        355                 360                 365

Lys Met Arg Arg Lys Met Ser Pro Ala Arg Pro Arg Thr Ser Cys Arg
    370                 375                 380

Glu Ala Cys Leu Gln Gly Trp Thr Glu Ala
385                 390

<210> SEQ ID NO 174
<211> LENGTH: 396
<212> TYPE: PRT
<213> ORGANISM: Homo sapiens

<400> SEQUENCE: 174

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
        50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
```

```
              115                 120                 125
Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Arg Arg Gln Arg Thr
            340                 345                 350

Arg Arg Met Met Arg Thr Lys Met Arg Met Arg Met Arg Arg Thr
        355                 360                 365

Arg Arg Lys Met Arg Arg Lys Met Ser Pro Ala Arg Pro Arg Thr Ser
    370                 375                 380

Cys Arg Glu Ala Cys Leu Gln Gly Trp Thr Glu Ala
385                 390                 395

<210> SEQ ID NO 175
<211> LENGTH: 394
<212> TYPE: PRT
<213> ORGANISM: Homo sapiens

<400> SEQUENCE: 175

Glu Pro Ala Val Tyr Phe Lys Glu Gln Phe Leu Asp Gly Asp Gly Trp
1               5                  10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
        50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95
```

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
                115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
                180                 185                 190

Asp Pro Asp Ala Ser Lys Pro Glu Asp Trp Asp Glu Arg Ala Lys Ile
                195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
                275                 280                 285

Tyr Ala Tyr Asp Asn Phe Gly Val Leu Gly Leu Asp Leu Trp Gln Val
                290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Arg Arg
                340                 345                 350

Met Met Arg Thr Lys Met Arg Met Arg Met Arg Thr Arg Arg
                355                 360                 365

Lys Met Arg Arg Lys Met Ser Pro Ala Arg Pro Arg Thr Ser Cys Arg
370                 375                 380

Glu Ala Cys Leu Gln Gly Trp Thr Glu Ala
385                 390

<210> SEQ ID NO 176
<211> LENGTH: 400
<212> TYPE: PRT
<213> ORGANISM: Homo sapiens

<400> SEQUENCE: 176

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Lys Asp Lys Gly
                35                  40                  45

Leu Gln Thr Ser Gln Asp Ala Arg Phe Tyr Ala Leu Ser Ala Ser Phe
50                  55                  60

Glu Pro Phe Ser Asn Lys Gly Gln Thr Leu Val Val Gln Phe Thr Val
65                  70                  75                  80

```
Lys His Glu Gln Asn Ile Asp Cys Gly Gly Gly Tyr Val Lys Leu Phe
                 85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Arg
            340                 345                 350

Arg Gln Arg Thr Arg Arg Met Met Arg Thr Lys Met Arg Met Arg Arg
            355                 360                 365

Met Arg Arg Thr Arg Lys Met Arg Lys Met Ser Pro Ala Arg
370                 375                 380

Pro Arg Thr Ser Cys Arg Glu Ala Cys Leu Gln Gly Trp Thr Glu Ala
385                 390                 395                 400
```

<210> SEQ ID NO 177
<211> LENGTH: 411
<212> TYPE: PRT
<213> ORGANISM: Homo sapiens

<400> SEQUENCE: 177

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
```

```
                 50                  55                  60

Glu Pro Phe Ser Asn Lys Gly Gln Thr Leu Val Val Gln Phe Thr Val
 65                  70                  75                  80

Lys His Glu Gln Asn Ile Asp Cys Gly Gly Gly Tyr Val Lys Leu Phe
                     85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Lys Lys Arg Lys Glu Glu Arg Gln Arg Thr Arg
        355                 360                 365

Arg Met Met Arg Thr Lys Met Arg Met Arg Met Arg Arg Thr Arg
370                 375                 380

Arg Lys Met Arg Lys Met Ser Pro Ala Arg Pro Arg Thr Ser Cys
385                 390                 395                 400

Arg Glu Ala Cys Leu Gln Gly Trp Thr Glu Ala
                405                 410

<210> SEQ ID NO 178
<211> LENGTH: 413
<212> TYPE: PRT
<213> ORGANISM: Homo sapiens

<400> SEQUENCE: 178

Glu Pro Ala Val Tyr Phe Lys Glu Gln Phe Leu Asp Gly Asp Gly Trp
 1               5                  10                  15
```

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
50                      55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Tyr Val Lys Leu Phe
                85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
                115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Lys Lys Arg Lys Glu Glu Glu Ala Glu Asp Met
        355                 360                 365

Cys Arg Arg Met Met Arg Thr Lys Met Arg Met Arg Arg Met Arg Arg
370                 375                 380

Thr Arg Arg Lys Met Arg Arg Lys Met Ser Pro Ala Arg Pro Arg Thr
385                 390                 395                 400

Ser Cys Arg Glu Ala Cys Leu Gln Gly Trp Thr Glu Ala
            405                 410

<210> SEQ ID NO 179
<211> LENGTH: 396
<212> TYPE: PRT

<213> ORGANISM: Homo sapiens

<400> SEQUENCE: 179

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Asp Gln Arg Gln Arg Thr
            340                 345                 350

Arg Arg Met Met Arg Thr Lys Met Arg Met Arg Met Arg Met Arg Thr
        355                 360                 365

Arg Arg Lys Met Arg Lys Met Ser Pro Ala Arg Pro Arg Thr Ser
    370                 375                 380

Cys Arg Glu Ala Cys Leu Gln Gly Trp Thr Glu Ala
385                 390                 395
```

<210> SEQ ID NO 180
<211> LENGTH: 400
<212> TYPE: PRT
<213> ORGANISM: Homo sapiens

<400> SEQUENCE: 180

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Arg Arg
            340                 345                 350

Arg Gln Arg Thr Arg Arg Met Met Arg Thr Lys Met Arg Met Arg Arg
        355                 360                 365

Met Arg Arg Thr Arg Arg Lys Met Arg Arg Lys Met Ser Pro Ala Arg
    370                 375                 380
```

Pro Arg Thr Ser Cys Arg Glu Ala Cys Leu Gln Gly Trp Thr Glu Ala
385                 390                 395                 400

<210> SEQ ID NO 181
<211> LENGTH: 400
<212> TYPE: PRT
<213> ORGANISM: Homo sapiens

<400> SEQUENCE: 181

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
        50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
        290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Gln Arg Arg
            340                 345                 350

Arg Gln Arg Thr Arg Arg Met Met Arg Thr Lys Met Arg Met Arg Arg

```
                    355                 360                 365
Met Arg Arg Thr Arg Arg Lys Met Arg Lys Met Ser Pro Ala Arg
        370                 375                 380

Pro Arg Thr Ser Cys Arg Glu Ala Cys Leu Gln Gly Trp Thr Glu Ala
385                 390                 395                 400

<210> SEQ ID NO 182
<211> LENGTH: 400
<212> TYPE: PRT
<213> ORGANISM: Homo sapiens

<400> SEQUENCE: 182

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335
```

Glu Lys Gln Met Lys Asp Lys Gln Asp Glu Gln Arg Leu Arg Arg
                340                 345                 350

Arg Gln Arg Thr Arg Arg Met Met Arg Thr Lys Met Arg Met Arg Arg
            355                 360                 365

Met Arg Arg Thr Arg Arg Lys Met Arg Arg Lys Met Ser Pro Ala Arg
    370                 375                 380

Pro Arg Thr Ser Cys Arg Glu Ala Cys Leu Gln Gly Trp Thr Glu Ala
385                 390                 395                 400

<210> SEQ ID NO 183
<211> LENGTH: 400
<212> TYPE: PRT
<213> ORGANISM: Homo sapiens

<400> SEQUENCE: 183

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

```
Tyr Ala Glu Glu Phe Gly Asn Glu Thr Trp Gly Val Thr Lys Ala Ala
                325                 330                 335

Glu Lys Gln Met Lys Asp Lys Gln Asp Glu Gln Arg Leu Arg Arg
            340                 345                 350

Arg Glu Arg Thr Arg Arg Met Met Arg Thr Lys Met Arg Met Arg Arg
            355                 360                 365

Met Arg Arg Thr Arg Arg Lys Met Arg Arg Lys Met Ser Pro Ala Arg
    370                 375                 380

Pro Arg Thr Ser Cys Arg Glu Ala Cys Leu Gln Gly Trp Thr Glu Ala
385                 390                 395                 400
```

<210> SEQ ID NO 184
<211> LENGTH: 400
<212> TYPE: PRT
<213> ORGANISM: Homo sapiens

<400> SEQUENCE: 184

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
```

```
            290                 295                 300
Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Gln Arg Leu Gln Arg
                340                 345                 350

Arg Gln Arg Thr Arg Arg Met Met Arg Thr Lys Met Arg Met Arg Arg
                355                 360                 365

Met Arg Arg Thr Arg Arg Lys Met Arg Arg Lys Met Ser Pro Ala Arg
                370                 375                 380

Pro Arg Thr Ser Cys Arg Glu Ala Cys Leu Gln Gly Trp Thr Glu Ala
385                 390                 395                 400

<210> SEQ ID NO 185
<211> LENGTH: 400
<212> TYPE: PRT
<213> ORGANISM: Homo sapiens

<400> SEQUENCE: 185

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
                115                 120                 125

Val Ile Phe Asn Tyr Lys Gly Lys Asn Val Leu Ile Asn Lys Asp Ile
            130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
            210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270
```

```
Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
            290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                    325                 330                 335

Glu Lys Gln Met Lys Asp Lys Gln Asp Glu Gln Arg Leu Lys Arg
                340                 345                 350

Arg Gln Trp Thr Arg Arg Met Met Arg Thr Lys Met Arg Met Arg Arg
            355                 360                 365

Met Arg Arg Thr Arg Arg Lys Met Arg Arg Lys Met Ser Pro Ala Arg
            370                 375                 380

Pro Arg Thr Ser Cys Arg Glu Ala Cys Leu Gln Gly Trp Thr Glu Ala
385                 390                 395                 400

<210> SEQ ID NO 186
<211> LENGTH: 394
<212> TYPE: PRT
<213> ORGANISM: Homo sapiens

<400> SEQUENCE: 186

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
        50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
        210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255
```

```
Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
            290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
            325                 330                 335

Glu Lys Gln Met Lys Asp Lys Gln Asp Glu Gln Arg Leu Lys Arg
            340                 345                 350

Met Met Arg Thr Lys Met Arg Met Arg Met Arg Thr Arg Arg
            355                 360                 365

Lys Met Arg Arg Lys Met Ser Pro Ala Arg Pro Arg Thr Ser Cys Arg
            370                 375                 380

Glu Ala Cys Leu Gln Gly Trp Thr Glu Ala
385                 390

<210> SEQ ID NO 187
<211> LENGTH: 401
<212> TYPE: PRT
<213> ORGANISM: Homo sapiens

<400> SEQUENCE: 187

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
        210                 215                 220

Ile Pro Asp Pro Asp Ala Lys Lys Pro Glu Asp Trp Asp Glu Glu Met
```

```
                225                 230                 235                 240
Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
                275                 280                 285

Tyr Ala Tyr Asp Asn Phe Gly Val Leu Gly Leu Asp Leu Trp Gln Val
                290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Gln Arg Leu Lys Glu
                340                 345                 350

Glu Arg Gln Arg Thr Arg Arg Met Met Arg Thr Lys Met Arg Met Arg
                355                 360                 365

Arg Met Arg Arg Thr Arg Arg Lys Met Arg Arg Lys Met Ser Pro Ala
370                 375                 380

Arg Pro Arg Thr Ser Cys Arg Glu Ala Cys Leu Gln Gly Trp Thr Glu
385                 390                 395                 400

Ala

<210> SEQ ID NO 188
<211> LENGTH: 405
<212> TYPE: PRT
<213> ORGANISM: Homo sapiens

<400> SEQUENCE: 188

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
                35                  40                  45

Leu Gln Thr Ser Gln Asp Ala Arg Phe Tyr Ala Leu Ser Ala Ser Phe
        50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
                115                 120                 125

Val Ile Phe Asn Tyr Lys Gly Lys Asn Val Leu Ile Asn Lys Asp Ile
                130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
                180                 185                 190

Asp Pro Asp Ala Ser Lys Pro Glu Asp Trp Asp Glu Arg Ala Lys Ile
```

```
                195                 200                 205
Asp Asp Pro Thr Asp Ser Lys Pro Glu Asp Trp Asp Lys Pro Glu His
    210                 215                 220
Ile Pro Asp Pro Asp Ala Lys Lys Pro Glu Asp Trp Asp Glu Glu Met
225                 230                 235                 240
Asp Gly Glu Trp Glu Pro Pro Val Ile Gln Asn Pro Glu Tyr Lys Gly
                245                 250                 255
Glu Trp Lys Pro Arg Gln Ile Asp Asn Pro Asp Tyr Lys Gly Thr Trp
            260                 265                 270
Ile His Pro Glu Ile Asp Asn Pro Glu Tyr Ser Pro Asp Pro Ser Ile
        275                 280                 285
Tyr Ala Tyr Asp Asn Phe Gly Val Leu Gly Leu Asp Leu Trp Gln Val
    290                 295                 300
Lys Ser Gly Thr Ile Phe Asp Asn Phe Leu Ile Thr Asn Asp Glu Ala
305                 310                 315                 320
Tyr Ala Glu Glu Phe Gly Asn Glu Thr Trp Gly Val Thr Lys Ala Ala
                325                 330                 335
Glu Lys Gln Met Lys Asp Lys Gln Asp Glu Glu Gln Arg Leu Lys Glu
            340                 345                 350
Glu Glu Glu Gly Arg Arg Gln Arg Thr Arg Arg Met Met Arg Thr Lys
        355                 360                 365
Met Arg Met Arg Met Arg Arg Thr Arg Arg Lys Met Arg Arg Lys
    370                 375                 380
Met Ser Pro Ala Arg Pro Arg Thr Ser Cys Arg Glu Ala Cys Leu Gln
385                 390                 395                 400
Gly Trp Thr Glu Ala
                405

<210> SEQ ID NO 189
<211> LENGTH: 404
<212> TYPE: PRT
<213> ORGANISM: Homo sapiens

<400> SEQUENCE: 189

Glu Pro Ala Val Tyr Phe Lys Glu Gln Phe Leu Asp Gly Asp Gly Trp
1               5                   10                  15
Thr Ser Arg Trp Ile Glu Ser Lys His Lys Ser Asp Phe Gly Lys Phe
            20                  25                  30
Val Leu Ser Ser Gly Lys Phe Tyr Gly Asp Glu Glu Lys Asp Lys Gly
        35                  40                  45
Leu Gln Thr Ser Gln Asp Ala Arg Phe Tyr Ala Leu Ser Ala Ser Phe
    50                  55                  60
Glu Pro Phe Ser Asn Lys Gly Gln Thr Leu Val Val Gln Phe Thr Val
65                  70                  75                  80
Lys His Glu Gln Asn Ile Asp Cys Gly Gly Gly Tyr Val Lys Leu Phe
                85                  90                  95
Pro Asn Ser Leu Asp Gln Thr Asp Met His Gly Asp Ser Glu Tyr Asn
            100                 105                 110
Ile Met Phe Gly Pro Asp Ile Cys Gly Pro Gly Thr Lys Lys Val His
        115                 120                 125
Val Ile Phe Asn Tyr Lys Gly Lys Asn Val Leu Ile Asn Lys Asp Ile
    130                 135                 140
Arg Cys Lys Asp Asp Glu Phe Thr His Leu Tyr Thr Leu Ile Val Arg
145                 150                 155                 160
```

-continued

```
Pro Asp Asn Thr Tyr Glu Val Lys Ile Asp Asn Ser Gln Val Glu Ser
                165                 170                 175
Gly Ser Leu Glu Asp Asp Trp Asp Phe Leu Pro Pro Lys Lys Ile Lys
            180                 185                 190
Asp Pro Asp Ala Ser Lys Pro Glu Asp Trp Asp Glu Arg Ala Lys Ile
        195                 200                 205
Asp Asp Pro Thr Asp Ser Lys Pro Glu Asp Trp Asp Lys Pro Glu His
    210                 215                 220
Ile Pro Asp Pro Asp Ala Lys Lys Pro Glu Asp Trp Asp Glu Glu Met
225                 230                 235                 240
Asp Gly Glu Trp Glu Pro Pro Val Ile Gln Asn Pro Glu Tyr Lys Gly
                245                 250                 255
Glu Trp Lys Pro Arg Gln Ile Asp Asn Pro Asp Tyr Lys Gly Thr Trp
            260                 265                 270
Ile His Pro Glu Ile Asp Asn Pro Glu Tyr Ser Pro Asp Pro Ser Ile
        275                 280                 285
Tyr Ala Tyr Asp Asn Phe Gly Val Leu Gly Leu Asp Leu Trp Gln Val
    290                 295                 300
Lys Ser Gly Thr Ile Phe Asp Asn Phe Leu Ile Thr Asn Asp Glu Ala
305                 310                 315                 320
Tyr Ala Glu Glu Phe Gly Asn Glu Thr Trp Gly Val Thr Lys Ala Ala
                325                 330                 335
Glu Lys Gln Met Lys Asp Lys Gln Asp Glu Gln Arg Leu Lys Glu
            340                 345                 350
Glu Glu Glu Ala Phe Lys Arg Thr Arg Arg Met Met Arg Thr Lys Met
        355                 360                 365
Arg Met Arg Arg Met Arg Arg Thr Arg Arg Lys Met Arg Arg Lys Met
    370                 375                 380
Ser Pro Ala Arg Pro Arg Thr Ser Cys Arg Glu Ala Cys Leu Gln Gly
385                 390                 395                 400
Trp Thr Glu Ala

<210> SEQ ID NO 190
<211> LENGTH: 410
<212> TYPE: PRT
<213> ORGANISM: Homo sapiens

<400> SEQUENCE: 190

Glu Pro Ala Val Tyr Phe Lys Glu Gln Phe Leu Asp Gly Asp Gly Trp
1               5                   10                  15
Thr Ser Arg Trp Ile Glu Ser Lys His Lys Ser Asp Phe Gly Lys Phe
                20                  25                  30
Val Leu Ser Ser Gly Lys Phe Tyr Gly Asp Glu Glu Lys Asp Lys Gly
            35                  40                  45
Leu Gln Thr Ser Gln Asp Ala Arg Phe Tyr Ala Leu Ser Ala Ser Phe
        50                  55                  60
Glu Pro Phe Ser Asn Lys Gly Gln Thr Leu Val Val Gln Phe Thr Val
65                  70                  75                  80
Lys His Glu Gln Asn Ile Asp Cys Gly Gly Gly Tyr Val Lys Leu Phe
                85                  90                  95
Pro Asn Ser Leu Asp Gln Thr Asp Met His Gly Asp Ser Glu Tyr Asn
            100                 105                 110
Ile Met Phe Gly Pro Asp Ile Cys Gly Pro Gly Thr Lys Lys Val His
        115                 120                 125
```

-continued

```
Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
                180                 185                 190

Asp Pro Asp Ala Ser Lys Pro Glu Asp Trp Asp Arg Ala Lys Ile
            195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
            290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
                340                 345                 350

Glu Glu Glu Asp Asn Ala Lys Arg Arg Arg Gln Arg Thr Arg Arg
            355                 360                 365

Met Met Arg Thr Lys Met Arg Met Arg Met Arg Thr Arg Arg
370                 375                 380

Lys Met Arg Arg Lys Met Ser Pro Ala Arg Pro Arg Thr Ser Cys Arg
385                 390                 395                 400

Glu Ala Cys Leu Gln Gly Trp Thr Glu Ala
                405                 410
```

<210> SEQ ID NO 191
<211> LENGTH: 409
<212> TYPE: PRT
<213> ORGANISM: Homo sapiens

<400> SEQUENCE: 191

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95
```

```
Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
            290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Cys Val Arg Arg Arg Gln Arg Thr Arg Arg Met
            355                 360                 365

Met Arg Thr Lys Met Arg Met Arg Arg Met Arg Thr Arg Arg Lys
370                 375                 380

Met Arg Arg Lys Met Ser Pro Ala Arg Pro Thr Ser Cys Arg Glu
385                 390                 395                 400

Ala Cys Leu Gln Gly Trp Thr Glu Ala
                405

<210> SEQ ID NO 192
<211> LENGTH: 405
<212> TYPE: PRT
<213> ORGANISM: Homo sapiens

<400> SEQUENCE: 192

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
```

```
            50                  55                  60
Glu Pro Phe Ser Asn Lys Gly Gln Thr Leu Val Val Gln Phe Thr Val
 65                  70                  75                  80

Lys His Glu Gln Asn Ile Asp Cys Gly Gly Gly Tyr Val Lys Leu Phe
                 85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
        210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
        290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Arg Arg Gln Arg Thr Arg Arg Met Met Arg Thr Lys
        355                 360                 365

Met Arg Met Arg Arg Met Arg Arg Thr Arg Arg Lys Met Arg Arg Lys
370                 375                 380

Met Ser Pro Ala Arg Pro Arg Thr Ser Cys Arg Glu Ala Cys Leu Gln
385                 390                 395                 400

Gly Trp Thr Glu Ala
            405

<210> SEQ ID NO 193
<211> LENGTH: 405
<212> TYPE: PRT
<213> ORGANISM: Homo sapiens

<400> SEQUENCE: 193

Glu Pro Ala Val Tyr Phe Lys Glu Gln Phe Leu Asp Gly Asp Gly Trp
 1               5                  10                  15
```

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
                35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
        130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Lys Arg Gln Arg Thr Arg Met Met Arg Thr Lys
        355                 360                 365

Met Arg Met Arg Met Arg Thr Arg Arg Lys Met Arg Arg Lys
370                 375                 380

Met Ser Pro Ala Arg Pro Arg Thr Ser Cys Arg Glu Ala Cys Leu Gln
385                 390                 395                 400

Gly Trp Thr Glu Ala
            405

<210> SEQ ID NO 194
<211> LENGTH: 411
<212> TYPE: PRT

<213> ORGANISM: Homo sapiens

<400> SEQUENCE: 194

```
Glu Pro Ala Val Tyr Phe Lys Glu Gln Phe Leu Asp Gly Asp Gly Trp
1               5                   10                  15
Thr Ser Arg Trp Ile Glu Ser Lys His Lys Ser Asp Phe Gly Lys Phe
            20                  25                  30
Val Leu Ser Ser Gly Lys Phe Tyr Gly Asp Glu Glu Lys Asp Lys Gly
        35                  40                  45
Leu Gln Thr Ser Gln Asp Ala Arg Phe Tyr Ala Leu Ser Ala Ser Phe
    50                  55                  60
Glu Pro Phe Ser Asn Lys Gly Gln Thr Leu Val Val Gln Phe Thr Val
65                  70                  75                  80
Lys His Glu Gln Asn Ile Asp Cys Gly Gly Gly Tyr Val Lys Leu Phe
                85                  90                  95
Pro Asn Ser Leu Asp Gln Thr Asp Met His Gly Asp Ser Glu Tyr Asn
            100                 105                 110
Ile Met Phe Gly Pro Asp Ile Cys Gly Pro Gly Thr Lys Lys Val His
        115                 120                 125
Val Ile Phe Asn Tyr Lys Gly Lys Asn Val Leu Ile Asn Lys Asp Ile
    130                 135                 140
Arg Cys Lys Asp Asp Glu Phe Thr His Leu Tyr Thr Leu Ile Val Arg
145                 150                 155                 160
Pro Asp Asn Thr Tyr Glu Val Lys Ile Asp Asn Ser Gln Val Glu Ser
                165                 170                 175
Gly Ser Leu Glu Asp Asp Trp Asp Phe Leu Pro Pro Lys Lys Ile Lys
            180                 185                 190
Asp Pro Asp Ala Ser Lys Pro Glu Asp Trp Asp Glu Arg Ala Lys Ile
        195                 200                 205
Asp Asp Pro Thr Asp Ser Lys Pro Glu Asp Trp Asp Lys Pro Glu His
    210                 215                 220
Ile Pro Asp Pro Asp Ala Lys Lys Pro Glu Asp Trp Asp Glu Glu Met
225                 230                 235                 240
Asp Gly Glu Trp Glu Pro Pro Val Ile Gln Asn Pro Glu Tyr Lys Gly
                245                 250                 255
Glu Trp Lys Pro Arg Gln Ile Asp Asn Pro Asp Tyr Lys Gly Thr Trp
            260                 265                 270
Ile His Pro Glu Ile Asp Asn Pro Glu Tyr Ser Pro Asp Pro Ser Ile
        275                 280                 285
Tyr Ala Tyr Asp Asn Phe Gly Val Leu Gly Leu Asp Leu Trp Gln Val
    290                 295                 300
Lys Ser Gly Thr Ile Phe Asp Asn Phe Leu Ile Thr Asn Asp Glu Ala
305                 310                 315                 320
Tyr Ala Glu Glu Phe Gly Asn Glu Thr Trp Gly Val Thr Lys Ala Ala
                325                 330                 335
Glu Lys Gln Met Lys Asp Lys Gln Asp Glu Glu Gln Arg Leu Lys Glu
            340                 345                 350
Glu Glu Glu Asp Lys Asn Ala Lys Arg Arg Arg Arg Gln Arg Thr Arg
        355                 360                 365
Arg Met Met Arg Thr Lys Met Arg Met Arg Met Arg Arg Thr Arg
    370                 375                 380
Arg Lys Met Arg Arg Lys Met Ser Pro Ala Arg Pro Arg Thr Ser Cys
385                 390                 395                 400
```

```
Arg Glu Ala Cys Leu Gln Gly Trp Thr Glu Ala
            405                 410
```

```
<210> SEQ ID NO 195
<211> LENGTH: 412
<212> TYPE: PRT
<213> ORGANISM: Homo sapiens

<400> SEQUENCE: 195
```

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Lys Cys Phe Ala Lys Arg Arg Arg Gln Arg Thr
        355                 360                 365
```

```
Arg Arg Met Met Arg Thr Lys Met Arg Met Arg Arg Met Arg Thr
            370                 375                 380

Arg Arg Lys Met Arg Lys Met Ser Pro Ala Arg Pro Arg Thr Ser
385                 390                 395                 400

Cys Arg Glu Ala Cys Leu Gln Gly Trp Thr Glu Ala
                405                 410
```

<210> SEQ ID NO 196
<211> LENGTH: 404
<212> TYPE: PRT
<213> ORGANISM: Homo sapiens

<400> SEQUENCE: 196

```
Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
    290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
```

```
                  325                 330                 335
Glu Lys Gln Met Lys Asp Lys Gln Asp Glu Glu Gln Arg Leu Lys Glu
                340                 345                 350

Glu Glu Glu Asp Lys Lys Arg Lys Arg Arg Met Met Arg Thr Lys Met
                355                 360                 365

Arg Met Arg Arg Met Arg Thr Arg Arg Lys Met Arg Lys Met
            370                 375                 380

Ser Pro Ala Arg Pro Arg Thr Ser Cys Arg Glu Ala Cys Leu Gln Gly
385                 390                 395                 400

Trp Thr Glu Ala

<210> SEQ ID NO 197
<211> LENGTH: 410
<212> TYPE: PRT
<213> ORGANISM: Homo sapiens

<400> SEQUENCE: 197

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
```

```
                290                 295                 300
Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Gln Arg Leu Lys Glu
                340                 345                 350

Glu Glu Glu Asp Lys Lys Arg Lys Glu Pro Pro Leu Cys Leu Arg Arg
            355                 360                 365

Met Met Arg Thr Lys Met Arg Met Arg Met Arg Arg Thr Arg Arg
        370                 375                 380

Lys Met Arg Arg Lys Met Ser Pro Ala Arg Pro Arg Thr Ser Cys Arg
385                 390                 395                 400

Glu Ala Cys Leu Gln Gly Trp Thr Glu Ala
                405                 410

<210> SEQ ID NO 198
<211> LENGTH: 409
<212> TYPE: PRT
<213> ORGANISM: Homo sapiens

<400> SEQUENCE: 198

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
            115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
            195                 200                 205

Asp Asp Pro Thr Asp Ser Lys Pro Glu Asp Trp Asp Lys Pro Glu His
            210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255
```

```
Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
            275                 280                 285

Tyr Ala Tyr Asp Asn Phe Gly Val Leu Gly Leu Asp Leu Trp Gln Val
        290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Lys Lys Arg Lys Glu Asp His Pro Cys Arg Arg Met
        355                 360                 365

Met Arg Thr Lys Met Arg Met Arg Met Arg Arg Thr Arg Arg Lys
            370                 375                 380

Met Arg Arg Lys Met Ser Pro Ala Arg Pro Arg Thr Ser Cys Arg Glu
385                 390                 395                 400

Ala Cys Leu Gln Gly Trp Thr Glu Ala
                405

<210> SEQ ID NO 199
<211> LENGTH: 413
<212> TYPE: PRT
<213> ORGANISM: Homo sapiens

<400> SEQUENCE: 199

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
    210                 215                 220
```

```
Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
            245                 250                 255

Glu Trp Lys Pro Arg Gln Ile Asp Asn Pro Asp Tyr Lys Gly Thr Trp
        260                 265                 270

Ile His Pro Glu Ile Asp Asn Pro Glu Tyr Ser Pro Asp Pro Ser Ile
    275                 280                 285

Tyr Ala Tyr Asp Asn Phe Gly Val Leu Gly Leu Asp Leu Trp Gln Val
290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
            325                 330                 335

Glu Lys Gln Met Lys Asp Lys Gln Asp Glu Glu Gln Arg Leu Lys Glu
        340                 345                 350

Glu Glu Glu Asp Lys Lys Arg Lys Glu Glu Glu Glu Ala Glu Gly Asn
    355                 360                 365

Cys Arg Arg Met Met Arg Thr Lys Met Arg Met Arg Arg Met Arg Arg
370                 375                 380

Thr Arg Arg Lys Met Arg Arg Lys Met Ser Pro Ala Arg Pro Arg Thr
385                 390                 395                 400

Ser Cys Arg Glu Ala Cys Leu Gln Gly Trp Thr Glu Ala
            405                 410

<210> SEQ ID NO 200
<211> LENGTH: 412
<212> TYPE: PRT
<213> ORGANISM: Homo sapiens

<400> SEQUENCE: 200

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
            85                  90                  95

Pro Asn Ser Leu Asp Gln Thr Asp Met His Gly Asp Ser Glu Tyr Asn
        100                 105                 110

Ile Met Phe Gly Pro Asp Ile Cys Gly Pro Gly Thr Lys Lys Val His
    115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
            165                 170                 175

Gly Ser Leu Glu Asp Asp Trp Asp Phe Leu Pro Pro Lys Lys Ile Lys
```

```
                180               185               190
Asp Pro Asp Ala Ser Lys Pro Glu Asp Trp Asp Glu Arg Ala Lys Ile
            195               200               205

Asp Asp Pro Thr Asp Ser Lys Pro Glu Asp Trp Asp Lys Pro Glu His
    210               215               220

Ile Pro Asp Pro Asp Ala Lys Lys Pro Glu Asp Trp Asp Glu Glu Met
225               230               235               240

Asp Gly Glu Trp Glu Pro Pro Val Ile Gln Asn Pro Glu Tyr Lys Gly
                245               250               255

Glu Trp Lys Pro Arg Gln Ile Asp Asn Pro Asp Tyr Lys Gly Thr Trp
            260               265               270

Ile His Pro Glu Ile Asp Asn Pro Glu Tyr Ser Pro Asp Pro Ser Ile
        275               280               285

Tyr Ala Tyr Asp Asn Phe Gly Val Leu Gly Leu Asp Leu Trp Gln Val
    290               295               300

Lys Ser Gly Thr Ile Phe Asp Asn Phe Leu Ile Thr Asn Asp Glu Ala
305               310               315               320

Tyr Ala Glu Glu Phe Gly Asn Glu Thr Trp Gly Val Thr Lys Ala Ala
                325               330               335

Glu Lys Gln Met Lys Asp Lys Gln Asp Glu Glu Arg Leu Lys Glu
                340               345               350

Glu Glu Glu Asp Lys Lys Arg Lys Glu Glu Glu Ala Glu Asp Cys
            355               360               365

Arg Arg Met Met Arg Thr Lys Met Arg Met Arg Arg Met Arg Thr
    370               375               380

Arg Arg Lys Met Arg Arg Lys Met Ser Pro Ala Arg Pro Arg Thr Ser
385               390               395               400

Cys Arg Glu Ala Cys Leu Gln Gly Trp Thr Glu Ala
                405               410

<210> SEQ ID NO 201
<211> LENGTH: 413
<212> TYPE: PRT
<213> ORGANISM: Homo sapiens

<400> SEQUENCE: 201

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
            20                  25                  30

Val Leu Ser Ser Gly Lys Phe Tyr Gly Asp Glu Glu Lys Asp Lys Gly
        35                  40                  45

Leu Gln Thr Ser Gln Asp Ala Arg Phe Tyr Ala Leu Ser Ala Ser Phe
    50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110

Ile Met Phe Gly Pro Asp Ile Cys Gly Pro Gly Thr Lys Lys Val His
        115                 120                 125

Val Ile Phe Asn Tyr Lys Gly Lys Asn Val Leu Ile Asn Lys Asp Ile
    130                 135                 140
```

```
Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
            180                 185                 190

Asp Pro Asp Ala Ser Lys Pro Glu Asp Trp Asp Glu Arg Ala Lys Ile
        195                 200                 205

Asp Asp Pro Thr Asp Ser Lys Pro Glu Asp Trp Asp Lys Pro Glu His
210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
            260                 265                 270

Ile His Pro Glu Ile Asp Asn Pro Glu Tyr Ser Pro Asp Pro Ser Ile
        275                 280                 285

Tyr Ala Tyr Asp Asn Phe Gly Val Leu Gly Leu Asp Leu Trp Gln Val
290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
            340                 345                 350

Glu Glu Glu Asp Lys Lys Arg Lys Glu Glu Glu Glu Ala Glu Asp Lys
        355                 360                 365

Cys Arg Arg Met Met Arg Thr Lys Met Arg Met Arg Arg Met Arg Arg
370                 375                 380

Thr Arg Arg Lys Met Arg Arg Lys Met Ser Pro Ala Arg Pro Arg Thr
385                 390                 395                 400

Ser Cys Arg Glu Ala Cys Leu Gln Gly Trp Thr Glu Ala
                405                 410

<210> SEQ ID NO 202
<211> LENGTH: 413
<212> TYPE: PRT
<213> ORGANISM: Homo sapiens

<400> SEQUENCE: 202

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30

Val Leu Ser Ser Gly Lys Phe Tyr Gly Asp Glu Glu Lys Asp Lys Gly
            35                  40                  45

Leu Gln Thr Ser Gln Asp Ala Arg Phe Tyr Ala Leu Ser Ala Ser Phe
50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
            100                 105                 110
```

-continued

```
Ile Met Phe Gly Pro Asp Ile Cys Gly Pro Gly Thr Lys Lys Val His
            115                 120                 125
Val Ile Phe Asn Tyr Lys Gly Lys Asn Val Leu Ile Asn Lys Asp Ile
        130                 135                 140
Arg Cys Lys Asp Glu Phe Thr His Leu Tyr Thr Leu Ile Val Arg
145                 150                 155                 160
Pro Asp Asn Thr Tyr Glu Val Lys Ile Asp Asn Ser Gln Val Glu Ser
                165                 170                 175
Gly Ser Leu Glu Asp Asp Trp Asp Phe Leu Pro Pro Lys Lys Ile Lys
            180                 185                 190
Asp Pro Asp Ala Ser Lys Pro Glu Asp Trp Asp Glu Arg Ala Lys Ile
        195                 200                 205
Asp Asp Pro Thr Asp Ser Lys Pro Glu Asp Trp Asp Lys Pro Glu His
210                 215                 220
Ile Pro Asp Pro Asp Ala Lys Lys Pro Glu Asp Trp Asp Glu Glu Met
225                 230                 235                 240
Asp Gly Glu Trp Glu Pro Pro Val Ile Gln Asn Pro Glu Tyr Lys Gly
                245                 250                 255
Glu Trp Lys Pro Arg Gln Ile Asp Asn Pro Asp Tyr Lys Gly Thr Trp
            260                 265                 270
Ile His Pro Glu Ile Asp Asn Pro Glu Tyr Ser Pro Asp Pro Ser Ile
        275                 280                 285
Tyr Ala Tyr Asp Asn Phe Gly Val Leu Gly Leu Asp Leu Trp Gln Val
        290                 295                 300
Lys Ser Gly Thr Ile Phe Asp Asn Phe Leu Ile Thr Asn Asp Glu Ala
305                 310                 315                 320
Tyr Ala Glu Glu Phe Gly Asn Glu Thr Trp Gly Val Thr Lys Ala Ala
                325                 330                 335
Glu Lys Gln Met Lys Asp Lys Gln Asp Glu Glu Gln Arg Leu Lys Glu
            340                 345                 350
Glu Glu Glu Asp Lys Lys Arg Lys Glu Glu Glu Glu Ala Glu Asp Thr
        355                 360                 365
Cys Arg Arg Met Met Arg Thr Lys Met Arg Met Arg Met Arg Met Arg
370                 375                 380
Thr Arg Arg Lys Met Arg Arg Lys Met Ser Pro Ala Arg Pro Arg Thr
385                 390                 395                 400
Ser Cys Arg Glu Ala Cys Leu Gln Gly Trp Thr Glu Ala
                405                 410
```

<210> SEQ ID NO 203
<211> LENGTH: 413
<212> TYPE: PRT
<213> ORGANISM: Homo sapiens

<400> SEQUENCE: 203

```
Glu Pro Ala Val Tyr Phe Lys Glu Gln Phe Leu Asp Gly Asp Gly Trp
1               5                   10                  15
Thr Ser Arg Trp Ile Glu Ser Lys His Lys Ser Asp Phe Gly Lys Phe
            20                  25                  30
Val Leu Ser Ser Gly Lys Phe Tyr Gly Asp Glu Lys Asp Lys Gly
        35                  40                  45
Leu Gln Thr Ser Gln Asp Ala Arg Phe Tyr Ala Leu Ser Ala Ser Phe
    50                  55                  60
Glu Pro Phe Ser Asn Lys Gly Gln Thr Leu Val Val Gln Phe Thr Val
```

```
            65                  70                  75                  80
Lys His Glu Gln Asn Ile Asp Cys Gly Gly Gly Tyr Val Lys Leu Phe
                85                  90                  95

Pro Asn Ser Leu Asp Gln Thr Asp Met His Gly Asp Ser Glu Tyr Asn
                100                 105                 110

Ile Met Phe Gly Pro Asp Ile Cys Gly Pro Gly Thr Lys Lys Val His
                115                 120                 125

Val Ile Phe Asn Tyr Lys Gly Lys Asn Val Leu Ile Asn Lys Asp Ile
                130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                165                 170                 175

Gly Ser Leu Glu Asp Asp Trp Asp Phe Leu Pro Pro Lys Lys Ile Lys
                180                 185                 190

Asp Pro Asp Ala Ser Lys Pro Glu Asp Trp Asp Glu Arg Ala Lys Ile
                195                 200                 205

Asp Asp Pro Thr Asp Ser Lys Pro Glu Asp Trp Asp Lys Pro Glu His
                210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                245                 250                 255

Glu Trp Lys Pro Arg Gln Ile Asp Asn Pro Asp Tyr Lys Gly Thr Trp
                260                 265                 270

Ile His Pro Glu Ile Asp Asn Pro Glu Tyr Ser Pro Asp Pro Ser Ile
                275                 280                 285

Tyr Ala Tyr Asp Asn Phe Gly Val Leu Gly Leu Asp Leu Trp Gln Val
                290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                325                 330                 335

Glu Lys Gln Met Lys Asp Lys Gln Asp Glu Glu Gln Arg Leu Lys Glu
                340                 345                 350

Glu Glu Glu Asp Lys Lys Arg Lys Glu Glu Glu Ala Glu Asp Ile
                355                 360                 365

Cys Arg Arg Met Met Arg Thr Lys Met Arg Met Arg Met Arg
370                 375                 380

Thr Arg Arg Lys Met Arg Lys Met Ser Pro Ala Arg Pro Arg Thr
385                 390                 395                 400

Ser Cys Arg Glu Ala Cys Leu Gln Gly Trp Thr Glu Ala
                405                 410

<210> SEQ ID NO 204
<211> LENGTH: 413
<212> TYPE: PRT
<213> ORGANISM: Homo sapiens

<400> SEQUENCE: 204

Glu Pro Ala Val Tyr Phe Lys Glu Gln Phe Leu Asp Gly Asp Gly Trp
1               5                   10                  15

Thr Ser Arg Trp Ile Glu Ser Lys His Lys Ser Asp Phe Gly Lys Phe
                20                  25                  30
```

```
Val Leu Ser Ser Gly Lys Phe Tyr Gly Asp Glu Lys Asp Lys Gly
         35                  40                  45

Leu Gln Thr Ser Gln Asp Ala Arg Phe Tyr Ala Leu Ser Ala Ser Phe
 50                  55                  60

Glu Pro Phe Ser Asn Lys Gly Gln Thr Leu Val Val Gln Phe Thr Val
65                  70                  75                  80

Lys His Glu Gln Asn Ile Asp Cys Gly Gly Gly Tyr Val Lys Leu Phe
                 85                  90                  95

Pro Asn Ser Leu Asp Gln Thr Asp Met His Gly Asp Ser Glu Tyr Asn
             100                 105                 110

Ile Met Phe Gly Pro Asp Ile Cys Gly Pro Gly Thr Lys Lys Val His
         115                 120                 125

Val Ile Phe Asn Tyr Lys Gly Lys Asn Val Leu Ile Asn Lys Asp Ile
130                 135                 140

Arg Cys Lys Asp Asp Glu Phe Thr His Leu Tyr Thr Leu Ile Val Arg
145                 150                 155                 160

Pro Asp Asn Thr Tyr Glu Val Lys Ile Asp Asn Ser Gln Val Glu Ser
                 165                 170                 175

Gly Ser Leu Glu Asp Asp Trp Asp Phe Leu Pro Pro Lys Lys Ile Lys
             180                 185                 190

Asp Pro Asp Ala Ser Lys Pro Glu Asp Trp Asp Glu Arg Ala Lys Ile
         195                 200                 205

Asp Asp Pro Thr Asp Ser Lys Pro Glu Asp Trp Asp Lys Pro Glu His
     210                 215                 220

Ile Pro Asp Pro Asp Ala Lys Lys Pro Glu Asp Trp Asp Glu Glu Met
225                 230                 235                 240

Asp Gly Glu Trp Glu Pro Pro Val Ile Gln Asn Pro Glu Tyr Lys Gly
                 245                 250                 255

Glu Trp Lys Pro Arg Gln Ile Asp Asn Pro Asp Tyr Lys Gly Thr Trp
             260                 265                 270

Ile His Pro Glu Ile Asp Asn Pro Glu Tyr Ser Pro Asp Pro Ser Ile
         275                 280                 285

Tyr Ala Tyr Asp Asn Phe Gly Val Leu Gly Leu Asp Leu Trp Gln Val
     290                 295                 300

Lys Ser Gly Thr Ile Phe Asp Asn Phe Leu Ile Thr Asn Asp Glu Ala
305                 310                 315                 320

Tyr Ala Glu Glu Phe Gly Asn Glu Thr Trp Gly Val Thr Lys Ala Ala
                 325                 330                 335

Glu Lys Gln Met Lys Asp Lys Gln Asp Glu Glu Gln Arg Leu Lys Glu
             340                 345                 350

Glu Glu Glu Asp Lys Lys Arg Lys Glu Glu Glu Ala Glu Asp Lys
         355                 360                 365

Cys Arg Arg Met Met Arg Thr Lys Met Arg Arg Met Arg Arg
370                 375                 380

Thr Arg Arg Lys Met Arg Arg Lys Met Ser Pro Ala Arg Pro Arg Thr
385                 390                 395                 400

Ser Cys Arg Glu Ala Cys Leu Gln Gly Trp Thr Glu Ala
                 405                 410

<210> SEQ ID NO 205

<400> SEQUENCE: 205

000
```

```
<210> SEQ ID NO 206
<400> SEQUENCE: 206
000

<210> SEQ ID NO 207
<400> SEQUENCE: 207
000

<210> SEQ ID NO 208
<400> SEQUENCE: 208
000

<210> SEQ ID NO 209
<400> SEQUENCE: 209
000

<210> SEQ ID NO 210
<400> SEQUENCE: 210
000

<210> SEQ ID NO 211
<400> SEQUENCE: 211
000

<210> SEQ ID NO 212
<400> SEQUENCE: 212
000

<210> SEQ ID NO 213
<400> SEQUENCE: 213
000

<210> SEQ ID NO 214
<400> SEQUENCE: 214
000

<210> SEQ ID NO 215
<400> SEQUENCE: 215
000

<210> SEQ ID NO 216
<400> SEQUENCE: 216
000

<210> SEQ ID NO 217
```

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 228
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Ala Lys Phe Ala Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Gly Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ala Gln Ser Ile
        115                 120                 125

Ile Ser Thr Leu Thr
        130

<210> SEQ ID NO 229
<211> LENGTH: 518
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Ile Trp Glu Leu Lys Lys Asp Val Tyr Val Val Glu Leu Asp Trp Tyr
1               5                   10                  15

```
Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
 50                  55                  60

Gln Tyr Thr Cys His Lys Gly Gly Glu Val Leu Ser His Ser Leu Leu
 65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
        130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
        210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
        290                 295                 300

Cys Ser Gly Gly Gly Ser Gly Gly Gly Gly Ser Gly Gly Gly Gly Gly
305                 310                 315                 320

Ser Arg Asn Leu Pro Val Ala Thr Pro Asp Pro Gly Met Phe Pro Cys
                325                 330                 335

Leu His His Ser Gln Asn Leu Leu Arg Ala Val Ser Asn Met Leu Gln
            340                 345                 350

Lys Ala Arg Gln Thr Leu Glu Phe Tyr Pro Cys Thr Ser Glu Glu Ile
        355                 360                 365

Asp His Glu Asp Ile Thr Lys Asp Lys Thr Ser Thr Val Glu Ala Cys
        370                 375                 380

Leu Pro Leu Glu Leu Thr Lys Asn Glu Ser Cys Leu Asn Ser Arg Glu
385                 390                 395                 400

Thr Ser Phe Ile Thr Asn Gly Ser Cys Leu Ala Ser Arg Lys Thr Ser
                405                 410                 415

Phe Met Met Ala Leu Cys Leu Ser Ser Ile Tyr Glu Asp Leu Lys Met
            420                 425                 430

Tyr Gln Val Glu Phe Lys Thr Met Asn Ala Lys Leu Leu Met Asp Pro
```

```
            435                 440                 445
Lys Arg Gln Ile Phe Leu Asp Gln Asn Met Leu Ala Val Ile Asp Glu
            450                 455                 460

Leu Met Gln Ala Leu Asn Phe Asn Ser Glu Thr Val Pro Gln Lys Ser
465                 470                 475                 480

Ser Leu Glu Glu Pro Asp Phe Tyr Lys Thr Lys Ile Lys Leu Cys Ile
                485                 490                 495

Leu Leu His Ala Phe Arg Ile Arg Ala Val Thr Ile Asp Arg Val Met
            500                 505                 510

Ser Tyr Leu Asn Ala Ser
            515

<210> SEQ ID NO 230
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Gly Gly Gly Gly Ser Gly Gly Gly Ser Gly Gly Gly Gly Ser Gly
                165                 170                 175

Gly Gly Ser Ser Pro Gly Gln Gly Thr Gln Ser Glu Asn Ser Cys
            180                 185                 190

Thr His Phe Pro Gly Asn Leu Pro Asn Met Leu Arg Asp Leu Arg Asp
        195                 200                 205

Ala Phe Ser Arg Val Lys Thr Phe Phe Gln Met Lys Asp Gln Leu Asp
        210                 215                 220

Asn Leu Leu Lys Glu Ser Leu Leu Glu Asp Phe Lys Gly Tyr Leu
225                 230                 235                 240

Gly Cys Gln Ala Leu Ser Glu Met Ile Gln Phe Tyr Leu Glu Glu Val
                245                 250                 255

Met Pro Gln Ala Glu Asn Gln Asp Pro Asp Ile Lys Ala His Val Asn
            260                 265                 270
```

```
Ser Leu Gly Glu Asn Leu Lys Thr Leu Arg Leu Arg Leu Arg Arg Cys
            275                 280                 285

His Arg Phe Leu Pro Cys Glu Asn Lys Ser Lys Ala Val Glu Gln Val
        290                 295                 300

Lys Asn Ala Phe Asn Lys Leu Gln Glu Lys Gly Ile Tyr Lys Ala Met
305                 310                 315                 320

Ser Glu Phe Asp Ile Phe Ile Asn Tyr Ile Glu Ala Tyr Met Thr Met
                325                 330                 335

Lys Ile Arg Asn
            340

<210> SEQ ID NO 231
<211> LENGTH: 166
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Gly Gly Gly Ser Gly Gly Lys Ser Lys Ala Val Glu
        115                 120                 125

Gln Val Lys Asn Ala Phe Asn Lys Leu Gln Glu Lys Gly Ile Tyr Lys
    130                 135                 140

Ala Met Ser Glu Phe Asp Ile Phe Ile Asn Tyr Ile Glu Ala Tyr Met
145                 150                 155                 160

Thr Met Lys Ile Arg Asn
                165

<210> SEQ ID NO 232
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45
```

Val Ile Ser Leu Ala Ser Gly Asp Ala Ser Ile His Asp Thr Val Glu
 50                  55                  60

Asn Leu Ile Ile Leu Ala Asn Asn Ser Leu Ser Ser Asn Gly Ala Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
             100                 105                 110

Thr Ser

<210> SEQ ID NO 233
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
                 20                  25                  30

Tyr Ile His Trp Val Arg Gln Ala Pro Gly Gln Gly Leu Glu Trp Ile
             35                  40                  45

Gly Tyr Ile Ser Ala Tyr Asn Gly Ala Ser Ser Tyr Asn Gln Lys Phe
     50                  55                  60

Lys Gly Arg Ala Thr Phe Thr Val Asp Thr Ser Thr Ser Thr Ala Tyr
 65                  70                  75                  80

Met Glu Leu Arg Ser Leu Arg Ser Asp Asp Met Ala Val Tyr Tyr Cys
                 85                  90                  95

Ala Ser Ser Met Asp Tyr Trp Gly Gln Gly Thr Leu Val Thr Val Ser
             100                 105                 110

Ser

<210> SEQ ID NO 234
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Thr Gly Tyr
                 20                  25                  30

Tyr Ile His Trp Val Arg Gln Ala Pro Gly Gln Gly Leu Glu Trp Ile
             35                  40                  45

Gly Tyr Ile Ser Ala Tyr Asn Gly Ala Ser Ser Tyr Asn Gln Lys Phe
     50                  55                  60

Lys Gly Arg Ala Thr Phe Thr Val Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Ser Ser Met Asp Tyr Trp Gly Gln Gly Thr Leu Val Thr Val Ser
             100                 105                 110

Ser

<210> SEQ ID NO 235
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Lys Gly Leu Glu Trp Ile
        35                  40                  45

Gly Tyr Ile Ser Ala Tyr Asn Gly Ala Ser Ser Tyr Asn Gln Lys Phe
    50                  55                  60

Lys Gly Arg Ala Thr Phe Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Met Asp Tyr Trp Gly Gln Gly Thr Leu Val Thr Val Ser
            100                 105                 110

Ser

<210> SEQ ID NO 236
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Ile
        35                  40                  45

Gly Tyr Ile Ser Ala Tyr Asn Gly Ala Ser Ser Tyr Asn Gln Lys Phe
    50                  55                  60

Lys Gly Arg Ala Thr Phe Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Ser Met Asp Tyr Trp Gly Gln Gly Thr Leu Val Thr Val Ser
            100                 105                 110

Ser

<210> SEQ ID NO 237
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Ile His Trp Val Arg Gln Ala Pro Gly Gln Gly Leu Glu Trp Ile
        35                  40                  45

Gly Tyr Ile Ser Ala Tyr Asn Gly Ala Ser Ser Tyr Asn Gln Lys Phe
    50                  55                  60

Lys Gly Arg Ala Thr Phe Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ser Met Asp Tyr Trp Gly Gln Gly Thr Leu Val Thr Val Ser
            100                 105                 110

Ser

<210> SEQ ID NO 238
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Gln Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Trp Gln Gly
                85                  90                  95

Thr His Phe Pro Tyr Thr Phe Gly Gln Gly Thr Lys Leu Glu Ile Lys
            100                 105                 110

<210> SEQ ID NO 239
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asp Val Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Lys Leu Leu Ile Tyr Leu Val Ser Lys Leu Asp Ser Gly Val Pro

```
                    50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr His Cys Trp Gln Gly
                     85                  90                  95

Thr His Phe Pro Tyr Thr Phe Gly Gln Gly Thr Lys Leu Glu Ile Lys
                100                 105                 110

<210> SEQ ID NO 240
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Asp Val Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Lys Pro Gly Gln Pro
             35                  40                  45

Pro Lys Leu Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr His Cys Trp Gln Gly
                     85                  90                  95

Thr His Phe Pro Tyr Thr Phe Gly Gln Gly Thr Lys Leu Glu Ile Lys
                100                 105                 110

<210> SEQ ID NO 241
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Asp Val Val Met Thr Gln Thr Pro Leu Ser Ser Val Thr Leu Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Gln Gln Arg Pro Gly Gln Pro
             35                  40                  45

Pro Lys Leu Leu Ile Tyr Leu Val Ser Lys Leu Asp Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr His Cys Trp Gln Gly
                     85                  90                  95

Thr His Phe Pro Tyr Thr Phe Gly Gln Gly Thr Lys Leu Glu Ile Lys
                100                 105                 110

<210> SEQ ID NO 242
<211> LENGTH: 112
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 242

Asp Val Val Met Thr Gln Ser Pro Leu Ser Leu Pro Val Thr Pro Gly
1               5                   10                  15

Glu Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Lys Leu Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr His Cys Trp Gln Gly
                85                  90                  95

Thr His Phe Pro Tyr Thr Phe Gly Gln Gly Thr Lys Leu Glu Ile Lys
                100                 105                 110

<210> SEQ ID NO 243
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Tyr Ile Ser Ala Tyr Asn Gly Ala Ser Ser Tyr Asn Gln Lys Phe Lys
1               5                   10                  15

Gly

<210> SEQ ID NO 244
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Gln or Lys
<220> FEATURE:
<221> NAME/KEY: MOD_RES
<222> LOCATION: (76)..(76)
<223> OTHER INFORMATION: Ile or Thr
<220> FEATURE:
<221> NAME/KEY: MOD_RES
<222> LOCATION: (84)..(84)
<223> OTHER INFORMATION: Ser or Arg
<220> FEATURE:
<221> NAME/KEY: MOD_RES
<222> LOCATION: (85)..(85)
<223> OTHER INFORMATION: Arg or Ser
<220> FEATURE:
<221> NAME/KEY: MOD_RES
<222> LOCATION: (91)..(91)
<223> OTHER INFORMATION: Thr or Met

<400> SEQUENCE: 244

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr

```
                20                  25                  30
Tyr Ile His Trp Val Arg Gln Ala Pro Gly Xaa Gly Leu Glu Trp Ile
            35                  40                  45

Gly Tyr Ile Ser Ala Tyr Asn Gly Ala Ser Ser Tyr Asn Gln Lys Phe
        50                  55                  60

Lys Gly Arg Ala Thr Phe Thr Val Asp Thr Ser Xaa Ser Thr Ala Tyr
 65                  70                  75                  80

Met Glu Leu Xaa Xaa Leu Arg Ser Asp Asp Xaa Ala Val Tyr Tyr Cys
                85                  90                  95

Ala Ser Ser Met Asp Tyr Trp Gly Gln Gly Thr Leu Val Thr Val Ser
                100                 105                 110

Ser

<210> SEQ ID NO 245
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (11)..(11)
<223> OTHER INFORMATION: Leu or Ser
<220> FEATURE:
<221> NAME/KEY: MOD_RES
<222> LOCATION: (12)..(12)
<223> OTHER INFORMATION: Pro or Ser
<220> FEATURE:
<221> NAME/KEY: MOD_RES
<222> LOCATION: (15)..(15)
<223> OTHER INFORMATION: Leu or Pro
<220> FEATURE:
<221> NAME/KEY: MOD_RES
<222> LOCATION: (17)..(17)
<223> OTHER INFORMATION: Gln or Glu
<220> FEATURE:
<221> NAME/KEY: MOD_RES
<222> LOCATION: (42)..(42)
<223> OTHER INFORMATION: Gln or Leu
<220> FEATURE:
<221> NAME/KEY: MOD_RES
<222> LOCATION: (44)..(44)
<223> OTHER INFORMATION: Arg or Lys
<220> FEATURE:
<221> NAME/KEY: MOD_RES
<222> LOCATION: (48)..(48)
<223> OTHER INFORMATION: Ser or Pro
<220> FEATURE:
<221> NAME/KEY: MOD_RES
<222> LOCATION: (51)..(51)
<223> OTHER INFORMATION: Arg or Leu
<220> FEATURE:
<221> NAME/KEY: MOD_RES
<222> LOCATION: (72)..(72)
<223> OTHER INFORMATION: Ser or Ala

<400> SEQUENCE: 245

Asp Val Val Met Thr Gln Xaa Pro Leu Ser Xaa Xaa Val Thr Xaa Gly
 1               5                   10                  15

Xaa Pro Ala Ser Ile Ser Cys Lys Ser Ser Gln Ser Leu Leu Asp Ser
                20                  25                  30

Asp Gly Lys Thr Tyr Leu Asn Trp Leu Xaa Gln Xaa Pro Gly Gln Xaa
            35                  40                  45
```

```
Pro Lys Xaa Leu Ile Tyr Leu Val Ser Lys Leu Asp Ser Gly Val Pro
     50                 55                  60
Asp Arg Phe Ser Gly Ser Gly Xaa Gly Thr Asp Phe Thr Leu Lys Ile
 65                  70                  75                  80
Ser Arg Val Glu Ala Glu Asp Val Gly Val Tyr His Cys Trp Gln Gly
                 85                  90                  95
Thr His Phe Pro Tyr Thr Phe Gly Gln Gly Thr Lys Leu Glu Ile Lys
                100                 105                 110
```

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

-continued

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292
<211> LENGTH: 390
<212> TYPE: PRT
<213> ORGANISM: Homo sapiens

<400> SEQUENCE: 292

Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
        115                 120                 125

His Ser Ile Tyr Met Phe Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

```
Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 293
<211> LENGTH: 414
<212> TYPE: PRT
<213> ORGANISM: Homo sapiens

<400> SEQUENCE: 293

Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
    50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
    130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
    210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
```

```
              260                 265                 270
Lys Asn Ser Gly Lys Thr Pro His Leu Leu Met Leu Leu Pro Ser
        275                 280                 285
Tyr Arg Leu Glu Ser Gln Gln Thr Asn Arg Arg Lys Arg Ala Leu
        290                 295                 300
Asp Ala Ala Tyr Cys Phe Arg Asn Val Gln Asp Asn Cys Cys Leu Arg
305                 310                 315                 320
Pro Leu Tyr Ile Asp Phe Lys Arg Asp Leu Gly Trp Lys Trp Ile His
                    325                 330                 335
Glu Pro Lys Gly Tyr Asn Ala Asn Phe Cys Ala Gly Ala Cys Pro Tyr
                    340                 345                 350
Leu Trp Ser Ser Asp Thr Gln His Ser Arg Val Leu Ser Leu Tyr Asn
                355                 360                 365
Thr Ile Asn Pro Glu Ala Ser Ala Ser Pro Cys Cys Val Ser Gln Asp
            370                 375                 380
Leu Glu Pro Leu Thr Ile Leu Tyr Tyr Ile Gly Lys Thr Pro Lys Ile
385                 390                 395                 400
Glu Gln Leu Ser Asn Met Ile Val Lys Ser Cys Lys Cys Ser
                405                 410

<210> SEQ ID NO 294
<211> LENGTH: 412
<212> TYPE: PRT
<213> ORGANISM: Homo sapiens

<400> SEQUENCE: 294

Met Lys Met His Leu Gln Arg Ala Leu Val Val Leu Ala Leu Leu Asn
1               5                   10                  15
Phe Ala Thr Val Ser Leu Ser Leu Ser Thr Cys Thr Thr Leu Asp Phe
                20                  25                  30
Gly His Ile Lys Lys Lys Arg Val Glu Ala Ile Arg Gly Gln Ile Leu
            35                  40                  45
Ser Lys Leu Arg Leu Thr Ser Pro Pro Glu Pro Thr Val Met Thr His
        50                  55                  60
Val Pro Tyr Gln Val Leu Ala Leu Tyr Asn Ser Thr Arg Glu Leu Leu
65                  70                  75                  80
Glu Glu Met His Gly Glu Arg Glu Glu Gly Cys Thr Gln Glu Asn Thr
                85                  90                  95
Glu Ser Glu Tyr Tyr Ala Lys Glu Ile His Lys Phe Asp Met Ile Gln
                100                 105                 110
Gly Leu Ala Glu His Asn Glu Leu Ala Val Cys Pro Lys Gly Ile Thr
            115                 120                 125
Ser Lys Val Phe Arg Phe Asn Val Ser Ser Val Glu Lys Asn Arg Thr
        130                 135                 140
Asn Leu Phe Arg Ala Glu Phe Arg Val Leu Arg Val Pro Asn Pro Ser
145                 150                 155                 160
Ser Lys Arg Asn Glu Gln Arg Ile Glu Leu Phe Gln Ile Leu Arg Pro
                165                 170                 175
Asp Glu His Ile Ala Lys Gln Arg Tyr Ile Gly Gly Lys Asn Leu Pro
                180                 185                 190
Thr Arg Gly Thr Ala Glu Trp Leu Ser Phe Asp Val Thr Asp Thr Val
            195                 200                 205
Arg Glu Trp Leu Leu Arg Arg Glu Ser Asn Leu Gly Leu Glu Ile Ser
        210                 215                 220
```

-continued

```
Ile His Cys Pro Cys His Thr Phe Gln Pro Asn Gly Asp Ile Leu Glu
225                 230                 235                 240

Asn Ile His Glu Val Met Glu Ile Lys Phe Lys Gly Val Asp Asn Glu
            245                 250                 255

Asp Asp His Gly Arg Gly Asp Leu Gly Arg Leu Lys Lys Gln Lys Asp
        260                 265                 270

His His Asn Pro His Leu Ile Leu Met Met Ile Pro Pro His Arg Leu
    275                 280                 285

Asp Asn Pro Gly Gln Gly Gly Gln Arg Lys Lys Arg Ala Leu Asp Thr
290                 295                 300

Asn Tyr Cys Phe Arg Asn Leu Glu Glu Asn Cys Cys Val Arg Pro Leu
305                 310                 315                 320

Tyr Ile Asp Phe Arg Gln Asp Leu Gly Trp Lys Trp Val His Glu Pro
                325                 330                 335

Lys Gly Tyr Tyr Ala Asn Phe Cys Ser Gly Pro Cys Pro Tyr Leu Arg
            340                 345                 350

Ser Ala Asp Thr Thr His Ser Thr Val Leu Gly Leu Tyr Asn Thr Leu
        355                 360                 365

Asn Pro Glu Ala Ser Ala Ser Pro Cys Cys Val Pro Gln Asp Leu Glu
370                 375                 380

Pro Leu Thr Ile Leu Tyr Tyr Val Gly Arg Thr Pro Lys Val Glu Gln
385                 390                 395                 400

Leu Ser Asn Met Val Val Lys Ser Cys Lys Cys Ser
                405                 410

<210> SEQ ID NO 295
<211> LENGTH: 503
<212> TYPE: PRT
<213> ORGANISM: Homo sapiens

<400> SEQUENCE: 295

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
    50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
    130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190
```

-continued

Leu Pro Leu Leu Val Gln Arg Thr Ile Ala Arg Thr Ile Val Leu Gln
            195                 200                 205

Glu Ser Ile Gly Lys Gly Arg Phe Gly Glu Val Trp Arg Gly Lys Trp
        210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
    290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
    370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
        435                 440                 445

Lys Leu Arg Pro Asn Ile Pro Asn Arg Trp Gln Ser Cys Glu Ala Leu
    450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
            500

<210> SEQ ID NO 296
<211> LENGTH: 507
<212> TYPE: PRT
<213> ORGANISM: Homo sapiens

<400> SEQUENCE: 296

Met Glu Ala Ala Val Ala Ala Pro Arg Pro Arg Leu Leu Leu Leu Val
1               5                   10                  15

Leu Ala Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys

-continued

```
                50                  55                  60
Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Pro Phe Ser Val Lys Ser Pro Gly Leu Gly Pro Val
            115                 120                 125

Glu Leu Ala Ala Val Ile Ala Gly Pro Val Cys Phe Val Cys Ile Ser
130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                165                 170                 175

Glu Gly Thr Thr Leu Lys Asp Leu Ile Tyr Asp Met Thr Thr Ser Gly
            180                 185                 190

Ser Gly Ser Gly Leu Pro Leu Leu Val Gln Arg Thr Ile Ala Arg Thr
            195                 200                 205

Ile Val Leu Gln Glu Ser Ile Gly Lys Gly Arg Phe Gly Glu Val Trp
210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                245                 250                 255

Met Leu Arg His Glu Asn Ile Leu Gly Phe Ile Ala Ala Asp Asn Lys
            260                 265                 270

Asp Asn Gly Thr Trp Thr Gln Leu Trp Leu Val Ser Asp Tyr His Glu
            275                 280                 285

His Gly Ser Leu Phe Asp Tyr Leu Asn Arg Tyr Thr Val Thr Val Glu
        290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
            340                 345                 350

Ile Ala Asp Leu Gly Leu Ala Val Arg His Asp Ser Ala Thr Asp Thr
            355                 360                 365

Ile Asp Ile Ala Pro Asn His Arg Val Gly Thr Lys Arg Tyr Met Ala
        370                 375                 380

Pro Glu Val Leu Asp Asp Ser Ile Asn Met Lys His Phe Glu Ser Phe
385                 390                 395                 400

Lys Arg Ala Asp Ile Tyr Ala Met Gly Leu Val Phe Trp Glu Ile Ala
                405                 410                 415

Arg Arg Cys Ser Ile Gly Gly Ile His Glu Asp Tyr Gln Leu Pro Tyr
            420                 425                 430

Tyr Asp Leu Val Pro Ser Asp Pro Ser Val Glu Glu Met Arg Lys Val
            435                 440                 445

Val Cys Glu Gln Lys Leu Arg Pro Asn Ile Pro Asn Arg Trp Gln Ser
        450                 455                 460

Cys Glu Ala Leu Arg Val Met Ala Lys Ile Met Arg Glu Cys Trp Tyr
465                 470                 475                 480
```

Ala Asn Gly Ala Ala Arg Leu Thr Ala Leu Arg Ile Lys Lys Thr Leu
            485                 490                 495

Ser Gln Leu Ser Gln Gln Glu Gly Ile Lys Met
            500                 505

<210> SEQ ID NO 297
<211> LENGTH: 426
<212> TYPE: PRT
<213> ORGANISM: Homo sapiens

<400> SEQUENCE: 297

Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
            85                  90                  95

Thr Thr Tyr Cys Cys Asn Gln Asp His Cys Asn Lys Ile Glu Leu Pro
            100                 105                 110

Thr Thr Gly Leu Pro Leu Leu Val Gln Arg Thr Ile Ala Arg Thr Ile
            115                 120                 125

Val Leu Gln Glu Ser Ile Gly Lys Gly Arg Phe Gly Glu Val Trp Arg
130                 135                 140

Gly Lys Trp Arg Gly Glu Glu Val Ala Val Lys Ile Phe Ser Ser Arg
145                 150                 155                 160

Glu Glu Arg Ser Trp Phe Arg Glu Ala Glu Ile Tyr Gln Thr Val Met
            165                 170                 175

Leu Arg His Glu Asn Ile Leu Gly Phe Ile Ala Ala Asp Asn Lys Asp
            180                 185                 190

Asn Gly Thr Trp Thr Gln Leu Trp Leu Val Ser Asp Tyr His Glu His
            195                 200                 205

Gly Ser Leu Phe Asp Tyr Leu Asn Arg Tyr Thr Val Thr Val Glu Gly
            210                 215                 220

Met Ile Lys Leu Ala Leu Ser Thr Ala Ser Gly Leu Ala His Leu His
225                 230                 235                 240

Met Glu Ile Val Gly Thr Gln Gly Lys Pro Ala Ile Ala His Arg Asp
            245                 250                 255

Leu Lys Ser Lys Asn Ile Leu Val Lys Lys Asn Gly Thr Cys Cys Ile
            260                 265                 270

Ala Asp Leu Gly Leu Ala Val Arg His Asp Ser Ala Thr Asp Thr Ile
            275                 280                 285

Asp Ile Ala Pro Asn His Arg Val Gly Thr Lys Arg Tyr Met Ala Pro
            290                 295                 300

Glu Val Leu Asp Asp Ser Ile Asn Met Lys His Phe Glu Ser Phe Lys
305                 310                 315                 320

Arg Ala Asp Ile Tyr Ala Met Gly Leu Val Phe Trp Glu Ile Ala Arg
            325                 330                 335

Arg Cys Ser Ile Gly Gly Ile His Glu Asp Tyr Gln Leu Pro Tyr Tyr

```
                340                 345                 350
Asp Leu Val Pro Ser Asp Pro Ser Val Glu Glu Met Arg Lys Val Val
            355                 360                 365

Cys Glu Gln Lys Leu Arg Pro Asn Ile Pro Asn Arg Trp Gln Ser Cys
370                 375                 380

Glu Ala Leu Arg Val Met Ala Lys Ile Met Arg Glu Cys Trp Tyr Ala
385                 390                 395                 400

Asn Gly Ala Ala Arg Leu Thr Ala Leu Arg Ile Lys Lys Thr Leu Ser
                405                 410                 415

Gln Leu Ser Gln Gln Glu Gly Ile Lys Met
            420                 425

<210> SEQ ID NO 298
<211> LENGTH: 567
<212> TYPE: PRT
<213> ORGANISM: Homo sapiens

<400> SEQUENCE: 298

Met Gly Arg Gly Leu Arg Gly Leu Trp Pro Leu His Ile Val Leu
1                5                  10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
            260                 265                 270

Thr Val Ala Val Lys Ile Phe Pro Tyr Glu Glu Tyr Ala Ser Trp Lys
        275                 280                 285
```

```
Thr Glu Lys Asp Ile Phe Ser Asp Ile Asn Leu Lys His Glu Asn Ile
290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
        355                 360                 365

Gly Arg Pro Lys Met Pro Ile Val His Arg Asp Leu Lys Ser Ser Asn
370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Val Glu Ser Phe Lys Gln Thr Asp Val Tyr
        435                 440                 445

Ser Met Ala Leu Val Leu Trp Glu Met Thr Ser Arg Cys Asn Ala Val
450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 299
<211> LENGTH: 592
<212> TYPE: PRT
<213> ORGANISM: Homo sapiens

<400> SEQUENCE: 299

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95
```

```
Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
            115                 120                 125

Pro Lys Leu Pro Tyr His Asp Phe Ile Leu Glu Asp Ala Ala Ser Pro
            130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Val Ile Phe Gln Val
            180                 185                 190

Thr Gly Ile Ser Leu Leu Pro Pro Leu Gly Val Ala Ile Ser Val Ile
            195                 200                 205

Ile Ile Phe Tyr Cys Tyr Arg Val Asn Arg Gln Gln Lys Leu Ser Ser
            210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
            245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
            290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
            325                 330                 335

Glu Arg Lys Thr Glu Leu Gly Lys Gln Tyr Trp Leu Ile Thr Ala Phe
            340                 345                 350

His Ala Lys Gly Asn Leu Gln Glu Tyr Leu Thr Arg His Val Ile Ser
            355                 360                 365

Trp Glu Asp Leu Arg Lys Leu Gly Ser Ser Leu Ala Arg Gly Ile Ala
            370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
            405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
            435                 440                 445

Tyr Met Ala Pro Glu Val Leu Glu Ser Arg Met Asn Leu Glu Asn Val
            450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
            485                 490                 495

Pro Pro Phe Gly Ser Lys Val Arg Glu His Pro Cys Val Glu Ser Met
            500                 505                 510
```

```
Lys Asp Asn Val Leu Arg Asp Arg Gly Arg Pro Glu Ile Pro Ser Phe
            515                 520                 525

Trp Leu Asn His Gln Gly Ile Gln Met Val Cys Glu Thr Leu Thr Glu
        530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 300
<211> LENGTH: 137
<212> TYPE: PRT
<213> ORGANISM: Homo sapiens

<400> SEQUENCE: 300

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 301
<211> LENGTH: 136
<212> TYPE: PRT
<213> ORGANISM: Homo sapiens

<400> SEQUENCE: 301

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110
```

Cys Ser Cys Ser Ser Asp Glu Cys Asn Asp Asn Ile Ile Phe Ser Glu
            115                 120                 125

Glu Tyr Asn Thr Ser Asn Pro Asp
        130                 135

<210> SEQ ID NO 302
<211> LENGTH: 162
<212> TYPE: PRT
<213> ORGANISM: Homo sapiens

<400> SEQUENCE: 302

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 303
<211> LENGTH: 101
<212> TYPE: PRT
<213> ORGANISM: Homo sapiens

<400> SEQUENCE: 303

Gln Leu Cys Lys Phe Cys Asp Val Arg Phe Ser Thr Cys Asp Asn Gln
1               5                   10                  15

Lys Ser Cys Met Ser Asn Cys Ser Ile Thr Ser Ile Cys Glu Lys Pro
            20                  25                  30

Gln Glu Val Cys Val Ala Val Trp Arg Lys Asn Asp Glu Asn Ile Thr
        35                  40                  45

Leu Glu Thr Val Cys His Asp Pro Lys Leu Pro Tyr His Asp Phe Ile
    50                  55                  60

Leu Glu Asp Ala Ala Ser Pro Lys Cys Ile Met Lys Glu Lys Lys Lys
65                  70                  75                  80

Pro Gly Glu Thr Phe Phe Met Cys Ser Cys Ser Ser Asp Glu Cys Asn
                85                  90                  95

Asp Asn Ile Ile Phe
            100

<210> SEQ ID NO 304
<211> LENGTH: 93
<212> TYPE: PRT

<213> ORGANISM: Homo sapiens

<400> SEQUENCE: 304

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
        35                  40                  45

Arg Pro Phe Val Cys Ala Pro Ser Ser Lys Thr Gly Ser Val Thr Thr
    50                  55                  60

Thr Tyr Cys Cys Asn Gln Asp His Cys Asn Lys Ile Glu Leu Pro Thr
65                  70                  75                  80

Thr Val Lys Ser Ser Pro Gly Leu Gly Pro Val Glu Leu
                85                  90

<210> SEQ ID NO 305
<211> LENGTH: 79
<212> TYPE: PRT
<213> ORGANISM: Homo sapiens

<400> SEQUENCE: 305

Ala Leu Gln Cys Phe Cys His Leu Cys Thr Lys Asp Asn Phe Thr Cys
1               5                   10                  15

Val Thr Asp Gly Leu Cys Phe Val Ser Val Thr Glu Thr Thr Asp Lys
            20                  25                  30

Val Ile His Asn Ser Met Cys Ile Ala Glu Ile Asp Leu Ile Pro Arg
        35                  40                  45

Asp Arg Pro Phe Val Cys Ala Pro Ser Ser Lys Thr Gly Ser Val Thr
    50                  55                  60

Thr Thr Tyr Cys Cys Asn Gln Asp His Cys Asn Lys Ile Glu Leu
65                  70                  75

<210> SEQ ID NO 306
<211> LENGTH: 851
<212> TYPE: PRT
<213> ORGANISM: Homo sapiens

<400> SEQUENCE: 306

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
        115                 120                 125

Val Ser Glu Gly Ser Val Val Gln Phe Ser Ser Ala Asn Phe Ser Leu
    130                 135                 140

```
Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
            165                 170                 175

Leu Lys Ile Ala Arg Asn Ile Tyr Ile Lys Val Gly Glu Asp Gln Val
        180                 185                 190

Phe Pro Pro Lys Cys Asn Ile Gly Lys Asn Phe Leu Ser Leu Asn Tyr
    195                 200                 205

Leu Ala Glu Tyr Leu Gln Pro Lys Ala Ala Glu Gly Cys Val Met Ser
210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
        275                 280                 285

Lys Gly Ser Leu Lys Ile Ile Ala Pro Asn Ser Ile Gly Phe Gly Lys
    290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
            340                 345                 350

Leu Arg Leu Glu Asn Asn Ala Glu Glu Met Gly Asp Glu Glu Val His
        355                 360                 365

Thr Ile Pro Pro Glu Leu Arg Ile Leu Leu Asp Pro Gly Ala Leu Pro
370                 375                 380

Ala Leu Gln Asn Pro Pro Ile Arg Gly Gly Glu Gly Gln Asn Gly Gly
385                 390                 395                 400

Leu Pro Phe Pro Phe Pro Asp Ile Ser Arg Arg Val Trp Asn Glu Glu
                405                 410                 415

Gly Glu Asp Gly Leu Pro Arg Pro Lys Asp Pro Val Ile Pro Ser Ile
            420                 425                 430

Gln Leu Phe Pro Gly Leu Arg Glu Pro Glu Glu Val Gln Gly Ser Val
        435                 440                 445

Asp Ile Ala Leu Ser Val Lys Cys Asp Asn Glu Lys Met Ile Val Ala
    450                 455                 460

Val Glu Lys Asp Ser Phe Gln Ala Ser Gly Tyr Ser Gly Met Asp Val
465                 470                 475                 480

Thr Leu Leu Asp Pro Thr Cys Lys Ala Lys Met Asn Gly Thr His Phe
                485                 490                 495

Val Leu Glu Ser Pro Leu Asn Gly Cys Gly Thr Arg Pro Arg Trp Ser
            500                 505                 510

Ala Leu Asp Gly Val Val Tyr Tyr Asn Ser Ile Val Ile Gln Val Pro
        515                 520                 525

Ala Leu Gly Asp Ser Ser Gly Trp Pro Asp Gly Tyr Glu Asp Leu Glu
    530                 535                 540

Ser Gly Asp Asn Gly Phe Pro Gly Asp Met Asp Glu Gly Asp Ala Ser
545                 550                 555                 560
```

Leu Phe Thr Arg Pro Glu Ile Val Val Phe Asn Cys Ser Leu Gln Gln
                565                 570                 575

Val Arg Asn Pro Ser Ser Phe Gln Glu Gln Pro His Gly Asn Ile Thr
            580                 585                 590

Phe Asn Met Glu Leu Tyr Asn Thr Asp Leu Phe Leu Val Pro Ser Gln
            595                 600                 605

Gly Val Phe Ser Val Pro Glu Asn Gly His Val Tyr Val Glu Val Ser
        610                 615                 620

Val Thr Lys Ala Glu Gln Glu Leu Gly Phe Ala Ile Gln Thr Cys Phe
625                 630                 635                 640

Ile Ser Pro Tyr Ser Asn Pro Asp Arg Met Ser His Tyr Thr Ile Ile
                645                 650                 655

Glu Asn Ile Cys Pro Lys Asp Glu Ser Val Lys Phe Tyr Ser Pro Lys
            660                 665                 670

Arg Val His Phe Pro Ile Pro Gln Ala Asp Met Asp Lys Lys Arg Phe
        675                 680                 685

Ser Phe Val Phe Lys Pro Val Phe Asn Thr Ser Leu Leu Phe Leu Gln
        690                 695                 700

Cys Glu Leu Thr Leu Cys Thr Lys Met Glu Lys His Pro Gln Lys Leu
705                 710                 715                 720

Pro Lys Cys Val Pro Pro Asp Glu Ala Cys Thr Ser Leu Asp Ala Ser
                725                 730                 735

Ile Ile Trp Ala Met Met Gln Asn Lys Lys Thr Phe Thr Lys Pro Leu
            740                 745                 750

Ala Val Ile His His Glu Ala Glu Ser Lys Lys Gly Pro Ser Met
        755                 760                 765

Lys Glu Pro Asn Pro Ile Ser Pro Ile Phe His Gly Leu Asp Thr
770                 775                 780

Leu Thr Val Met Gly Ile Ala Phe Ala Ala Phe Val Ile Gly Ala Leu
785                 790                 795                 800

Leu Thr Gly Ala Leu Trp Tyr Ile Tyr Ser His Thr Gly Glu Thr Ala
                805                 810                 815

Gly Arg Gln Gln Val Pro Thr Ser Pro Pro Ala Ser Glu Asn Ser Ser
            820                 825                 830

Ala Ala His Ser Ile Gly Ser Thr Gln Ser Thr Pro Cys Ser Ser Ser
        835                 840                 845

Ser Thr Ala
    850

<210> SEQ ID NO 307
<211> LENGTH: 850
<212> TYPE: PRT
<213> ORGANISM: Homo sapiens

<400> SEQUENCE: 307

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

```
Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
        115                 120                 125

Val Ser Glu Gly Ser Val Val Gln Phe Ser Ser Ala Asn Phe Ser Leu
    130                 135                 140

Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
        195                 200                 205

Leu Ala Glu Tyr Leu Gln Pro Lys Ala Ala Glu Gly Cys Val Met Ser
    210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
        275                 280                 285

Lys Gly Ser Leu Lys Ile Ile Ala Pro Asn Ser Ile Gly Phe Gly Lys
    290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
            340                 345                 350

Leu Arg Leu Glu Asn Asn Glu Glu Met Gly Asp Glu Val His Thr
        355                 360                 365

Ile Pro Pro Glu Leu Arg Ile Leu Leu Asp Pro Gly Ala Leu Pro Ala
370                 375                 380

Leu Gln Asn Pro Pro Ile Arg Gly Gly Glu Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Val Gln Gly Ser Val Asp
        435                 440                 445

Ile Ala Leu Ser Val Lys Cys Asp Asn Glu Lys Met Ile Val Ala Val
    450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val
                485                 490                 495
```

```
Leu Glu Ser Pro Leu Asn Gly Cys Gly Thr Arg Pro Arg Trp Ser Ala
                500                 505                 510

Leu Asp Gly Val Val Tyr Tyr Asn Ser Ile Val Ile Gln Val Pro Ala
            515                 520                 525

Leu Gly Asp Ser Ser Gly Trp Pro Asp Gly Tyr Glu Asp Leu Glu Ser
        530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
            580                 585                 590

Asn Met Glu Leu Tyr Asn Thr Asp Leu Phe Leu Val Pro Ser Gln Gly
        595                 600                 605

Val Phe Ser Val Pro Glu Asn Gly His Val Tyr Val Glu Val Ser Val
610                 615                 620

Thr Lys Ala Glu Gln Leu Gly Phe Ala Ile Gln Thr Cys Phe Ile
625                 630                 635                 640

Ser Pro Tyr Ser Asn Pro Asp Arg Met Ser His Tyr Thr Ile Ile Glu
                645                 650                 655

Asn Ile Cys Pro Lys Asp Glu Ser Val Lys Phe Tyr Ser Pro Lys Arg
            660                 665                 670

Val His Phe Pro Ile Pro Gln Ala Asp Met Asp Lys Lys Arg Phe Ser
        675                 680                 685

Phe Val Phe Lys Pro Val Phe Asn Thr Ser Leu Leu Phe Leu Gln Cys
690                 695                 700

Glu Leu Thr Leu Cys Thr Lys Met Glu Lys His Pro Gln Lys Leu Pro
705                 710                 715                 720

Lys Cys Val Pro Pro Asp Glu Ala Cys Thr Ser Leu Asp Ala Ser Ile
                725                 730                 735

Ile Trp Ala Met Met Gln Asn Lys Lys Thr Phe Thr Lys Pro Leu Ala
            740                 745                 750

Val Ile His His Glu Ala Glu Ser Lys Glu Lys Gly Pro Ser Met Lys
        755                 760                 765

Glu Pro Asn Pro Ile Ser Pro Ile Phe His Gly Leu Asp Thr Leu
770                 775                 780

Thr Val Met Gly Ile Ala Phe Ala Ala Phe Val Ile Gly Ala Leu Leu
785                 790                 795                 800

Thr Gly Ala Leu Trp Tyr Ile Tyr Ser His Thr Gly Glu Thr Ala Gly
                805                 810                 815

Arg Gln Gln Val Pro Thr Ser Pro Pro Ala Ser Glu Asn Ser Ser Ala
            820                 825                 830

Ala His Ser Ile Gly Ser Thr Gln Ser Thr Pro Cys Ser Ser Ser Ser
        835                 840                 845

Thr Ala
    850

<210> SEQ ID NO 308
<211> LENGTH: 767
<212> TYPE: PRT
<213> ORGANISM: Homo sapiens

<400> SEQUENCE: 308

Gly Pro Glu Pro Gly Ala Leu Cys Glu Leu Ser Pro Val Ser Ala Ser
1               5                   10                  15
```

His Pro Val Gln Ala Leu Met Glu Ser Phe Thr Val Leu Ser Gly Cys
                20                  25                  30

Ala Ser Arg Gly Thr Thr Gly Leu Pro Gln Glu Val His Val Leu Asn
            35                  40                  45

Leu Arg Thr Ala Gly Gln Gly Pro Gly Gln Leu Gln Arg Glu Val Thr
50                  55                  60

Leu His Leu Asn Pro Ile Ser Ser Val His Ile His Lys Ser Val
65                  70                  75                  80

Val Phe Leu Leu Asn Ser Pro His Pro Leu Val Trp His Leu Lys Thr
                85                  90                  95

Glu Arg Leu Ala Thr Gly Val Ser Arg Leu Phe Leu Val Ser Glu Gly
                100                 105                 110

Ser Val Val Gln Phe Ser Ser Ala Asn Phe Ser Leu Thr Ala Glu Thr
            115                 120                 125

Glu Glu Arg Asn Phe Pro His Gly Asn Glu His Leu Leu Asn Trp Ala
130                 135                 140

Arg Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Lys
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Met Ser Ser Gln Pro Gln
            195                 200                 205

Asn Glu Glu Val His Ile Ile Glu Leu Ile Thr Pro Asn Ser Asn Pro
            210                 215                 220

Tyr Ser Ala Phe Gln Val Asp Ile Thr Ile Asp Ile Arg Pro Ser Gln
225                 230                 235                 240

Glu Asp Leu Glu Val Val Lys Asn Leu Ile Leu Ile Leu Lys Cys Lys
                245                 250                 255

Lys Ser Val Asn Trp Val Ile Lys Ser Phe Asp Val Lys Gly Ser Leu
            260                 265                 270

Lys Ile Ile Ala Pro Asn Ser Ile Gly Phe Gly Lys Glu Ser Glu Arg
            275                 280                 285

Ser Met Thr Met Thr Lys Ser Ile Arg Asp Asp Ile Pro Ser Thr Gln
290                 295                 300

Gly Asn Leu Val Lys Trp Ala Leu Asp Asn Gly Tyr Ser Pro Ile Thr
305                 310                 315                 320

Ser Tyr Thr Met Ala Pro Val Ala Asn Arg Phe His Leu Arg Leu Glu
                325                 330                 335

Asn Asn Ala Glu Glu Met Gly Asp Glu Val His Thr Ile Pro Pro
            340                 345                 350

Glu Leu Arg Ile Leu Leu Asp Pro Gly Ala Leu Pro Ala Leu Gln Asn
            355                 360                 365

Pro Pro Ile Arg Gly Gly Glu Gly Gln Asn Gly Leu Pro Phe Pro
            370                 375                 380

Phe Pro Asp Ile Ser Arg Arg Val Trp Asn Glu Glu Gly Glu Asp Gly
385                 390                 395                 400

Leu Pro Arg Pro Lys Asp Pro Val Ile Pro Ser Ile Gln Leu Phe Pro
                405                 410                 415

Gly Leu Arg Glu Pro Glu Glu Val Gln Gly Ser Val Asp Ile Ala Leu
            420                 425                 430

Ser Val Lys Cys Asp Asn Glu Lys Met Ile Val Ala Val Glu Lys Asp
435 440 445

Ser Phe Gln Ala Ser Gly Tyr Ser Gly Met Asp Val Thr Leu Leu Asp
450 455 460

Pro Thr Cys Lys Ala Lys Met Asn Gly Thr His Phe Val Leu Glu Ser
465 470 475 480

Pro Leu Asn Gly Cys Gly Thr Arg Pro Arg Trp Ser Ala Leu Asp Gly
485 490 495

Val Val Tyr Tyr Asn Ser Ile Val Ile Gln Val Pro Ala Leu Gly Asp
500 505 510

Ser Ser Gly Trp Pro Asp Gly Tyr Glu Asp Leu Glu Ser Gly Asp Asn
515 520 525

Gly Phe Pro Gly Asp Met Asp Glu Gly Asp Ala Ser Leu Phe Thr Arg
530 535 540

Pro Glu Ile Val Val Phe Asn Cys Ser Leu Gln Gln Val Arg Asn Pro
545 550 555 560

Ser Ser Phe Gln Glu Gln Pro His Gly Asn Ile Thr Phe Asn Met Glu
565 570 575

Leu Tyr Asn Thr Asp Leu Phe Leu Val Pro Ser Gln Gly Val Phe Ser
580 585 590

Val Pro Glu Asn Gly His Val Tyr Val Glu Val Ser Val Thr Lys Ala
595 600 605

Glu Gln Glu Leu Gly Phe Ala Ile Gln Thr Cys Phe Ile Ser Pro Tyr
610 615 620

Ser Asn Pro Asp Arg Met Ser His Tyr Thr Ile Ile Glu Asn Ile Cys
625 630 635 640

Pro Lys Asp Glu Ser Val Lys Phe Tyr Ser Pro Lys Arg Val His Phe
645 650 655

Pro Ile Pro Gln Ala Asp Met Asp Lys Lys Arg Phe Ser Phe Val Phe
660 665 670

Lys Pro Val Phe Asn Thr Ser Leu Leu Phe Leu Gln Cys Glu Leu Thr
675 680 685

Leu Cys Thr Lys Met Glu Lys His Pro Gln Lys Leu Pro Lys Cys Val
690 695 700

Pro Pro Asp Glu Ala Cys Thr Ser Leu Asp Ala Ser Ile Ile Trp Ala
705 710 715 720

Met Met Gln Asn Lys Lys Thr Phe Thr Lys Pro Leu Ala Val Ile His
725 730 735

His Glu Ala Glu Ser Lys Glu Lys Gly Pro Ser Met Lys Glu Pro Asn
740 745 750

Pro Ile Ser Pro Pro Ile Phe His Gly Leu Asp Thr Leu Thr Val
755 760 765

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317
<211> LENGTH: 361
<212> TYPE: PRT
<213> ORGANISM: Homo sapiens

<400> SEQUENCE: 317

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
```

```
                    165                 170                 175
Gln Trp Leu Ser Arg Gly Gly Glu Ile Glu Gly Phe Arg Leu Ser Ala
            180                 185                 190
His Cys Ser Cys Asp Ser Arg Asp Asn Thr Leu Gln Val Asp Ile Asn
            195                 200                 205
Gly Phe Thr Thr Gly Arg Arg Gly Asp Leu Ala Thr Ile His Gly Met
210                 215                 220
Asn Arg Pro Phe Leu Leu Leu Met Ala Thr Pro Leu Glu Arg Ala Gln
225                 230                 235                 240
His Leu Gln Ser Ser Arg His Arg Arg Ala Leu Asp Thr Asn Tyr Cys
            245                 250                 255
Phe Ser Ser Thr Glu Lys Asn Cys Cys Val Arg Gln Leu Tyr Ile Asp
            260                 265                 270
Phe Arg Lys Asp Leu Gly Trp Lys Trp Ile His Glu Pro Lys Gly Tyr
            275                 280                 285
His Ala Asn Phe Cys Leu Gly Pro Cys Pro Tyr Ile Trp Ser Leu Asp
            290                 295                 300
Thr Gln Tyr Ser Lys Val Leu Ala Leu Tyr Asn Gln His Asn Pro Gly
305                 310                 315                 320
Ala Ser Ala Ala Pro Cys Cys Val Pro Gln Ala Leu Glu Pro Leu Pro
            325                 330                 335
Ile Val Tyr Tyr Val Gly Arg Lys Pro Lys Val Glu Gln Leu Ser Asn
            340                 345                 350
Met Ile Val Arg Ser Cys Lys Cys Ser
            355                 360

<210> SEQ ID NO 318
<211> LENGTH: 394
<212> TYPE: PRT
<213> ORGANISM: Homo sapiens

<400> SEQUENCE: 318

Leu Ser Thr Cys Ser Thr Leu Asp Met Asp Gln Phe Met Arg Lys Arg
1               5                   10                  15
Ile Glu Ala Ile Arg Gly Gln Ile Leu Ser Lys Leu Lys Leu Thr Ser
            20                  25                  30
Pro Pro Glu Asp Tyr Pro Glu Pro Glu Glu Val Pro Pro Glu Val Ile
            35                  40                  45
Ser Ile Tyr Asn Ser Thr Arg Asp Leu Leu Gln Glu Lys Ala Ser Arg
        50                  55                  60
Arg Ala Ala Ala Cys Glu Arg Glu Arg Ser Asp Glu Glu Tyr Tyr Ala
65                  70                  75                  80
Lys Glu Val Tyr Lys Ile Asp Met Pro Pro Phe Phe Pro Ser Glu Asn
                85                  90                  95
Ala Ile Pro Pro Thr Phe Tyr Arg Pro Tyr Phe Arg Ile Val Arg Phe
            100                 105                 110
Asp Val Ser Ala Met Glu Lys Asn Ala Ser Asn Leu Val Lys Ala Glu
            115                 120                 125
Phe Arg Val Phe Arg Leu Gln Asn Pro Lys Ala Arg Val Pro Glu Gln
            130                 135                 140
Arg Ile Glu Leu Tyr Gln Ile Leu Lys Ser Lys Asp Leu Thr Ser Pro
145                 150                 155                 160
Thr Gln Arg Tyr Ile Asp Ser Lys Val Val Lys Thr Arg Ala Glu Gly
                165                 170                 175
```

-continued

```
Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
        195                 200                 205

Cys Thr Phe Val Pro Ser Asn Asn Tyr Ile Ile Pro Asn Lys Ser Glu
    210                 215                 220

Glu Leu Glu Ala Arg Phe Ala Gly Ile Asp Gly Thr Ser Thr Tyr Thr
225                 230                 235                 240

Ser Gly Asp Gln Lys Thr Ile Lys Ser Thr Arg Lys Lys Asn Ser Gly
                245                 250                 255

Lys Thr Pro His Leu Leu Met Leu Leu Pro Ser Tyr Arg Leu Glu
            260                 265                 270

Ser Gln Gln Thr Asn Arg Arg Lys Lys Arg Ala Leu Asp Ala Ala Tyr
        275                 280                 285

Cys Phe Arg Asn Val Gln Asp Asn Cys Cys Leu Arg Pro Leu Tyr Ile
    290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
                325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
        355                 360                 365

Thr Ile Leu Tyr Tyr Ile Gly Lys Thr Pro Lys Ile Glu Gln Leu Ser
    370                 375                 380

Asn Met Ile Val Lys Ser Cys Lys Cys Ser
385                 390

<210> SEQ ID NO 319
<211> LENGTH: 389
<212> TYPE: PRT
<213> ORGANISM: Homo sapiens

<400> SEQUENCE: 319

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Thr Val Met Thr His Val Pro Tyr Gln Val Leu Ala
        35                  40                  45

Leu Tyr Asn Ser Thr Arg Glu Leu Leu Glu Glu Met His Gly Glu Arg
    50                  55                  60

Glu Glu Gly Cys Thr Gln Glu Asn Thr Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Arg Thr Asn Leu Phe Arg Ala Glu Phe
        115                 120                 125

Arg Val Leu Arg Val Pro Asn Pro Ser Ser Lys Arg Asn Glu Gln Arg
    130                 135                 140

Ile Glu Leu Phe Gln Ile Leu Arg Pro Asp Glu His Ile Ala Lys Gln
145                 150                 155                 160
```

-continued

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
        195                 200                 205

Phe Gln Pro Asn Gly Asp Ile Leu Glu Asn Ile His Glu Val Met Glu
    210                 215                 220

Ile Lys Phe Lys Gly Val Asp Asn Glu Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Asn Pro Gly Gln Gly Gly
            260                 265                 270

Gln Arg Lys Lys Arg Ala Leu Asp Thr Asn Tyr Cys Phe Arg Asn Leu
        275                 280                 285

Glu Glu Asn Cys Cys Val Arg Pro Leu Tyr Ile Asp Phe Arg Gln Asp
    290                 295                 300

Leu Gly Trp Lys Trp Val His Glu Pro Lys Gly Tyr Tyr Ala Asn Phe
305                 310                 315                 320

Cys Ser Gly Pro Cys Pro Tyr Leu Arg Ser Ala Asp Thr Thr His Ser
                325                 330                 335

Thr Val Leu Gly Leu Tyr Asn Thr Leu Asn Pro Glu Ala Ser Ala Ser
            340                 345                 350

Pro Cys Cys Val Pro Gln Asp Leu Glu Pro Leu Thr Ile Leu Tyr Tyr
        355                 360                 365

Val Gly Arg Thr Pro Lys Val Glu Gln Leu Ser Asn Met Val Val Lys
    370                 375                 380

Ser Cys Lys Cys Ser
385

<210> SEQ ID NO 320
<211> LENGTH: 470
<212> TYPE: PRT
<213> ORGANISM: Homo sapiens

<400> SEQUENCE: 320

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
        35                  40                  45

Arg Pro Phe Val Cys Ala Pro Ser Ser Lys Thr Gly Ser Val Thr Thr
    50                  55                  60

Thr Tyr Cys Cys Asn Gln Asp His Cys Asn Lys Ile Glu Leu Pro Thr
65                  70                  75                  80

Thr Val Lys Ser Ser Pro Gly Leu Gly Pro Val Glu Leu Ala Ala Val
                85                  90                  95

Ile Ala Gly Pro Val Cys Phe Val Cys Ile Ser Leu Met Leu Met Val
            100                 105                 110

Tyr Ile Cys His Asn Arg Thr Val Ile His His Arg Val Pro Asn Glu
        115                 120                 125

Glu Asp Pro Ser Leu Asp Arg Pro Phe Ile Ser Glu Gly Thr Thr Leu

```
                130                 135                 140
Lys Asp Leu Ile Tyr Asp Met Thr Thr Ser Gly Ser Gly Ser Gly Leu
145                 150                 155                 160

Pro Leu Leu Val Gln Arg Thr Ile Ala Arg Thr Ile Val Leu Gln Glu
                165                 170                 175

Ser Ile Gly Lys Gly Arg Phe Gly Glu Val Trp Arg Gly Lys Trp Arg
            180                 185                 190

Gly Glu Glu Val Ala Val Lys Ile Phe Ser Ser Arg Glu Glu Arg Ser
        195                 200                 205

Trp Phe Arg Glu Ala Glu Ile Tyr Gln Thr Val Met Leu Arg His Glu
    210                 215                 220

Asn Ile Leu Gly Phe Ile Ala Ala Asp Asn Lys Asp Asn Gly Thr Trp
225                 230                 235                 240

Thr Gln Leu Trp Leu Val Ser Asp Tyr His Glu His Gly Ser Leu Phe
                245                 250                 255

Asp Tyr Leu Asn Arg Tyr Thr Val Thr Val Glu Gly Met Ile Lys Leu
            260                 265                 270

Ala Leu Ser Thr Ala Ser Gly Leu Ala His Leu His Met Glu Ile Val
        275                 280                 285

Gly Thr Gln Gly Lys Pro Ala Ile Ala His Arg Asp Leu Lys Ser Lys
    290                 295                 300

Asn Ile Leu Val Lys Lys Asn Gly Thr Cys Cys Ile Ala Asp Leu Gly
305                 310                 315                 320

Leu Ala Val Arg His Asp Ser Ala Thr Asp Thr Ile Asp Ile Ala Pro
                325                 330                 335

Asn His Arg Val Gly Thr Lys Arg Tyr Met Ala Pro Glu Val Leu Asp
            340                 345                 350

Asp Ser Ile Asn Met Lys His Phe Glu Ser Phe Lys Arg Ala Asp Ile
        355                 360                 365

Tyr Ala Met Gly Leu Val Phe Trp Glu Ile Ala Arg Arg Cys Ser Ile
    370                 375                 380

Gly Gly Ile His Glu Asp Tyr Gln Leu Pro Tyr Tyr Asp Leu Val Pro
385                 390                 395                 400

Ser Asp Pro Ser Val Glu Glu Met Arg Lys Val Val Cys Glu Gln Lys
                405                 410                 415

Leu Arg Pro Asn Ile Pro Asn Arg Trp Gln Ser Cys Glu Ala Leu Arg
            420                 425                 430

Val Met Ala Lys Ile Met Arg Glu Cys Trp Tyr Ala Asn Gly Ala Ala
        435                 440                 445

Arg Leu Thr Ala Leu Arg Ile Lys Lys Thr Leu Ser Gln Leu Ser Gln
    450                 455                 460

Gln Glu Gly Ile Lys Met
465                 470

<210> SEQ ID NO 321
<211> LENGTH: 474
<212> TYPE: PRT
<213> ORGANISM: Homo sapiens

<400> SEQUENCE: 321

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30
```

```
Ile His Asn Ser Met Cys Ile Ala Glu Ile Asp Leu Ile Pro Arg Asp
         35                  40                  45

Arg Pro Phe Val Cys Ala Pro Ser Ser Lys Thr Gly Ser Val Thr Thr
 50                  55                  60

Thr Tyr Cys Cys Asn Gln Asp His Cys Asn Lys Ile Glu Leu Pro Thr
 65                  70                  75                  80

Thr Gly Pro Phe Ser Val Lys Ser Ser Pro Gly Leu Gly Pro Val Glu
                 85                  90                  95

Leu Ala Ala Val Ile Ala Gly Pro Val Cys Phe Val Cys Ile Ser Leu
                100                 105                 110

Met Leu Met Val Tyr Ile Cys His Asn Arg Thr Val Ile His His Arg
            115                 120                 125

Val Pro Asn Glu Glu Asp Pro Ser Leu Asp Arg Pro Phe Ile Ser Glu
130                 135                 140

Gly Thr Thr Leu Lys Asp Leu Ile Tyr Asp Met Thr Thr Ser Gly Ser
145                 150                 155                 160

Gly Ser Gly Leu Pro Leu Leu Val Gln Arg Thr Ile Ala Arg Thr Ile
                165                 170                 175

Val Leu Gln Glu Ser Ile Gly Lys Gly Arg Phe Gly Glu Val Trp Arg
            180                 185                 190

Gly Lys Trp Arg Gly Glu Val Ala Val Lys Ile Phe Ser Ser Arg
            195                 200                 205

Glu Glu Arg Ser Trp Phe Arg Glu Ala Glu Ile Tyr Gln Thr Val Met
210                 215                 220

Leu Arg His Glu Asn Ile Leu Gly Phe Ile Ala Ala Asp Asn Lys Asp
225                 230                 235                 240

Asn Gly Thr Trp Thr Gln Leu Trp Leu Val Ser Asp Tyr His Glu His
                245                 250                 255

Gly Ser Leu Phe Asp Tyr Leu Asn Arg Tyr Thr Val Thr Val Glu Gly
                260                 265                 270

Met Ile Lys Leu Ala Leu Ser Thr Ala Ser Gly Leu Ala His Leu His
            275                 280                 285

Met Glu Ile Val Gly Thr Gln Gly Lys Pro Ala Ile Ala His Arg Asp
    290                 295                 300

Leu Lys Ser Lys Asn Ile Leu Val Lys Asn Gly Thr Cys Cys Ile
305                 310                 315                 320

Ala Asp Leu Gly Leu Ala Val Arg His Asp Ser Ala Thr Asp Thr Ile
                325                 330                 335

Asp Ile Ala Pro Asn His Arg Val Gly Thr Lys Arg Tyr Met Ala Pro
                340                 345                 350

Glu Val Leu Asp Asp Ser Ile Asn Met Lys His Phe Glu Ser Phe Lys
                355                 360                 365

Arg Ala Asp Ile Tyr Ala Met Gly Leu Val Phe Trp Glu Ile Ala Arg
370                 375                 380

Arg Cys Ser Ile Gly Gly Ile His Glu Asp Tyr Gln Leu Pro Tyr Tyr
385                 390                 395                 400

Asp Leu Val Pro Ser Asp Pro Ser Val Glu Glu Met Arg Lys Val Val
                405                 410                 415

Cys Glu Gln Lys Leu Arg Pro Asn Ile Pro Asn Arg Trp Gln Ser Cys
            420                 425                 430

Glu Ala Leu Arg Val Met Ala Lys Ile Met Arg Glu Cys Trp Tyr Ala
            435                 440                 445

Asn Gly Ala Ala Arg Leu Thr Ala Leu Arg Ile Lys Lys Thr Leu Ser
```

Gln Leu Ser Gln Gln Glu Gly Ile Lys Met
465                 470

<210> SEQ ID NO 322
<211> LENGTH: 393
<212> TYPE: PRT
<213> ORGANISM: Homo sapiens

<400> SEQUENCE: 322

Leu Gln Cys Phe Cys His Leu Cys Thr Lys Asp Asn Phe Thr Cys Val
1               5                   10                  15

Thr Asp Gly Leu Cys Phe Val Ser Val Thr Glu Thr Thr Asp Lys Val
            20                  25                  30

Ile His Asn Ser Met Cys Ile Ala Glu Ile Asp Leu Ile Pro Arg Asp
                35                  40                  45

Arg Pro Phe Val Cys Ala Pro Ser Ser Lys Thr Gly Ser Val Thr Thr
    50                  55                  60

Thr Tyr Cys Cys Asn Gln Asp His Cys Asn Lys Ile Glu Leu Pro Thr
65              70                  75                  80

Thr Gly Leu Pro Leu Leu Val Gln Arg Thr Ile Ala Arg Thr Ile Val
                85                  90                  95

Leu Gln Glu Ser Ile Gly Lys Gly Arg Phe Gly Glu Val Trp Arg Gly
            100                 105                 110

Lys Trp Arg Gly Glu Glu Val Ala Val Lys Ile Phe Ser Ser Arg Glu
        115                 120                 125

Glu Arg Ser Trp Phe Arg Glu Ala Glu Ile Tyr Gln Thr Val Met Leu
    130                 135                 140

Arg His Glu Asn Ile Leu Gly Phe Ile Ala Ala Asp Asn Lys Asp Asn
145                 150                 155                 160

Gly Thr Trp Thr Gln Leu Trp Leu Val Ser Asp Tyr His Glu His Gly
                165                 170                 175

Ser Leu Phe Asp Tyr Leu Asn Arg Tyr Thr Val Thr Val Glu Gly Met
            180                 185                 190

Ile Lys Leu Ala Leu Ser Thr Ala Ser Gly Leu Ala His Leu His Met
        195                 200                 205

Glu Ile Val Gly Thr Gln Gly Lys Pro Ala Ile Ala His Arg Asp Leu
    210                 215                 220

Lys Ser Lys Asn Ile Leu Val Lys Lys Asn Gly Thr Cys Cys Ile Ala
225                 230                 235                 240

Asp Leu Gly Leu Ala Val Arg His Asp Ser Ala Thr Asp Thr Ile Asp
                245                 250                 255

Ile Ala Pro Asn His Arg Val Gly Thr Lys Arg Tyr Met Ala Pro Glu
            260                 265                 270

Val Leu Asp Asp Ser Ile Asn Met Lys His Phe Glu Ser Phe Lys Arg
        275                 280                 285

Ala Asp Ile Tyr Ala Met Gly Leu Val Phe Trp Glu Ile Ala Arg Arg
    290                 295                 300

Cys Ser Ile Gly Gly Ile His Glu Asp Tyr Gln Leu Pro Tyr Tyr Asp
305                 310                 315                 320

Leu Val Pro Ser Asp Pro Ser Val Glu Glu Met Arg Lys Val Val Cys
                325                 330                 335

Glu Gln Lys Leu Arg Pro Asn Ile Pro Asn Arg Trp Gln Ser Cys Glu
            340                 345                 350

```
Ala Leu Arg Val Met Ala Lys Ile Met Arg Glu Cys Trp Tyr Ala Asn
            355                 360                 365

Gly Ala Ala Arg Leu Thr Ala Leu Arg Ile Lys Lys Thr Leu Ser Gln
    370                 375                 380

Leu Ser Gln Gln Glu Gly Ile Lys Met
385                 390

<210> SEQ ID NO 323
<211> LENGTH: 545
<212> TYPE: PRT
<213> ORGANISM: Homo sapiens

<400> SEQUENCE: 323

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Val Ile Phe Gln
    130                 135                 140

Val Thr Gly Ile Ser Leu Leu Pro Pro Leu Gly Val Ala Ile Ser Val
145                 150                 155                 160

Ile Ile Ile Phe Tyr Cys Tyr Arg Val Asn Arg Gln Gln Lys Leu Ser
                165                 170                 175

Ser Thr Trp Glu Thr Gly Lys Thr Arg Lys Leu Met Glu Phe Ser Glu
            180                 185                 190

His Cys Ala Ile Ile Leu Glu Asp Asp Arg Ser Asp Ile Ser Ser Thr
        195                 200                 205

Cys Ala Asn Asn Ile Asn His Asn Thr Glu Leu Leu Pro Ile Glu Leu
    210                 215                 220

Asp Thr Leu Val Gly Lys Gly Arg Phe Ala Glu Val Tyr Lys Ala Lys
225                 230                 235                 240

Leu Lys Gln Asn Thr Ser Glu Gln Phe Glu Thr Val Ala Val Lys Ile
                245                 250                 255

Phe Pro Tyr Glu Glu Tyr Ala Ser Trp Lys Thr Glu Lys Asp Ile Phe
            260                 265                 270

Ser Asp Ile Asn Leu Lys His Glu Asn Ile Leu Gln Phe Leu Thr Ala
        275                 280                 285

Glu Glu Arg Lys Thr Glu Leu Gly Lys Gln Tyr Trp Leu Ile Thr Ala
    290                 295                 300

Phe His Ala Lys Gly Asn Leu Gln Glu Tyr Leu Thr Arg His Val Ile
305                 310                 315                 320

Ser Trp Glu Asp Leu Arg Lys Leu Gly Ser Ser Leu Ala Arg Gly Ile
                325                 330                 335
```

```
Ala His Leu His Ser Asp His Thr Pro Cys Gly Arg Pro Lys Met Pro
                340                 345                 350

Ile Val His Arg Asp Leu Lys Ser Asn Ile Leu Val Lys Asn Asp
            355                 360                 365

Leu Thr Cys Cys Leu Cys Asp Phe Gly Leu Ser Leu Arg Leu Asp Pro
        370                 375                 380

Thr Leu Ser Val Asp Asp Leu Ala Asn Ser Gly Gln Val Gly Thr Ala
385                 390                 395                 400

Arg Tyr Met Ala Pro Glu Val Leu Glu Ser Arg Met Asn Leu Glu Asn
                405                 410                 415

Val Glu Ser Phe Lys Gln Thr Asp Val Tyr Ser Met Ala Leu Val Leu
            420                 425                 430

Trp Glu Met Thr Ser Arg Cys Asn Ala Val Gly Glu Val Lys Asp Tyr
        435                 440                 445

Glu Pro Pro Phe Gly Ser Lys Val Arg Glu His Pro Cys Val Glu Ser
    450                 455                 460

Met Lys Asp Asn Val Leu Arg Asp Arg Gly Arg Pro Glu Ile Pro Ser
465                 470                 475                 480

Phe Trp Leu Asn His Gln Gly Ile Gln Met Val Cys Glu Thr Leu Thr
                485                 490                 495

Glu Cys Trp Asp His Asp Pro Glu Ala Arg Leu Thr Ala Gln Cys Val
            500                 505                 510

Ala Glu Arg Phe Ser Glu Leu Glu His Leu Asp Arg Leu Ser Gly Arg
        515                 520                 525

Ser Cys Ser Glu Glu Lys Ile Pro Glu Asp Gly Ser Leu Asn Thr Thr
    530                 535                 540

Lys
545

<210> SEQ ID NO 324
<211> LENGTH: 570
<212> TYPE: PRT
<213> ORGANISM: Homo sapiens

<400> SEQUENCE: 324

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
```

```
            145                 150                 155                 160
        Pro Asp Leu Leu Leu Val Ile Phe Gln Val Thr Gly Ile Ser Leu Leu
                        165                 170                 175
        Pro Pro Leu Gly Val Ala Ile Ser Val Ile Ile Phe Tyr Cys Tyr
                        180                 185                 190
        Arg Val Asn Arg Gln Gln Lys Leu Ser Ser Thr Trp Glu Thr Gly Lys
                        195                 200                 205
        Thr Arg Lys Leu Met Glu Phe Ser Glu His Cys Ala Ile Ile Leu Glu
                        210                 215                 220
        Asp Asp Arg Ser Asp Ile Ser Ser Thr Cys Ala Asn Asn Ile Asn His
        225                 230                 235                 240
        Asn Thr Glu Leu Leu Pro Ile Glu Leu Asp Thr Leu Val Gly Lys Gly
                        245                 250                 255
        Arg Phe Ala Glu Val Tyr Lys Ala Lys Leu Lys Gln Asn Thr Ser Glu
                        260                 265                 270
        Gln Phe Glu Thr Val Ala Val Lys Ile Phe Pro Tyr Glu Glu Tyr Ala
                        275                 280                 285
        Ser Trp Lys Thr Glu Lys Asp Ile Phe Ser Asp Ile Asn Leu Lys His
                        290                 295                 300
        Glu Asn Ile Leu Gln Phe Leu Thr Ala Glu Glu Arg Lys Thr Glu Leu
        305                 310                 315                 320
        Gly Lys Gln Tyr Trp Leu Ile Thr Ala Phe His Ala Lys Gly Asn Leu
                        325                 330                 335
        Gln Glu Tyr Leu Thr Arg His Val Ile Ser Trp Glu Asp Leu Arg Lys
                        340                 345                 350
        Leu Gly Ser Ser Leu Ala Arg Gly Ile Ala His Leu His Ser Asp His
                        355                 360                 365
        Thr Pro Cys Gly Arg Pro Lys Met Pro Ile Val His Arg Asp Leu Lys
                        370                 375                 380
        Ser Ser Asn Ile Leu Val Lys Asn Asp Leu Thr Cys Cys Leu Cys Asp
        385                 390                 395                 400
        Phe Gly Leu Ser Leu Arg Leu Asp Pro Thr Leu Ser Val Asp Asp Leu
                        405                 410                 415
        Ala Asn Ser Gly Gln Val Gly Thr Ala Arg Tyr Met Ala Pro Glu Val
                        420                 425                 430
        Leu Glu Ser Arg Met Asn Leu Glu Asn Val Glu Ser Phe Lys Gln Thr
                        435                 440                 445
        Asp Val Tyr Ser Met Ala Leu Val Leu Trp Glu Met Thr Ser Arg Cys
                        450                 455                 460
        Asn Ala Val Gly Glu Val Lys Asp Tyr Glu Pro Pro Phe Gly Ser Lys
        465                 470                 475                 480
        Val Arg Glu His Pro Cys Val Glu Ser Met Lys Asp Asn Val Leu Arg
                        485                 490                 495
        Asp Arg Gly Arg Pro Glu Ile Pro Ser Phe Trp Leu Asn His Gln Gly
                        500                 505                 510
        Ile Gln Met Val Cys Glu Thr Leu Thr Glu Cys Trp Asp His Asp Pro
                        515                 520                 525
        Glu Ala Arg Leu Thr Ala Gln Cys Val Ala Glu Arg Phe Ser Glu Leu
                        530                 535                 540
        Glu His Leu Asp Arg Leu Ser Gly Arg Ser Cys Ser Glu Glu Lys Ile
        545                 550                 555                 560
        Pro Glu Asp Gly Ser Leu Asn Thr Thr Lys
                        565                 570
```

```
<210> SEQ ID NO 325
<211> LENGTH: 831
<212> TYPE: PRT
<213> ORGANISM: Homo sapiens

<400> SEQUENCE: 325

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
            20                  25                  30

Ala Ser Arg Gly Thr Thr Gly Leu Pro Gln Glu Val His Val Leu Asn
        35                  40                  45

Leu Arg Thr Ala Gly Gln Gly Pro Gly Gln Leu Gln Arg Glu Val Thr
    50                  55                  60

Leu His Leu Asn Pro Ile Ser Ser Val His Ile His His Lys Ser Val
65                  70                  75                  80

Val Phe Leu Leu Asn Ser Pro His Pro Leu Val Trp His Leu Lys Thr
                85                  90                  95

Glu Arg Leu Ala Thr Gly Val Ser Arg Leu Phe Leu Val Ser Glu Gly
            100                 105                 110

Ser Val Val Gln Phe Ser Ser Ala Asn Phe Ser Leu Thr Ala Glu Thr
        115                 120                 125

Glu Glu Arg Asn Phe Pro His Gly Asn Glu His Leu Leu Asn Trp Ala
    130                 135                 140

Arg Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Lys
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Met Ser Ser Gln Pro Gln
        195                 200                 205

Asn Glu Glu Val His Ile Ile Glu Leu Ile Thr Pro Asn Ser Asn Pro
    210                 215                 220

Tyr Ser Ala Phe Gln Val Asp Ile Thr Ile Asp Ile Arg Pro Ser Gln
225                 230                 235                 240

Glu Asp Leu Glu Val Val Lys Asn Leu Ile Leu Ile Leu Lys Cys Lys
                245                 250                 255

Lys Ser Val Asn Trp Val Ile Lys Ser Phe Asp Val Lys Gly Ser Leu
            260                 265                 270

Lys Ile Ile Ala Pro Asn Ser Ile Gly Phe Gly Lys Glu Ser Glu Arg
        275                 280                 285

Ser Met Thr Met Thr Lys Ser Ile Arg Asp Asp Ile Pro Ser Thr Gln
    290                 295                 300

Gly Asn Leu Val Lys Trp Ala Leu Asp Asn Gly Tyr Ser Pro Ile Thr
305                 310                 315                 320

Ser Tyr Thr Met Ala Pro Val Ala Asn Arg Phe His Leu Arg Leu Glu
                325                 330                 335

Asn Asn Ala Glu Glu Met Gly Asp Glu Val His Thr Ile Pro Pro
            340                 345                 350

Glu Leu Arg Ile Leu Leu Asp Pro Gly Ala Leu Pro Ala Leu Gln Asn
        355                 360                 365

Pro Pro Ile Arg Gly Gly Glu Gly Gln Asn Gly Gly Leu Pro Phe Pro
```

```
            370                 375                 380
Phe Pro Asp Ile Ser Arg Arg Val Trp Asn Glu Glu Gly Glu Asp Gly
385                 390                 395                 400

Leu Pro Arg Pro Lys Asp Pro Val Ile Pro Ser Ile Gln Leu Phe Pro
                405                 410                 415

Gly Leu Arg Glu Pro Glu Val Gln Gly Ser Val Asp Ile Ala Leu
                420                 425                 430

Ser Val Lys Cys Asp Asn Glu Lys Met Ile Val Ala Val Glu Lys Asp
                435                 440                 445

Ser Phe Gln Ala Ser Gly Tyr Ser Gly Met Asp Val Thr Leu Leu Asp
            450                 455                 460

Pro Thr Cys Lys Ala Lys Met Asn Gly Thr His Phe Val Leu Glu Ser
465                 470                 475                 480

Pro Leu Asn Gly Cys Gly Thr Arg Pro Arg Trp Ser Ala Leu Asp Gly
                485                 490                 495

Val Val Tyr Tyr Asn Ser Ile Val Ile Gln Val Pro Ala Leu Gly Asp
                500                 505                 510

Ser Ser Gly Trp Pro Asp Gly Tyr Glu Asp Leu Glu Ser Gly Asp Asn
            515                 520                 525

Gly Phe Pro Gly Asp Met Asp Glu Gly Asp Ala Ser Leu Phe Thr Arg
            530                 535                 540

Pro Glu Ile Val Val Phe Asn Cys Ser Leu Gln Gln Val Arg Asn Pro
545                 550                 555                 560

Ser Ser Phe Gln Glu Gln Pro His Gly Asn Ile Thr Phe Asn Met Glu
                565                 570                 575

Leu Tyr Asn Thr Asp Leu Phe Leu Val Pro Ser Gln Gly Val Phe Ser
            580                 585                 590

Val Pro Glu Asn Gly His Val Tyr Val Glu Val Ser Val Thr Lys Ala
            595                 600                 605

Glu Gln Glu Leu Gly Phe Ala Ile Gln Thr Cys Phe Ile Ser Pro Tyr
            610                 615                 620

Ser Asn Pro Asp Arg Met Ser His Tyr Thr Ile Ile Glu Asn Ile Cys
625                 630                 635                 640

Pro Lys Asp Glu Ser Val Lys Phe Tyr Ser Pro Lys Arg Val His Phe
                645                 650                 655

Pro Ile Pro Gln Ala Asp Met Asp Lys Lys Arg Phe Ser Phe Val Phe
                660                 665                 670

Lys Pro Val Phe Asn Thr Ser Leu Leu Phe Leu Gln Cys Glu Leu Thr
                675                 680                 685

Leu Cys Thr Lys Met Glu Lys His Pro Gln Lys Leu Pro Lys Cys Val
            690                 695                 700

Pro Pro Asp Glu Ala Cys Thr Ser Leu Asp Ala Ser Ile Ile Trp Ala
705                 710                 715                 720

Met Met Gln Asn Lys Lys Thr Phe Thr Lys Pro Leu Ala Val Ile His
                725                 730                 735

His Glu Ala Glu Ser Lys Glu Lys Gly Pro Ser Met Lys Glu Pro Asn
                740                 745                 750

Pro Ile Ser Pro Pro Ile Phe His Gly Leu Asp Thr Leu Thr Val Met
            755                 760                 765

Gly Ile Ala Phe Ala Ala Phe Val Ile Gly Ala Leu Leu Thr Gly Ala
            770                 775                 780

Leu Trp Tyr Ile Tyr Ser His Thr Gly Glu Thr Ala Gly Arg Gln Gln
785                 790                 795                 800
```

-continued

```
Val Pro Thr Ser Pro Pro Ala Ser Glu Asn Ser Ser Ala Ala His Ser
            805                 810                 815

Ile Gly Ser Thr Gln Ser Thr Pro Cys Ser Ser Ser Ser Thr Ala
            820                 825                 830

<210> SEQ ID NO 326
<211> LENGTH: 830
<212> TYPE: PRT
<213> ORGANISM: Homo sapiens

<400> SEQUENCE: 326

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
            20                  25                  30

Ala Ser Arg Gly Thr Thr Gly Leu Pro Gln Glu Val His Val Leu Asn
        35                  40                  45

Leu Arg Thr Ala Gly Gln Gly Pro Gly Gln Leu Gln Arg Glu Val Thr
    50                  55                  60

Leu His Leu Asn Pro Ile Ser Ser Val His Ile His His Lys Ser Val
65                  70                  75                  80

Val Phe Leu Leu Asn Ser Pro His Pro Leu Val Trp His Leu Lys Thr
                85                  90                  95

Glu Arg Leu Ala Thr Gly Val Ser Arg Leu Phe Leu Val Ser Glu Gly
            100                 105                 110

Ser Val Val Gln Phe Ser Ser Ala Asn Phe Ser Leu Thr Ala Glu Thr
        115                 120                 125

Glu Glu Arg Asn Phe Pro His Gly Asn Glu His Leu Leu Asn Trp Ala
    130                 135                 140

Arg Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Lys
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Met Ser Ser Gln Pro Gln
        195                 200                 205

Asn Glu Glu Val His Ile Ile Glu Leu Ile Thr Pro Asn Ser Asn Pro
    210                 215                 220

Tyr Ser Ala Phe Gln Val Asp Ile Thr Ile Asp Ile Arg Pro Ser Gln
225                 230                 235                 240

Glu Asp Leu Glu Val Val Lys Asn Leu Ile Leu Ile Leu Lys Cys Lys
                245                 250                 255

Lys Ser Val Asn Trp Val Ile Lys Ser Phe Asp Val Lys Gly Ser Leu
            260                 265                 270

Lys Ile Ile Ala Pro Asn Ser Ile Gly Phe Gly Lys Glu Ser Glu Arg
        275                 280                 285

Ser Met Thr Met Thr Lys Ser Ile Arg Asp Asp Ile Pro Ser Thr Gln
    290                 295                 300

Gly Asn Leu Val Lys Trp Ala Leu Asp Asn Gly Tyr Ser Pro Ile Thr
305                 310                 315                 320

Ser Tyr Thr Met Ala Pro Val Ala Asn Arg Phe His Leu Arg Leu Glu
                325                 330                 335

Asn Asn Glu Glu Met Gly Asp Glu Glu Val His Thr Ile Pro Pro Glu
```

```
              340                 345                 350
Leu Arg Ile Leu Leu Asp Pro Gly Ala Leu Ala Leu Gln Asn Pro
            355                 360                 365

Pro Ile Arg Gly Gly Glu Gly Gln Asn Gly Gly Leu Pro Phe Pro Phe
            370                 375                 380

Pro Asp Ile Ser Arg Arg Val Trp Asn Glu Glu Gly Glu Asp Gly Leu
385                 390                 395                 400

Pro Arg Pro Lys Asp Pro Val Ile Pro Ser Ile Gln Leu Phe Pro Gly
                405                 410                 415

Leu Arg Glu Pro Glu Glu Val Gln Gly Ser Val Asp Ile Ala Leu Ser
            420                 425                 430

Val Lys Cys Asp Asn Glu Lys Met Ile Val Ala Val Glu Lys Asp Ser
            435                 440                 445

Phe Gln Ala Ser Gly Tyr Ser Gly Met Asp Val Thr Leu Leu Asp Pro
            450                 455                 460

Thr Cys Lys Ala Lys Met Asn Gly Thr His Phe Val Leu Glu Ser Pro
465                 470                 475                 480

Leu Asn Gly Cys Gly Thr Arg Pro Arg Trp Ser Ala Leu Asp Gly Val
                485                 490                 495

Val Tyr Tyr Asn Ser Ile Val Ile Gln Val Pro Ala Leu Gly Asp Ser
            500                 505                 510

Ser Gly Trp Pro Asp Gly Tyr Glu Asp Leu Glu Ser Gly Asp Asn Gly
            515                 520                 525

Phe Pro Gly Asp Met Asp Glu Gly Asp Ala Ser Leu Phe Thr Arg Pro
            530                 535                 540

Glu Ile Val Val Phe Asn Cys Ser Leu Gln Gln Val Arg Asn Pro Ser
545                 550                 555                 560

Ser Phe Gln Glu Gln Pro His Gly Asn Ile Thr Phe Asn Met Glu Leu
                565                 570                 575

Tyr Asn Thr Asp Leu Phe Leu Val Pro Ser Gln Gly Val Phe Ser Val
            580                 585                 590

Pro Glu Asn Gly His Val Tyr Val Glu Val Ser Val Thr Lys Ala Glu
            595                 600                 605

Gln Glu Leu Gly Phe Ala Ile Gln Thr Cys Phe Ile Ser Pro Tyr Ser
            610                 615                 620

Asn Pro Asp Arg Met Ser His Tyr Thr Ile Ile Glu Asn Ile Cys Pro
625                 630                 635                 640

Lys Asp Glu Ser Val Lys Phe Tyr Ser Pro Lys Arg Val His Phe Pro
                645                 650                 655

Ile Pro Gln Ala Asp Met Asp Lys Lys Arg Phe Ser Phe Val Phe Lys
            660                 665                 670

Pro Val Phe Asn Thr Ser Leu Leu Phe Leu Gln Cys Glu Leu Thr Leu
            675                 680                 685

Cys Thr Lys Met Glu Lys His Pro Gln Lys Leu Pro Lys Cys Val Pro
            690                 695                 700

Pro Asp Glu Ala Cys Thr Ser Leu Asp Ala Ser Ile Ile Trp Ala Met
705                 710                 715                 720

Met Gln Asn Lys Lys Thr Phe Thr Lys Pro Leu Ala Val Ile His His
                725                 730                 735

Glu Ala Glu Ser Lys Glu Lys Gly Pro Ser Met Lys Glu Pro Asn Pro
            740                 745                 750

Ile Ser Pro Pro Ile Phe His Gly Leu Asp Thr Leu Thr Val Met Gly
            755                 760                 765
```

```
Ile Ala Phe Ala Ala Phe Val Ile Gly Ala Leu Leu Thr Gly Ala Leu
        770                 775                 780
Trp Tyr Ile Tyr Ser His Thr Gly Glu Thr Ala Gly Arg Gln Gln Val
785                 790                 795                 800
Pro Thr Ser Pro Pro Ala Ser Glu Asn Ser Ser Ala Ala His Ser Ile
                805                 810                 815
Gly Ser Thr Gln Ser Thr Pro Cys Ser Ser Ser Ser Thr Ala
            820                 825                 830
```

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370

-continued

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382
<400> SEQUENCE: 382
000

<210> SEQ ID NO 383
<400> SEQUENCE: 383
000

<210> SEQ ID NO 384
<400> SEQUENCE: 384
000

<210> SEQ ID NO 385
<400> SEQUENCE: 385
000

<210> SEQ ID NO 386
<400> SEQUENCE: 386
000

<210> SEQ ID NO 387
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<211> LENGTH: 481
<212> TYPE: PRT
<213> ORGANISM: Artificial Sequence
<220> FEATURE:

```
<223> OTHER INFORMATION: Description of Artificial Sequence: Synthetic
      polypeptide
<220> FEATURE:
<221> NAME/KEY: MOD_RES
<222> LOCATION: (330)..(330)
<223> OTHER INFORMATION: Lys or absent

<400> SEQUENCE: 392

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Cys Thr Leu Pro Pro Ser Arg Glu Glu
225                 230                 235                 240

Met Thr Lys Asn Gln Val Ser Leu Ser Cys Ala Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Val Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Xaa Gly Gly Gly Ser Gly
                325                 330                 335

Gly Gly Gly Ser Gly Gly Gly Ser Ile Pro His Val Gln Lys
            340                 345                 350

Ser Val Asn Asn Asp Met Ile Val Thr Asp Asn Asn Gly Ala Val Lys
        355                 360                 365

Phe Pro Gln Leu Cys Lys Phe Cys Asp Val Arg Phe Ser Thr Cys Asp
```

```
                 370                 375                 380
Asn Gln Lys Ser Cys Met Ser Asn Cys Ser Ile Thr Ser Ile Cys Glu
385                 390                 395                 400

Lys Pro Gln Glu Val Cys Val Ala Val Trp Arg Lys Asn Asp Glu Asn
                405                 410                 415

Ile Thr Leu Glu Thr Val Cys His Asp Pro Lys Leu Pro Tyr His Asp
                420                 425                 430

Phe Ile Leu Glu Asp Ala Ala Ser Pro Lys Cys Ile Met Lys Glu Lys
                435                 440                 445

Lys Lys Pro Gly Glu Thr Phe Phe Met Cys Ser Cys Ser Ser Asp Glu
                450                 455                 460

Cys Asn Asp Asn Ile Ile Phe Ser Glu Glu Tyr Asn Thr Ser Asn Pro
465                 470                 475                 480

Asp

<210> SEQ ID NO 393
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (330)..(330)
<223> OTHER INFORMATION: Lys or absent

<400> SEQUENCE: 393

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Cys Arg Glu Glu
225                 230                 235                 240

Met Thr Lys Asn Gln Val Ser Leu Trp Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Xaa Gly Gly Gly Ser Gly
            325                 330                 335

Gly Gly Gly Ser Gly Gly Gly Ser Ile Pro Pro His Val Gln Lys
            340                 345                 350

Ser Val Asn Asn Asp Met Ile Val Thr Asp Asn Asn Gly Ala Val Lys
    355                 360                 365

Phe Pro Gln Leu Cys Lys Phe Cys Asp Val Arg Phe Ser Thr Cys Asp
370                 375                 380

Asn Gln Lys Ser Cys Met Ser Asn Cys Ser Ile Thr Ser Ile Cys Glu
385                 390                 395                 400

Lys Pro Gln Glu Val Cys Val Ala Val Trp Arg Lys Asn Asp Glu Asn
                405                 410                 415

Ile Thr Leu Glu Thr Val Cys His Asp Pro Lys Leu Pro Tyr His Asp
            420                 425                 430

Phe Ile Leu Glu Asp Ala Ala Ser Pro Lys Cys Ile Met Lys Glu Lys
        435                 440                 445

Lys Lys Pro Gly Glu Thr Phe Phe Met Cys Ser Cys Ser Ser Asp Glu
    450                 455                 460

Cys Asn Asp Asn Ile Ile Phe Ser Glu Glu Tyr Asn Thr Ser Asn Pro
465                 470                 475                 480

Asp

<210> SEQ ID NO 394
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (227)..(227)
<223> OTHER INFORMATION: Lys or absent

<400> SEQUENCE: 394

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80
```

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Glu Glu Met Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Xaa Gly Gly Gly Ser Gly Gly Gly Ser Gly Gly Gly
225                 230                 235                 240

Gly Ser Ile Pro Pro His Val Gln Lys Ser Val Asn Asn Asp Met Ile
                245                 250                 255

Val Thr Asp Asn Asn Gly Ala Val Lys Phe Pro Gln Leu Cys Lys Phe
            260                 265                 270

Cys Asp Val Arg Phe Ser Thr Cys Asp Asn Gln Lys Ser Cys Met Ser
        275                 280                 285

Asn Cys Ser Ile Thr Ser Ile Cys Glu Lys Pro Gln Glu Val Cys Val
    290                 295                 300

Ala Val Trp Arg Lys Asn Asp Glu Asn Ile Thr Leu Glu Thr Val Cys
305                 310                 315                 320

His Asp Pro Lys Leu Pro Tyr His Asp Phe Ile Leu Glu Asp Ala Ala
                325                 330                 335

Ser Pro Lys Cys Ile Met Lys Glu Lys Lys Pro Gly Glu Thr Phe
            340                 345                 350

Phe Met Cys Ser Cys Ser Ser Asp Glu Cys Asn Asp Asn Ile Ile Phe
        355                 360                 365

Ser Glu Glu Tyr Asn Thr Ser Asn Pro Asp
    370                 375

<210> SEQ ID NO 395
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (227)..(227)
<223> OTHER INFORMATION: Lys or absent

<400> SEQUENCE: 395

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Glu Glu Met Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Xaa Gly Gly Gly Ser Gly Gly Gly Ser Gly Gly
225                 230                 235                 240

Gly Ser Ile Pro Pro His Val Gln Lys Ser Val Asn Asn Asp Met Ile
                245                 250                 255

Val Thr Asp Asn Asn Gly Ala Val Lys Phe Pro Gln Leu Cys Lys Phe
            260                 265                 270

Cys Asp Val Arg Phe Ser Thr Cys Asp Asn Gln Lys Ser Cys Met Ser
        275                 280                 285

Asn Cys Ser Ile Thr Ser Ile Cys Glu Lys Pro Gln Glu Val Cys Val
290                 295                 300

Ala Val Trp Arg Lys Asn Asp Glu Asn Ile Thr Leu Glu Thr Val Cys
305                 310                 315                 320

His Asp Pro Lys Leu Pro Tyr His Asp Phe Ile Leu Glu Asp Ala Ala
                325                 330                 335

Ser Pro Lys Cys Ile Met Lys Glu Lys Lys Lys Pro Gly Glu Thr Phe
            340                 345                 350

Phe Met Cys Ser Cys Ser Ser Asp Glu Cys Asn Asp Asn Ile Ile Phe
        355                 360                 365

Ser Glu Glu Tyr Asn Thr Ser Asn Pro Asp
370                 375

<210> SEQ ID NO 396
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (481)..(481)
<223> OTHER INFORMATION: Lys or absent

```
<400> SEQUENCE: 396

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65              70                  75                  80

Pro Lys Leu Pro Tyr His Asp Phe Ile Leu Glu Asp Ala Ala Ser Pro
            85                  90                  95

Lys Cys Ile Met Lys Glu Lys Lys Pro Gly Glu Thr Phe Phe Met
        100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Arg Val Glu Pro Lys Ser Cys Asp Lys
                245                 250                 255

Thr His Thr Cys Pro Pro Cys Pro Ala Pro Glu Leu Leu Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Cys Thr
    370                 375                 380

Leu Pro Pro Ser Arg Glu Glu Met Thr Lys Asn Gln Val Ser Leu Ser
385                 390                 395                 400

Cys Ala Val Lys Gly Phe Tyr Pro Ser Asp Ile Ala Val Glu Trp Glu
                405                 410                 415
```

Ser Asn Gly Gln Pro Glu Asn Asn Tyr Lys Thr Thr Pro Pro Val Leu
            420                 425                 430

Asp Ser Asp Gly Ser Phe Phe Leu Val Ser Lys Leu Thr Val Asp Lys
            435                 440                 445

Ser Arg Trp Gln Gln Gly Asn Val Phe Ser Cys Ser Val Met His Glu
450                 455                 460

Ala Leu His Asn His Tyr Thr Gln Lys Ser Leu Ser Leu Ser Pro Gly
465                 470                 475                 480

Xaa

<210> SEQ ID NO 397
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (481)..(481)
<223> OTHER INFORMATION: Lys or absent

<400> SEQUENCE: 397

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Ser Gly Gly Gly
    130                 135                 140

Gly Ser Gly Gly Gly Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
            180                 185                 190

Asn Ser Gly Ala Leu Thr Ser Gly Val His Thr Phe Pro Ala Val Leu
        195                 200                 205

Gln Ser Ser Gly Leu Tyr Ser Leu Ser Val Val Thr Val Pro Ser
    210                 215                 220

Ser Ser Leu Gly Thr Gln Thr Tyr Ile Cys Asn Val Asn His Lys Pro
225                 230                 235                 240

Ser Asn Thr Lys Val Asp Lys Arg Val Glu Pro Lys Ser Cys Asp Lys
                245                 250                 255

Thr His Thr Cys Pro Pro Cys Pro Ala Pro Glu Leu Leu Gly Gly Pro

```
              260                 265                 270
Ser Val Phe Leu Phe Pro Pro Lys Pro Lys Asp Thr Leu Met Ile Ser
            275                 280                 285

Arg Thr Pro Glu Val Thr Cys Val Val Asp Val Ser His Glu Asp
290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Cys Arg Glu Glu Met Thr Lys Asn Gln Val Ser Leu Trp
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Xaa

<210> SEQ ID NO 398
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
        115                 120                 125

Glu Tyr Asn Thr Ser Asn Pro Asp Gly Gly Gly Gly Ser Gly Gly Gly
```

```
              130                 135                 140
Gly Ser Gly Gly Gly Ser Gly Gln Pro Lys Ala Asn Pro Thr Val
145                 150                 155                 160

Thr Leu Phe Pro Pro Ser Ser Glu Glu Leu Gln Ala Asn Lys Ala Thr
                165                 170                 175

Leu Val Cys Leu Ile Ser Asp Phe Tyr Pro Gly Ala Val Thr Val Ala
            180                 185                 190

Trp Lys Ala Asp Gly Ser Pro Val Lys Ala Gly Val Glu Thr Thr Lys
                195                 200                 205

Pro Ser Lys Gln Ser Asn Asn Lys Tyr Ala Ala Ser Ser Tyr Leu Ser
    210                 215                 220

Leu Thr Pro Glu Gln Trp Lys Ser His Arg Ser Tyr Ser Cys Gln Val
225                 230                 235                 240

Thr His Glu Gly Ser Thr Val Glu Lys Thr Val Ala Pro Thr Glu Cys
                245                 250                 255

Ser
```

<210> SEQ ID NO 399
<211> LENGTH: 258
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

```
Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
                20                  25                  30

Val Arg Phe Ser Thr Cys Asp Asn Gln Lys Ser Cys Met Ser Asn Cys
            35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp Gly Gly Gly Ser Gly Gly Gly
    130                 135                 140

Gly Ser Gly Gly Gly Gly Ser Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
                195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
```

```
225                 230                 235                 240
Thr His Gln Gly Leu Ser Ser Pro Val Thr Lys Ser Phe Asn Arg Gly
                245                 250                 255

Glu Cys

<210> SEQ ID NO 400
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (2)..(26)
<223> OTHER INFORMATION: This region may encompass 2-5 "Glu Ala Ala Ala
      Lys" repeating units

<400> SEQUENCE: 400

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
                20                  25
```

MULTIFUNCTIONAL MOLECULES THAT BIND TO CALRETICULIN AND USES THEREOF

RELATED APPLICATIONS

This application is a U.S. National Phase Application under 35 U.S.C. § 371 of International Application No. PCT/US2019/022282, filed Mar. 14, 2019, which claims priority to U.S. Ser. No. 62/642,647 filed Mar. 14, 2018, the contents of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 6, 2019, is named.53671-726-831_SL, txt and is 7,101,367 bytes in size.

BACKGROUND

Myeloproliferative neoplasms (MPNs) are a group of conditions that cause blood cells to grow abnormally in the bone marrow. Common myeloproliferative neoplasms include primary or idiopathic myelofibrosis (MF), essential thrombocytosis (ET), polycythemia vera (PV), and chronic myelogenous leukemia (CML). Primary myelofibrosis is a chronic blood cancer in which excessive scar tissue forms in the bone marrow and impairs its ability to produce normal blood cells. Given the ongoing need for improved treatment of myeloproliferative neoplasms such as myelofibrosis, new compositions and treatments targeting myeloproliferative neoplasms are highly desirable.

SUMMARY OF THE INVENTION

The disclosure relates, inter alia, to novel multispecific or multifunctional molecules that include (i) an antigen binding domain that binds to a calreticulin mutant protein; and one, two or all of: (ii) an immune cell engager (e.g., chosen from an NK cell engager, a T cell engager, a B cell engager, a dendritic cell engager, or a macrophage cell engager); (iii) a cytokine molecule or a modulator of a cytokine molecule; and/or (iv) a stromal modifying moiety. The terms "multi-specific" or "multifunctional" are used interchangeably herein.

Without wishing to be bound by theory, the multispecific or multifunctional molecules disclosed herein are expected to target (e.g., localize, bridge and/or activate) an immune cell (e.g., an immune effector cell chosen from an NK cell, a T cell, a B cell, a dendritic cell or a macrophage), at a target cell, e.g., a cancer cell, expressing a calreticulin mutant protein, and/or alter the tumor stroma, e.g., alter the tumor microenvironment near the cancer site. Increasing the proximity and/or activity of the immune cell using the multispecific molecules described herein is expected to enhance an immune response against the target cell (e.g., the cancer cell), thereby providing a more effective therapy (e.g., a more effective cancer therapy). Without being bound by theory, a targeted, localized immune response against the target cell (e.g., the cancer cell) is believed to reduce the effects of systemic toxicity of the multispecific molecules described herein.

Accordingly, provided herein are, inter alia, multispecific molecules (e.g., multispecific or multifunctional antibody molecules) that include the aforesaid moieties, nucleic acids encoding the same, methods of producing the aforesaid molecules, and methods of treating a cancer using the aforesaid molecules.

Accordingly, in one aspect, the disclosure features a multifunctional molecule (e.g., polypeptide or nucleic acid encoding the same) that includes:
  (i) a first antigen binding domain that preferentially binds to a first calreticulin mutant protein over a wild type calreticulin protein,
  and
  (ii) one, two, or all of:
    (a) an immune cell engager chosen from a T cell engager, an NK cell engager, a B cell engager, a dendritic cell engager, or a macrophage cell engager;
    (b) a cytokine molecule or a modulator of a cytokine molecule; and
    (c) a stromal modifying moiety In some embodiments, the first calreticulin mutant protein comprises the amino acid sequence of SEQ ID NO: 141. In some embodiments, the wild type calreticulin protein comprises the amino acid sequence of SEQ ID NO: 140.

In some embodiments, the first antigen binding domain comprises a heavy chain variable region (VH) comprising a heavy chain complementarity determining region 1 (VHCDR1) amino acid sequence of SEQ ID NO: 107, a VHCDR2 amino acid sequence of SEQ ID NO: 243, and a VHCDR3 amino acid sequence of SEQ ID NO: 109, and a light chain variable region (VL) comprising a light chain complementarity determining region 1 (VLCDR1) amino acid sequence of SEQ ID NO: 113, a VLCDR2 amino acid sequence of SEQ ID NO: 114, and/or a VLCDR3 amino acid sequence of SEQ ID NO: 115.

In some embodiments, the first antigen binding domain comprises a heavy chain variable region (VH) comprising a heavy chain framework region 1 (VHFWR1) amino acid sequence of SEQ ID NO: 80, a VHFWR2 amino acid sequence of SEQ ID NO: 81, a VHFWR3 amino acid sequence of SEQ ID NO: 82, or a VHFWR4 amino acid sequence of SEQ ID NO: 83. In some embodiments, the first antigen binding domain comprises a heavy chain variable region (VH) comprising a heavy chain framework region 1 (VHFWR1) amino acid sequence of SEQ ID NO: 84, a VHFWR2 amino acid sequence of SEQ ID NO: 85, a VHFWR3 amino acid sequence of SEQ ID NO: 86, or a VHFWR4 amino acid sequence of SEQ ID NO: 83. In some embodiments, the first antigen binding domain comprises a light chain variable region (VL) comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, or a VLFWR4 amino acid sequence of SEQ ID NO: 90.

In some embodiments, the first calreticulin mutant protein comprises an amino acid sequence chosen from SEQ ID NOs: 142-168. In some embodiments, the first calreticulin mutant protein comprises an amino acid sequence chosen from SEQ ID NOs: 169-204. In some embodiments, the first calreticulin mutant protein is a calreticulin mutant protein disclosed in Table 2 or 3. In some embodiments, the first calreticulin mutant protein comprises the amino acid sequence of SEQ ID NO: 142. In some embodiments, the first calreticulin mutant protein comprises the amino acid sequence of SEQ ID NO: 169. In some embodiments, the first calreticulin mutant protein comprises the amino acid sequence of SEQ ID NO: 143. In some embodiments, the first calreticulin mutant protein comprises the amino acid sequence of SEQ ID NO: 170.

In some embodiments, the multifunctional molecule further comprising a second antigen binding domain that preferentially binds to a second calreticulin mutant protein over a wild type calreticulin protein. In some embodiments, the second calreticulin mutant protein comprises the amino acid sequence of SEQ ID NO: 141. In some embodiments, the second antigen binding domain is different from the first antigen binding domain. In some embodiments, the second antigen binding domain is the same as the first antigen binding domain. In some embodiments, the second calreticulin mutant protein comprises an amino acid sequence chosen from SEQ ID NOs: 142-168. In some embodiments, the second calreticulin mutant protein comprises an amino acid sequence chosen from SEQ ID NOs: 169-204. In some embodiments, the second calreticulin mutant protein is a calreticulin mutant protein disclosed in Table 2 or 3. In some embodiments, the second calreticulin mutant protein comprises the amino acid sequence of SEQ ID NO: 142. In some embodiments, the second calreticulin mutant protein comprises the amino acid sequence of SEQ ID NO: 169. In some embodiments, the second calreticulin mutant protein comprises the amino acid sequence of SEQ ID NO: 143. In some embodiments, the second calreticulin mutant protein comprises the amino acid sequence of SEQ ID NO: 170.

In some embodiments, the first calreticulin mutant protein is a Type 1 calreticulin mutant protein, and the second calreticulin mutant protein is a Type 2 calreticulin mutant protein. In some embodiments, the first calreticulin mutant protein comprises the amino acid sequence of SEQ ID NO: 142, and the second calreticulin mutant protein comprises the amino acid sequence of SEQ ID NO: 143. In some embodiments, the first calreticulin mutant protein comprises the amino acid sequence of SEQ ID NO: 169, and the first calreticulin mutant protein comprises the amino acid sequence of SEQ ID NO: 170.

In some embodiments, the wild type calreticulin protein comprises the amino acid sequence of SEQ ID NO: 140.

In some embodiments, the first antigen binding domain has a higher affinity for the first calreticulin mutant protein than for the wild type calreticulin protein. In some embodiments, the Kp for the binding between the first antigen binding domain and the first calreticulin mutant protein is no more than 40%, 30%, 20%, 10%, 1%, 0.1%, or 0.01% of the Kp for the binding between the first antigen binding domain and the wild type calreticulin protein. In some embodiments, the first antigen binding domain binds to an epitope located within the C-terminus of the first calreticulin mutant protein. In some embodiments, the first antigen binding domain binds to an epitope located within the amino acid sequence of SEQ ID NO: 141. In some embodiments, the first antigen binding domain does not bind to the wild type calreticulin protein. In some embodiments, the wild type calreticulin protein comprises the amino acid sequence of SEQ ID NO: 140.

In some embodiments, the second antigen binding domain has a higher affinity for the second calreticulin mutant protein than for the wild type calreticulin protein. In some embodiments, the Kp for the binding between the second antigen binding domain and the second calreticulin mutant protein is no more than 40%, 30%, 20%, 10%, 1%, 0.1%, or 0.01% of the Kp for the binding between the second antigen binding domain and the wild type calreticulin protein. In some embodiments, the second antigen binding domain binds to an epitope located within the C-terminus of the second calreticulin mutant protein. In some embodiments, the second antigen binding domain binds to an epitope located within the amino acid sequence of SEQ ID NO: 141.

In some embodiments, the second antigen binding domain does not bind to the wild type calreticulin protein. In some embodiments, the wild type calreticulin protein comprises the amino acid sequence of SEQ ID NO: 140.

In some embodiments, the multifunctional molecule preferentially binds to a myeloproliferative neoplasm cell over a non-tumor cell. In some embodiments, the binding between the multifunctional molecule and the myeloproliferative neoplasm cell is more than 10, 20, 30, 40, 50-fold greater than the binding between the multifunctional molecule and a non-tumor cell. In some embodiments, the myeloproliferative neoplasm cell is chosen from a myelofibrosis cell, an essential thrombocythemia cell, a polycythemia vera cell, or a chronic myeloid cancer cell. In some embodiments, the myeloproliferative neoplasm cell does not comprise a JAK2 V617F mutation. In some embodiments, the myeloproliferative neoplasm cell does not comprise a MPL mutation.

In some embodiments, the first and/or second antigen binding domain comprises a heavy chain variable region (VH) comprising a heavy chain complementarity determining region 1 (VHCDR1) amino acid sequence of SEQ ID NO: 107, a VHCDR2 amino acid sequence of SEQ ID NO: 243, and a VHCDR3 amino acid sequence of SEQ ID NO: 109, and a light chain variable region (VL) comprising a light chain complementarity determining region 1 (VLCDR1) amino acid sequence of SEQ ID NO: 113, a VLCDR2 amino acid sequence of SEQ ID NO: 114, and/or a VLCDR3 amino acid sequence of SEQ ID NO: 115. In some embodiments, the first and/or second antigen binding domain comprises a VH comprising the amino acid sequence of SEQ ID NO: 244 or an amino acid sequence having at least about 80%, 85%, 90%, 95%, or 99% sequence identity thereto. In some embodiments, the first and/or second antigen binding domain comprises a VL comprising the amino acid sequence of SEQ ID NO: 245 or an amino acid sequence having at least about 90%, 95%, or 99% sequence identity thereto. In some embodiments, the first and/or second antigen binding domain comprises a VH comprising the amino acid sequence of SEQ ID NO: 244 and a VL comprising the amino acid sequence of SEQ ID NO: 245. In some embodiments, the first and/or second antigen binding domain comprises a VH comprising the amino acid sequence of SEQ ID NO: 233, 234, 235, 236, or 237, or an amino acid sequence having at least about 80%, 85%, 90%, 95%, or 99% sequence identity thereto. In some embodiments, the first and/or second antigen binding domain comprises a VL comprising the amino acid sequence of SEQ ID NO: 238, 239, 240, 241, or 242, or an amino acid sequence having at least about 90%, 95%, or 99% sequence identity thereto. In some embodiments, the first and/or second antigen binding domain comprises a VH comprising any one of SEQ ID NOs: 233, 234, 235, 236, and 237 and a VL comprising any one of SEQ ID NOs: 238, 239, 240, 241, and 242. In some embodiments, the first and/or second antigen binding domain comprises a VH comprising the amino acid sequence of SEQ ID NO: 236 (or an amino acid sequence having at least about 80%, 85%, 90%, 95%, or 99% sequence identity thereto) and a VL comprising the amino acid sequence of SEQ ID NO: 238 (or an amino acid sequence having at least about 90%, 95%, or 99% sequence identity thereto). In some embodiments, the first and/or second antigen binding domain comprises a VH comprising the amino acid sequence of SEQ ID NO: 236 and a VL comprising the amino acid sequence of SEQ ID NO: 238.

In some embodiments, the first and/or second antigen binding domain comprises a heavy chain variable region (VH) comprising a heavy chain complementarity determining region 1 (VHCDR1) amino acid sequence of SEQ ID NO: 107 (or a sequence with no more than 1, 2, 3, or 4 mutations, e.g., substitutions, additions, or deletions), a VHCDR2 amino acid sequence of SEQ ID NO: 108 (or a sequence with no more than 1, 2, 3, or 4 mutations, e.g., substitutions, additions, or deletions), and/or a VHCDR3 amino acid sequence of SEQ ID NO: 109 (or a sequence with no more than 1, 2, 3, or 4 mutations, e.g., substitutions, additions, or deletions). In some embodiments, the first and/or second antigen binding domain comprises a light chain variable region (VL) comprising a light chain complementarity determining region 1 (VLCDR1) amino acid sequence of SEQ ID NO: 113 (or a sequence with no more than 1, 2, 3, or 4 mutations, e.g., substitutions, additions, or deletions), a VLCDR2 amino acid sequence of SEQ ID NO: 114 (or a sequence with no more than 1, 2, 3, or 4 mutations, e.g., substitutions, additions, or deletions), and/or a VLCDR3 amino acid sequence of SEQ ID NO: 115 (or a sequence with no more than 1, 2, 3, or 4 mutations, e.g., substitutions, additions, or deletions).

In some embodiments, the first and/or second antigen binding domain comprises:
(i) a heavy chain variable region (VH) comprising a heavy chain complementarity determining region 1 (VHCDR1) amino acid sequence of SEQ ID NO: 107 (or a sequence with no more than 1, 2, 3, or 4 mutations, e.g., substitutions, additions, or deletions), a VHCDR2 amino acid sequence of SEQ ID NO: 108 (or a sequence with no more than 1, 2, 3, or 4 mutations, e.g., substitutions, additions, or deletions), and/or a VHCDR3 amino acid sequence of SEQ ID NO: 109 (or a sequence with no more than 1, 2, 3, or 4 mutations, e.g., substitutions, additions, or deletions), and
(ii) a light chain variable region (VL) comprising a light chain complementarity determining region 1 (VLCDR1) amino acid sequence of SEQ ID NO: 113 (or a sequence with no more than 1, 2, 3, or 4 mutations, e.g., substitutions, additions, or deletions), a VLCDR2 amino acid sequence of SEQ ID NO: 114 (or a sequence with no more than 1, 2, 3, or 4 mutations, e.g., substitutions, additions, or deletions), and/or a VLCDR3 amino acid sequence of SEQ ID NO: 115 (or a sequence with no more than 1, 2, 3, or 4 mutations, e.g., substitutions, additions, or deletions).

In some embodiments, the first and/or second antigen binding domain comprises a VH comprising a VHCDR1 amino acid sequence of SEQ ID NO: 107, a VHCDR2 amino acid sequence of SEQ ID NO: 108, and a VHCDR3 amino acid sequence of SEQ ID NO: 109. In some embodiments, the first and/or second antigen binding domain comprises a VL comprising a VLCDR1 amino acid sequence of SEQ ID NO: 113, a VLCDR2 amino acid sequence of SEQ ID NO: 114, and a VLCDR3 amino acid sequence of SEQ ID NO: 115.

In some embodiments, the first and/or second antigen binding domain comprises:
(i) a VH comprising a VHCDR1 amino acid sequence of SEQ ID NO: 107, a VHCDR2 amino acid sequence of SEQ ID NO: 108, and a VHCDR3 amino acid sequence of SEQ ID NO: 109, and
(ii) a VL comprising a VLCDR1 amino acid sequence of SEQ ID NO: 113, a VLCDR2 amino acid sequence of SEQ ID NO: 114, and a VLCDR3 amino acid sequence of SEQ ID NO: 115.

In some embodiments, the first and/or second antigen binding domain comprises a VH comprising a heavy chain framework region 1 (VHFWR1) amino acid sequence of SEQ ID NO: 80, a VHFWR2 amino acid sequence of SEQ ID NO: 81, a VHFWR3 amino acid sequence of SEQ ID NO: 82, and/or a VHFWR4 amino acid sequence of SEQ ID NO: 83. In some embodiments, the first and/or second antigen binding domain comprises a VL comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, and/or a VLFWR4 amino acid sequence of SEQ ID NO: 90.

In some embodiments, the first and/or second antigen binding domain comprises:
(i) a VH comprising a heavy chain framework region 1 (VHFWR1) amino acid sequence of SEQ ID NO: 80, a VHFWR2 amino acid sequence of SEQ ID NO: 81, a VHFWR3 amino acid sequence of SEQ ID NO: 82, and/or a VHFWR4 amino acid sequence of SEQ ID NO: 83, and
(ii) a VL comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, and/or a VLFWR4 amino acid sequence of SEQ ID NO: 90.

In some embodiments, the first and/or second antigen binding domain comprises a VH comprising a VHFWR1 amino acid sequence of SEQ ID NO: 117 (or a sequence with no more than 1, 2, 3, 4, 5, or 6 mutations, e.g., substitutions, additions, or deletions), a VHFWR2 amino acid sequence of SEQ ID NO: 118 (or a sequence with no more than 1, 2, 3, 4, 5, or 6 mutations, e.g., substitutions, additions, or deletions), a VHFWR3 amino acid sequence of SEQ ID NO: 119 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 120. In some embodiments, the first and/or second antigen binding domain comprises a VL comprising a VLFWR1 amino acid sequence of SEQ ID NO: 132 (or a sequence with no more than 1, 2, or 3 mutations, e.g., substitutions, additions, or deletions), a VLFWR2 amino acid sequence of SEQ ID NO: 133 (or a sequence with no more than 1 mutation, e.g., substitution, addition, or deletion), a VLFWR3 amino acid sequence of SEQ ID NO: 134 (or a sequence with no more than 1 mutation, e.g., substitution, addition, or deletion), and/or a VLFWR4 amino acid sequence of SEQ ID NO: 135.

In some embodiments, the first and/or second antigen binding domain comprises:
(i) a VH comprising a VHFWR1 amino acid sequence of SEQ ID NO: 117 (or a sequence with no more than 1, 2, 3, 4, 5, or 6 mutations, e.g., substitutions, additions, or deletions), a VHFWR2 amino acid sequence of SEQ ID NO: 118 (or a sequence with no more than 1, 2, 3, 4, 5, or 6 mutations, e.g., substitutions, additions, or deletions), a VHFWR3 amino acid sequence of SEQ ID NO: 119 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 120, and
(ii) a VL comprising a VLFWR1 amino acid sequence of SEQ ID NO: 132 (or a sequence with no more than 1, 2, or 3 mutations, e.g., substitutions, additions, or deletions), a VLFWR2 amino acid sequence of SEQ ID NO: 133 (or a sequence with no more than 1 mutation, e.g., substitution, addition, or deletion), a VLFWR3 amino acid sequence of SEQ ID NO: 134 (or a sequence with no more than 1 mutation, e.g., substitution, addition, or deletion), and/or a VLFWR4 amino acid sequence of SEQ ID NO: 135.

In some embodiments, the first and/or second antigen binding domain comprises a VH comprising a VHFWR1 amino acid sequence of SEQ ID NO: 117, a VHFWR2 amino acid sequence of SEQ ID NO: 118, a VHFWR3 amino acid sequence of SEQ ID NO: 119, and/or a VHFWR4 amino acid sequence of SEQ ID NO: 120. In some embodiments, the first and/or second antigen binding domain comprises a VL comprising a VLFWR1 amino acid sequence of SEQ ID NO: 132, a VLFWR2 amino acid sequence of SEQ ID NO: 133, a VLFWR3 amino acid sequence of SEQ ID NO: 134, and/or a VLFWR4 amino acid sequence of SEQ ID NO: 135.

In some embodiments, the first and/or second antigen binding domain comprises:
  (i) a VH comprising a VHFWR1 amino acid sequence of SEQ ID NO: 117, a VHFWR2 amino acid sequence of SEQ ID NO: 118, a VHFWR3 amino acid sequence of SEQ ID NO: 119, and/or a VHFWR4 amino acid sequence of SEQ ID NO: 120, and
  (ii) a VL comprising a VLFWR1 amino acid sequence of SEQ ID NO: 132, a VLFWR2 amino acid sequence of SEQ ID NO: 133, a VLFWR3 amino acid sequence of SEQ ID NO: 134, and/or a VLFWR4 amino acid sequence of SEQ ID NO: 135.

In some embodiments, the first and/or second antigen binding domain comprises a VH comprising the amino acid sequence of SEQ ID NO: 101 (or an amino acid sequence having at least about 77%, 80%, 85%, 90%, 95%, or 99% sequence identity to SEQ ID NO: 101). In some embodiments, the first and/or second antigen binding domain comprises a VL comprising the amino acid sequence of SEQ ID NO: 103 (or an amino acid sequence having at least about 93%, 95%, or 99% sequence identity to SEQ ID NO: 103).

In some embodiments, the first and/or second antigen binding domain comprises:
  (i) a VH comprising the amino acid sequence of SEQ ID NO: 101 (or an amino acid sequence having at least about 77%, 80%, 85%, 90%, 95%, or 99% sequence identity to SEQ ID NO: 101), and
  (ii) a VL comprising the amino acid sequence of SEQ ID NO: 103 (or an amino acid sequence having at least about 93%, 95%, or 99% sequence identity to SEQ ID NO: 103).

In some embodiments, the first and/or second antigen binding domain comprises a VH comprising the amino acid sequence of SEQ ID NO: 101. In some embodiments, the first and/or second antigen binding domain comprises a VL comprising the amino acid sequence of SEQ ID NO: 103. In some embodiments, the first and/or second antigen binding domain comprises (i) a VH comprising the amino acid sequence of SEQ ID NO: 101, and (ii) a VL comprising the amino acid sequence of SEQ ID NO: 103.

In some embodiments, the first and/or second antigen binding domain comprises a VH comprising an amino acid sequence of at least 70% or 75% sequence identity to SEQ ID NO: 104. In some embodiments, the first and/or second antigen binding domain comprises a VL comprising an amino acid sequence of at least 85% or 90% sequence identity to SEQ ID NO: 106. In some embodiments, the first and/or second antigen binding domain comprises (i) a VH comprising an amino acid sequence of at least 70% or 75% sequence identity to SEQ ID NO: 104, and (ii) a VL comprising an amino acid sequence of at least 85% or 90% sequence identity to SEQ ID NO: 106.

In some embodiments, the first and/or second antigen binding domain comprises a heavy chain variable region (VH) comprising a heavy chain complementarity determining region 1 (VHCDR1) amino acid sequence of SEQ ID NO: 110 (or a sequence with no more than 1, 2, 3, or 4 mutations, e.g., substitutions, additions, or deletions), a VHCDR2 amino acid sequence of SEQ ID NO: 111 (or a sequence with no more than 1, 2, 3, or 4 mutations, e.g., substitutions, additions, or deletions), and/or a VHCDR3 amino acid sequence of SEQ ID NO: 112 or 116 (or a sequence with no more than 1, 2, 3, or 4 mutations, e.g., substitutions, additions, or deletions). In some embodiments, the first and/or second antigen binding domain comprises a light chain variable region (VL) comprising a light chain complementarity determining region 1 (VLCDR1) amino acid sequence of SEQ ID NO: 113 (or a sequence with no more than 1, 2, 3, or 4 mutations, e.g., substitutions, additions, or deletions), a VLCDR2 amino acid sequence of SEQ ID NO: 114 (or a sequence with no more than 1, 2, 3, or 4 mutations, e.g., substitutions, additions, or deletions), and/or a VLCDR3 amino acid sequence of SEQ ID NO: 115 (or a sequence with no more than 1, 2, 3, or 4 mutations, e.g., substitutions, additions, or deletions).

In some embodiments, the first and/or second antigen binding domain comprises:
  (i) a heavy chain variable region (VH) comprising a heavy chain complementarity determining region 1 (VHCDR1) amino acid sequence of SEQ ID NO: 110 (or a sequence with no more than 1, 2, 3, or 4 mutations, e.g., substitutions, additions, or deletions), a VHCDR2 amino acid sequence of SEQ ID NO: 111 (or a sequence with no more than 1, 2, 3, or 4 mutations, e.g., substitutions, additions, or deletions), and/or a VHCDR3 amino acid sequence of SEQ ID NO: 112 or 116 (or a sequence with no more than 1, 2, 3, or 4 mutations, e.g., substitutions, additions, or deletions), and
  (ii) a light chain variable region (VL) comprising a light chain complementarity determining region 1 (VLCDR1) amino acid sequence of SEQ ID NO: 113 (or a sequence with no more than 1, 2, 3, or 4 mutations, e.g., substitutions, additions, or deletions), a VLCDR2 amino acid sequence of SEQ ID NO: 114 (or a sequence with no more than 1, 2, 3, or 4 mutations, e.g., substitutions, additions, or deletions), and/or a VLCDR3 amino acid sequence of SEQ ID NO: 115 (or a sequence with no more than 1, 2, 3, or 4 mutations, e.g., substitutions, additions, or deletions).

In some embodiments, the first and/or second antigen binding domain comprises a VH comprising a heavy chain framework region 1 (VHFWR1) amino acid sequence of SEQ ID NO: 84, a VHFWR2 amino acid sequence of SEQ ID NO: 85, a VHFWR3 amino acid sequence of SEQ ID NO: 86, and/or a VHFWR4 amino acid sequence of SEQ ID NO: 83. In some embodiments, the first and/or second antigen binding domain comprises a VL comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, and/or a VLFWR4 amino acid sequence of SEQ ID NO: 90.

In some embodiments, the first and/or second antigen binding domain comprises:
  (i) a VH comprising a heavy chain framework region 1 (VHFWR1) amino acid sequence of SEQ ID NO: 84, a VHFWR2 amino acid sequence of SEQ ID NO: 85, a VHFWR3 amino acid sequence of SEQ ID NO: 86, and/or a VHFWR4 amino acid sequence of SEQ ID NO: 83, and (ii) a VL comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, and/or a VLFWR4 amino acid sequence of SEQ ID NO: 90.

In some embodiments, the first and/or second antigen binding domain comprises a VH comprising a heavy chain framework 1 (VHFWR1) amino acid sequence of SEQ ID NO: 121 (or a sequence with no more than 1, 2, 3, 4, 5, 6, 7, 8, or 9 mutations, e.g., substitutions, additions, or deletions), a VHFWR2 amino acid sequence of SEQ ID NO: 122 (or a sequence with no more than 1, 2, 3, or 4 mutations, e.g., substitutions, additions, or deletions), a VHFWR3 amino acid sequence of SEQ ID NO: 123 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 124. In some embodiments, the first and/or second antigen binding domain comprises a VL comprising a VLFWR1 amino acid sequence of SEQ ID NO: 132 (or a sequence with no more than 1, 2, or 3 mutations, e.g., substitutions, additions, or deletions), a VLFWR2 amino acid sequence of SEQ ID NO: 133 (or a sequence with no more than 1 mutation, e.g., substitution, addition, or deletion), a VLFWR3 amino acid sequence of SEQ ID NO: 134 (or a sequence with no more than 1 mutation, e.g., substitution, addition, or deletion), and/or a VLFWR4 amino acid sequence of SEQ ID NO: 135.

In some embodiments, the first and/or second antigen binding domain comprises:

(i) a VH comprising a heavy chain framework 1 (VHFWR1) amino acid sequence of SEQ ID NO: 121 (or a sequence with no more than 1, 2, 3, 4, 5, 6, 7, 8, or 9 mutations, e.g., substitutions, additions, or deletions), a VHFWR2 amino acid sequence of SEQ ID NO: 122 (or a sequence with no more than 1, 2, 3, or 4 mutations, e.g., substitutions, additions, or deletions), a VHFWR3 amino acid sequence of SEQ ID NO: 123 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 124, and (ii) a VL comprising a VLFWR1 amino acid sequence of SEQ ID NO: 132 (or a sequence with no more than 1, 2, or 3 mutations, e.g., substitutions, additions, or deletions), a VLFWR2 amino acid sequence of SEQ ID NO: 133 (or a sequence with no more than 1 mutation, e.g., substitution, addition, or deletion), a VLFWR3 amino acid sequence of SEQ ID NO: 134 (or a sequence with no more than 1 mutation, e.g., substitution, addition, or deletion), and/or a VLFWR4 amino acid sequence of SEQ ID NO: 135.

In some embodiments, the first and/or second antigen binding domain comprises a VH comprising the amino acid sequence of SEQ ID NO: 102 (or an amino acid sequence having at least about 75%, 80%, 85%, 90%, 95%, or 99% sequence identity to SEQ ID NO: 102). In some embodiments, the first and/or second antigen binding domain comprises a VL comprising the amino acid sequence of SEQ ID NO: 103 (or an amino acid sequence having at least about 93%, 95%, or 99% sequence identity to SEQ ID NO: 103). In some embodiments, the first and/or second antigen binding domain comprises (i) a VH comprising the amino acid sequence of SEQ ID NO: 102 (or an amino acid sequence having at least about 75%, 80%, 85%, 90%, 95%, or 99% sequence identity to SEQ ID NO: 102), and (ii) a VL comprising the amino acid sequence of SEQ ID NO: 103 (or an amino acid sequence having at least about 93%, 95%, or 99% sequence identity to SEQ ID NO: 103).

In some embodiments, the first and/or second antigen binding domain comprises a VH comprising the amino acid sequence of SEQ ID NO: 102. In some embodiments, the first and/or second antigen binding domain comprises a VL comprising the amino acid sequence of SEQ ID NO: 103. In some embodiments, the first and/or second antigen binding domain comprises (i) a VH comprising the amino acid sequence of SEQ ID NO: 102, and (ii) a VL comprising the amino acid sequence of SEQ ID NO: 103.

In some embodiments, the first and/or second antigen binding domain comprises a VH comprising an amino acid sequence of at least 70% or 74% sequence identity to SEQ ID NO: 105. In some embodiments, the first and/or second antigen binding domain comprises a VL comprising an amino acid sequence of at least 85% or 90% sequence identity to SEQ ID NO: 106. In some embodiments, the first and/or second antigen binding domain comprises (i) a VH comprising an amino acid sequence of at least 70% or 74% sequence identity to SEQ ID NO: 105, and/or (ii) a VL comprising an amino acid sequence of at least 85% or 90% sequence identity to SEQ ID NO: 106.

In some embodiments, the multifunctional molecule comprises an immune cell engager chosen from a T cell engager, an NK cell engager, a B cell engager, a dendritic cell engager, or a macrophage cell engager. In some embodiments, the immune cell engager binds to and activates an immune cell, e.g., an effector cell. In some embodiments, the immune cell engager binds to, but does not activate, an immune cell, e.g., an effector cell.

In some embodiments, the immune cell engager is a T cell engager, e.g., a T cell engager that mediates binding to and activation of a T cell, or a T cell engager that mediates binding to but not activation of a T cell. In some embodiments, the T cell engager binds to CD3, TCRa, TCRβ, TCRγ, TCRγ, ICOζ, CD28, CD27, HVEM, LIGHT, CD40, 4-1BB, OX40, DR3, GITR, CD30, TIM1, SLAM, CD2, or CD226. In some embodiments, the T cell engager is an anti-CD3 antibody molecule. In some embodiments, the T cell engager is an anti-TCRß antibody molecule.

In some embodiments, the immune cell engager is an NK cell engager, e.g., an NK cell engager that mediates binding to and activation of an NK cell, or an NK cell engager that mediates binding to but not activation of an NK cell. In some embodiments, the NK cell engager is chosen from an antibody molecule, e.g., an antigen binding domain, or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80, CD244 (also known as SLAMF4 or 2B4), SLAMF6, SLAMF7, KIR2DS2, KIR2DS4, KIR3DS1, KIR2DS3, KIR2DS5, KIR2DS1, CD94, NKG2C, NKG2E, or CD160. In some embodiments, the NK cell engager is an antibody molecule or ligand that binds to (e.g., activates) NKp30. In some embodiments, the NK cell engager is an antibody molecule, e.g., an antigen binding domain. In some embodiments, the NK cell engager is an antibody molecule, e.g., an antigen binding domain, that binds to NKp30 or NKp46. In some embodiments, the NK cell engager is a ligand, optionally, the ligand further comprises an immunoglobulin constant region, e.g., an Fc region. In some embodiments, the NK cell engager is a ligand of NKp44 or NKp46, e.g., a viral HA. In some embodiments, the NK cell engager is a ligand of DAP10, e.g., a coreceptor for NKG2D. In some embodiments, the NK cell engager is a ligand of CD16, e.g., a CD16a/b ligand, e.g., a CD16a/b ligand further comprising an antibody Fc region. In some embodiments, the immune cell engager mediates binding to, or activation of, or both of, one or more of a B cell, a macrophage, and/or a dendritic cell.

In some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); an agonist of a Toll-like receptor (e.g., a TLR4, e.g., a constitutively active TLR4 (caTLR4) or a TLR9 agonist); a 41BB; a CD2 agonist; a CD47; or a STING agonist, or a combination thereof. In some embodiments, the immune cell engager is a B cell engager, e.g., a CD40L, an OX40L, or a CD70 ligand, or an antibody molecule that binds to OX40, CD40 or CD70. In some embodiments, the immune cell engager is a macrophage cell engager, e.g., a CD2 agonist; a CD40L; an OX40L; an antibody molecule that binds to OX40, CD40 or CD70; an agonist of a Toll-like receptor (TLR) (e.g., a TLR4, e.g., a constitutively active TLR4 (caTLR4) or a TLR9 agonist); CD47; or a STING agonist. In some embodiments, the immune cell engager is a dendritic cell engager, e.g., a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist. In some embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages, e.g., wherein the STING agonist is covalently coupled to the multifunctional molecule.

In some embodiments, the multifunctional molecule comprises a cytokine molecule. In some embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. In some embodiments, the cytokine molecule is a monomer or a dimer. In some embodiments, the cytokine molecule further comprises a receptor dimerizing domain, e.g., an IL 15Ralpha dimerizing domain. In some embodiments, the cytokine molecule (e.g., IL-15) and the receptor dimerizing domain (e.g., an IL 15Ralpha dimerizing domain) are not covalently linked, e.g., are non-covalently associated.

In some embodiments, the multifunctional molecule comprises a modulator of a cytokine molecule. In some embodiments, the modulator of a cytokine molecule is a TGF-beta inhibitor disclosed herein. In some embodiments, the TGF-beta inhibitor comprises a portion of a TGF-beta receptor (e.g., an extracellular domain of a TGF-beta receptor) that is capable of inhibiting (e.g., reducing the activity of) TGF-beta, or functional fragment or variant thereof. In some embodiments, the TGF-beta inhibitor comprises an extracellular domain of TGFBR1 or a sequence substantially identical thereto (e.g., a sequence that is at least 80%, 85%, 90%, or 95% identical thereto). In some embodiments, the TGF-beta inhibitor comprises an extracellular domain of TGFBR2 or a sequence substantially identical thereto (e.g., a sequence that is at least 80%, 85%, 90%, or 95% identical thereto). In some embodiments, the TGF-beta inhibitor comprises an extracellular domain of TGFBR3 or a sequence substantially identical thereto (e.g., a sequence that is at least 80%, 85%, 90%, or 95% identical thereto). In some embodiments, the TGF-beta inhibitor comprises an amino acid sequence disclosed in Table 12 or a sequence that is at least 80%, 85%, 90%, or 95% identical thereto.

In some embodiments, the multifunctional molecule comprises a stromal modifying moiety. In some embodiments, the stromal modifying moiety causes one or more of: decreases the level or production of a stromal or extracellular matrix (ECM) component; decreases tumor fibrosis; increases interstitial tumor transport; improves tumor perfusion; expands the tumor microvasculature; decreases interstitial fluid pressure (IFP) in a tumor; or decreases or enhances penetration or diffusion of an agent, e.g., a cancer therapeutic or a cellular therapy, into a tumor or tumor vasculature. In some embodiments, the stromal or ECM component decreased is chosen from a glycosaminoglycan or an extracellular protein, or a combination thereof. In some embodiments, the glycosaminoglycan is chosen from hyaluronan (also known as hyaluronic acid or HA), chondroitin sulfate, chondroitin, dermatan sulfate, heparan sulfate, heparin, entactin, tenascin, aggrecan or keratin sulfate. In some embodiments, the extracellular protein is chosen from collagen, laminin, elastin, fibrinogen, fibronectin, or vitronectin. In some embodiments, the stromal modifying moiety comprises an enzyme molecule that degrades a tumor stroma or extracellular matrix (ECM). In some embodiments, the enzyme molecule is chosen from a hyaluronidase molecule, a collagenase molecule, a chondroitinase molecule, a matrix metalloproteinase molecule (e.g., macrophage metalloelastase), or a variant (e.g., a fragment) of any of the aforesaid. In some embodiments, the stromal modifying moiety decreases the level or production of hyaluronic acid. In some embodiments, the stromal modifying moiety comprises a hyaluronan degrading enzyme, an agent that inhibits hyaluronan synthesis, or an antibody molecule against hyaluronic acid. In some embodiments, the hyaluronan degrading enzyme is a hyaluronidase molecule or a variant (e.g., fragment thereof) thereof. In some embodiments, the hyaluronan degrading enzyme is active in neutral or acidic pH, e.g., pH of about 4-5. In some embodiments, the hyaluronidase molecule is a mammalian hyaluronidase molecule, e.g., a recombinant human hyaluronidase molecule, or a variant thereof (e.g., a truncated form thereof). In some embodiments, the hyaluronidase molecule is chosen from HYAL1, HYAL2, or PH-20/SPAM1, or a variant thereof (e.g., a truncated form thereof). In some embodiments, the truncated form lacks a C-terminal glycosylphosphatidylinositol (GPI) attachment site or a portion of the GPI attachment site. In some embodiments, the hyaluronidase molecule is glycosylated, e.g., comprises at least one N-linked glycan. In some embodiments, the hyaluronidase molecule comprises the amino acid sequence of SEQ ID NO:61, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 61). In some embodiments, the hyaluronidase molecule comprises the amino acid residues 36-464 of SEQ ID NO: 61. In some embodiments, the hyaluronidase molecule comprises the amino acid residues 36-481, 36-482, or 36-483 of PH20, wherein PH20 has the amino acid sequence of SEQ ID NO: 61. In some embodiments, the hyaluronidase molecule comprises an amino acid sequence having at least 95% to 100% sequence identity to the polypeptide or truncated form of the amino acid sequence of SEQ ID NO: 61. In some embodiments, the hyaluronidase molecule comprises an amino acid sequence having 30, 20, 10, 5 or fewer amino acid substitutions to the amino acid sequence of SEQ ID NO: 61. In some embodiments, the hyaluronidase molecule comprises an amino acid sequence at least 95% (e.g., at least 95%, 96%, 97%, 98%, 99%, 100%) identical to the amino acid sequence of SEQ ID NO: 61. In some embodiments, the hyaluronidase molecule is encoded by a nucleotide sequence at least 95% (e.g., at least 96%, 97%, 98%, 99%, 100%) identical to the nucleotide sequence of SEQ ID NO: 61. In some embodiments, the hyaluronidase molecule is PH20, e.g., rHuPH20. In some embodiments, the hyaluronidase molecule is HYAL1 and comprises the amino acid sequence of SEQ ID NO: 62, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62). In some embodiments, the hyaluronan degrading enzyme, e.g., the hyaluronidase molecule, further comprises a polymer, e.g., is conjugated to a polymer, e.g., PEG. In some embodiments, the hyaluronan-degrading enzyme is a PEGylated PH20 enzyme (PEGPH20). In some embodiments, the hyaluronan degrading enzyme, e.g., the hyaluronidase molecule, further comprises an immunoglobulin chain constant region (e.g., Fc region) chosen from, e.g., the heavy chain constant regions of IgG1, IgG2, IgG3, or IgG4, more particularly, the heavy chain constant region of human IgG1, IgG2, IgG3, or IgG4. In some embodiments, the immunoglobulin constant region (e.g., the Fc region) is linked, e.g., covalently linked to, the hyaluronan degrading enzyme, e.g., the hyaluronidase molecule. In some embodiments, the immunoglobulin chain constant region (e.g., Fc region) is altered, e.g., mutated, to increase or decrease one or more of: Fc receptor binding, antibody glycosylation, the number of cysteine residues, effector cell function, or complement function. In some embodiments, the hyaluronan degrading enzyme, e.g., the hyaluronidase molecule, forms a dimer. In some embodiments, the stromal modifying moiety comprises an inhibitor of the synthesis of hyaluronan, e.g., an HA synthase. In some embodiments, the inhibitor comprises a sense or an antisense nucleic acid molecule against an HA synthase or is a small molecule drug. In some embodiments, the inhibitor is 4-methylumbelliferone (MU) or a derivative thereof (e.g., 6,7-dihydroxy-4-methyl coumarin or 5,7-dihydroxy-4-methyl coumarin), or leflunomide or a derivative thereof. In some embodiments, the stromal modifying moiety comprises a collagenase molecule, e.g., a mammalian collagenase molecule, or a variant (e.g., fragment) thereof. In some embodiments, the collagenase molecule is collagenase molecule IV, e.g., comprising the amino acid sequence of SEQ ID NO: 63, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63.

In some embodiments, the multifunctional molecule comprises an immune cell engager (e.g., a T cell engager, an NK cell engager, a B cell engager, a dendritic cell engager, or a macrophage cell engager) and a cytokine molecule. In some embodiments, the multifunctional molecule comprises an immune cell engager (e.g., a T cell engager, an NK cell engager, a B cell engager, a dendritic cell engager, or a macrophage cell engager) and a modulator of a cytokine molecule. In some embodiments, the multifunctional molecule comprises an immune cell engager (e.g., a T cell engager, an NK cell engager, a B cell engager, a dendritic cell engager, or a macrophage cell engager) and a stromal modifying moiety. In some embodiments, the multifunctional molecule comprises a cytokine molecule and a stromal modifying moiety. In some embodiments, the multifunctional molecule comprises a modulator of a cytokine molecule and a stromal modifying moiety. In some embodiments, the multifunctional molecule comprises an immune cell engager (e.g., a T cell engager, an NK cell engager, a B cell engager, a dendritic cell engager, or a macrophage cell engager), a cytokine molecule, and a stromal modifying moiety. In some embodiments, the multifunctional molecule comprises an immune cell engager (e.g., a T cell engager, an NK cell engager, a B cell engager, a dendritic cell engager, or a macrophage cell engager), a modulator of a cytokine molecule, and a stromal modifying moiety. In some embodiments, the multifunctional molecule comprises at least two non-contiguous polypeptide chains.

In some embodiments, the multifunctional molecule comprises the following configuration:

A,B-[dimerization module]-C,-D e.g., the configuration shown in FIGS. 1A, 1B, and 1C, wherein:
(1) the dimerization module comprises an immunoglobulin constant domain, e.g., a heavy chain constant domain (e.g., a homodimeric or heterodimeric heavy chain constant region, e.g., an Fc region), or a constant domain of an immunoglobulin variable region (e.g., a Fab region); and
(2) A, B, C, and D are independently absent; (i) an antigen binding domain that preferentially binds to a calreticulin mutant protein over a wild type calreticulin protein, wherein the calreticulin mutant protein comprises the amino acid sequence of SEQ ID NO: 141; (ii) an immune cell engager chosen from a T cell engager, an NK cell engager, a B cell engager, a dendritic cell engager, or a macrophage cell engager; (iii) a cytokine molecule (or a modulator of a cytokine molecule); or (iv) a stromal modifying moiety, provided that:
at least one, two, or three of A, B, C, and D comprises an antigen binding domain that preferentially binds to a calreticulin mutant protein over a wild type calreticulin protein, wherein the calreticulin mutant protein comprises the amino acid sequence of SEQ ID NO: 141, and
any of the remaining A, B, C, and D is absent or comprises one of an immune cell engager, a cytokine molecule (or a modulator of a cytokine molecule), or a stromal modifying moiety.
In some embodiments,
(i) A comprises an antigen binding domain that preferentially binds to a calreticulin mutant protein over a wild type calreticulin protein, wherein the calreticulin mutant protein comprises the amino acid sequence of SEQ ID NO: 141, and B, C, or D comprises an immune cell engager, e.g., a T cell engager, e.g., an anti-CD3 antibody molecule;
(ii) A comprises an antigen binding domain that preferentially binds to a calreticulin mutant protein over a wild type calreticulin protein, wherein the calreticulin mutant protein comprises the amino acid sequence of SEQ ID NO: 141, and B, C, or D comprises a cytokine molecule (or a modulator of a cytokine molecule);

(iii) A comprises an antigen binding domain that preferentially binds to a calreticulin mutant protein over a wild type calreticulin protein, wherein the calreticulin mutant protein comprises the amino acid sequence of SEQ ID NO: 141, and B, C, or D comprises a stromal modifying moiety;

(iv) A comprises a first antigen binding domain that preferentially binds to a first calreticulin mutant protein over a wild type calreticulin protein, wherein the first calreticulin mutant protein comprises the amino acid sequence of SEQ ID NO: 141, B comprises a second antigen binding domain that preferentially binds to a second calreticulin mutant protein over a wild type calreticulin protein, wherein the second calreticulin mutant protein comprises the amino acid sequence of SEQ ID NO: 141, and C or D comprises an immune cell engager, e.g., a T cell engager, e.g., an anti-CD3 antibody molecule;

(v) A comprises a first antigen binding domain that preferentially binds to a first calreticulin mutant protein over a wild type calreticulin protein, wherein the first calreticulin mutant protein comprises the amino acid sequence of SEQ ID NO: 141, B comprises a second antigen binding domain that preferentially binds to a second calreticulin mutant protein over a wild type calreticulin protein, wherein the second calreticulin mutant protein comprises the amino acid sequence of SEQ ID NO: 141, and C or D comprises a cytokine molecule (or a modulator of a cytokine molecule);

(vi) A comprises a first antigen binding domain that preferentially binds to a first calreticulin mutant protein over a wild type calreticulin protein, wherein the first calreticulin mutant protein comprises the amino acid sequence of SEQ ID NO: 141, B comprises a second antigen binding domain that preferentially binds to a second calreticulin mutant protein over a wild type calreticulin protein, wherein the second calreticulin mutant protein comprises the amino acid sequence of SEQ ID NO: 141, and C or D comprises a stromal modifying moiety;

(vii) A comprises a first antigen binding domain that preferentially binds to a first calreticulin mutant protein over a wild type calreticulin protein, wherein the first calreticulin mutant protein comprises the amino acid sequence of SEQ ID NO: 141, C comprises a second antigen binding domain that preferentially binds to a second calreticulin mutant protein over a wild type calreticulin protein, wherein the second calreticulin mutant protein comprises the amino acid sequence of SEQ ID NO: 141, and B or D comprises an immune cell engager, e.g., a T cell engager, e.g., an anti-CD3 antibody molecule;

(viii) A comprises a first antigen binding domain that preferentially binds to a first calreticulin mutant protein over a wild type calreticulin protein, wherein the first calreticulin mutant protein comprises the amino acid sequence of SEQ ID NO: 141, C comprises a second antigen binding domain that preferentially binds to a second calreticulin mutant protein over a wild type calreticulin protein, wherein the second calreticulin mutant protein comprises the amino acid sequence of SEQ ID NO: 141, and B or D comprises a cytokine molecule (or a modulator of a cytokine molecule);

(ix) A comprises a first antigen binding domain that preferentially binds to a first calreticulin mutant protein over a wild type calreticulin protein, wherein the first calreticulin mutant protein comprises the amino acid sequence of SEQ ID NO: 141, C comprises a second antigen binding domain that preferentially binds to a second calreticulin mutant protein over a wild type calreticulin protein, wherein the second calreticulin mutant protein comprises the amino acid sequence of SEQ ID NO: 141, and B or D comprises a stromal modifying moiety;

(x) A comprises a first antigen binding domain that preferentially binds to a first calreticulin mutant protein over a wild type calreticulin protein, wherein the first calreticulin mutant protein comprises the amino acid sequence of SEQ ID NO: 141, and B, C, or D comprises (a) an immune cell engager, e.g., a T cell engager, e.g., an anti-CD3 antibody molecule and (b) a cytokine molecule (or a modulator of a cytokine molecule);

(xi) A comprises a first antigen binding domain that preferentially binds to a first calreticulin mutant protein over a wild type calreticulin protein, wherein the first calreticulin mutant protein comprises the amino acid sequence of SEQ ID NO: 141, and B, C, or D comprises (a) an immune cell engager, e.g., a T cell engager, e.g., an anti-CD3 antibody molecule and (b) a stromal modifying moiety;

(xii) A comprises a first antigen binding domain that preferentially binds to a first calreticulin mutant protein over a wild type calreticulin protein, wherein the first calreticulin mutant protein comprises the amino acid sequence of SEQ ID NO: 141, and B, C, or D comprises (a) a cytokine molecule (or a modulator of a cytokine molecule) and (b) a stromal modifying moiety;

(xiii) A comprises a first antigen binding domain that preferentially binds to a first calreticulin mutant protein over a wild type calreticulin protein, wherein the first calreticulin mutant protein comprises the amino acid sequence of SEQ ID NO: 141, B comprises a second antigen binding domain that preferentially binds to a second calreticulin mutant protein over a wild type calreticulin protein, wherein the second calreticulin mutant protein comprises the amino acid sequence of SEQ ID NO: 141, and C or D comprises (a) an immune cell engager, e.g., a T cell engager, e.g., an anti-CD3 antibody molecule and (b) a cytokine molecule (or a modulator of a cytokine molecule);

(xiv) A comprises a first antigen binding domain that preferentially binds to a first calreticulin mutant protein over a wild type calreticulin protein, wherein the first calreticulin mutant protein comprises the amino acid sequence of SEQ ID NO: 141, B comprises a second antigen binding domain that preferentially binds to a second calreticulin mutant protein over a wild type calreticulin protein, wherein the second calreticulin mutant protein comprises the amino acid sequence of SEQ ID NO: 141, and C or D comprises (a) an immune cell engager, e.g., a T cell engager, e.g., an anti-CD3 antibody molecule and (b) a stromal modifying moiety;

(xv) A comprises a first antigen binding domain that preferentially binds to a first calreticulin mutant protein over a wild type calreticulin protein, wherein the first calreticulin mutant protein comprises the amino acid sequence of SEQ ID NO: 141, B comprises a second antigen binding domain that preferentially binds to a second calreticulin mutant protein over a wild type calreticulin protein, wherein the second calreticulin mutant protein comprises the amino acid sequence of SEQ ID NO: 141, and C or D comprises (a) a cytokine molecule (or a modulator of a cytokine molecule) and (b) a stromal modifying moiety;

(xvi) A comprises a first antigen binding domain that preferentially binds to a first calreticulin mutant protein over a wild type calreticulin protein, wherein the first calreticulin mutant protein comprises the amino acid sequence of SEQ ID NO: 141, C comprises a second antigen binding domain that preferentially binds to a second calreticulin mutant protein over a wild type calreticulin protein, wherein the second calreticulin mutant protein comprises the amino acid sequence of SEQ ID NO: 141, and B or D comprises (a) an immune cell engager, e.g., a T cell engager, e.g., an anti-CD3 antibody molecule and (b) a cytokine molecule (or a modulator of a cytokine molecule);

(xvii) A comprises a first antigen binding domain that preferentially binds to a first calreticulin mutant protein over a wild type calreticulin protein, wherein the first calreticulin mutant protein comprises the amino acid sequence of SEQ ID NO: 141, C comprises a second antigen binding domain that preferentially binds to a second calreticulin mutant protein over a wild type calreticulin protein, wherein the second calreticulin mutant protein comprises the amino acid sequence of SEQ ID NO: 141, and B or D comprises (a) an immune cell engager, e.g., a T cell engager, e.g., an anti-CD3 antibody molecule and (b) a stromal modifying moiety;

(xviii) A comprises a first antigen binding domain that preferentially binds to a first calreticulin mutant protein over a wild type calreticulin protein, wherein the first calreticulin mutant protein comprises the amino acid sequence of SEQ ID NO: 141, C comprises a second antigen binding domain that preferentially binds to a second calreticulin mutant protein over a wild type calreticulin protein, wherein the second calreticulin mutant protein comprises the amino acid sequence of SEQ ID NO: 141, and B or D comprises (a) a cytokine molecule (or a modulator of a cytokine molecule) and (b) a stromal modifying moiety;

(xix) A comprises a first antigen binding domain that preferentially binds to a first calreticulin mutant protein over a wild type calreticulin protein, wherein the first calreticulin mutant protein comprises the amino acid sequence of SEQ ID NO: 141, and B, C, or D comprises (a) an immune cell engager, e.g., a T cell engager, e.g., an anti-CD3 antibody molecule, (b) a cytokine molecule (or a modulator of a cytokine molecule), and (c) a stromal modifying moiety;

(xx) A comprises a first antigen binding domain that preferentially binds to a first calreticulin mutant protein over a wild type calreticulin protein, wherein the first calreticulin mutant protein comprises the amino acid sequence of SEQ ID NO: 141, B comprises a second antigen binding domain that preferentially binds to a second calreticulin mutant protein over a wild type calreticulin protein, wherein the second calreticulin mutant protein comprises the amino acid sequence of SEQ ID NO: 141, and C or D comprises (a) an immune cell engager, e.g., a T cell engager, e.g., an anti-CD3 antibody molecule, (b) a cytokine molecule (or a modulator of a cytokine molecule), and (c) a stromal modifying moiety; or (xxi) A comprises a first antigen binding domain that preferentially binds to a first calreticulin mutant protein over a wild type calreticulin protein, wherein the first calreticulin mutant protein comprises the amino acid sequence of SEQ ID NO: 141, C comprises a second antigen binding domain that preferentially binds to a second calreticulin mutant protein over a wild type calreticulin protein, wherein the second calreticulin mutant protein comprises the amino acid sequence of SEQ ID NO: 141, and B or D comprises (a) an immune cell engager, e.g., a T cell engager, e.g., an anti-CD3 antibody molecule, (b) a cytokine molecule (or a modulator of a cytokine molecule), and (c) a stromal modifying moiety.

In some embodiments, the dimerization module comprises one or more immunoglobulin chain constant regions (e.g., Fc regions) comprising one or more of: a paired cavity-protuberance ("knob-in-a hole"), an electrostatic interaction, or a strand-exchange. In some embodiments, the one or more immunoglobulin chain constant regions (e.g., Fc regions) comprise an amino acid substitution at a position chosen from one or more of 347, 349, 350, 351, 366, 368, 370, 392, 394, 395, 397, 398, 399, 405, 407, or 409, e.g., of the Fc region of human IgG1. In some embodiments, the one or more immunoglobulin chain constant regions (e.g., Fc regions) comprise an amino acid substitution chosen from: T366S, L368A, or Y407V (e.g., corresponding to a cavity or hole), or T366W (e.g., corresponding to a protuberance or knob), or a combination thereof.

In some embodiments, the multifunctional molecule further comprises a linker, e.g., a linker between one or more of: the antigen binding domain and the immune cell engager, the antigen binding domain and the cytokine molecule (or the modulator of a cytokine molecule), the antigen binding domain and the stromal modifying moiety, the immune cell engager and the cytokine molecule (or the modulator of a cytokine molecule), the immune cell engager and the stromal modifying moiety, the cytokine molecule (or the modulator of a cytokine molecule) and the stromal modifying moiety, the antigen binding domain and the dimerization module, the immune cell engager and the dimerization module, the cytokine molecule (or the modulator of a cytokine molecule) and the dimerization module, or the stromal modifying moiety and the dimerization module. In some embodiments, the linker is chosen from: a cleavable linker, a non-cleavable linker, a peptide linker, a flexible linker, a rigid linker, a helical linker, or a non-helical linker. In some embodiments, the linker is a peptide linker. In some embodiments, the peptide linker comprises Gly and Ser. In some embodiments, the peptide linker comprises an amino acid sequence chosen from SEQ ID NOs: 42-45 or 75-78.

In one aspect, the invention provides a multifunctional molecule, comprising:
(i) an antigen binding domain that preferentially binds to a calreticulin mutant protein over a wild type calreticulin protein, e.g., wherein the calreticulin mutant protein comprises the amino acid sequence of SEQ ID NO: 141, and
(ii) a moiety that binds to CD3, e.g., an antibody molecule that binds to CD3.

In some embodiments, the multifunctional molecule comprises:
a first polypeptide comprising, e.g., from N-terminus to C-terminus, a first VL and a first CL,
a second polypeptide comprising, e.g., from N-terminus to C-terminus, a first VH, a first CH1, a first dimerization domain (e.g., a first Fc), and a first moiety that binds to CD3 (e.g., a first scFv that binds to CD3),
a third polypeptide comprising, e.g., from N-terminus to C-terminus, a second VH, a second CH1, a second dimerization domain (e.g., a second Fc), and optionally a second moiety that binds to CD3 (e.g., a second scFv that binds to CD3), a fourth polypeptide comprising, e.g., from N-terminus to C-terminus, a second VL and a second CL, wherein:

the first VL and the first VH form a first antigen binding domain that binds to a first calreticulin mutant protein, and the second VL and the second VH form a second antigen binding domain that binds to a second calreticulin mutant protein, wherein the first and second calreticulin mutant proteins comprise the amino acid sequence of SEQ ID NO: 141, optionally wherein the first and second calreticulin mutant proteins are each independently chosen from: a molecule comprising the amino acid sequence of SEQ ID NO: 169, or a molecule comprising the amino acid sequence of SEQ ID NO: 170.

In some embodiments, the multifunctional molecule comprises the configuration of FIG. 2A or 2B.

In one aspect, the invention provides a multifunctional molecule, comprising:

(i) an antigen binding domain that preferentially binds to a calreticulin mutant protein over a wild type calreticulin protein, e.g., wherein the calreticulin mutant protein comprises the amino acid sequence of SEQ ID NO: 141, and (ii) a moiety that binds to TCR (e.g., TCRβ), e.g., an antibody molecule that binds to TCR (e.g., TCRβ).

In some embodiments, the multifunctional molecule comprises:

a first polypeptide comprising, e.g., from N-terminus to C-terminus, a first VL and a first CL, a second polypeptide comprising, e.g., from N-terminus to C-terminus, a first VH, a first CH1, a first dimerization domain (e.g., a first Fc), and a first moiety that binds to TCR (e.g., TCRβ) (e.g., a first scFv that binds to TCR (e.g., TCRβ)), a third polypeptide comprising, e.g., from N-terminus to C-terminus, a second VH, a second CH1, a second dimerization domain (e.g., a second Fc), and optionally a second moiety that binds to TCR (e.g., TCRβ) (e.g., a second scFv that binds to TCR (e.g., TCRβ)), a fourth polypeptide comprising, e.g., from N-terminus to C-terminus, a second VL and a second CL, wherein:

the first VL and the first VH form a first antigen binding domain that binds to a first calreticulin mutant protein, and the second VL and the second VH form a second antigen binding domain that binds to a second calreticulin mutant protein, wherein the first and second calreticulin mutant proteins comprise the amino acid sequence of SEQ ID NO: 141, optionally wherein the first and second calreticulin mutant proteins are each independently chosen from: a molecule comprising the amino acid sequence of SEQ ID NO: 169, or a molecule comprising the amino acid sequence of SEQ ID NO: 170.

In some embodiments, the multifunctional molecule comprises the configuration of FIG. 3A or 3B.

In one aspect, the invention provides a multifunctional molecule, comprising:

(i) an antigen binding domain that preferentially binds to a calreticulin mutant protein over a wild type calreticulin protein, e.g., wherein the calreticulin mutant protein comprises the amino acid sequence of SEQ ID NO: 141, and (ii) a moiety that binds to NKp30, e.g., an antibody molecule or ligand that binds to (e.g., activates) NKp30.

In some embodiments, the multifunctional molecule comprises:

a first polypeptide comprising, e.g., from N-terminus to C-terminus, a first VL and a first CL, a second polypeptide comprising, e.g., from N-terminus to C-terminus, a first VH, a first CH1, a first dimerization domain (e.g., a first Fc), and a first moiety that binds to NKp30 (e.g., a first antibody molecule or ligand that binds to NKp30), a third polypeptide comprising, e.g., from N-terminus to C-terminus, a second VH, a second CH1, a second dimerization domain (e.g., a second Fc), and optionally a second moiety that binds to NKp30 (e.g., a second antibody molecule or ligand that binds to NKp30), a fourth polypeptide comprising, e.g., from N-terminus to C-terminus, a second VL and a second CL, wherein:

the first VL and the first VH form a first antigen binding domain that binds to a first calreticulin mutant protein, and the second VL and the second VH form a second antigen binding domain that binds to a second calreticulin mutant protein, wherein the first and second calreticulin mutant proteins comprise the amino acid sequence of SEQ ID NO: 141, optionally wherein the first and second calreticulin mutant proteins are each independently chosen from: a molecule comprising the amino acid sequence of SEQ ID NO: 169, or a molecule comprising the amino acid sequence of SEQ ID NO: 170.

In some embodiments, the multifunctional molecule comprises the configuration of FIG. 4A or 4B.

In another aspect, the disclosure provides an isolated nucleic acid molecule encoding any multispecific or multifunctional molecule described herein. In another aspect, the disclosure provides an isolated nucleic acid molecule, which comprises the nucleotide sequence encoding any of the multispecific or multifunctional molecules described herein, or a nucleotide sequence substantially homologous thereto (e.g., at least 80%, 90%, 95%, or 99.9% identical thereto). In another aspect, the disclosure provides a host cell comprising a nucleic acid molecule or a vector described herein.

In another aspect, the disclosure provides a method of making, e.g., producing, a multispecific or multifunctional molecule polypeptide described herein, comprising culturing a host cell described herein, under suitable conditions, e.g., conditions suitable for gene expression and/or homo- or heterodimerization.

In another aspect, the disclosure provides a pharmaceutical composition comprising a multispecific or multifunctional molecule polypeptide described herein and a pharmaceutically acceptable carrier, excipient, or stabilizer.

In another aspect, the disclosure provides a method of treating a cancer, comprising administering to a subject in need thereof a multispecific or multifunctional molecule polypeptide described herein, wherein the multispecific antibody is administered in an amount effective to treat the cancer. In some embodiments, the subject has cancer cells that express the first and/or second calreticulin mutant. In some embodiments, the subject has the JAK2 V617F mutation. In some embodiments, the subject does not have the JAK2 V617F mutation. In some embodiments, the subject has a MPL mutation. In some embodiments, the subject does not have a MPL mutation. In some embodiments, the cancer is a hematological cancer, optionally wherein the cancer is a myeloproliferative neoplasm, e.g., primary or idiopathic myelofibrosis (MF), essential thrombocytosis (ET), polycythemia vera (PV), or chronic myelogenous leukemia (CML). In some embodiments, the cancer is myelofibrosis. In some embodiments, the cancer is a solid tumor cancer. In some embodiments, the solid tumor cancer is one or more of pancreatic (e.g., pancreatic adenocarcinoma), breast, colorectal, lung (e.g., small or non-small cell lung cancer), skin, ovarian, or liver cancer.

In some embodiments, the method further comprises administering a second therapeutic treatment. In some embodiments, second therapeutic treatment comprises a therapeutic agent (e.g., a chemotherapeutic agent, a biologic agent, hormonal therapy), radiation, or surgery. In some embodiments, therapeutic agent is selected from: a chemotherapeutic agent, or a biologic agent.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIGS. 1A-1C are schematic representations of exemplary formats and configurations of functional moieties attached to a dimerization module, e.g., an immunoglobulin constant domain. FIG. 1A depicts moieties A, B, C and D, covalently linked to a heterodimeric Fc domain. FIG. 1B depicts moieties A, B, C and D, covalently linked to a homodimeric Fc domain. FIG. 1C depicts moieties A, B, C and D, covalently linked to heterodimeric heavy and light constant domains (e.g., a Fab CH$_1$ and a Fab CL). In some embodiments, the functional moiety is an antigen binding domain that preferentially binds to a calreticulin mutant protein over a wild type calreticulin protein, e.g., wherein the first calreticulin mutant protein comprises the amino acid sequence of SEQ ID NO: 141 and the wild type calreticulin protein comprises the amino acid sequence of SEQ ID NO: 140. In some embodiments, the functional moiety is an immune cell engager chosen from a T cell engager, an NK cell engager, a B cell engager, a dendritic cell engager, or a macrophage cell engager. In some embodiments, the functional moiety is a cytokine molecule. In some embodiments, the functional moiety is a modulator of a cytokine molecule. In some embodiments, the functional moiety is a stromal modifying moiety.

In FIGS. 5A and 5B, the two TGFBR ECD domains are linked to the C-terminus of two Fc regions. In some embodiments, the CH1-Fc-TGFBR ECD region shown in FIG. 5A or 5B comprises the amino acid sequence of SEQ ID NO: 392 or 393. In some embodiments, the Fc-TGFBR ECD region shown in FIG. 5A or 5B comprises the amino acid sequence of SEQ ID NO: 394 or 395. In FIGS. 5C and 5D, the two TGFBR ECD domains are linked to CH1 and CL, respectively. In some embodiments, the TGFBR ECD-CH1-Fc region shown in FIG. 5C or 5D comprises the amino acid sequence of SEQ ID NO: 396 or 397. In some embodiments, the TGFBR ECD-CL region shown in FIG. 5C or 5D comprises the amino acid sequence of SEQ ID NO: 398 or 399. In some embodiments, the multispecific molecule comprises a binding moiety A and a binding moiety B. In some embodiments, the binding moiety A or binding moiety B is an anti-mutant calreticulin binding moiety.

DETAILED DESCRIPTION OF THE INVENTION

Figure 2A:
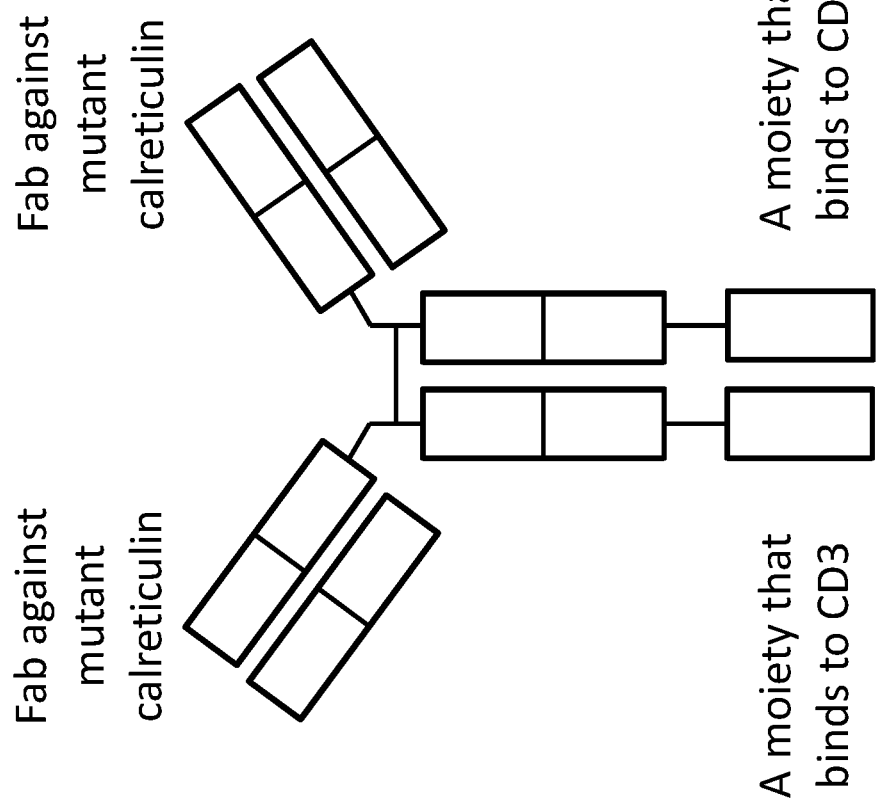
FIGS. 2A and 2B are schematic representations of exemplary formats and configurations of a multifunctional molecule comprising a first antigen binding domain (e.g., a first Fab) that binds to a calreticulin mutant protein, a second antigen binding domain (e.g., a second Fab) that binds to a calreticulin mutant protein, and one or more moieties that bind to CD3 (e.g., an scFv that binds to CD3). In one embodiment, the first antigen binding domain (e.g., the first Fab) binds to a calreticulin mutant protein disclosed herein, e.g., a calreticulin mutant protein disclosed in Table 2 or 3, e.g., Type 1 or Type 2 calreticulin mutant protein disclosed in Table 2 or 3, e.g., a calreticulin mutant protein comprising the amino acid sequence of SEQ ID NO: 169 or 170. In one embodiment, the second antigen binding domain (e.g., the second Fab) binds to a calreticulin mutant protein disclosed herein, e.g., a calreticulin mutant protein disclosed in Table 2 or 3, e.g., Type 1 or Type 2 calreticulin mutant protein disclosed in Table 2 or 3, e.g., a calreticulin mutant protein comprising the amino acid sequence of SEQ ID NO: 169 or 170.
Figure 2B:
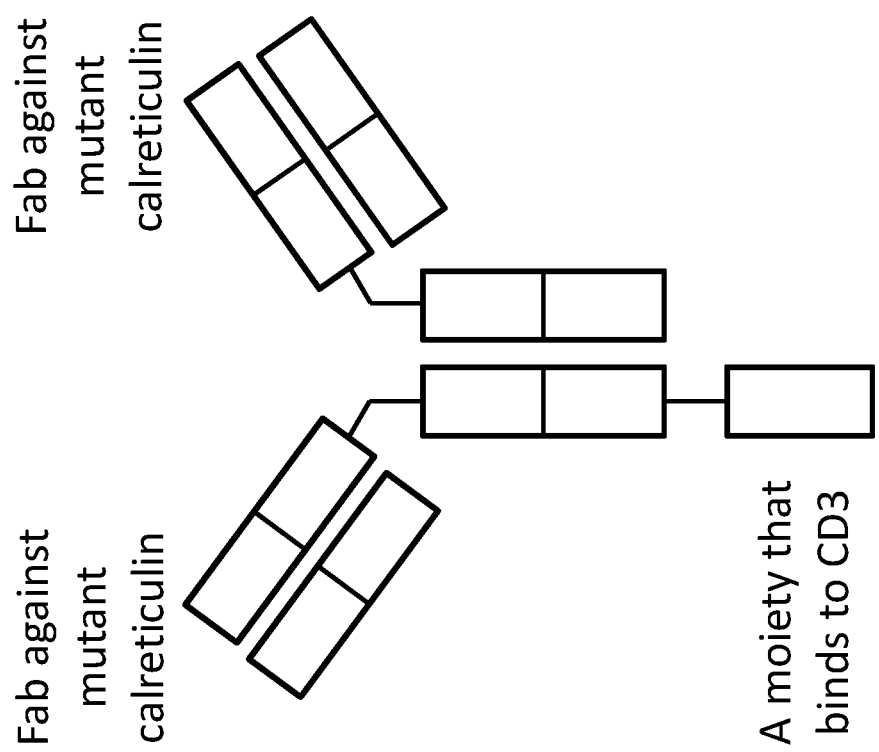
Figure 3A:
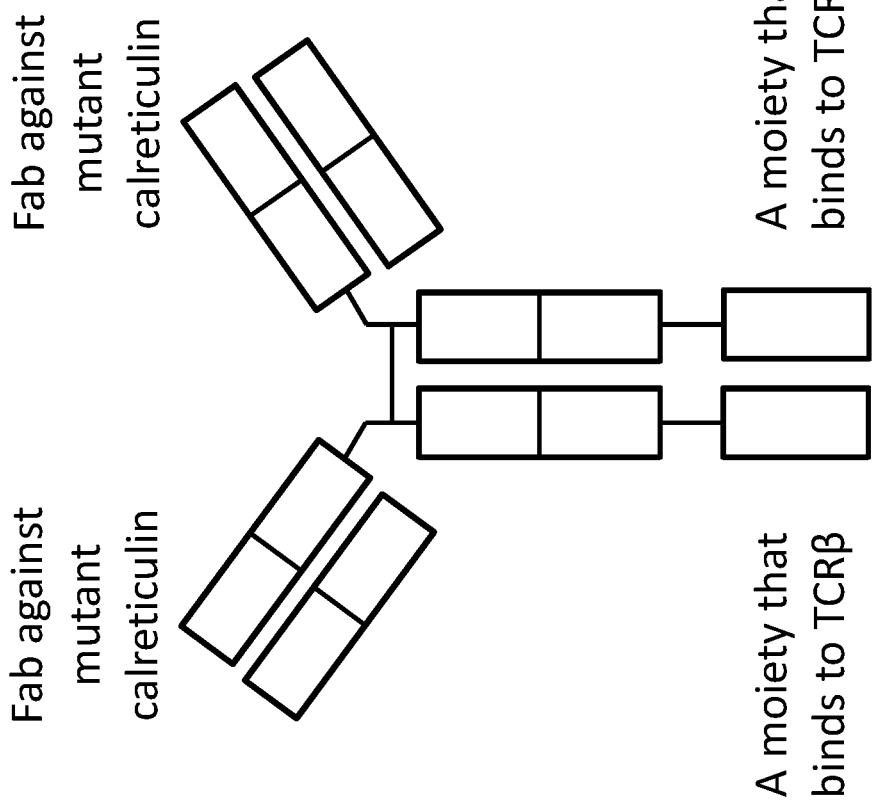
FIGS. 3A and 3B are schematic representations of exemplary formats and configurations of a multifunctional molecule comprising a first antigen binding domain (e.g., a first Fab) that binds to a calreticulin mutant protein, a second antigen binding domain (e.g., a second Fab) that binds to a calreticulin mutant protein, and one or more moieties that bind to TCR (e.g., TCRβ) (e.g., an scFv that binds to TCR (e.g., TCRβ)). In one embodiment, the first antigen binding domain (e.g., the first Fab) binds to a calreticulin mutant protein disclosed herein, e.g., a calreticulin mutant protein disclosed in Table 2 or 3, e.g., Type 1 or Type 2 calreticulin mutant protein disclosed in Table 2 or 3, e.g., a calreticulin mutant protein comprising the amino acid sequence of SEQ ID NO: 169 or 170. In one embodiment, the second antigen binding domain (e.g., the second Fab) binds to a calreticulin mutant protein disclosed herein, e.g., a calreticulin mutant protein disclosed in Table 2 or 3, e.g., Type 1 or Type 2 calreticulin mutant protein disclosed in Table 2 or 3, e.g., a calreticulin mutant protein comprising the amino acid sequence of SEQ ID NO: 169 or 170.
Figure 3B:
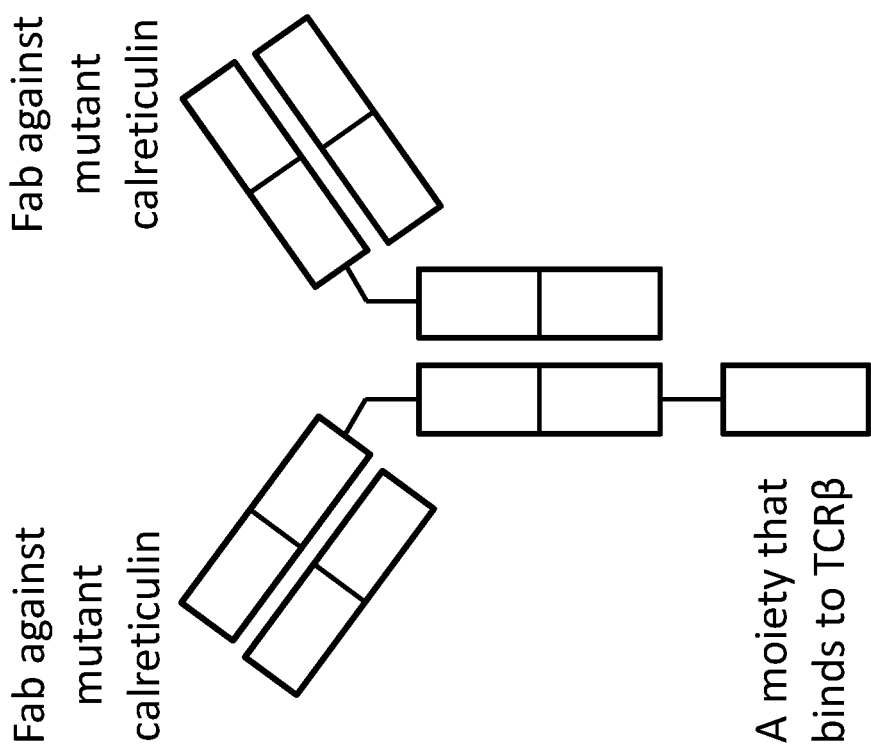
Figure 4A:
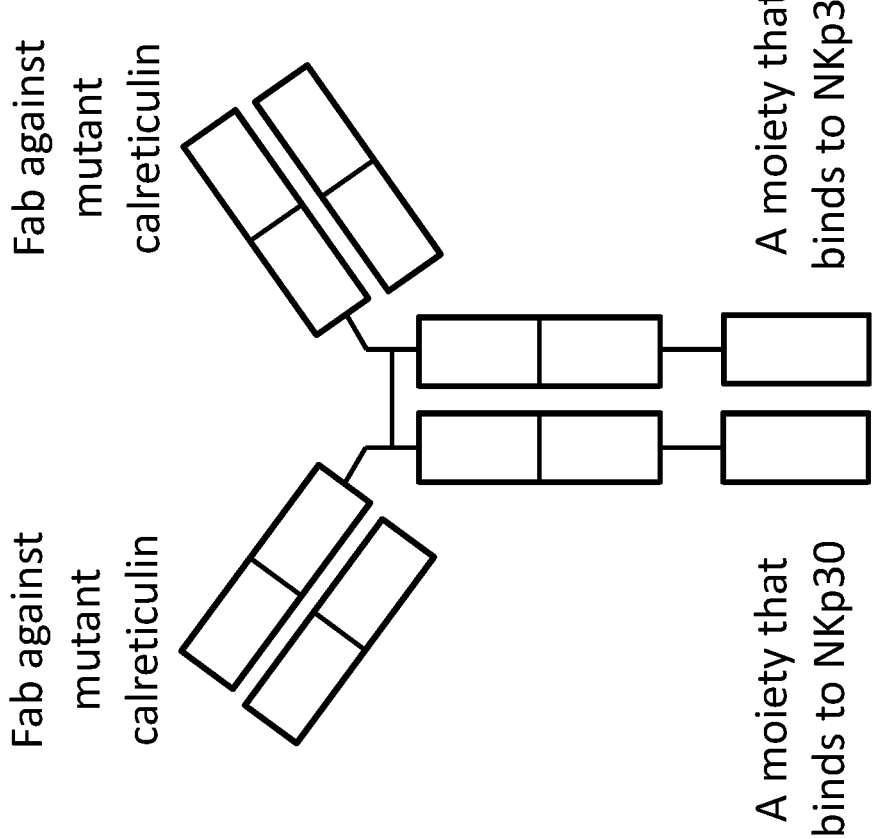
FIGS. 4A and 4B are schematic representations of exemplary formats and configurations of a multifunctional molecule comprising a first antigen binding domain (e.g., a first Fab) that binds to a calreticulin mutant protein, a second antigen binding domain (e.g., a second Fab) that binds to a calreticulin mutant protein, and one or more moieties that bind to NKp30 (e.g., an antibody molecule or ligand that binds to NKp30). In one embodiment, the first antigen binding domain (e.g., the first Fab) binds to a calreticulin mutant protein disclosed herein, e.g., a calreticulin mutant protein disclosed in Table 2 or 3, e.g., Type 1 or Type 2 calreticulin mutant protein disclosed in Table 2 or 3, e.g., a calreticulin mutant protein comprising the amino acid sequence of SEQ ID NO: 169 or 170. In one embodiment, the second antigen binding domain (e.g., the second Fab) binds to a calreticulin mutant protein disclosed herein, e.g., a calreticulin mutant protein disclosed in Table 2 or 3, e.g., Type 1 or Type 2 calreticulin mutant protein disclosed in Table 2 or 3, e.g., a calreticulin mutant protein comprising the amino acid sequence of SEQ ID NO: 169 or 170.
Figure 4B:
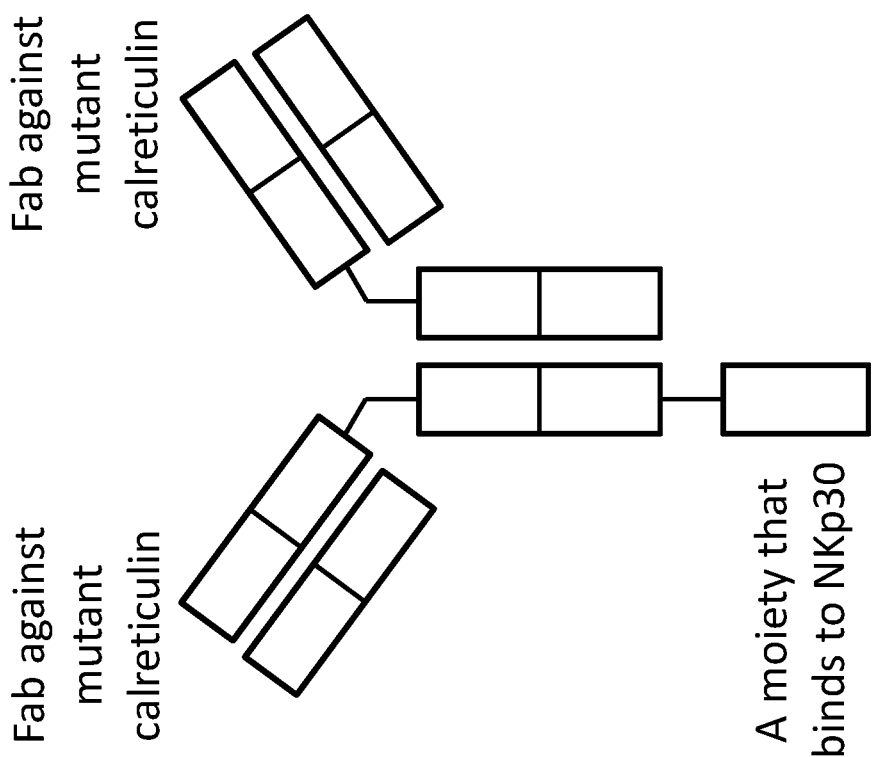

Disclosed herein are multifunctional molecules (also referred to herein as "multispecific molecules") that include a plurality of (e.g., two or more) functionalities (or binding specificities), comprising (i) an antigen binding domain that preferentially binds to a calreticulin mutant protein over a wild type calreticulin protein, wherein the calreticulin mutant protein comprises the amino acid sequence of SEQ ID NO: 141, and (ii) one, two, or all of: (a) an immune cell engager chosen from a T cell engager, an NK cell engager, a B cell engager, a dendritic cell engager, or a macrophage cell engager; (b) a cytokine molecule or a modulator of a cytokine molecule; and (c) a stromal modifying moiety. In some embodiments, the antigen binding domain binds to a calreticulin mutant protein disclosed in Table 2 or Table 3. In some embodiments, the antigen binding domain binds to Type 1 calreticulin mutant protein disclosed in Table 2 or Table 3. In some embodiments, the antigen binding domain binds to Type 2 calreticulin mutant protein disclosed in Table 2 or Table 3. In some embodiments, the antigen binding domain binds to both Type 1 and Type 2 calreticulin mutant proteins disclosed in Table 2 or Table 3.

In an embodiment, the multispecific or multifunctional molecule is a bispecific (or bifunctional) molecule, a trispecific (or trifunctional) molecule, or a tetraspecific (or tetrafunctional) molecule.

Without being bound by theory, the multispecific or multifunctional molecules disclosed herein are expected to localize (e.g., bridge) and/or activate an immune cell (e.g., an immune effector cell chosen from a T cell, an NK cell, a B cell, a dendritic cell or a macrophage), in the presence of a cell expressing the calreticulin mutant protein, e.g., on the surface. Increasing the proximity and/or activity of the immune cell, in the presence of the cell expressing the calreticulin mutant protein, using the multispecific or multifunctional molecules described herein is expected to enhance an immune response against the target cell, thereby providing a more effective therapy.

Novel multifunctional, e.g., multispecific, molecules that include (i) a stromal modifying moiety and (ii) an antigen binding domain that preferentially binds to a calreticulin mutant protein over a wild type calreticulin protein, wherein the calreticulin mutant protein comprises the amino acid sequence of SEQ ID NO: 141 are disclosed. Without being bound by theory, the multifunctional molecules disclosed herein are believed to inter alia target (e.g., localize to) a cancer site, and alter the tumor stroma, e.g., alter the tumor microenvironment near the cancer site. The multifunctional molecules can further include one or both of: an immune cell engager (e.g., chosen from one, two, three, or all of a T cell engager, NK cell engager, a B cell engager, a dendritic cell engager, or a macrophage cell engager); and/or a cytokine molecule (or a modulator of a cytokine molecule). Accordingly, provided herein are, inter alia, multifunctional, e.g., multispecific molecules, that include the aforesaid moieties, nucleic acids encoding the same, methods of producing the aforesaid molecules, and methods of treating a cancer using the aforesaid molecules.

Accordingly, provided herein are, inter alia, multispecific or multifunctional molecules (e.g., multispecific or multifunctional antibody molecules) that include the aforesaid moieties, nucleic acids encoding the same, methods of producing the aforesaid molecules, and methods of treating a disease or disorder, e.g., cancer, using the aforesaid molecules.

Definitions

In some embodiments, the multifunctional molecule includes an immune cell engager. "An immune cell engager" refers to one or more binding specificities that bind and/or activate an immune cell, e.g., a cell involved in an immune response. In embodiments, the immune cell is chosen from a T cell, an NK cell, a B cell, a dendritic cell, and/or the macrophage cell. The immune cell engager can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the immune cell antigen (e.g., the T cell, the NK cell antigen, the B cell antigen, the dendritic cell antigen, and/or the macrophage cell antigen). In embodiments, the immune cell engager specifically binds to the target immune cell, e.g., binds preferentially to the target immune cell. For example, when the immune cell engager is an antibody molecule, it binds to an immune cell antigen (e.g., a T cell antigen, an NK cell antigen, a B cell antigen, a dendritic cell antigen, and/or a macrophage cell antigen) with a dissociation constant of less than about 10 nM.

In some embodiments, the multifunctional molecule includes a cytokine molecule. As used herein, a "cytokine molecule" refers to full length, a fragment or a variant of a cytokine; a cytokine further comprising a receptor domain, e.g., a cytokine receptor dimerizing domain; or an agonist of a cytokine receptor, e.g., an antibody molecule (e.g., an agonistic antibody) to a cytokine receptor, that elicits at least one activity of a naturally-occurring cytokine. In some embodiments the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain. In other embodiments, the cytokine molecule is an agonist of a cytokine receptor, e.g., an antibody molecule (e.g., an agonistic antibody) to a cytokine receptor chosen from an IL-15Ra or IL-21R.

As used herein, the term "molecule" as used in, e.g., antibody molecule, cytokine molecule, receptor molecule, includes full-length, naturally-occurring molecules, as well as variants, e.g., functional variants (e.g., truncations, fragments, mutated (e.g., substantially similar sequences) or derivatized form thereof), so long as at least one function and/or activity of the unmodified (e.g., naturally-occurring) molecule remains.

In some embodiments, the multifunctional molecule includes a stromal modifying moiety. A "stromal modifying moiety," as used herein refers to an agent, e.g., a protein (e.g., an enzyme), that is capable of altering, e.g., degrading a component of, the stroma. In embodiments, the component of the stroma is chosen from, e.g., an ECM component, e.g., a glycosaminoglycan, e.g., hyaluronan (also known as hyaluronic acid or HA), chondroitin sulfate, chondroitin, dermatan sulfate, heparin sulfate, heparin, entactin, tenascin, aggrecan and keratin sulfate; or an extracellular protein, e.g., collagen, laminin, elastin, fibrinogen, fibronectin, and vitronectin.

Certain terms are defined below.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

"Antibody molecule" as used herein refers to a protein, e.g., an immunoglobulin chain or fragment thereof, comprising at least one immunoglobulin variable domain sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', F(ab')2, F (ab) 2, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and F(ab')$_2$ fragments, and single chain variable fragments (scFvs).

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a molecule that can provoke an immune response, e.g., involving activation of certain immune cells and/or antibody generation. Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site," or "binding portion" of an antibody molecule refers to the part of an antibody molecule, e.g., an immunoglobulin (Ig) molecule, that participates in antigen binding. In embodiments, the antigen binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions," (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4.

"Cancer" as used herein can encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. Innate leukocytes include phagocytes (e.g., macrophages, neutrophils, and dendritic cells), mast cells, eosinophils, basophils, and natural killer cells. Innate leukocytes identify and eliminate pathogens, either by attacking larger pathogens through contact or by engulfing and then killing microorganisms, and are mediators in the activation of an adaptive immune response. The cells of the adaptive immune system are special types of leukocytes, called lymphocytes. B cells and T cells are important types of lymphocytes and are derived from hematopoietic stem cells in the bone marrow. B cells are involved in the humoral immune response, whereas T cells are involved in cell-mediated immune response. The term "immune cell" includes immune effector cells.

"Immune effector cell," as that term is used herein, refers to a cell that is involved in an immune response, e.g., in the promotion of an immune effector response. Examples of immune effector cells include, but are not limited to, T cells, e.g., alpha/beta T cells and gamma/delta T cells, B cells, natural killer (NK) cells, natural killer T (NK T) cells, and mast cells.

The term "effector function" or "effector response" refers to a specialized function of a cell. Effector function of a T cell, for example, may be cytolytic activity or helper activity including the secretion of cytokines.

The compositions and methods of the present invention encompass polypeptides and nucleic acids having the sequences specified, or sequences substantially identical or similar thereto, e.g., sequences at least 80%, 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 80%, 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 80%, 85%, 90%, 91%, 92%, 93%, 94%, 95%, 96%, 97%, 98% or 99% identity to a reference sequence, e.g., a sequence provided herein.

The term "variant" refers to a polypeptide that has a substantially identical amino acid sequence to a reference amino acid sequence, or is encoded by a substantially identical nucleotide sequence. In some embodiments, the variant is a functional variant.

The term "functional variant" refers to a polypeptide that has a substantially identical amino acid sequence to a reference amino acid sequence, or is encoded by a substantially identical nucleotide sequence, and is capable of having one or more activities of the reference amino acid sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) (*CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.*

25:3389-3402. When utilizing BLAST and Gapped BLAST programs, the default parameters of the respective programs (e.g., XBLAST and NBLAST) can be used. See http://www.ncbi.nlm.nih.gov.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

As used herein, the term "transforming growth factor beta-1 (TGF-beta 1)" refers to a protein that in humans is encoded by the gene TGFB1, or its orthologs. Swiss-Prot accession number P01137 provides exemplary human TGF-beta 1 amino acid sequences. An exemplary immature human TGF-beta 1 amino acid sequence is provided in SEQ ID NO: 292. An exemplary mature human TGF-beta 1 amino acid sequence is provided in SEQ ID NO: 317.

As used herein, the term "transforming growth factor beta-2 (TGF-beta 2)" refers to a protein that in humans is encoded by the gene TGFB2, or its orthologs. Swiss-Prot accession number P61812 provides exemplary human TGF-beta 2 amino acid sequences. An exemplary immature human TGF-beta 2 amino acid sequence is provided in SEQ ID NO: 293. An exemplary mature human TGF-beta 2 amino acid sequence is provided in SEQ ID NO: 318.

As used herein, the term "transforming growth factor beta-3 (TGF-beta 3)" refers to a protein that in humans is encoded by the gene TGFB3, or its orthologs. Swiss-Prot accession number P10600 provides exemplary human TGF-beta 3 amino acid sequences. An exemplary immature human TGF-beta 3 amino acid sequence is provided in SEQ ID NO: 294. An exemplary mature human TGF-beta 3 amino acid sequence is provided in SEQ ID NO: 319.

As used herein, a "TGF-beta receptor polypeptide" refers to a TGF-beta receptor (e.g., TGFBR1, TGFBR2, or TGFBR3) or its fragment, or variant thereof.

As used herein, the term "transforming growth factor beta receptor type 1 (TGFBR1)" (also known as ALK-5 or SKR4) refers to a protein that in humans is encoded by the gene TGFBR1, or its orthologs. Swiss-Prot accession number P36897 provides exemplary human TGFBR1 amino acid sequences. Exemplary immature human TGFBR1 amino acid sequences are provided in SEQ ID NOs: 295, 296, and 297. Exemplary mature human TGFBR1 amino acid sequences are provided in SEQ ID NOs: 320, 321, and 322. As used herein, a "TGFBR1 polypeptide" refers to a TGFBR1 or its fragment, or variant thereof.

As used herein, the term "transforming growth factor beta receptor type 2 (TGFBR2)" refers to a protein that in humans is encoded by the gene TGFBR2, or its orthologs. Swiss-Prot accession number P37173 provides exemplary human TGFBR2 amino acid sequences. Exemplary immature human TGFBR2 amino acid sequences are provided in SEQ ID NOs: 298 and 299. Exemplary mature human TGFBR2 amino acid sequences are provided in SEQ ID NOs: 323 and 324. As used herein, a "TGFBR2 polypeptide" refers to a TGFBR2 or its fragment, or variant thereof.

As used herein, the term "transforming growth factor beta receptor type 3 (TGFBR3)" refers to a protein that in humans is encoded by the gene TGFBR3, or its orthologs. Swiss-Prot accession number Q03167 provides exemplary human TGFBR3 amino acid sequences. Exemplary immature human TGFBR3 amino acid sequences are provided in SEQ ID NOs: 306 and 307. Exemplary mature human TGFBR3 amino acid sequences are provided in SEQ ID NOs: 325 and 326. As used herein, a "TGFBR3 polypeptide" refers to a TGFBR3 or its fragment, or variant thereof.

Various aspects of the invention are described in further detail below. Additional definitions are set out throughout the specification.

Antibody Molecules

In one embodiment, the antibody molecule binds to a cancer antigen, e.g., a tumor antigen or a stromal antigen. In some embodiments, the cancer antigen is, e.g., a mammalian, e.g., a human, cancer antigen. In other embodiments, the antibody molecule binds to an immune cell antigen, e.g., a mammalian, e.g., a human, immune cell antigen. For example, the antibody molecule binds specifically to an epitope, e.g., linear or conformational epitope, on the cancer antigen or the immune cell antigen.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific or multifunctional antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. A preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in (Camelidae species, for example in camel, llama, dromedary, alpaca and guanaco. Other species besides (Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains.* In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273,927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibody molecules generated in a non-human organism, e.g., a rat or mouse, and then modified, e.g., in the variable framework or constant region, to decrease antigenicity in a human are within the invention.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.,* 32:180-190 (1990)) and also because of potential allergic reactions (see, e.g., LoBuglio et al., *Hybridoma,* 5:5117-5123 (1986)).

Chimeric antibodies can be produced by recombinant DNA techniques known in the art (see Robinson et al., International Patent Publication PCT/US86/02269; Akira, et al., European Patent Application 184, 187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125, 023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239: 1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibody molecules in which specific amino acids have been substituted, deleted or added. Criteria for selecting amino acids from the donor are described in U.S. Pat. No. 5,585, 089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann N Y Acad Sci* 880:263-80; and Reiter, Y. (1996) (*Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Multispecific or Multifunctional Antibody Molecules

Exemplary structures of multispecific and multifunctional molecules defined herein are described throughout. Exemplary structures are further described in: Weidle U et al. (2013) The Intriguing Options of Multispecific Antibody Formats for Treatment of Cancer. *Cancer Genomics & Proteomics* 10:1-18 (2013); and Spiess C et al. (2015) Alternative molecular formats and therapeutic applications for bispecific antibodies. *Molecular Immunology* 67:95-106; the full contents of each of which is incorporated by reference herein).

In embodiments, multispecific antibody molecules can comprise more than one antigen-binding site, where different sites are specific for different antigens. In embodiments, multispecific antibody molecules can bind more than one (e.g., two or more) epitopes on the same antigen. In embodiments, multispecific antibody molecules comprise an antigen-binding site specific for a target cell (e.g., cancer cell) and a different antigen-binding site specific for an immune effector cell. In one embodiment, the multispecific antibody molecule is a bispecific antibody molecule. Bispecific antibody molecules can be classified into five different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates.

BsIgG is a format that is monovalent for each antigen. Exemplary BsIgG formats include but are not limited to crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, KA-body, orthogonal Fab. See Spiess et al. Mol. Immunol. 67 (2015): 95-106. Exemplary BsIgGs include catumaxomab (Fresenius Biotech, Trion Pharma, Neopharm), which contains an anti-CD3 arm and an anti-EpCAM arm; and ertumaxomab (Neovii Biotech, Fresenius Biotech), which targets CD3 and HER2. In some embodiments, BsIgG comprises heavy chains that are engineered for heterodimerization. For example, heavy chains can be engineered for heterodimerization using a "knobs-into-holes" strategy, a SEED platform, a common heavy chain (e.g., in KA-bodies), and use of heterodimeric Fc regions. See Spiess et al. Mol. Immunol. 67 (2015): 95-106. Strategies that have been used to avoid heavy chain pairing of homodimers in BsIgG include knobs-in-holes, duobody, azymetric, charge pair, HA-TF, SEEDbody, and differential protein A affinity. See Id. BsIgG can be produced by separate expression of the component antibodies in different host cells and subsequent purification/assembly into a BsIgG. BsIgG can also be produced by expression of the component antibodies in a single host cell. BsIgG can be purified using affinity chromatography, e.g., using protein A and sequential pH elution.

IgG appended with an additional antigen-binding moiety is another format of bispecific antibody molecules. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). See Id. Examples of appended IgG formats include dual variable domain IgG (DVD-Ig), IgG (H)-scFv, scFv-(H) IgG, IgG (L)-scFv, scFv-(L) IgG, IgG (L,H)-Fv, IgG (H)-V, V(H)-IgG, IgG (L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67 (2015): 95-106. An example of an IgG-scFv is MM-141 (Merrimack Pharmaceuticals), which binds IGF-IR and HER3. Examples of DVD-Ig include ABT-981 (AbbVie), which binds IL-1α and IL-1β; and ABT-122 (Abb Vie), which binds TNF and IL-17A.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Exemplary bispecific antibody fragments include but are not limited to nanobody, nanobody-HAS, BITE, Diabody, DART, TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody. See Id. For example, the BiTE format comprises tandem scFvs, where the component scFvs bind to CD3 on T cells and a surface antigen on cancer cells Bispecific fusion proteins include antibody fragments linked to other proteins, e.g., to add additional specificity and/or functionality. An example of a bispecific fusion protein is an immTAC, which comprises an anti-CD3 scFv linked to an affinity-matured T-cell receptor that recognizes HLA-presented peptides. In embodiments, the dock-and-lock (DNL) method can be used to generate bispecific antibody molecules with higher valency. Also, fusions to albumin binding proteins or human serum albumin can be extend the serum half-life of antibody fragments. See Id.

In embodiments, chemical conjugation, e.g., chemical conjugation of antibodies and/or antibody fragments, can be used to create BsAb molecules. See Id. An exemplary bispecific antibody conjugate includes the CovX-body format, in which a low molecular weight drug is conjugated site-specifically to a single reactive lysine in each Fab arm or an antibody or fragment thereof. In embodiments, the conjugation improves the serum half-life of the low molecular weight drug. An exemplary CovX-body is CVX-241 (NCT01004822), which comprises an antibody conjugated to two short peptides inhibiting either VEGF or Ang2. See Id.

The antibody molecules can be produced by recombinant expression, e.g., of at least one or more component, in a host system. Exemplary host systems include eukaryotic cells (e.g., mammalian cells, e.g., CHO cells, or insect cells, e.g., SF9 or S2 cells) and prokaryotic cells (e.g., *E. coli*). Bispecific antibody molecules can be produced by separate expression of the components in different host cells and subsequent purification/assembly. Alternatively, the antibody molecules can be produced by expression of the components in a single host cell. Purification of bispecific antibody molecules can be performed by various methods such as affinity chromatography, e.g., using protein A and sequential pH elution. In other embodiments, affinity tags can be used for purification, e.g., histidine-containing tag, myc tag, or streptavidin tag.

CDR-Grafted Scaffolds

In embodiments, the antibody molecule is a CDR-grafted scaffold domain. In embodiments, the scaffold domain is based on a fibronectin domain, e.g., fibronectin type III domain. The overall fold of the fibronectin type III (Fn3) domain is closely related to that of the smallest functional antibody fragment, the variable domain of the antibody heavy chain. There are three loops at the end of Fn3; the positions of BC, DE and FG loops approximately correspond to those of CDR1, 2 and 3 of the VH domain of an antibody. Fn3 does not have disulfide bonds; and therefore Fn3 is stable under reducing conditions, unlike antibodies and their fragments (see, e.g., WO 98/56915; WO 01/64942; WO 00/34784). An Fn3 domain can be modified (e.g., using CDRs or hypervariable loops described herein) or varied, e.g., to select domains that bind to an antigen/marker/cell described herein.

In embodiments, a scaffold domain, e.g., a folded domain, is based on an antibody, e.g., a "minibody" scaffold created by deleting three beta strands from a heavy chain variable domain of a monoclonal antibody (see, e.g., Tramontano et al., 1994, J Mol. Recognit. 7:9; and Martin et al., 1994, EMBO J. 13:5303-5309). The "minibody" can be used to present two hypervariable loops. In embodiments, the scaffold domain is a V-like domain (see, e.g., Coia et al. WO 99/45110) or a domain derived from tendamistatin, which is a 74 residue, six-strand beta sheet sandwich held together by two disulfide bonds (see, e.g., McConnell and Hoess, 1995, J Mol. Biol. 250:460). For example, the loops of tendamistatin can be modified (e.g., using CDRs or hypervariable loops) or varied, e.g., to select domains that bind to a marker/antigen/cell described herein. Another exemplary scaffold domain is a beta-sandwich structure derived from the extracellular domain of CTLA-4 (see, e.g., WO 00/60070).

Other exemplary scaffold domains include but are not limited to T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). See, e.g., US20040009530 and U.S. Pat. No. 7,501,121, incorporated herein by reference.

In embodiments, a scaffold domain is evaluated and chosen, e.g., by one or more of the following criteria: (1) amino acid sequence, (2) sequences of several homologous domains, (3) 3-dimensional structure, and/or (4) stability data over a range of pH, temperature, salinity, organic solvent, oxidant concentration. In embodiments, the scaffold domain is a small, stable protein domain, e.g., a protein of less than 100, 70, 50, 40 or 30 amino acids. The domain may include one or more disulfide bonds or may chelate a metal, e.g., zinc.

Antibody-Based Fusions

A variety of formats can be generated which contain additional binding entities attached to the N or C terminus of antibodies. These fusions with single chain or disulfide stabilized Fvs or Fabs result in the generation of tetravalent molecules with bivalent binding specificity for each antigen. Combinations of scFvs and scFabs with IgGs enable the production of molecules which can recognize three or more different antigens.

Antibody-Fab Fusion

Antibody-Fab fusions are bispecific antibodies comprising a traditional antibody to a first target and a Fab to a second target fused to the C terminus of the antibody heavy chain. Commonly the antibody and the Fab will have a common light chain. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) Nature Biotech 15:159.

Antibody-scFv Fusion

Antibody-scFv Fusions are bispecific antibodies comprising a traditional antibody and a scFv of unique specificity fused to the C terminus of the antibody heavy chain. The scFv can be fused to the C terminus through the Heavy Chain of the scFv either directly or through a linker peptide. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) Nature Biotech 15:159.

Variable Domain Immunoglobulin DVD

A related format is the dual variable domain immunoglobulin (DVD), which are composed of VH and VL domains of a second specificity place upon the N termini of the V domains by shorter linker sequences.

Other exemplary multispecific antibody formats include, e.g., those described in the following US20160114057A1, US20130243775A1, US20140051833, US20130022601, US20150017187A1, US20120201746A1, US20150133638A1, US20130266568A1, US20160145340A1, WO2015127158A1, US20150203591A1, US20140322221A1, US20130303396A1, US20110293613, US20130017200A1, US20160102135A1, WO2015197598A2, WO2015197582A1, U.S. Pat. No. 9,359,437, US20150018529, WO2016115274A1, WO2016087416A1, US20080069820A1, U.S. Pat. Nos. 9,145,588B, 7,919,257, and US20150232560A1.

Exemplary multispecific molecules utilizing a full antibody-Fab/scFab format include those described in the following, U.S. Pat. No. 9,382,323B2, US20140072581A1, US20140308285A1, US20130165638A1, US20130267686A1, US20140377269A1, U.S. Pat. No. 7,741,446B2, and WO1995009917A1. Exemplary multispecific molecules utilizing a domain exchange format include those described in the following, US20150315296A1, WO2016087650A1, US20160075785A1, WO2016016299A1, US20160130347A1, US20150166670, U.S. Pat. No. 8,703,132B2, US20100316645, U.S. Pat. No. 8,227,577B2, US20130078249.

Fc-Containing Entities (Mini-Antibodies)

Fc-containing entities, also known as mini-antibodies, can be generated by fusing scFv to the C-termini of constant heavy region domain 3 (CH3-scFv) and/or to the hinge region (scFv-hinge-Fc) of an antibody with a different specificity. Trivalent entities can also be made which have disulfide stabilized variable domains (without peptide linker) fused to the C-terminus of CH3 domains of IgGs.

Fc-Containing Multispecific Molecules

In some embodiments, the multispecific molecules disclosed herein includes an immunoglobulin constant region (e.g., an Fc region). Exemplary Fc regions can be chosen from the heavy chain constant regions of IgG1, IgG2, IgG3 or IgG4; more particularly, the heavy chain constant region of human IgG1, IgG2, IgG3, or IgG4.

In some embodiments, the immunoglobulin chain constant region (e.g., the Fc region) is altered, e.g., mutated, to increase or decrease one or more of: Fc receptor binding, antibody glycosylation, the number of cysteine residues, effector cell function, or complement function.

In other embodiments, an interface of a first and second immunoglobulin chain constant regions (e.g., a first and a second Fc region) is altered, e.g., mutated, to increase or decrease dimerization, e.g., relative to a non-engineered interface, e.g., a naturally-occurring interface. For example, dimerization of the immunoglobulin chain constant region (e.g., the Fc region) can be enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface.

In some embodiments, the multispecific molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) can include a paired an amino acid substitution chosen from: T366S, L368A, or Y407V (e.g., corresponding to a cavity or hole), and T366W (e.g., corresponding to a protuberance or knob).

In other embodiments, the multifunctional molecule includes a half-life extender, e.g., a human serum albumin or an antibody molecule to human serum albumin.

Heterodimerized Antibody Molecules & Methods of Making

Various methods of producing multispecific antibodies have been disclosed to address the problem of incorrect heavy chain pairing. Exemplary methods are described below. Exemplary multispecific antibody formats and methods of making said multispecific antibodies are also disclosed in e.g., Speiss et al. Molecular Immunology 67 (2015) 95-106; and Klein et al mAbs 4:6, 653-663; November/December 2012; the entire contents of each of which are incorporated by reference herein.

Heterodimerized bispecific antibodies are based on the natural IgG structure, wherein the two binding arms recognize different antigens. IgG derived formats that enable defined monovalent (and simultaneous) antigen binding are generated by forced heavy chain heterodimerization, combined with technologies that minimize light chain mispairing (e.g., common light chain). Forced heavy chain heterodimerization can be obtained using, e.g., knob-in-hole OR strand exchange engineered domains (SEED).

Knob-In-Hole

Knob-in-Hole as described in U.S. Pat. Nos. 5,731,116, 7,476,724 and Ridgway, J. et al. (1996) *Prot. Engineering* 9(7): 617-621, broadly involves: (1) mutating the CH3 domain of one or both antibodies to promote heterodimerization; and (2) combining the mutated antibodies under conditions that promote heterodimerization. "Knobs" or "protuberances" are typically created by replacing a small amino acid in a parental antibody with a larger amino acid (e.g., T366Y or T366W); "Holes" or "cavities" are created by replacing a larger residue in a parental antibody with a smaller amino acid (e.g., Y407T, T366S, L368A and/or Y407V).

For bispecific antibodies including an Fc domain, introduction of specific mutations into the constant region of the heavy chains to promote the correct heterodimerization of the Fc portion can be utilized. Several such techniques are reviewed in Klein et al. (mAbs (2012) 4:6, 1-11), the contents of which are incorporated herein by reference in their entirety. These techniques include the "knobs-into-holes" (KiH) approach which involves the introduction of a bulky residue into one of the CH3 domains of one of the antibody heavy chains. This bulky residue fits into a complementary "hole" in the other CH3 domain of the paired heavy chain so as to promote correct pairing of heavy chains (see e.g., U.S. Pat. No. 7,642,228).

Exemplary KiH mutations include S354C, T366W in the "knob" heavy chain and Y349C, T366S, L368A, Y407V in the "hole" heavy chain. Other exemplary KiH mutations are provided in Table 1, with additional optional stabilizing Fc cysteine mutations.

TABLE 1

Exemplary Fc KiH mutations and optional Cysteine mutations

| Position | Knob Mutation | Hole Mutation |
|---|---|---|
| T366 | T366W | T366S |
| L368 | — | L368A |
| Y407 | — | Y407V |

Additional Cysteine Mutations to form a stabilizing disulfide bridge

| Position | Knob CH3 | Hole CH3 |
|---|---|---|
| S354 | S354C | — |
| Y349 | — | Y349C |

Other Fc mutations are provided by Igawa and Tsunoda who identified 3 negatively charged residues in the CH3 domain of one chain that pair with three positively charged residues in the CH3 domain of the other chain. These specific charged residue pairs are: E356-K439, E357-K370, D399-K409 and vice versa. By introducing at least two of the following three mutations in chain A: E356K, E357K and D399K, as well as K370E, K409D, K439E in chain B, alone or in combination with newly identified disulfide bridges, they were able to favor very efficient heterodimerization while suppressing homodimerization at the same time (Martens T et al. A novel one-armed antic-Met antibody inhibits glioblastoma growth in vivo. Clin Cancer Res 2006; 12:6144-52; PMID:17062691). Xencor defined 41 variant pairs based on combining structural calculations and sequence information that were subsequently screened for maximal heterodimerization, defining the combination of S364H, F405A (HA) on chain A and Y349T, T394F on chain B (TF) (Moore G L et al. A novel bispecific antibody format enables simultaneous bivalent and monovalent co-engagement of distinct target antigens. MAbs 2011; 3:546-57; PMID: 22123055).

Other exemplary Fc mutations to promote heterodimerization of multispecific antibodies include those described in the following references, the contents of each of which is incorporated by reference herein, WO2016071377A1, US20140079689A1, US20160194389A1, US20160257763, WO2016071376A2, WO2015107026A1, WO2015107025A1, WO2015107015A1, US20150353636A1, US20140199294A1, U.S. Pat. No. 7,750,128B2, US20160229915A1, US20150344570A1, U.S. Pat. No. 8,003,774A1, US20150337049A1, US20150175707A1, US20140242075A1, US20130195849A1, US20120149876A1, US20140200331A1, U.S. Pat. Nos. 9,309,311B2, 8,586,713, US20140037621A1, US20130178605A1, US20140363426A1, US20140051835A1 and US20110054151A1.

Stabilizing cysteine mutations have also been used in combination with KiH and other Fc heterodimerization promoting variants, see e.g., U.S. Pat. No. 7,183,076. Other exemplary cysteine modifications include, e.g., those disclosed in US20140348839A1, U.S. Pat. Nos. 7,855,275B2, and 9,000,130B2.

Strand Exchange Engineered Domains (SEED)

Heterodimeric Fc platform that support the design of bispecific and asymmetric fusion proteins by devising strand-exchange engineered domain (SEED) C(H)3 heterodimers are known. These derivatives of human IgG and IgA C(H)3 domains create complementary human SEED C(H)3 heterodimers that are composed of alternating segments of human IgA and IgG C(H)3 sequences. The resulting pair of SEED C(H)3 domains preferentially associates to form heterodimers when expressed in mammalian cells. SEEDbody (Sb) fusion proteins consist of [IgG1 hinge]-C(H)2-[SEED C(H)3], that may be genetically linked to one or more fusion partners (see e.g., Davis J H et al. SEEDbodies: fusion proteins based on strand exchange engineered domain (SEED) CH3 heterodimers in an Fc analogue platform for asymmetric binders or immunofusions and bispecific antibodies. Protein Eng Des Sel 2010; 23:195-202; PMID:20299542 and U.S. Pat. No. 8,871,912. The contents of each of which are incorporated by reference herein).

Duobody

"Duobody" technology to produce bispecific antibodies with correct heavy chain pairing are known. The DuoBody technology involves three basic steps to generate stable bispecific human IgG1antibodies in a post-production exchange reaction. In a first step, two IgG1s, each containing single matched mutations in the third constant (CH3) domain, are produced separately using standard mammalian recombinant cell lines. Subsequently, these IgG1 antibodies are purified according to standard processes for recovery and purification. After production and purification (post-production), the two antibodies are recombined under tailored laboratory conditions resulting in a bispecific antibody product with a very high yield (typically >95%) (see e.g., Labrijn et al, PNAS 2013; 110(13):5145-5150 and Labrijn et al. Nature Protocols 2014; 9(10):2450-63, the contents of each of which are incorporated by reference herein).

Electrostatic Interactions

Methods of making multispecific antibodies using CH3 amino acid changes with charged amino acids such that homodimer formation is electrostatically unfavorable are disclosed. EP1870459 and WO 2009089004 describe other strategies for favoring heterodimer formation upon co-expression of different antibody domains in a host cell. In these methods, one or more residues that make up the heavy chain constant domain 3 (CH3), CH3-CH3 interfaces in both CH3 domains are replaced with a charged amino acid such that homodimer formation is electrostatically unfavorable and heterodimerization is electrostatically favorable. Additional methods of making multispecific molecules using electrostatic interactions are described in the following references, the contents of each of which is incorporated by reference herein, include US20100015133, U.S. Pat. Nos. 8,592,562B2, 9,200,060B2, US20140154254A1, and U.S. Pat. No. 9,358,286A1.

Common Light Chain

Light chain mispairing needs to be avoided to generate homogenous preparations of bispecific IgGs. One way to achieve this is through the use of the common light chain principle, i.e. combining two binders that share one light chain but still have separate specificities. An exemplary method of enhancing the formation of a desired bispecific antibody from a mixture of monomers is by providing a common variable light chain to interact with each of the heteromeric variable heavy chain regions of the bispecific antibody. Compositions and methods of producing bispecific antibodies with a common light chain as disclosed in, e.g., U.S. Pat. No. 7,183,076B2, US20110177073A1, EP2847231A1, WO2016079081A1, and EP3055329A1, the contents of each of which is incorporated by reference herein.

CrossMab

Another option to reduce light chain mispairing is the CrossMab technology which avoids non-specific L chain mispairing by exchanging CH1 and CL domains in the Fab of one half of the bispecific antibody. Such crossover variants retain binding specificity and affinity, but make the two arms so different that L chain mispairing is prevented. The CrossMab technology (as reviewed in Klein et al. Supra) involves domain swapping between heavy and light chains so as to promote the formation of the correct pairings. Briefly, to construct a bispecific IgG-like CrossMab antibody that could bind to two antigens by using two distinct light chain-heavy chain pairs, a two-step modification process is applied. First, a dimerization interface is engineered into the C-terminus of each heavy chain using a heterodimerization approach, e.g., Knob-into-hole (KiH) technology, to ensure that only a heterodimer of two distinct heavy chains from one antibody (e.g., Antibody A) and a second antibody (e.g., Antibody B) is efficiently formed. Next, the constant heavy 1 (CH1) and constant light (CL) domains of one antibody are exchanged (Antibody A), keeping the variable heavy (VH) and variable light (VL) domains consistent. The exchange of the CH1 and CL domains ensured that the modified antibody (Antibody A) light chain would only efficiently dimerize with the modified antibody (antibody A) heavy chain, while the unmodified antibody (Antibody B) light chain would only efficiently dimerize with the unmodified antibody (Antibody B) heavy chain; and thus only the desired bispecific CrossMab would be efficiently formed (see e.g., Cain, C. SciBX 4(28); doi:10.1038/scibx.2011.783, the contents of which are incorporated by reference herein).

Common Heavy Chain

An exemplary method of enhancing the formation of a desired bispecific antibody from a mixture of monomers is by providing a common variable heavy chain to interact with each of the heteromeric variable light chain regions of the bispecific antibody. Compositions and methods of producing bispecific antibodies with a common heavy chain are disclosed in, e.g., US20120184716, US20130317200, and US20160264685A1, the contents of each of which is incorporated by reference herein.

Amino Acid Modifications

Alternative compositions and methods of producing multispecific antibodies with correct light chain pairing include various amino acid modifications. For example, Zymeworks describes heterodimers with one or more amino acid modifications in the CH1 and/or CL domains, one or more amino acid modifications in the VH and/or VL domains, or a combination thereof, which are part of the interface between the light chain and heavy chain and create preferential pairing between each heavy chain and a desired light chain such that when the two heavy chains and two light chains of the heterodimer pair are co-expressed in a cell, the heavy chain of the first heterodimer preferentially pairs with one of the light chains rather than the other (see e.g., WO2015181805). Other exemplary methods are described in WO2016026943 (Argen-X), US20150211001, US20140072581A1, US20160039947A1, and US20150368352.

Lambda Kappa Formats

Multispecific molecules (e.g., multispecific antibody molecules) that include the lambda light chain polypeptide and a kappa light chain polypeptides, can be used to allow for heterodimerization. Methods for generating bispecific antibody molecules comprising the lambda light chain polypeptide and a kappa light chain polypeptides are disclosed in PCT/US17/53053 filed on Sep. 22, 2017, incorporated herein by reference in its entirety.

In embodiments, the multispecific molecules includes a multispecific antibody molecule, e.g., an antibody molecule comprising two binding specificities, e.g., a bispecific antibody molecule. The multispecific antibody molecule includes:

a lambda light chain polypeptide 1 (LLCP1) specific for a first epitope;

a heavy chain polypeptide 1 (HCP1) specific for the first epitope;

a kappa light chain polypeptide 2 (KLCP2) specific for a second epitope; and a heavy chain polypeptide 2 (HCP2) specific for the second epitope.

"Lambda light chain polypeptide 1 (LLCP1)", as that term is used herein, refers to a polypeptide comprising sufficient light chain (LC) sequence, such that when combined with a cognate heavy chain variable region, can mediate specific binding to its epitope and complex with an HCP1. In an embodiment it comprises all or a fragment of a CH1 region. In an embodiment, an LLCP1 comprises LC-CDR1, LC-CDR2, LC-CDR3, FR1, FR2, FR3, FR4, and CH1, or sufficient sequence therefrom to mediate specific binding of its epitope and complex with an HCP1. LLCP1, together with its HCP1, provide specificity for a first epitope (while KLCP2, together with its HCP2, provide specificity for a second epitope). As described elsewhere herein, LLCP1 has a higher affinity for HCP1 than for HCP2.

"Kappa light chain polypeptide 2 (KLCP2)", as that term is used herein, refers to a polypeptide comprising sufficient light chain (LC) sequence, such that when combined with a cognate heavy chain variable region, can mediate specific binding to its epitope and complex with an HCP2. In an embodiments it comprises all or a fragment of a CH1 region. In an embodiment, a KLCP2 comprises LC-CDR1, LC-CDR2, LC-CDR3, FR1, FR2, FR3, FR4, and CH1, or sufficient sequence therefrom to mediate specific binding of its epitope and complex with an HCP2. KLCP2, together with its HCP2, provide specificity for a second epitope (while LLCP1, together with its HCP1, provide specificity for a first epitope).

"Heavy chain polypeptide 1 (HCP1)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an LLCP1, (ii) to complex preferentially, as described herein to LLCP1 as opposed to KLCP2; and (iii) to complex preferentially, as described herein, to an HCP2, as opposed to another molecule of HCP1. HCP1, together with its LLCP1, provide specificity for a first epitope (while KLCP2, together with its HCP2, provide specificity for a second epitope).

"Heavy chain polypeptide 2 (HCP2)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In an embodiments it comprises all or a fragment of a CH1 region. In an embodiments it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an KLCP2, (ii) to complex preferentially, as described herein to KLCP2 as opposed to LLCP1; and (iii) to complex preferentially, as described herein, to an HCP1, as opposed to another molecule of HCP2. HCP2, together with its KLCP2, provide specificity for a second epitope (while LLCP1, together with its HCP1, provide specificity for a first epitope).

In some embodiments of the multispecific antibody molecule disclosed herein:

LLCP1 has a higher affinity for HCP1 than for HCP2; and/or

KLCP2 has a higher affinity for HCP2 than for HCP1.

In embodiments, the affinity of LLCP1 for HCP1 is sufficiently greater than its affinity for HCP2, such that under preselected conditions, e.g., in aqueous buffer, e.g., at pH 7, in saline, e.g., at pH 7, or under physiological conditions, at least 75, 80, 90, 95, 98, 99, 99.5, or 99.9% of the multispecific antibody molecule molecules have a LLCP1complexed, or interfaced with, a HCP1.

In some embodiments of the multispecific antibody molecule disclosed herein:

the HCP1 has a greater affinity for HCP2, than for a second molecule of HCP1; and/or the HCP2 has a greater affinity for HCP1, than for a second molecule of HCP2.

In embodiments, the affinity of HCP1 for HCP2 is sufficiently greater than its affinity for a second molecule of HCP1, such that under preselected conditions, e.g., in aqueous buffer, e.g., at pH 7, in saline, e.g., at pH 7, or under physiological conditions, at least 75%, 80, 90, 95, 98, 99 99.5 or 99.9% of the multispecific antibody molecule molecules have a HCP1 complexed, or interfaced with, a HCP2.

In another aspect, disclosed herein is a method for making, or producing, a multispecific antibody molecule. The method includes:

(i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both));
(ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));
(iii) providing a lambda chain polypeptide (e.g., a lambda light variable region (VL), a lambda light constant chain (VL), or both) that preferentially associates with the first heavy chain polypeptide (e.g., the first VH); and
(iv) providing a kappa chain polypeptide (e.g., a lambda light variable region (VLc), a lambda light constant chain (VLx), or both) that preferentially associates with the second heavy chain polypeptide (e.g., the second VH), under conditions where (i)-(iv) associate.

In embodiments, the first and second heavy chain polypeptides form an Fc interface that enhances heterodimerization.

In embodiments, (i)-(iv) (e.g., nucleic acid encoding (i)-(iv)) are introduced in a single cell, e.g., a single mammalian cell, e.g., a CHO cell. In embodiments, (i)-(iv) are expressed in the cell.

In embodiments, (i)-(iv) (e.g., nucleic acid encoding (i)-(iv)) are introduced in different cells, e.g., different mammalian cells, e.g., two or more CHO cell. In embodiments, (i)-(iv) are expressed in the cells.

In one embodiments, the method further comprises purifying a cell-expressed antibody molecule, e.g., using a lambda—and/or—kappa-specific purification, e.g., affinity chromatography.

In embodiments, the method further comprises evaluating the cell-expressed multispecific antibody molecule. For example, the purified cell-expressed multispecific antibody molecule can be analyzed by techniques known in the art, include mass spectrometry. In one embodiment, the purified cell-expressed antibody molecule is cleaved, e.g., digested with papain to yield the Fab moieties and evaluated using mass spectrometry.

In embodiments, the method produces correctly paired kappa/lambda multispecific, e.g., bispecific, antibody molecules in a high yield, e.g., at least 75%, 80, 90, 95, 98, 99 99.5 or 99.9%.

In other embodiments, the multispecific, e.g., a bispecific, antibody molecule that includes:
(i) a first heavy chain polypeptide (HCP1) (e.g., a heavy chain polypeptide comprising one, two, three or all of a first heavy chain variable region (first VH), a first CH1, a first heavy chain constant region (e.g., a first CH2, a first CH3, or both)), e.g., wherein the HCP1 binds to a first epitope;
(ii) a second heavy chain polypeptide (HCP2) (e.g., a heavy chain polypeptide comprising one, two, three or all of a second heavy chain variable region (second VH), a second CH1, a second heavy chain constant region (e.g., a second CH2, a second CH3, or both)), e.g., wherein the HCP2 binds to a second epitope;
(iii) a lambda light chain polypeptide (LLCP1) (e.g., a lambda light variable region (VL1), a lambda light constant chain (VL1), or both) that preferentially associates with the first heavy chain polypeptide (e.g., the first VH), e.g., wherein the LLCP1 binds to a first epitope; and
(iv) a kappa light chain polypeptide (KLCP2) (e.g., a lambda light variable region (VLk), a lambda light constant chain (VLk), or both) that preferentially associates with the second heavy chain polypeptide (e.g., the second VH), e.g., wherein the KLCP2 binds to a second epitope.

In embodiments, the first and second heavy chain polypeptides form an Fc interface that enhances heterodimerization. In embodiments, the multispecific antibody molecule has a first binding specificity that includes a hybrid VL1-CL1 heterodimerized to a first heavy chain variable region connected to the Fc constant, CH2-CH3 domain (having a knob modification) and a second binding specificity that includes a hybrid VLk-CLk heterodimerized to a second heavy chain variable region connected to the Fc constant, CH2-CH3 domain (having a hole modification).

Calreticulin-Targeting Antigen Binding Domains

The present disclosure provides, inter alia, multispecific (e.g., bi-, tri-, tetra-specific) or multifunctional molecules, that include, e.g., are engineered to contain, one or more antigen binding domains that bind to calreticulin, e.g., a calreticulin mutant protein. In some embodiments, the multifunctional molecule preferentially binds to a calreticulin mutant protein over a wild type calreticulin protein.

An exemplary wild type human calreticulin is shown as SEQ ID NO: 140.

(SEQ ID NO: 140)
EPAVYFKEQFLDGDGWTSRWIESKHKSDFGKFVLSSGKFYGDEEKDKGL

QTSQDARFYALSASFEPFSNKGQTLVVQFTVKHEQNIDCGGGYVKLFPN

SLDQTDMHGDSEYNIMFGPDICGPGTKKVHVIFNYKGKNVLINKDIRCK

DDEFTHLYTLIVRPDNTYEVKIDNSQVESGSLEDDWDFLPPKKIKDPDA

SKPEDWDERAKIDDPTDSKPEDWDKPEHIPDPDAKKPEDWDEEMDGEWE

PPVIQNPEYKGEWKPRQIDNPDYKGTWIHPEIDNPEYSPDPSIYAYDNF

GVLGLDLWQVKSGTIFDNFLITNDEAYAEEFGNETWGVTKAAEKQMKDK

QDEEQRLKEEEEDKKRKEEEEAEDKEDDEDKDEDEEDEEDKEEDEEEDV

PGQAKDEL

Calreticulin mutant proteins have been identified and found to be associated with myeloid cancers, e.g., see Nangalia et al., N Engl J Med. 2013 Dec. 19; 369(25):2391-2405, Klampfl et al., N Engl J Med. 2013 Dec. 19; 369(25): 2379-90, and US20170269092, herein incorporated by reference in their entirety. Mutant calreticulin has a frameshift in exon 9 of the coding sequence of wild type calreticulin, resulting in the replacement of the C-terminal negatively charged amino acids of wild type calreticulin by a predominantly positively charged polypeptide. Table 2 discloses full-length amino acid sequences of 36 calreticulin mutant proteins. Table 3 discloses the C-terminal amino acid sequences of the 36 calreticulin mutant proteins. All 36 calreticulin mutant proteins comprise the amino acid sequence of RRKMSPARPRTSCREACLQGWTEA (SEQ ID NO: 141).

The predominant mutations of calreticulin are Type 1 and Type 2 mutations (see Tables 2 and 3). Type 1 mutation is a 52-bp deletion (c.1092_1143del) whereas Type 2 mutation is a 5-bp insertion (c.1154_1155insTTGTC).

TABLE 2

Full-length amino acid sequences of calreticulin mutants

| SEQ ID NO | Type | Full length sequences of insertion/deletion frameshift mutations of calreticulin |
|---|---|---|
| SEQ ID NO: 169 | Type 1 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRTRRMMRTKMRMRRMRRTRRKMRRKMSPARPRTSCREACLQGWTEA |
| SEQ ID NO: 170 | Type 2 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDKKRKEEEEAEDNCRRMMRTKMRMRRMRRTRRKMRRKMS<br>PARPRTSCREACLQGWTEA |
| SEQ ID NO: 171 | Type 3 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRQRTRRMMRTKMRMRRMRRTRRKMRRKMSPARPRTSCREACLQGWT<br>EA |
| SEQ ID NO: 172 | Type 4 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLRRQRTRRMMRTKMRMRRMRRTRRKMRRKMSPARPRTSCREACL<br>QGWTEA |
| SEQ ID NO: 173 | Type 5 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEG<br>QRTRRMMRTKMRMRRMRRTRRKMRRKMSPARPRTSCREACLQGWTEA |
| SEQ ID NO: 174 | Type 6 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>RRQRTRRMMRTKMRMRRMRRTRRKMRRKMSPARPRTSCREACLQGWT<br>EA |
| SEQ ID NO: 175 | Type 7 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLRRMMRTKMRMRRMRRTRRKMRRKMSPARPRTSCREACLQGWTEA |
| SEQ ID NO: 176 | Type 8 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI |

TABLE 2-continued

Full-length amino acid sequences of calreticulin mutants

| SEQ ID NO | Type | Full length sequences of insertion/deletion frameshift mutations of calreticulin |
|---|---|---|
| | | QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKRRQRTRRMMRTKMRMRRMRRTRRKMRRKMSPARPRTSCREACL QGWTEA |
| SEQ ID NO: 177 | Type 9 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEERQRTRRMMRTKMRMRRMRRTRRKMRRKMSPA RPRTSCREACLQGWTEA |
| SEQ ID NO: 178 | Type 10 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEEEAEDMCRRMMRTKMRMRRMRRTRRKMRRKMS PARPRTSCREACLQGWTEA |
| SEQ ID NO: 179 | Type 11 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDED QRQRTRRMMRTKMRMRRMRRTRRKMRRKMSPARPRTSCREACLQGWT EA |
| SEQ ID NO: 180 | Type 12 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRRRRQRTRRMMRTKMRMRRMRRTRRKMRRKMSPARPRTSCREACL QGWTEA |
| SEQ ID NO: 181 | Type 13 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRQRRRQRTRRMMRTKMRMRRMRRTRRKMRRKMSPARPRTSCREACL QGWTEA |
| SEQ ID NO: 182 | Type 14 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLRRRQRTRRMMRTKMRMRRMRRTRRKMRRKMSPARPRTSCREACL QGWTEA |
| SEQ ID NO: 183 | Type 15 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLRRRERTRRMMRTKMRMRRMRRTRRKMRRKMSPARPRTSCREACL QGWTEA |

TABLE 2-continued

Full-length amino acid sequences of calreticulin mutants

| SEQ ID NO | Type | Full length sequences of insertion/deletion frameshift mutations of calreticulin |
|---|---|---|
| SEQ ID NO: 184 | Type 16 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLQRRQRTRRMMRTKMRMRRMRRTRRKMRRKMSPARPRTSCREACL QGWTEA |
| SEQ ID NO: 185 | Type 17 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKRRQWTRRMMRTKMRMRRMRRTRRKMRRKMSPARPRTSCREACL QGWTEA |
| SEQ ID NO: 186 | Type 18 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKRMMRTKMRMRRMRRTRRKMRRKMSPARPRTSCREACLQGWTEA |
| SEQ ID NO: 187 | Type 19 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEERQRTRRMMRTKMRMRRMRRTRRKMRRKMSPARPRTSCREAC LQGWTEA |
| SEQ ID NO: 188 | Type 20 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEGRRQRTRRMMRTKMRMRRMRRTRRKMRRKMSPARPRTSC REACLQGWTEA |
| SEQ ID NO: 189 | Type 21 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEAFKRTRRMMRTKMRMRRMRRTRRKMRRKMSPARPRTSCRE ACLQGWTEA |
| SEQ ID NO: 190 | Type 22 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDNAKRRRQRTRRMMRTKMRMRRMRRTRRKMRRKMSPAR PRTSCREACLQGWTEA |
| SEQ ID NO: 191 | Type 23 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL |

TABLE 2-continued

Full-length amino acid sequences of calreticulin mutants

| SEQ ID NO | Type | Full length sequences of insertion/deletion frameshift mutations of calreticulin |
|---|---|---|
| | | DLWQVKSGTIFDNFLITNDEAYAEEFGNETWGVTKAAEKQMKDKQDEE<br>QRLKEEEEDCVRRRRQRTRRMMRTKMRMRRMRRTRRKMRRKMSPARP<br>RTSCREACLQGWTEA |
| SEQ ID NO: 192 | Type 24 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDRRQRTRRMMRTKMRMRRMRRTRRKMRRKMSPARPRTSC<br>REACLQGWTEA |
| SEQ ID NO: 193 | Type 25 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDKRQRTRRMMRTKMRMRRMRRTRRKMRRKMSPARPRTSC<br>REACLQGWTEA |
| SEQ ID NO: 194 | Type 26 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDKNAKRRRRQRTRRMMRTKMRMRRMRRTRRKMRRKMSPA<br>RPRTSCREACLQGWTEA |
| SEQ ID NO: 195 | Type 27 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDKCFAKRRRRQRTRRMMRTKMRMRRMRRTRRKMRRKMSP<br>ARPRTSCREACLQGWTEA |
| SEQ ID NO: 196 | Type 28 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDKKRRRMMRTKMRMRRMRRTRRKMRRKMSPARPRTSCR<br>EACLQGWTEA |
| SEQ ID NO: 197 | Type 29 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDKKRKEPPLCLRRMMRTKMRMRRMRRTRRKMRRKMSPAR<br>PRTSCREACLQGWTEA |
| SEQ ID NO: 198 | Type 30 | EPAVYFKEQFLDGDGWTSRWIESKHKSDFGKFVLSSGKFYGDEEKDKGL<br>QTSQDARFYALSASFEPFSNKGQTLVVQFTVKHEQNIDCGGGYVKLFPNS<br>LDQTDMHGDSEYNIMFGPDICGPGTKKVHVIFNYKGKNVLINKDIRCKDD<br>EFTHLYTLIVRPDNTYEVKIDNSQVESGSLEDDWDFLPPKKIKDPDASKPE<br>DWDERAKIDDPTDSKPEDWDKPEHIPDPDAKKPEDWDEEMDGEWEPPVI<br>QNPEYKGEWKPRQIDNPDYKGTWIHPEIDNPEYSPDPSIYAYDNFGVLGL<br>DLWQVKSGTIFDNFLITNDEAYAEEFGNETWGVTKAAEKQMKDKQDEE<br>QRLKEEEEDKKRKEDHPCRRMMRTKMRMRRMRRTRRKMRRKMSPARP<br>RTSCREACLQGWTEA |

TABLE 2-continued

Full-length amino acid sequences of calreticulin mutants

| SEQ ID NO | Type | Full length sequences of insertion/deletion frameshift mutations of calreticulin |
|---|---|---|
| SEQ ID NO: 199 | Type 31 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEEEAEGNCRRMMRTKMRMRRMRRTRRKMRRKMS PARPRTSCREACLQGWTEA |
| SEQ ID NO: 200 | Type 32 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEEEAEDCRRMMRTKMRMRRMRRTRRKMRRKMSP ARPRTSCREACLQGWTEA |
| SEQ ID NO: 201 | Type 33 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEEEAEDKCRRMMRTKMRMRRMRRTRRKMRRKMS PARPRTSCREACLQGWTEA |
| SEQ ID NO: 202 | Type 34 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEEEAEDTCRRMMRTKMRMRRMRRTRRKMRRKMS PARPRTSCREACLQGWTEA |
| SEQ ID NO: 203 | Type 35 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEEEAEDICRRMMRTKMRMRRMRRTRRKMRRKMSP ARPRTSCREACLQGWTEA |
| SEQ ID NO: 204 | Type 36 | EPAVYFKEQFLDGDGWTSRWIESKHKSDFGKFVLSSGKFYGDEEKDKGL QTSQDARFYALSASFEPFSNKGQTLVVQFTVKHEQNIDCGGGYVKLFPNS LDQTDMHGDSEYNIMFGPDICGPGTKKVHVIFNYKGKNVLINKDIRCKDD EFTHLYTLIVRPDNTYEVKIDNSQVESGSLEDDWDFLPPKKIKDPDASKPE DWDERAKIDDPTDSKPEDWDKPEHIPDPDAKKPEDWDEEMDGEWEPPVI QNPEYKGEWKPRQIDNPDYKGTWIHPEIDNPEYSPDPSIYAYDNFGVLGL DLWQVKSGTIFDNFLITNDEAYAEEFGNETWGVTKAAEKQMKDKQDEE QRLKEEEEDKKRKEEEEAEDKCRRMMRTKMRMRRMRRTRRKMRRKMS PARPRTSCREACLQGWTEA |

TABLE 3

The C-terminal amino acid sequences of calreticulin mutants

| SEQ ID NO | Type | C-terminal sequences of insertion/deletion frameshift mutations of calreticulin |
|---|---|---|
| SEQ ID NO: 142 | Type 1 | TRRMMRTKMRMRRMRRTRRKMRRKMSPARPRTSCREACLQGWTEA |
| SEQ ID NO: 143 | Type 2 | NCRRMMRTKMRMRRMRRTRRKMRRKMSPARPRTSCREACLQGWTEA |
| SEQ ID NO: 144 | Type 3 | QRTRRMMRTKMRMRRMRRTRRKMRRKMSPARPRTSCREACLQGWTEA |
| SEQ ID NO: 145 | Type 4 | RRRQRTRRMMRTKMRMRRMRRTRRKMRRKMSPARPRTSCREACLQGWTEA |
| SEQ ID NO: 146 | Type 5 | GQRTRRMMRTKMRMRRMRRTRRKMRRKMSPARPRTSCREACLQGWTEA |
| SEQ ID NO: 147 | Type 6 | RRQRTRRMMRTKMRMRRMRRTRRKMRRKMSPARPRTSCREACLQGWTEA |
| SEQ ID NO: 148 | Type 7 | RRMMRTKMRMRRMRRTRRKMRRKMSPARPRTSCREACLQGWTEA |
| SEQ ID NO: 147 | Type 8 | RRQRTRRMMRTKMRMRRMRRTRRKMRRKMSPARPRTSCREACLQGWTEA |
| SEQ ID NO: 149 | Type 9 | RQRTRRMMRTKMRMRRMRRTRRKMRRKMSPARPRTSCREACLQGWTEA |
| SEQ ID NO: 150 | Type 10 | MCRRMMRTKMRMRRMRRTRRKMRRKMSPARPRTSCREACLQGWTEA |
| SEQ ID NO: 151 | Type 11 | DQRQRTRRMMRTKMRMRRMRRTRRKMRRKMSPARPRTSCREACLQGWTEA |
| SEQ ID NO: 152 | Type 12 | RRRRQRTRRMMRTKMRMRRMRRTRRKMRRKMSPARPRTSCREACLQGWTEA |
| SEQ ID NO: 153 | Type 13 | QRRQRTRRMMRTKMRMRRMRRTRRKMRRKMSPARPRTSCREACLQGWTEA |
| SEQ ID NO: 145 | Type 14 | RRRQRTRRMMRTKMRMRRMRRTRRKMRRKMSPARPRTSCREACLQGWTEA |
| SEQ ID NO: 154 | Type 15 | RRRERTRRMMRTKMRMRRMRRTRRKMRRKMSPARPRTSCREACLQGWTEA |
| SEQ ID NO: 155 | Type 16 | QRRQRTRRMMRTKMRMRRMRRTRRKMRRKMSPARPRTSCREACLQGWTEA |
| SEQ ID NO: 156 | Type 17 | RRQWTRRMMRTKMRMRRMRRTRRKMRRKMSPARPRTSCREACLQGWTEA |
| SEQ ID NO: 157 | Type 18 | RMMRTKMRMRRMRRTRRKMRRKMSPARPRTSCREACLQGWTEA |
| SEQ ID NO: 149 | Type 19 | RQRTRRMMRTKMRMRRMRRTRRKMRRKMSPARPRTSCREACLQGWTEA |
| SEQ ID NO: 158 | Type 20 | GRRQRTRRMMRTKMRMRRMRRTRRKMRRKMSPARPRTSCREACLQGWTEA |
| SEQ ID NO: 159 | Type 21 | AFKRTRRMMRTKMRMRRMRRTRRKMRRKMSPARPRTSCREACLQGWTEA |
| SEQ ID NO: 160 | Type 22 | NAKRRRQRTRRMMRTKMRMRRMRRTRRKMRRKMSPARPRTSCREACLQGWTEA |
| SEQ ID NO: 161 | Type 23 | CVRRRQRTRRMMRTKMRMRRMRRTRRKMRRKMSPARPRTSCREACLQGWTEA |
| SEQ ID NO: 147 | Type 24 | RRQRTRRMMRTKMRMRRMRRTRRKMRRKMSPARPRTSCREACLQGWTEA |
| SEQ ID NO: 149 | Type 25 | RQRTRRMMRTKMRMRRMRRTRRKMRRKMSPARPRTSCREACLQGWTEA |

TABLE 3-continued

The C-terminal amino acid sequences of calreticulin mutants

| SEQ ID NO | Type | C-terminal sequences of insertion/deletion frameshift mutations of calreticulin |
|---|---|---|
| SEQ ID NO: 160 | Type 26 | NAKRRRRQRTRRMMRTKMRMRRMRRTRRKMRRKMSPARPRTSCREACLQGWTEA |
| SEQ ID NO: 162 | Type 27 | CFAKRRRRQRTRRMMRTKMRMRRMRRTRRKMRRKMSPARPRTSCREACLQGWTEA |
| SEQ ID NO: 148 | Type 28 | RRMMRTKMRMRRMRRTRRKMRRKMSPARPRTSCREACLQGWTEA |
| SEQ ID NO: 163 | Type 29 | PPLCLRRMMRTKMRMRRMRRTRRKMRRKMSPARPRTSCREACLQGWTEA |
| SEQ ID NO: 164 | Type 30 | DHPCRRMMRTKMRMRRMRRTRRKMRRKMSPARPRTSCREACLQGWTEA |
| SEQ ID NO: 165 | Type 31 | GNCRRMMRTKMRMRRMRRTRRKMRRKMSPARPRTSCREACLQGWTEA |
| SEQ ID NO: 166 | Type 32 | CRRMMRTKMRMRRMRRTRRKMRRKMSPARPRTSCREACLQGWTEA |
| SEQ ID NO: 166 | Type 33 | CRRMMRTKMRMRRMRRTRRKMRRKMSPARPRTSCREACLQGWTEA |
| SEQ ID NO: 167 | Type 34 | TCRRMMRTKMRMRRMRRTRRKMRRKMSPARPRTSCREACLQGWTEA |
| SEQ ID NO: 168 | Type 35 | ICRRMMRTKMRMRRMRRTRRKMRRKMSPARPRTSCREACLQGWTEA |
| SEQ ID NO: 166 | Type 36 | CRRMMRTKMRMRRMRRTRRKMRRKMSPARPRTSCREACLQGWTEA |

In some embodiments, the calreticulin-targeting antigen binding domain comprises any CDR amino acid sequence, framework region (FWR) amino acid sequence, or variable region amino acid sequence disclosed in Tables 4-7. In some embodiments, the calreticulin-targeting antigen binding domain comprises a VH comprising a heavy chain complementarity determining region 1 (VHCDR1) amino acid sequence of SEQ ID NO: 107 (or a sequence with no more than 1, 2, 3, or 4 mutations, e.g., substitutions, additions, or deletions), a VHCDR2 amino acid sequence of SEQ ID NO: 108 (or a sequence with no more than 1, 2, 3, or 4 mutations, e.g., substitutions, additions, or deletions), and/or a VHCDR3 amino acid sequence of SEQ ID NO: 109 (or a sequence with no more than 1, 2, 3, or 4 mutations, e.g., substitutions, additions, or deletions). In some embodiments, the calreticulin-targeting antigen binding domain comprises a VH comprising a VHCDR1 amino acid sequence of SEQ ID NO: 107, a VHCDR2 amino acid sequence of SEQ ID NO: 108, and/or a VHCDR3 amino acid sequence of SEQ ID NO: 109. In some embodiments, the calreticulin-targeting antigen binding domain comprises a VL comprising a light chain complementarity determining region 1 (VLCDR1) amino acid sequence of SEQ ID NO: 113 (or a sequence with no more than 1, 2, 3, or 4 mutations, e.g., substitutions, additions, or deletions), a VLCDR2 amino acid sequence of SEQ ID NO: 114 (or a sequence with no more than 1, 2, 3, or 4 mutations, e.g., substitutions, additions, or deletions), and/or a VLCDR3 amino acid sequence of SEQ ID NO: 115 (or a sequence with no more than 1, 2, 3, or 4 mutations, e.g., substitutions, additions, or deletions). In some embodiments, the calreticulin-targeting antigen binding domain comprises a VL comprising a VLCDR1 amino acid sequence of SEQ ID NO: 113, a VLCDR2 amino acid sequence of SEQ ID NO: 114, and a VLCDR3 amino acid sequence of SEQ ID NO: 115. In some embodiments, the calreticulin-targeting antigen binding domain comprises a VH comprising a heavy chain framework region 1 (VHFWR1) amino acid sequence of SEQ ID NO: 80, a VHFWR2 amino acid sequence of SEQ ID NO: 81, a VHFWR3 amino acid sequence of SEQ ID NO: 82, and/or a VHFWR4 amino acid sequence of SEQ ID NO: 83. In some embodiments, the calreticulin-targeting antigen binding domain comprises a VL comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, and/or a VLFWR4 amino acid sequence of SEQ ID NO: 90. In some embodiments, the calreticulin-targeting antigen binding domain comprises a VH comprising a VHFWR1 amino acid sequence of SEQ ID NO: 117 (or a sequence with no more than 1, 2, 3, 4, 5, or 6 mutations, e.g., substitutions, additions, or deletions), a VHFWR2 amino acid sequence of SEQ ID NO: 118 (or a sequence with no more than 1, 2, 3, 4, 5, or 6 mutations, e.g., substitutions, additions, or deletions), a VHFWR3 amino acid sequence of SEQ ID NO: 119 (or a sequence with no more than 1, 2, 3, 4, 5, 6, 7, 8, 9, 10, or 11 mutations, e.g., substitutions, additions, or deletions), and/or a VHFWR4 amino acid sequence of SEQ ID NO: 120. In some embodiments, the calreticulin-targeting antigen binding domain comprises a VL comprising a VLFWR1 amino acid sequence of SEQ ID NO: 132 (or a sequence with no more than 1, 2, or 3 mutations, e.g., substitutions, additions, or deletions), a VLFWR2 amino acid sequence of SEQ ID NO: 133 (or a sequence with no more than 1 mutation, e.g., substitution, addition, or deletion), a VLFWR3 amino acid sequence of SEQ ID NO: 134 (or a sequence with no more than 1 mutation, e.g., substitution, addition, or deletion), and/or a VLFWR4 amino acid sequence of SEQ ID NO: 135. In some embodiments, the calreticulin-targeting antigen binding domain comprises a VH comprising a VHFWR1 amino acid sequence of SEQ ID NO: 117, a VHFWR2 amino acid sequence of SEQ ID NO: 118, a VHFWR3 amino acid sequence of SEQ ID NO: 119, and/or a VHFWR4 amino acid sequence of SEQ ID NO: 120. In some embodiments, the calreticulin-targeting antigen binding domain comprises a VL comprising a VLFWR1 amino acid sequence of SEQ ID NO: 132, a VLFWR2 amino acid sequence of SEQ ID NO: 133, a VLFWR3 amino acid sequence of SEQ ID NO: 134, and/or a VLFWR4 amino acid sequence of SEQ ID NO: 135. In some embodiments, the calreticulin-targeting antigen binding domain comprises a VH comprising the amino acid sequence of SEQ ID NO: 101 (or an amino acid sequence having at least about 7700, 8000, 8500, 9000, 9500 or 9900 sequence identity to SEQ ID NO: 101). In some embodiments, the calreticulin-targeting antigen binding domain comprises a VL comprising the amino acid sequence of SEQ ID NO: 103 (or an amino acid sequence having at least about 93%, 95% or 99% sequence identity to SEQ ID NO: 103). In some embodiments, the calreticulin-targeting antigen binding domain comprises a VH comprising the amino acid sequence of SEQ ID NO: 101. In some embodiments, the calreticulin-targeting antigen binding domain comprises a VL comprising the amino acid sequence of SEQ ID NO: 103. In some embodiments, the calreticulin-targeting antigen binding domain comprises a VH comprising the amino acid sequence of SEQ ID NO: 101, and a VL comprising the amino acid sequence of SEQ ID NO: 103.

TABLE 4

Exemplary heavy chain CDRs and FWRs of calreticulin-targeting antigen binding domains

| Ab ID | VHFWR1 | VHCDR1 | VHFWR2 | VHCDR2 | VHFWR3 | VHCDR3 | VHFWR4 |
|---|---|---|---|---|---|---|---|
| AbH-1H | QVQLVQS GAEVKKP GASVKVS CKASG (SEQ ID NO: 117) | YSFTGYYI H (SEQ ID NO: 107) | WVRQAP GQELGW MG (SEQ ID NO: 118) | YISCYNG ASSYNQK FKG (SEQ ID NO: 108) | RVTMTVD TSISTAYT ELSSLRSE DTATYYC A (SEQ ID NO: 119) | SSMDY (SEQ ID NO: 109) | WGQGTL VTVSS (SEQ ID NO: 120) |
| AbH-2H | QVTLKES GPVL VKP TETLTLTC TVSG (SEQ ID NO: 121) | YSITSDYA WN (SEQ ID NO: 110) | WIRQPPG KALEWLA (SEQ ID NO: 122) | YISYSGST SYNPSLK S (SEQ ID NO: 111) | RLSITKDT SKSQVVL TMTNMD PVDTATY YCAR (SEQ ID NO: 123) | DPPYYYG S (SEQ ID NO: 112) | WGQGTT VTVSS (SEQ ID NO: 124) |
| AbM-1H | EVQLEQS GPEL VKT GASVKIS CKASG (SEQ ID NO: 125) | YSFTGYYI H (SEQ ID NO: 107) | WVKQSH GKSLEWI G (SEQ ID NO: 126) | YISCYNG ASSYNQK FKG (SEQ ID NO: 108) | KATFTVD TSSSTAY MQFNSLT SGDSAVY YCA (SEQ ID NO: 127) | SSMDY (SEQ ID NO: 109) | WGQGTS VTVSS (SEQ ID NO: 128) |
| AbM-2H | DVQLQES GPGLVKN SQSLSLTC TVTG (SEQ ID NO: 129) | YSITSDYA WN (SEQ ID NO: 110) | WIRQFPG NKLEWM G (SEQ ID NO: 130) | YISYSGST SYNPSLK S (SEQ ID NO: 111) | RISITRDT SKNQFFL QLNSVTP EDTATYY CAR (SEQ ID NO: 131) | DPPYYYG SNGT (SEQ ID NO: 116) | WGQGTS VTVSS (SEQ ID NO: 128) |

TABLE 5

Exemplary light chain CDRs and FWRs of calreticulin-targeting antigen binding domains

| Ab ID | FWR1 | CDR1 | FWR2 | CDR2 | FWR3 | CDR3 | FWR4 |
|---|---|---|---|---|---|---|---|
| AbH-1L/ AbH-2L | DVVMTQS PLSLPVTL GQPASISC (SEQ ID NO: 132) | KSSQSLL DSDGKTY LN (SEQ ID NO: 113) | WLQQRPG QSPRRLIY (SEQ ID NO: 133) | LVSKLDS (SEQ ID NO: 114) | GVPDRFS GSGSGTD FTLKISRV EAEDVGV YHC (SEQ ID NO: 134) | WQGTHFP YT (SEQ ID NO: 115) | FGGGTKV EIK (SEQ ID NO: 135) |

TABLE 5-continued

Exemplary light chain CDRs and FWRs of calreticulin-targeting antigen binding domains

| Ab ID | FWR1 | CDR1 | FWR2 | CDR2 | FWR3 | CDR3 | FWR4 |
|---|---|---|---|---|---|---|---|
| AbM-1L/ AbM-2L | DVVMTQ TPLTLSVT IGQPASIS C (SEQ ID NO: 136) | KSSQSLL DSDGKTY LN (SEQ ID NO: 113) | WLLQRPG QSPKRLIY (SEQ ID NO: 137) | LVSKLDS (SEQ ID NO: 114) | GVPDRFT GSGSGTD FTLKISRV EAEDLGV YHC (SEQ ID NO: 138) | WQGTHFP YT (SEQ ID NO: 115) | FGGGTKL EIK (SEQ ID NO: 139) |

TABLE 6

Exemplary FWRs of calreticulin-targeting antigen binding domains

| SEQ ID NO | Description | Sequence |
|---|---|---|
| SEQ ID NO: 80 | Ab-1 VHFWR1 | $X_1$VQLX$_2$QSGX$_3$EX$_4$X$_5$KX$_6$GASVKX$_7$SCKASG, wherein:<br>$X_1$ is not E,<br>$X_2$ is not E,<br>$X_3$ is not P,<br>$X_4$ is not L,<br>$X_5$ is not V,<br>$X_6$ is not T, or<br>$X_7$ is not I |
| SEQ ID NO: 81 | Ab-1 VHFWR2 | WVX$_1$QX$_2$X$_3$GX$_4$X$_5$LX$_6$WX$_7$G, wherein:<br>$X_1$ is not K,<br>$X_2$ is not S,<br>$X_3$ is not H,<br>$X_4$ is not K,<br>$X_5$ is not S,<br>$X_6$ is not E, or<br>$X_7$ is not I |
| SEQ ID NO: 82 | Ab-1 VHFWR3 | $X_1$X$_2$TX$_3$TVDTSX$_4$STAYX$_5$X$_6$X$_7$X$_8$SLX$_9$SX$_{10}$DX$_{11}$AX$_{12}$YYCA, wherein:<br>$X_1$ is not K,<br>$X_2$ is not A,<br>$X_3$ is not F,<br>$X_4$ is not S,<br>$X_5$ is not M,<br>$X_6$ is not Q,<br>$X_7$ is not F,<br>$X_8$ is not N,<br>$X_9$ is not T,<br>$X_{10}$ is not G,<br>$X_{11}$ is not S, or<br>$X_{12}$ is not V |
| SEQ ID NO: 83 | Ab-1 VHFWR4 | WGQGTX$_1$VTVSS, wherein:<br>$X_1$ is not S |
| SEQ ID NO: 84 | Ab-2 VHFWR1 | $X_1$VX$_2$LX$_3$ESGPX$_4$LVKX$_5$X$_6$X$_7$X$_8$LX$_9$LTCTVX$_{10}$G, wherein:<br>$X_1$ is not D,<br>$X_2$ is not Q,<br>$X_3$ is not Q,<br>$X_4$ is not G,<br>$X_5$ is not N,<br>$X_6$ is not S,<br>$X_7$ is not Q,<br>$X_8$ is not S,<br>$X_9$ is not S, or<br>$X_{10}$ is not T |
| SEQ ID NO: 85 | Ab-2 VHFWR2 | WIRQX$_1$PGX$_2$X$_3$LEWX$_4$X$_5$, wherein:<br>$X_1$ is not F,<br>$X_2$ is not N,<br>$X_3$ is not K,<br>$X_4$ is not M, or<br>$X_5$ is not G |

TABLE 6-continued

Exemplary FWRs of calreticulin-targeting antigen binding domains

| SEQ ID NO | Description | Sequence |
|---|---|---|
| SEQ ID NO: 86 | Ab-2 VHFWR3 | $RX_1SITX_2DTSKX_3QX_4X_5LX_6X_7X_8X_9X_{10}X_{11}PX_{12}DTATYYCAR$, wherein:<br>$X_1$ is not I,<br>$X_2$ is not R,<br>$X_3$ is not N,<br>$X_4$ is not F,<br>$X_5$ is not F,<br>$X_6$ is not Q,<br>$X_7$ is not L,<br>$X_8$ is not N,<br>$X_9$ is not S,<br>$X_{10}$ is not V,<br>$X_{11}$ is not T, or<br>$X_{12}$ is not E |
| SEQ ID NO: 83 | Ab-2 VHFWR4 | $WGQGTX_1VTVSS$, wherein:<br>$X_1$ is not S |
| SEQ ID NO: 87 | Ab-1/2 VLFWR1 | $DVVMTQX_1PLX_2LX_3VTX_4GQPASISC$, wherein:<br>$X_1$ is not T,<br>$X_2$ is not T,<br>$X_3$ is not S, or<br>$X_4$ is not I |
| SEQ ID NO: 88 | Ab-1/2 VLFWR2 | $WLX_1QRPGQSPX_2RLIY$, wherein:<br>$X_1$ is not L, or<br>$X_2$ is not K |
| SEQ ID NO: 89 | Ab-1/2 VLFWR3 | $GVPDRFX_1GSGSGTDFTLKISRVEAEDX_2GVYHC$, wherein:<br>$X_1$ is not T, or<br>$X_2$ is not L |
| SEQ ID NO: 90 | Ab-1/2 VLFWR4 | $FGGGTKX_1EIK$, wherein:<br>X1 is not L |

TABLE 7

Exemplary variable regions of calreticulin-targeting antigen binding domains

| SEQ ID NO | Description | Sequence |
|---|---|---|
| SEQ ID NO: 101 | AbH-1 heavy chain variable region | QVQLVQSGAEVKKPGASVKVSCKASGYSFTGYYIHWVRQAP GQELGWMGYISCYNGASSYNQKFKGRVTMTVDTSISTAYTEL SSLRSEDTATYYCA SSMDYWGQGTLVTVSS |
| SEQ ID NO: 102 | AbH-2 heavy chain variable region | QVTLKESGPVLVKPTETLTLTCTVSGYSITSDYAWNWIRQPPG KALEWLAYISYSGSTSYNPSLKSRLSITKDTSKSQVVLTMTNM DPVDTATYYCARDPPYYYGSWGQGTTVTVSS |
| SEQ ID NO: 103 | AbH-1/AbH-2 light chain variable region | DVVMTQSPLSLPVTLGQPASISCKSSQSLLDSDGKTYLNWLQQ RPGQSPRRLIYLVSKLDSGVPDRFSGSGSGTDFTLKISRVEAED VGVYHCWQGTHFPYTFGGGTKVEIK |
| SEQ ID NO: 104 | AbM-1 heavy chain variable region | EVQLEQSGPELVKTGASVKISCKASGYSFTGYYIHWVKQSHG KSLEWIGYISCYNGASSYNQKFKGKATFTVDTSSSTAYMQFNS LTSGDSAVYYCA SSMDYWGQGTSVTVSS |
| SEQ ID NO: 105 | AbM-2 heavy chain variable region | DVQLQESGPGLVKNSQSLSLTCTVTGYSITSDYAWNWIRQFPG NKLEWMGYISYSGSTSYNPSLKSRISITRDTSKNQFFLQLNSVT PEDTATYYCA RDPPYYYGSNGTWGQGTSVTVSS |
| SEQ ID NO: 106 | AbM-1/AbM-2 light chain variable region | DVVMTQTPLTLSVTIGQPASISCKSSQSLLDSDGKTYLNWLLQ RPGQSPKRLIYLVSKLDSGVPDRFTGSGSGTDFTLKISRVEAED LGVYHCWQGTHFPYTFGGGTKLEIK |

In some embodiments, the calreticulin-targeting antigen binding domain comprises any CDR amino acid sequence or variable region amino acid sequence disclosed in Tables 8-11. In some embodiments, the calreticulin-targeting antigen binding domain comprises a VH comprising a heavy chain complementarity determining region 1 (VHCDR1) amino acid sequence of SEQ ID NO: 107 (or a sequence with no more than 1, 2, 3, or 4 mutations, e.g., substitutions, additions, or deletions), a VHCDR2 amino acid sequence of SEQ ID NO: 243 (or a sequence with no more than 1, 2, 3, or 4 mutations, e.g., substitutions, additions, or deletions), and/or a VHCDR3 amino acid sequence of SEQ ID NO: 109

(or a sequence with no more than 1, 2, 3, or 4 mutations, e.g., substitutions, additions, or deletions). In some embodiments, the calreticulin-targeting antigen binding domain comprises a VH comprising a VHCDR1 amino acid sequence of SEQ ID NO: 107, a VHCDR2 amino acid sequence of SEQ ID NO: 243, and/or a VHCDR3 amino acid sequence of SEQ ID NO: 109. In some embodiments, the calreticulin-targeting antigen binding domain comprises a VL comprising a light chain complementarity determining region 1 (VLCDR1) amino acid sequence of SEQ ID NO: 113 (or a sequence with no more than 1, 2, 3, or 4 mutations, e.g., substitutions, additions, or deletions), a VLCDR2 amino acid sequence of SEQ ID NO: 114 (or a sequence with no more than 1, 2, 3, or 4 mutations, e.g., substitutions, additions, or deletions), and/or a VLCDR3 amino acid sequence of SEQ ID NO: 115 (or a sequence with no more than 1, 2, 3, or 4 mutations, e.g., substitutions, additions, or deletions). In some embodiments, the calreticulin-targeting antigen binding domain comprises a VL comprising a VLCDR1 amino acid sequence of SEQ ID NO: 113, a VLCDR2 amino acid sequence of SEQ ID NO: 114, and a VLCDR3 amino acid sequence of SEQ ID NO: 115. In some embodiments, the calreticulin-targeting antigen binding domain comprises a VH comprising the amino acid sequence of SEQ ID NO: 244 (or an amino acid sequence having at least about 77%, 80%, 85%, 90%, 95%, or 99% sequence identity to SEQ ID NO: 244). In some embodiments, the calreticulin-targeting antigen binding domain comprises a VL comprising the amino acid sequence of SEQ ID NO: 245 (or an amino acid sequence having at least about 93%, 95%, or 99% sequence identity to SEQ ID NO: 245). In some embodiments, the calreticulin-targeting antigen binding domain comprises a VH comprising the amino acid sequence of SEQ ID NO: 244 and/or a VL comprising the amino acid sequence of SEQ ID NO: 245. In some embodiments, the calreticulin-targeting antigen binding domain comprises a VH comprising the amino acid sequence of SEQ ID NO: 233, 234, 235, 236, or 237, or an amino acid sequence having at least about 80%, 85%, 90%, 95%, or 99% sequence identity thereto. In some embodiments, the calreticulin-targeting antigen binding domain comprises a VL comprising the amino acid sequence of SEQ ID NO: 238, 239, 240, 241, or 242, or an amino acid sequence having at least about 80%, 85%, 90%, 95%, or 99% sequence identity thereto. In some embodiments, the calreticulin-targeting antigen binding domain comprises a VH comprising the amino acid sequence of SEQ ID NO: 233 (or an amino acid sequence having at least about 80%, 85%, 90%, 95%, or 99% sequence identity thereto) and a VL comprising the amino acid sequence of SEQ ID NO: 238 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 233 and a VL comprising the amino acid sequence of SEQ ID NO: 238. In some embodiments, the calreticulin-targeting antigen binding domain comprises a VH comprising the amino acid sequence of SEQ ID NO: 234 (or an amino acid sequence having at least about 80%, 85%, 90%, 95%, or 99% sequence identity thereto) and a VL comprising the amino acid sequence of SEQ ID NO: 238 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 234 and a VL comprising the amino acid sequence of SEQ ID NO: 238. In some embodiments, the calreticulin-targeting antigen binding domain comprises a VH comprising the amino acid sequence of SEQ ID NO: 235 (or an amino acid sequence having at least about 80%, 85%, 90%, 95%, or 99% sequence identity thereto) and a VL comprising the amino acid sequence of SEQ ID NO: 238 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 235 and a VL comprising the amino acid sequence of SEQ ID NO: 238. In some embodiments, the calreticulin-targeting antigen binding domain comprises a VH comprising the amino acid sequence of SEQ ID NO: 236 (or an amino acid sequence having at least about 80%, 85%, 90%, 95%, or 99% sequence identity thereto) and a VL comprising the amino acid sequence of SEQ ID NO: 238 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 236 and a VL comprising the amino acid sequence of SEQ ID NO: 238. In some embodiments, the calreticulin-targeting antigen binding domain comprises a VH comprising the amino acid sequence of SEQ ID NO: 237 (or an amino acid sequence having at least about 80%, 85%, 90%, 95%, or 99% sequence identity thereto) and a VL comprising the amino acid sequence of SEQ ID NO: 238 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 237 and a VL comprising the amino acid sequence of SEQ ID NO: 238. In some embodiments, the calreticulin-targeting antigen binding domain comprises a VH comprising the amino acid sequence of SEQ ID NO: 233 (or an amino acid sequence having at least about 80%, 85%, 90%, 95%, or 99% sequence identity thereto) and a VL comprising the amino acid sequence of SEQ ID NO: 239 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 233 and a VL comprising the amino acid sequence of SEQ ID NO: 239. In some embodiments, the calreticulin-targeting antigen binding domain comprises a VH comprising the amino acid sequence of SEQ ID NO: 234 (or an amino acid sequence having at least about 80%, 85%, 90%, 95%, or 99% sequence identity thereto) and a VL comprising the amino acid sequence of SEQ ID NO: 239 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 234 and a VL comprising the amino acid sequence of SEQ ID NO: 239. In some embodiments, the calreticulin-targeting antigen binding domain comprises a VH comprising the amino acid sequence of SEQ ID NO: 235 (or an amino acid sequence having at least about 80%, 85%, 90%, 95%, or 99% sequence identity thereto) and a VL comprising the amino acid sequence of SEQ ID NO: 239 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 235 and a VL comprising the amino acid sequence of SEQ ID NO: 239. In some embodiments, the calreticulin-targeting antigen binding domain comprises a VH comprising the amino acid sequence of SEQ ID NO: 236 (or an amino acid sequence having at least about 80%, 85%, 90%, 95%, or 99% sequence identity thereto) and a VL comprising the amino acid sequence of SEQ ID NO: 239 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 236 and a VL comprising the amino acid sequence of SEQ ID NO: 239. In some embodiments, the calreticulin-targeting antigen binding domain comprises a VH comprising the amino acid sequence of SEQ ID NO: 237 (or an amino acid sequence having at least about 80%, 85%, 90%, 95%, or 99% sequence identity thereto) and a VL comprising the amino acid sequence of SEQ ID NO: 239 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 237 and a VL comprising the amino acid sequence of SEQ ID NO: 239. In some embodiments, the calreticulin-targeting antigen binding domain comprises a VH comprising the amino acid sequence of SEQ ID NO: 233 (or an amino acid sequence having at least about 80%, 85%, 90%, 95%, or 99% sequence identity thereto) and a VL comprising the amino acid sequence of SEQ ID NO: 240 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 233 and a VL comprising the amino acid sequence of SEQ ID NO: 240. In some embodiments, the calreticulin-targeting antigen binding domain comprises a VH comprising the amino acid sequence of SEQ ID NO: 234 (or an amino acid sequence having at least about 80%, 85%, 90%, 95%, or 99% sequence identity thereto) and a VL comprising the amino acid sequence of SEQ ID NO: 240 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 234 and a VL comprising the amino acid sequence of SEQ ID NO: 240. In some embodiments, the calreticulin-targeting antigen binding domain comprises a VH comprising the amino acid sequence of SEQ ID NO: 235 (or an amino acid sequence having at least about 80%, 85%, 90%, 95%, or 99% sequence identity thereto) and a VL comprising the amino acid sequence of SEQ ID NO: 240 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 235 and a VL comprising the amino acid sequence of SEQ ID NO: 240. In some embodiments, the calreticulin-targeting antigen binding domain comprises a VH comprising the amino acid sequence of SEQ ID NO: 236 (or an amino acid sequence having at least about 80%, 85%, 90%, 95%, or 99% sequence identity thereto) and a VL comprising the amino acid sequence of SEQ ID NO: 240 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 236 and a VL comprising the amino acid sequence of SEQ ID NO: 240. In some embodiments, the calreticulin-targeting antigen binding domain comprises a VH comprising the amino acid sequence of SEQ ID NO: 237 (or an amino acid sequence having at least about 80%, 85%, 90%, 95%, or 99% sequence identity thereto) and a VL comprising the amino acid sequence of SEQ ID NO: 240 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 237 and a VL comprising the amino acid sequence of SEQ ID NO: 240. In some embodiments, the calreticulin-targeting antigen binding domain comprises a VH comprising the amino acid sequence of SEQ ID NO: 233 (or an amino acid sequence having at least about 80%, 85%, 90%, 95%, or 99% sequence identity thereto) and a VL comprising the amino acid sequence of SEQ ID NO: 241 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 233 and a VL comprising the amino acid sequence of SEQ ID NO: 241. In some embodiments, the calreticulin-targeting antigen binding domain comprises a VH comprising the amino acid sequence of SEQ ID NO: 234 (or an amino acid sequence having at least about 80%, 85%, 90%, 95%, or 99% sequence identity thereto) and a VL comprising the amino acid sequence of SEQ ID NO: 241 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 234 and a VL comprising the amino acid sequence of SEQ ID NO: 241. In some embodiments, the calreticulin-targeting antigen binding domain comprises a VH comprising the amino acid sequence of SEQ ID NO: 235 (or an amino acid sequence having at least about 80%, 85%, 90%, 95%, or 99% sequence identity thereto) and a VL comprising the amino acid sequence of SEQ ID NO: 241 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 235 and a VL comprising the amino acid sequence of SEQ ID NO: 241. In some embodiments, the calreticulin-targeting antigen binding domain comprises a VH comprising the amino acid sequence of SEQ ID NO: 236 (or an amino acid sequence having at least about 80%, 85%, 90%, 95%, or 99% sequence identity thereto) and a VL comprising the amino acid sequence of SEQ ID NO: 241 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 236 and a VL comprising the amino acid sequence of SEQ ID NO: 241. In some embodiments, the calreticulin-targeting antigen binding domain comprises a VH comprising the amino acid sequence of SEQ ID NO: 237 (or an amino acid sequence having at least about 80%, 85%, 90%, 95%, or 99% sequence identity thereto) and a VL comprising the amino acid sequence of SEQ ID NO: 241 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 237 and a VL comprising the amino acid sequence of SEQ ID NO: 241. In some embodiments, the calreticulin-targeting antigen binding domain comprises a VH comprising the amino acid sequence of SEQ ID NO: 233 (or an amino acid sequence having at least about 80%, 85%, 90%, 95%, or 99% sequence identity thereto) and a VL comprising the amino acid sequence of SEQ ID NO: 242 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 233 and a VL comprising the amino acid sequence of SEQ ID NO: 242. In some embodiments, the calreticulin-targeting antigen binding domain comprises a VH comprising the amino acid sequence of SEQ ID NO: 234 (or an amino acid sequence having at least about 80%, 85%, 90%, 95%, or 99% sequence identity thereto) and a VL comprising the amino acid sequence of SEQ ID NO: 242 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 234 and a VL comprising the amino acid sequence of SEQ ID NO: 242. In some embodiments, the calreticulin-targeting antigen binding domain comprises a VH comprising the amino acid sequence of SEQ ID NO: 235 (or an amino acid sequence having at least about 80%, 85%, 90%, 95%, or 99% sequence identity thereto) and a VL comprising the amino acid sequence of SEQ ID NO: 242 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 235 and a VL comprising the amino acid sequence of SEQ ID NO: 242. In some embodiments, the calreticulin-targeting antigen binding domain comprises a VH comprising the amino acid sequence of SEQ ID NO: 236 (or an amino acid sequence having at least about 80%, 85%, 90%, 95%, or 99% sequence identity thereto) and a VL comprising the amino acid sequence of SEQ ID NO: 242 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 236 and a VL comprising the amino acid sequence of SEQ ID NO: 242. In some embodiments, the calreticulin-targeting antigen binding domain comprises a VH comprising the amino acid sequence of SEQ ID NO: 237 (or an amino acid sequence having at least about 80%, 85%, 90%, 95%, or 99% sequence identity thereto) and a VL comprising the amino acid sequence of SEQ ID NO: 242 (or an amino acid sequence having at least about 80%, 85%, 90%, 95%, or 99% sequence identity thereto). In some embodiments, the calreticulin-targeting antigen binding domain comprises a VH comprising the amino acid sequence of SEQ ID NO: 237 and a VL comprising the amino acid sequence of SEQ ID NO: 242.

In some embodiments, the calreticulin-targeting antigen binding domain comprises a VH comprising the amino acid sequence of SEQ ID NO: 236 and a VL comprising the amino acid sequence of SEQ ID NO: 238.

TABLE 8

Exemplary variable regions of additional calreticulin-targeting antigen binding domains

| SEQ ID NO | Description | Sequence |
| --- | --- | --- |
| SEQ ID NO: 233 | BJ092 (VH) | QVQLVQSGAEVKKPGASVKVSCKASGYSFTGYYIHWVRQAPGQGLEWIGYISAYNGASSYNQKFKGRATFTVDTSTSTAYMELRSLRSDDMAVYYCASSMDYWGQGTLVTVSS |
| SEQ ID NO: 234 | BJ093 (VH) | QVQLVQSGAEVKKPGASVKVSCKASGYSFTGYYIHWVRQAPGQGLEWIGYISAYNGASSYNQKFKGRATFTVDTSTSTAYMELRSLRSDDTAVYYCASSMDYWGQGTLVTVSS |
| SEQ ID NO: 235 | BJ094 (VH) | QVQLVQSGAEVKKPGASVKVSCKASGYSFTGYYIHWVRQAPGKGLEWIGYISAYNGASSYNQKFKGRATFTVDTSTSTAYMELSSLRSEDTAVYYCASSMDYWGQGTLVTVSS |
| SEQ ID NO: 236 | BJ095 (VH) | QVQLVQSGAEVKKPGASVKVSCKASGYSFTGYYIHWVRQAPGQGLEWIGYISAYNGASSYNQKFKGRATFTVDTSISTAYMELSRLRSDDTAVYYCASSMDYWGQGTLVTVSS |
| SEQ ID NO: 237 | BJ096 (VH) | QVQLVQSGAEVKKPGASVKVSCKASGYSFTGYYIHWVRQAPGQGLEWIGYISAYNGASSYNQKFKGRATFTVDTSTSTAYMELSSLRSEDTAVYYCASSMDYWGQGTLVTVSS |
| SEQ ID NO: 244 | VH consensus | QVQLVQSGAEVKKPGASVKVSCKASGYSFTGYYIHWVRQAPGX$_1$GLEWIGYISAYNGASSYNQKFKGRATFTVDTSX$_2$STAYMELX$_3$X$_4$LRSDDX$_5$AVYYCASSMDYWGQGTLVTVSS, wherein:<br>X$_1$ is Q or K,<br>X$_2$ is I or T,<br>X$_3$ is S or R,<br>X$_4$ is R or S, or<br>X$_5$ is T or M |
| SEQ ID NO: 238 | BJ097 (VL) | DVVMTQSPLSLPVTLGQPASISCKSSQSLLDSDGKTYLNWLQQRPGQSPKRLIYLVSKLDSGVPDRFSGSGSGTDFTLKISRVEAEDVGVYHCWQGTHEPYTFGQGTKLEIK |
| SEQ ID NO: 239 | BJ098 (VL) | DVVMTQTPLSLSVTPGQPASISCKSSQSLLDSDGKTYLNWLLQKPGQSPKLLIYLVSKLDSGVPDRFSGSGSGTDFTLKISRVEAEDVGVYHCWQGTHFPYTFGQGTKLEIK |

TABLE 8-continued

Exemplary variable regions of additional calreticulin-targeting antigen binding domains

| SEQ ID NO | Description | Sequence |
|---|---|---|
| SEQ ID NO: 240 | BJ099 (VL) | DVVMTQTPLSLSVTPGQPASISCKSSQSLLDSDGKTYLNWLLQ KPGQPPKLLIYLVSKLDSGVPDRFSGSGSGTDFTLKISRVEAED VGVYHCWQGTHEPYTFGQGTKLEIK |
| SEQ ID NO: 241 | BJ100 (VL) | DVVMTQTPLSSPVTLGQPASISCKSSQSLLDSDGKTYLNWLQQ RPGQPPKLLIYLVSKLDSGVPDRFSGSGAGTDFTLKISRVEAED VGVYHCWQGTHFPYTFGQGTKLEIK |
| SEQ ID NO: 242 | BJ101 (VL) | DVVMTQSPLSLPVTPGEPASISCKSSQSLLDSDGKTYLNWLLQ KPGQSPKLLIYLVSKLDSGVPDRFSGSGSGTDFTLKISRVEAED VGVYHCWQGTHEPYTFGQGTKLEIK |
| SEQ ID NO: 245 | VL consensus | DVVMTQX$_1$PLSX$_2$X$_3$VTX$_4$GX$_5$PASISCKSSQSLLDSDGKTYLN WLX$_6$QX$_7$PGQX$_8$PKX$_9$LIYLVSKLDSGVPDRFSGSGX$_{10}$GTDFTL KISRVEAEDVGVYHCWQGTHEPYTFGQGTKLEIK, wherein: X$_1$ is S or T, X$_2$ is L or S, X$_3$ is P or S, X$_4$ is L or P, X$_5$ is Q or E, X$_6$ is Q or L, X$_7$ is R or K, X$_8$ is S or P, X$_9$ is R or L, or X$_{10}$ is S or A |

TABLE 9

Exemplary heavy chain CDRs of calreticulin-targeting antigen binding domains

| VH (SEQ ID NO) | VHCDR1 (SEQ ID NO) | VHCDR2 (SEQ ID NO) | VHCDR3 (SEQ ID NO) |
|---|---|---|---|
| BJ092 (SEQ ID NO: 233) | YSFTGYYIH (SEQ ID NO: 107) | YISAYNGASSYNQKFKG (SEQ ID NO: 243) | SSMDY (SEQ ID NO: 109) |
| BJ093 (SEQ ID NO: 234) | YSFTGYYIH (SEQ ID NO: 107) | YISAYNGASSYNQKFKG (SEQ ID NO: 243) | SSMDY (SEQ ID NO: 109) |
| BJ094 (SEQ ID NO: 235) | YSFTGYYIH (SEQ ID NO: 107) | YISAYNGASSYNQKFKG (SEQ ID NO: 243) | SSMDY (SEQ ID NO: 109) |
| BJ095 (SEQ ID NO: 236) | YSFTGYYIH (SEQ ID NO: 107) | YISAYNGASSYNQKFKG (SEQ ID NO: 243) | SSMDY (SEQ ID NO: 109) |
| BJ096 (SEQ ID NO: 237) | YSFTGYYIH (SEQ ID NO: 107) | YISAYNGASSYNQKFKG (SEQ ID NO: 243) | SSMDY (SEQ ID NO: 109) |

TABLE 10

Exemplary light chain CDRs of calreticulin-targeting antigen binding domains

| VL (SEQ ID NO) | VLCDR1 (SEQ ID NO) | VLCDR2 (SEQ ID NO) | VLCDR3 (SEQ ID NO) |
|---|---|---|---|
| BJ097 (SEQ ID NO: 238) | KSSQSLLDSDGKTYLN (SEQ ID NO: 113) | LVSKLDS (SEQ ID NO: 114) | WQGTHFPYT (SEQ ID NO: 115) |
| BJ098 (SEQ ID NO: 239) | KSSQSLLDSDGKTYLN (SEQ ID NO: 113) | LVSKLDS (SEQ ID NO: 114) | WQGTHFPYT (SEQ ID NO: 115) |
| BJ099 (SEQ ID NO: 240) | KSSQSLLDSDGKTYLN (SEQ ID NO: 113) | LVSKLDS (SEQ ID NO: 114) | WQGTHFPYT (SEQ ID NO: 115) |
| BJ100 (SEQ ID NO: 241) | KSSQSLLDSDGKTYLN (SEQ ID NO: 113) | LVSKLDS (SEQ ID NO: 114) | WQGTHFPYT (SEQ ID NO: 115) |
| BJ101 (SEQ ID NO: 242) | KSSQSLLDSDGKTYLN (SEQ ID NO: 113) | LVSKLDS (SEQ ID NO: 114) | WQGTHFPYT (SEQ ID NO: 115) |

TABLE 11

Exemplary calreticulin-targeting antigen binding domains

| Antibody code | VH code | VH germline | VL code | VL germline |
|---|---|---|---|---|
| BJM0040 | BJ092 (SEQ ID NO: 233) | IGHV1-18*03 | BJ097 (SEQ ID NO: 238) | IGKV2-30*01 |
| BJM0041 | BJ093 (SEQ ID NO: 234) | IGHV1-18*01 | BJ097 (SEQ ID NO: 238) | IGKV2-30*01 |
| BJM0042 | BJ094 (SEQ ID NO: 235) | IGHV1-2*02 | BJ097 (SEQ ID NO: 238) | IGKV2-30*01 |
| BJM0043 | BJ095 (SEQ ID NO: 236) | IGHV1-2*02 | BJ097 (SEQ ID NO: 238) | IGKV2-30*01 |
| BJM0044 | BJ096 (SEQ ID NO: 237) | IGHV1-2*02 | BJ097 (SEQ ID NO: 238) | IGKV2-30*01 |
| BJM0045 | BJ092 (SEQ ID NO: 233) | IGHV1-18*03 | BJ098 (SEQ ID NO: 239) | IGKV2-29*02 |
| BJM0046 | BJ093 (SEQ ID NO: 234) | IGHV1-18*01 | BJ098 (SEQ ID NO: 239) | IGKV2-29*02 |
| BJM0047 | BJ094 (SEQ ID NO: 235) | IGHV1-2*02 | BJ098 (SEQ ID NO: 239) | IGKV2-29*02 |
| BJM0048 | BJ095 (SEQ ID NO: 236) | IGHV1-2*02 | BJ098 (SEQ ID NO: 239) | IGKV2-29*02 |
| BJM0049 | BJ096 (SEQ ID NO: 237) | IGHV1-2*02 | BJ098 (SEQ ID NO: 239) | IGKV2-29*02 |
| BJM0050 | BJ092 (SEQ ID NO: 233) | IGHV1-18*03 | BJ099 (SEQ ID NO: 240) | IGKV2D-29*01 |
| BJM0051 | BJ093 (SEQ ID NO: 234) | IGHV1-18*01 | BJ099 (SEQ ID NO: 240) | IGKV2D-29*01 |
| BJM0052 | BJ094 (SEQ ID NO: 235) | IGHV1-2*02 | BJ099 (SEQ ID NO: 240) | IGKV2D-29*01 |
| BJM0053 | BJ095 (SEQ ID NO: 236) | IGHV1-2*02 | BJ099 (SEQ ID NO: 240) | IGKV2D-29*01 |
| BJM0054 | BJ096 (SEQ ID NO: 237) | IGHV1-2*02 | BJ099 (SEQ ID NO: 240) | IGKV2D-29*01 |
| BJM0055 | BJ092 (SEQ ID NO: 233) | IGHV1-18*03 | BJ100 (SEQ ID NO: 241) | IGKV2-24*01 |
| BJM0056 | BJ093 (SEQ ID NO: 234) | IGHV1-18*01 | BJ100 (SEQ ID NO: 241) | IGKV2-24*01 |
| BJM0057 | BJ094 (SEQ ID NO: 235) | IGHV1-2*02 | BJ100 (SEQ ID NO: 241) | IGKV2-24*01 |
| BJM0058 | BJ095 (SEQ ID NO: 236) | IGHV1-2*02 | BJ100 (SEQ ID NO: 241) | IGKV2-24*01 |
| BJM0059 | BJ096 (SEQ ID NO: 237) | IGHV1-2*02 | BJ100 (SEQ ID NO: 241) | IGKV2-24*01 |
| BJM0060 | BJ092 (SEQ ID NO: 233) | IGHV1-18*03 | BJ101 (SEQ ID NO: 242) | IGKV2-28*01 |
| BJM0061 | BJ093 (SEQ ID NO: 234) | IGHV1-18*01 | BJ101 (SEQ ID NO: 242) | IGKV2-28*01 |
| BJM0062 | BJ094 (SEQ ID NO: 235) | IGHV1-2*02 | BJ101 (SEQ ID NO: 242) | IGKV2-28*01 |
| BJM0063 | BJ095 (SEQ ID NO: 236) | IGHV1-2*02 | BJ101 (SEQ ID NO: 242) | IGKV2-28*01 |
| BJM0064 | BJ096 (SEQ ID NO: 237) | IGHV1-2*02 | BJ101 (SEQ ID NO: 242) | IGKV2-28*01 |

TGF-Beta Inhibitor

In one aspect, provided herein is a multispecific antibody molecule comprising a TGF-beta inhibitor. In some embodiments, the TGF-beta inhibitor binds to and inhibits TGF-beta, e.g., reduces the activity of TGF-beta. In some embodiments, the TGF-beta inhibitor inhibits (e.g., reduces the activity of) TGF-beta 1. In some embodiments, the TGF-beta inhibitor inhibits (e.g., reduces the activity of) TGF-beta 2. In some embodiments, the TGF-beta inhibitor inhibits (e.g., reduces the activity of) TGF-beta 3. In some embodiments, the TGF-beta inhibitor inhibits (e.g., reduces the activity of) TGF-beta 1 and TGF-beta 3. In some embodiments, the TGF-beta inhibitor inhibits (e.g., reduces the activity of) TGF-beta 1, TGF-beta 2, and TGF-beta 3.

In some embodiments, the TGF-beta inhibitor comprises a portion of a TGF-beta receptor (e.g., an extracellular domain of a TGF-beta receptor) that is capable of inhibiting (e.g., reducing the activity of) TGF-beta, or functional fragment or variant thereof. In some embodiments, the TGF-beta inhibitor comprises a TGFBR1 polypeptide (e.g., an extracellular domain of TGFBR1 or functional variant thereof). In some embodiments, the TGF-beta inhibitor comprises a TGFBR2 polypeptide (e.g., an extracellular domain of TGFBR2 or functional variant thereof). In some embodiments, the TGF-beta inhibitor comprises a TGFBR3 polypeptide (e.g., an extracellular domain of TGFBR3 or functional variant thereof). In some embodiments, the TGF-beta inhibitor comprises a TGFBR1 polypeptide (e.g., an extracellular domain of TGFBR1 or functional variant thereof) and a TGFBR2 polypeptide (e.g., an extracellular domain of TGFBR2 or functional variant thereof). In some embodiments, the TGF-beta inhibitor comprises a TGFBR1 polypeptide (e.g., an extracellular domain of TGFBR1 or functional variant thereof) and a TGFBR3 polypeptide (e.g., an extracellular domain of TGFBR3 or functional variant thereof). In some embodiments, the TGF-beta inhibitor comprises a TGFBR2 polypeptide (e.g., an extracellular domain of TGFBR2 or functional variant thereof) and a TGFBR3 polypeptide (e.g., an extracellular domain of TGFBR3 or functional variant thereof).

Exemplary TGF-beta receptor polypeptides that can be used as TGF-beta inhibitors have been disclosed in U.S. Pat. Nos. 8,993,524, 9,676,863, 8,658,135, US20150056199, US20070184052, and WO2017037634, all of which are herein incorporated by reference in their entirety.

In some embodiments, the TGF-beta inhibitor comprises an extracellular domain of TGFBR1 or a sequence substantially identical thereto (e.g., a sequence that is at least 80%, 85%, 90%, or 95% identical thereto). In some embodiments, the TGF-beta inhibitor comprises an extracellular domain of SEQ ID NO: 295, or a sequence substantially identical thereto (e.g., a sequence that is at least 80%, 85%, 90%, or 95% identical thereto). In some embodiments, the TGF-beta inhibitor comprises an extracellular domain of SEQ ID NO: 296, or a sequence substantially identical thereto (e.g., a sequence that is at least 80%, 85%, 90%, or 95% identical thereto). In some embodiments, the TGF-beta inhibitor comprises an extracellular domain of SEQ ID NO: 297, or a sequence substantially identical thereto (e.g., a sequence that is at least 80%, 85%, 90%, or 95% identical thereto). In some embodiments, the TGF-beta inhibitor comprises the amino acid sequence of SEQ ID NO: 304, or a sequence substantially identical thereto (e.g., a sequence that is at least 80%, 85%, 90%, or 95% identical thereto). In some embodiments, the TGF-beta inhibitor comprises the amino acid sequence of SEQ ID NO: 305, or a sequence substantially identical thereto (e.g., a sequence that is at least 80%, 85%, 90%, or 95% identical thereto).

In some embodiments, the TGF-beta inhibitor comprises an extracellular domain of TGFBR2 or a sequence substantially identical thereto (e.g., a sequence that is at least 80%, 85%, 90%, or 95% identical thereto). In some embodiments, the TGF-beta inhibitor comprises an extracellular domain of SEQ ID NO: 298, or a sequence substantially identical thereto (e.g., a sequence that is at least 80%, 85%, 90%, or 95% identical thereto). In some embodiments, the TGF-beta inhibitor comprises an extracellular domain of SEQ ID NO: 299, or a sequence substantially identical thereto (e.g., a sequence that is at least 80%, 85%, 90%, or 95% identical thereto). In some embodiments, the TGF-beta inhibitor comprises the amino acid sequence of SEQ ID NO: 300, or a sequence substantially identical thereto (e.g., a sequence that is at least 80%, 85%, 90%, or 95% identical thereto). In some embodiments, the TGF-beta inhibitor comprises the amino acid sequence of SEQ ID NO: 301, or a sequence substantially identical thereto (e.g., a sequence that is at least 80%, 85%, 90%, or 95% identical thereto). In some embodiments, the TGF-beta inhibitor comprises the amino acid sequence of SEQ ID NO: 302, or a sequence substantially identical thereto (e.g., a sequence that is at least 80%, 85%, 90%, or 95% identical thereto). In some embodiments, the TGF-beta inhibitor comprises the amino acid sequence of SEQ ID NO: 303, or a sequence substantially identical thereto (e.g., a sequence that is at least 80%, 85%, 90%, or 95% identical thereto).

In some embodiments, the TGF-beta inhibitor comprises an extracellular domain of TGFBR3 or a sequence substantially identical thereto (e.g., a sequence that is at least 80%, 85%, 90%, or 95% identical thereto). In some embodiments, the TGF-beta inhibitor comprises an extracellular domain of SEQ ID NO: 306, or a sequence substantially identical thereto (e.g., a sequence that is at least 80%, 85%, 90%, or 95% identical thereto). In some embodiments, the TGF-beta inhibitor comprises an extracellular domain of SEQ ID NO: 307, or a sequence substantially identical thereto (e.g., a sequence that is at least 80%, 85%, 90%, or 95% identical thereto). In some embodiments, the TGF-beta inhibitor comprises the amino acid sequence of SEQ ID NO: 308, or a sequence substantially identical thereto (e.g., a sequence that is at least 80%, 85%, 90%, or 95% identical thereto).

In some embodiments, the TGF-beta inhibitor comprises no more than one TGF-beta receptor extracellular domain. In some embodiments, the TGF-beta inhibitor comprises two or more (e.g., two, three, four, five, or more) TGF-beta receptor extracellular domains, linked together, e.g., via a linker.

Figures 5A, 5B:
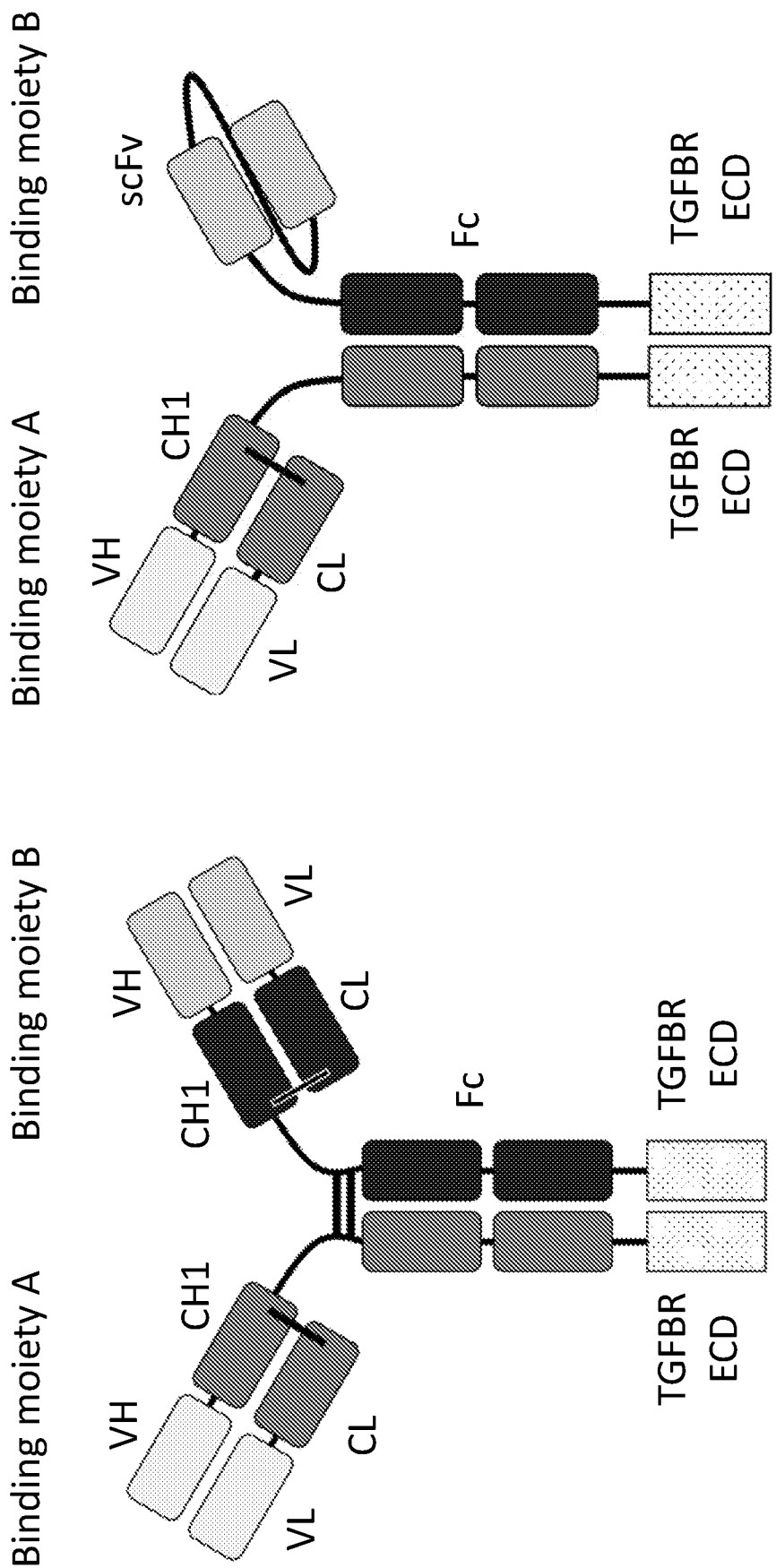
FIGS. 5A-5D are schematics showing exemplary multispecific molecules comprising a TGFβ inhibitor. In some embodiments, the TGFβ inhibitor comprises a TGF-beta receptor ECD homodimer. In some embodiments, the TGFß inhibitor comprises a TGFBR2 ECD heterodimer.
Figures 5C, 5D:
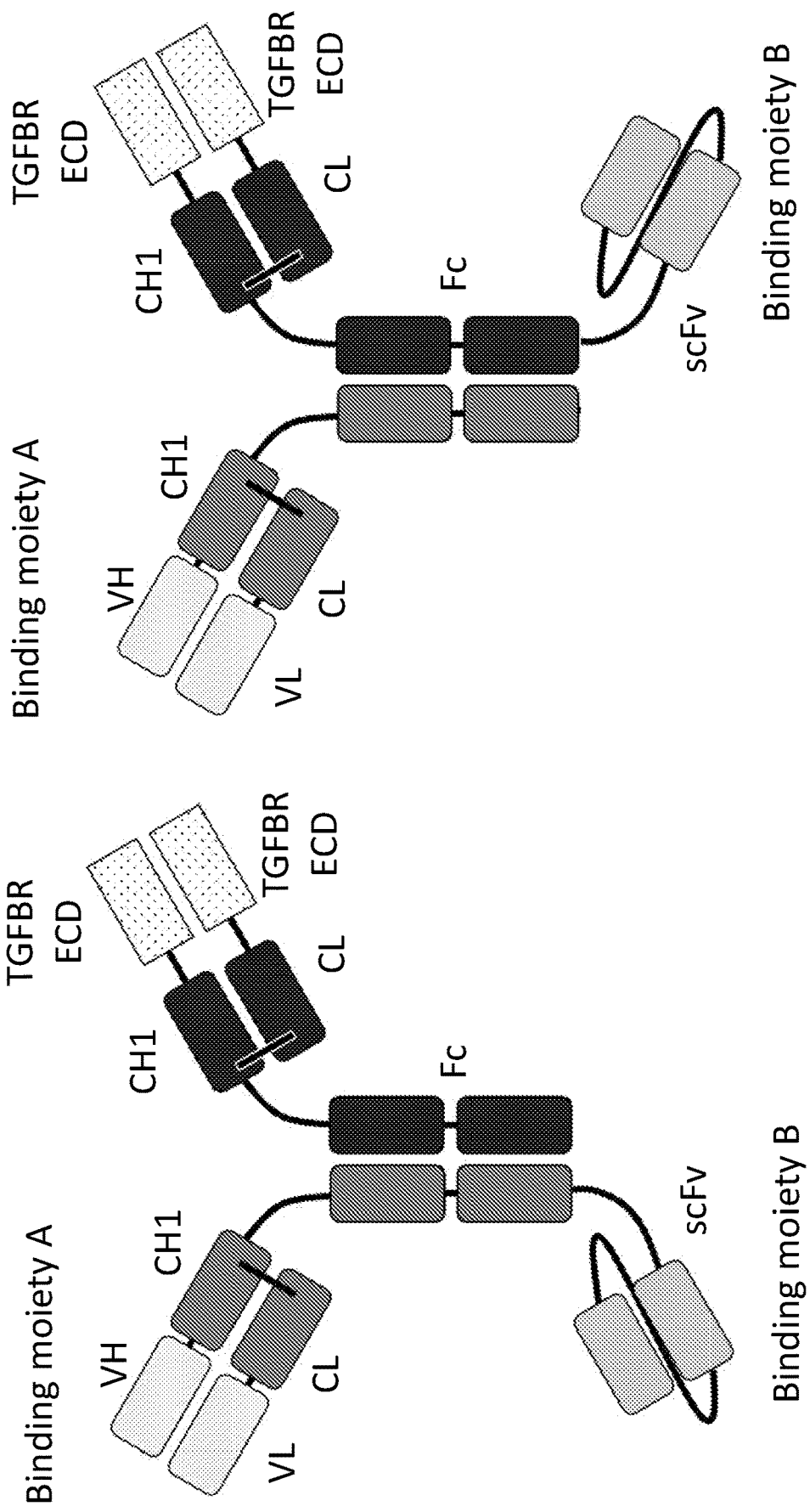

In some embodiments, the multispecific molecule comprises a configuration shown in FIGS. 5A-5D. In some embodiments, the TGFβ inhibitor comprises a TGF-beta receptor ECD homodimer. In some embodiments, the TGFβ inhibitor comprises a TGF-beta receptor ECD heterodimer. In some embodiments, the two TGFBR ECD domains are linked to two Fc regions, e.g., the C-terminus of two Fc regions. In some embodiments, the two TGFBR ECD domains are linked to CH1 and CL, respectively.

TABLE 12

Exemplary amino acid sequences of TGF-beta polypeptides or
TGF-beta receptor polypeptides

| SEQ ID NO | Description | Amino acid sequence |
|---|---|---|
| SEQ ID NO: 292 | Immature human TGF-beta 1 (P01137-1) | MPPSGLRLLLLLLPLLWLLVLTPGRPAAGLSTCKTIDMELVKRKRIE AIRGQILSKLRLASPPSQGEVPPGPLPEAVLALYNSTRDRVAGESAEP EPEPEADYYAKEVTRVLMVETHNEIYDKFKQSTHSIYMFFNTSELRE AVPEPVLLSRAELRLLRLKLKVEQHVELYQKYSNNSWRYLSNRLLA PSDSPEWLSFDVTGVVRQWLSRGGEIEGFRLSAHCSCDSRDNTLQV DINGFTTGRRGDLATIHGMNRPFLLLMATPLERAQHLQSSRHRRAL DTNYCFSSTEKNCCVRQLYIDFRKDLGWKWIHEPKGYHANFCLGP CPYIWSLDTQYSKVLALYNQHNPGASAAPCCVPQALEPLPIVYYVG RKPKVEQLSNMIVRSCKCS |
| SEQ ID NO: 317 | Human TGF-beta 1 (P01137-1) | LSTCKTIDMELVKRKRIEAIRGQILSKLRLASPPSQGEVPPGPLPEAV LALYNSTRDRVAGESAEPEPEPEADYYAKEVTRVLMVETHNEIYDK FKQSTHSIYMFFNTSELREAVPEPVLLSRAELRLLRLKLKVEQHVEL YQKYSNNSWRYLSNRLLAPSDSPEWLSFDVTGVVRQWLSRGGEIE GFRLSAHCSCDSRDNTLQVDINGFTTGRRGDLATIHGMNRPFLLLM ATPLERAQHLQSSRHRRALDTNYCFSSTEKNCCVRQLYIDFRKDLG WKWIHEPKGYHANFCLGPCPYIWSLDTQYSKVLALYNQHNPGASA APCCVPQALEPLPIVYYVGRKPKVEQLSNMIVRSCKCS |
| SEQ ID NO: 293 | Immature human TGF-beta 2 (P61812-1) | MHYCVLSAFLILHLVTVALSLSTCSTLDMDQFMRKRIEAIRGQILSK LKLTSPPEDYPEPEEVPPEVISIYNSTRDLLQEKASRRAAACERERSD EEYYAKEVYKIDMPPFFPSENAIPPTFYRPYFRIVRFDVSAMEKNAS NLVKAEFRVFRLQNPKARVPEQRIELYQILKSKDLTSPTQRYIDSKV VKTRAEGEWLSFDVTDAVHEWLHHKDRNLGFKISLHCPCCTFVPS NNYIIPNKSEELEARFAGIDGTSTYTSGDQKTIKSTRKKNSGKTPHLL LMLLPSYRLESQQTNRRKKRALDAAYCFRNVQDNCCLRPLYIDFKR DLGWKWIHEPKGYNANFCAGACPYLWSSDTQHSRVLSLYNTINPE ASASPCCVSQDLEPLTILYYIGKTPKIEQLSNMIVKSCKCS |
| SEQ ID NO: 318 | Human TGF-beta 2 (P61812-1) | LSTCSTLDMDQFMRKRIEAIRGQILSKLKLTSPPEDYPEPEEVPPEVIS IYNSTRDLLQEKASRRAAACERERSDEEYYAKEVYKIDMPPFFPSEN AIPPTFYRPYFRIVRFDVSAMEKNASNLVKAEFRVFRLQNPKARVPE QRIELYQILKSKDLTSPTQRYIDSKVVKTRAEGEWLSFDVTDAVHE WLHHKDRNLGFKISLHCPCCTFVPSNNYIIPNKSEELEARFAGIDGTS TYTSGDQKTIKSTRKKNSGKTPHLLLMLLPSYRLESQQTNRRKKRA LDAAYCFRNVQDNCCLRPLYIDFKRDLGWKWIHEPKGYNANFCAG ACPYLWSSDTQHSRVLSLYNTINPEASASPCCVSQDLEPLTILYYIGK TPKIEQLSNMIVKSCKCS |
| SEQ ID NO: 294 | Immature human TGF-beta 3 (P10600-1) | MKMHLQRALVVLALLNFATVSLSLSTCTTLDFGHIKKKRVEAIRGQ ILSKLRLTSPPEPTVMTHVPYQVLALYNSTRELLEEMHGEREEGCTQ ENTESEYYAKEIHKFDMIQGLAEHNELAVCPKGITSKVFRFNVSSVE KNRTNLFRAEFRVLRVPNPSSKRNEQRIELFQILRPDEHIAKQRYIGG KNLPTRGTAEWLSFDVTDTVREWLLRRESNLGLEISIHCPCHTFQPN GDILENIHEVMEIKFKGVDNEDDHGRGDLGRLKKQKDHHNPHLIL MMIPPHRLDNPGQGGQRKKRALDTNYCFRNLEENCCVRPLYIDFRQ DLGWKWVHEPKGYYANFCSGPCPYLRSADTTHSTVLGLYNTLNPE ASASPCCVPQDLEPLTILYYVGRTPKVEQLSNMVVKSCKCS |
| SEQ ID NO: 319 | Human TGF-beta 3 (P10600-1) | LSTCTTLDFGHIKKKRVEAIRGQILSKLRLTSPPEPTVMTHVPYQVL ALYNSTRELLEEMHGEREEGCTQENTESEYYAKEIHKFDMIQGLAE HNELAVCPKGITSKVFRFNVSSVEKNRTNLFRAEFRVLRVPNPSSKR NEQRIELFQILRPDEHIAKQRYIGGKNLPTRGTAEWLSFDVTDTVRE WLLRRESNLGLEISIHCPCHTFQPNGDILENIHEVMEIKFKGVDNED DHGRGDLGRLKKQKDHHNPHLILMMIPPHRLDNPGQGGQRKKRAL DTNYCFRNLEENCCVRPLYIDFRQDLGWKWVHEPKGYYANFCSGP CPYLRSADTTHSTVLGLYNTLNPEASASPCCVPQDLEPLTILYYVGR TPKVEQLSNMVVKSCKCS |
| SEQ ID NO: 295 | Immature human TGFBR1 isoform 1 (P36897-1) | MEAAVAAPRPRLLLLVLAAAAAAAAALLPGATALQCFCHLCTKDN FTCVTDGLCFVSVTETTDKVIHNSMCIAEIDLIPRDRPFVCAPSSKTG SVTTTYCCNQDHCNKIELPTTVKSSPGLGPVELAAVIAGPVCFVCISL MLMVYICHNRTVIHHRVPNEEDPSLDRPFISEGTTLKDLIYDMTTSG SGSGLPLLVQRTIARTIVLQESIGKGRFGEVWRGKWRGEEVAVKIFS SREERSWFREAEIYQTVMLRHENILGFIAADNKDNGTWTQLWLVSD YHEHGSLFDYLNRYTVTVEGMIKLALSTASGLAHLHMEIVGTQGKP AIAHRDLKSKNILVKKNGTCCIADLGLAVRHDSATDTIDIAPNHRVG TKRYMAPEVLDDSINMKHFESFKRADIYAMGLVFWEIARRCSIGGI HEDYQLPYYDLVPSDPSVEEMRKVVCEQKLRPNIPNRWQSCEALR VMAKIMRECWYANGAARLTALRIKKTLSQLSQQEGIKM |

TABLE 12-continued

Exemplary amino acid sequences of TGF-beta polypeptides or TGF-beta receptor polypeptides

| SEQ ID NO | Description | Amino acid sequence |
|---|---|---|
| SEQ ID NO: 320 | Human TGFBR1 isoform 1 (P36897-1) | LQCFCHLCTKDNFTCVTDGLCFVSVTETTDKVIHNSMCIAEIDLIPR<br>DRPFVCAPSSKTGSVTTTYCCNQDHCNKIELPTTVKSSPGLGPVELA<br>AVIAGPVCFVCISLMLMVYICHNRTVIHHRVPNEEDPSLDRPFISEGT<br>TLKDLIYDMTTSGSGSGLPLLVQRTIARTIVLQESIGKGRFGEVWRG<br>KWRGEEVAVKIFSSREERSWFREAEIYQTVMLRHENILGFIAADNK<br>DNGTWTQLWLVSDYHEHGSLFDYLNRYTVTVEGMIKLALSTASGL<br>AHLHMEIVGTQGKPAIAHRDLKSKNILVKKNGTCCIADLGLAVRHD<br>SATDTIDIAPNHRVGTKRYMAPEVLDDSINMKHFESFKRADIYAMG<br>LVFWEIARRCSIGGIHEDYQLPYYDLVPSDPSVEEMRKVVCEQKLRP<br>NIPNRWQSCEALRVMAKIMRECWYANGAARLTALRIKKTLSQLSQ<br>QEGIKM |
| SEQ ID NO: 296 | Immature human TGFBR1 isoform 2 (P36897-2) | MEAAVAAPRPRLLLLVLAAAAAAAAALLPGATALQCFCHLCTKDN<br>FTCVTDGLCFVSVTETTDKVIHNSMCIAEIDLIPRDRPFVCAPSSKTG<br>SVTTTYCCNQDHCNKIELPTTGPFSVKSSPGLGPVELAAVIAGPVCF<br>VCISLMLMVYICHNRTVIHHRVPNEEDPSLDRPFISEGTTLKDLIYD<br>MTTSGSGSGLPLLVQRTIARTIVLQESIGKGRFGEVWRGKWRGEEV<br>AVKIFSSREERSWFREAEIYQTVMLRHENILGFIAADNKDNGTWTQ<br>LWLVSDYHEHGSLFDYLNRYTVTVEGMIKLALSTASGLAHLHMEI<br>VGTQGKPAIAHRDLKSKNILVKKNGTCCIADLGLAVRHDSATDTIDI<br>APNHRVGTKRYMAPEVLDDSINMKHFESFKRADIYAMGLVFWEIA<br>RRCSIGGIHEDYQLPYYDLVPSDPSVEEMRKVVCEQKLRPNIPNRW<br>QSCEALRVMAKIMRECWYANGAARLTALRIKKTLSQLSQQEGIKM |
| SEQ ID NO: 321 | Human TGFBR1 isoform 2 (P36897-2) | LQCFCHLCTKDNFTCVTDGLCFVSVTETTDKVIHNSMCIAEIDLIPR<br>DRPFVCAPSSKTGSVTTTYCCNQDHCNKIELPTTGPFSVKSSPGLGP<br>VELAAVIAGPVCFVCISLMLMVYICHNRTVIHHRVPNEEDPSLDRPFI<br>SEGTTLKDLIYDMTTSGSGSGLPLLVQRTIARTIVLQESIGKGRFGEV<br>WRGKWRGEEVAVKIFSSREERSWFREAEIYQTVMLRHENILGFIAA<br>DNKDNGTWTQLWLVSDYHEHGSLFDYLNRYTVTVEGMIKLALST<br>ASGLAHLHMEIVGTQGKPAIAHRDLKSKNILVKKNGTCCIADLGLA<br>VRHDSATDTIDIAPNHRVGTKRYMAPEVLDDSINMKHFESFKRADI<br>YAMGLVFWEIARRCSIGGIHEDYQLPYYDLVPSDPSVEEMRKVVCE<br>QKLRPNIPNRWQSCEALRVMAKIMRECWYANGAARLTALRIKKTL<br>SQLSQQEGIKM |
| SEQ ID NO: 297 | Immature human TGFBR1 isoform 3 (P36897-3) | MEAAVAAPRPRLLLLVLAAAAAAAAALLPGATALQCFCHLCTKDN<br>FTCVTDGLCFVSVTETTDKVIHNSMCIAEIDLIPRDRPFVCAPSSKTG<br>SVTTTYCCNQDHCNKIELPTTGLPLLVQRTIARTIVLQESIGKGRFGE<br>VWRGKWRGEEVAVKIFSSREERSWFREAEIYQTVMLRHENILGFIA<br>ADNKDNGTWTQLWLVSDYHEHGSLFDYLNRYTVTVEGMIKLALS<br>TASGLAHLHMEIVGTQGKPAIAHRDLKSKNILVKKNGTCCIADLGL<br>AVRHDSATDTIDIAPNHRVGTKRYMAPEVLDDSINMKHFESFKRAD<br>IYAMGLVFWEIARRCSIGGIHEDYQLPYYDLVPSDPSVEEMRKVVC<br>EQKLRPNIPNRWQSCEALRVMAKIMRECWYANGAARLTALRIKKT<br>LSQLSQQEGIKM |
| SEQ ID NO: 322 | Human TGFBR1 isoform 3 (P36897-3) | LQCFCHLCTKDNFTCVTDGLCFVSVTETTDKVIHNSMCIAEIDLIPR<br>DRPFVCAPSSKTGSVTTTYCCNQDHCNKIELPTTGLPLLVQRTIARTI<br>VLQESIGKGRFGEVWRGKWRGEEVAVKIFSSREERSWFREAEIYQT<br>VMLRHENILGFIAADNKDNGTWTQLWLVSDYHEHGSLFDYLNRYT<br>VTVEGMIKLALSTASGLAHLHMEIVGTQGKPAIAHRDLKSKNILVK<br>KNGTCCIADLGLAVRHDSATDTIDIAPNHRVGTKRYMAPEVLDDSI<br>NMKHFESFKRADIYAMGLVFWEIARRCSIGGIHEDYQLPYYDLVPS<br>DPSVEEMRKVVCEQKLRPNIPNRWQSCEALRVMAKIMRECWYAN<br>GAARLTALRIKKTLSQLSQQEGIKM |
| SEQ ID NO: 304 | Human TGFBR1 fragment 1 | LQCFCHLCTKDNFTCVTDGLCFVSVTETTDKVIHNSMCIAEIDLIPR<br>DRPFVCAPSSKTGSVTTTYCCNQDHCNKIELPTTVKSSPGLGPVEL |
| SEQ ID NO: 305 | Human TGFBR1 fragment 2 | ALQCFCHLCTKDNFTCVTDGLCFVSVTETTDKVIHNSMCIAEIDLIP<br>RDRPFVCAPSSKTGSVTTTYCCNQDHCNKIEL |
| SEQ ID NO: 298 | Immature human TGFBR2 isoform B (short isoform) (P37173-1) | MGRGLLRGLWPLHIVLWTRIASTIPPHVQKSVNNDMIVTDNNGAV<br>KFPQLCKFCDVRFSTCDNQKSCMSNCSITSICEKPQEVCVAVWRKN<br>DENITLETVCHDPKLPYHDFILEDAASPKCIMKEKKKPGETFFMCSC<br>SSDECNDNIIFSEEYNTSNPDLLLVIFQVTGISLLPPLGVAISVIIIFYCY<br>RVNRQQKLSSTWETGKTRKLMEFSEHCAIILEDDRSDISSTCANNIN<br>HNTELLPIELDTLVGKGRFAEVYKAKLKQNTSEQFETVAVKIFPYEE<br>YASWKTEKDIFSDINLKHENILQFLTAEERKTELGKQYWLITAFHAK<br>GNLQEYLTRHVISWEDLRKLGSSLARGIAHLHSDHTPCGRPKMPIV |

TABLE 12-continued

Exemplary amino acid sequences of TGF-beta polypeptides or TGF-beta receptor polypeptides

| SEQ ID NO | Description | Amino acid sequence |
|---|---|---|
| | | HRDLKSSNILVKNDLTCCLCDFGLSLRLDPTLSVDDLANSGQVGTA<br>RYMAPEVLESRMNLENVESFKQTDVYSMALVLWEMTSRCNAVGE<br>VKDYEPPFGSKVREHPCVESMKDNVLRDRGRPEIPSFWLNHQGIQM<br>VCETLTECWDHDPEARLTAQCVAERFSELEHLDRLSGRSCSEEKIPE<br>DGSLNTTK |
| SEQ ID NO: 323 | Human TGFBR2 isoform B (short isoform) (P37173-1) | TIPPHVQKSVNNDMIVTDNNGAVKFPQLCKFCDVRFSTCDNQKSC<br>MSNCSITSICEKPQEVCVAVWRKNDENITLETVCHDPKLPYHDFILE<br>DAASPKCIMKEKKKPGETFFMCSCSSDECNDNIIFSEEYNTSNPDLLL<br>VIFQVTGISLLPPLGVAISVIIIFYCYRVNRQQKLSSTWETGKTRKLM<br>EFSEHCAIILEDDRSDISSTCANNINHNTELLPIELDTLVGKGRFAEVY<br>KAKLKQNTSEQFETVAVKIFPYEEYASWKTEKDIFSDINLKHENILQ<br>FLTAEERKTELGKQYWLITAFHAKGNLQEYLTRHVISWEDLRKLGS<br>SLARGIAHLHSDHTPCGRPKMPIVHRDLKSSNILVKNDLTCCLCDFG<br>LSLRLDPTLSVDDLANSGQVGTARYMAPEVLESRMNLENVESFKQT<br>DVYSMALVLWEMTSRCNAVGEVKDYEPPFGSKVREHPCVESMKD<br>NVLRDRGRPEIPSFWLNHQGIQMVCETLTECWDHDPEARLTAQCV<br>AERFSELEHLDRLSGRSCSEEKIPEDGSLNTTK |
| SEQ ID NO: 299 | Immature human TGFBR2 isoform A (long isoform) (P37173-2) | MGRGLLRGLWPLHIVLWTRIASTIPPHVQKSDVEMEAQKDEIICPSC<br>NRTAHPLRHINNDMIVTDNNGAVKFPQLCKFCDVRFSTCDNQKSC<br>MSNCSITSICEKPQEVCVAVWRKNDENITLETVCHDPKLPYHDFILE<br>DAASPKCIMKEKKKPGETFFMCSCSSDECNDNIIFSEEYNTSNPDLLL<br>VIFQVTGISLLPPLGVAISVIIIFYCYRVNRQQKLSSTWETGKTRKLM<br>EFSEHCAIILEDDRSDISSTCANNINHNTELLPIELDTLVGKGRFAEVY<br>KAKLKQNTSEQFETVAVKIFPYEEYASWKTEKDIFSDINLKHENILQ<br>FLTAEERKTELGKQYWLITAFHAKGNLQEYLTRHVISWEDLRKLGS<br>SLARGIAHLHSDHTPCGRPKMPIVHRDLKSSNILVKNDLTCCLCDFG<br>LSLRLDPTLSVDDLANSGQVGTARYMAPEVLESRMNLENVESFKQT<br>DVYSMALVLWEMTSRCNAVGEVKDYEPPFGSKVREHPCVESMKD<br>NVLRDRGRPEIPSFWLNHQGIQMVCETLTECWDHDPEARLTAQCV<br>AERFSELEHLDRLSGRSCSEEKIPEDGSLNTTK |
| SEQ ID NO: 324 | Human TGFBR2 isoform A (long isoform) (P37173-2) | TIPPHVQKSDVEMEAQKDEIICPSCNRTAHPLRHINNDMIVTDNNGA<br>VKFPQLCKFCDVRFSTCDNQKSCMSNCSITSICEKPQEVCVAVWRK<br>NDENITLETVCHDPKLPYHDFILEDAASPKCIMKEKKKPGETFFMCS<br>CSSDECNDNIIFSEEYNTSNPDLLLVIFQVTGISLLPPLGVAISVIIIFYC<br>YRVNRQQKLSSTWETGKTRKLMEFSEHCAIILEDDRSDISSTCANNI<br>NHNTELLPIELDTLVGKGRFAEVYKAKLKQNTSEQFETVAVKIFPYE<br>EYASWKTEKDIFSDINLKHENILQFLTAEERKTELGKQYWLITAFHA<br>KGNLQEYLTRHVISWEDLRKLGSSLARGIAHLHSDHTPCGRPKMPI<br>VHRDLKSSNILVKNDLTCCLCDFGLSLRLDPTLSVDDLANSGQVGT<br>ARYMAPEVLESRMNLENVESFKQTDVYSMALVLWEMTSRCNAVG<br>EVKDYEPPFGSKVREHPCVESMKDNVLRDRGRPEIPSFWLNHQGIQ<br>MVCETLTECWDHDPEARLTAQCVAERFSELEHLDRLSGRSCSEEKI<br>PEDGSLNTTK |
| SEQ ID NO: 300 | Human TGFBR2 fragment 1 (ECD of human TGFBR2 isoform B) | TIPPHVQKSVNNDMIVTDNNGAVKFPQLCKFCDVRFSTCDNQKSC<br>MSNCSITSICEKPQEVCVAVWRKNDENITLETVCHDPKLPYHDFILE<br>DAASPKCIMKEKKKPGETFFMCSCSSDECNDNIIFSEEYNTSNPD |
| SEQ ID NO: 301 | Human TGFBR2 fragment 2 | IPPHVQKSVNNDMIVTDNNGAVKFPQLCKFCDVRFSTCDNQKSCMS<br>NCSITSICEKPQEVCVAVWRKNDENITLETVCHDPKLPYHDFILEDA<br>ASPKCIMKEKKKPGETFFMCSCSSDECNDNIIFSEEYNTSNPD |
| SEQ ID NO: 302 | Human TGFBR2 fragment 3 (ECD of human TGFBR2 isoform A) | TIPPHVQKSDVEMEAQKDEIICPSCNRTAHPLRHINNDMIVTDNNGA<br>VKFPQLCKFCDVRFSTCDNQKSCMSNCSITSICEKPQEVCVAVWRK<br>NDENITLETVCHDPKLPYHDFILEDAASPKCIMKEKKKPGETFFMCS<br>CSSDECNDNIIFSEEYNTSNPD |
| SEQ ID NO: 303 | Human TGFBR2 fragment 4 | QLCKFCDVRFSTCDNQKSCMSNCSITSICEKPQEVCVAVWRKNDEN<br>ITLETVCHDPKLPYHDFILEDAASPKCIMKEKKKPGETFFMCSCSSD<br>ECNDNIIF |

TABLE 12-continued

Exemplary amino acid sequences of TGF-beta polypeptides or TGF-beta receptor polypeptides

| SEQ ID NO | Description | Amino acid sequence |
|---|---|---|
| SEQ ID NO: 306 | Immature human TGFBR3 isoform 1 (Q03167-1) | MTSHYVIAIFALMSSCLATAGPEPGALCELSPVSASHPVQALMESFT VLSGCASRGTTGLPQEVHVLNLRTAGQGPGQLQREVTLHLNPISSV HIHHKSVVFLLNSPHPLVWHLKTERLATGVSRLFLVSEGSVVQFSSA NFSLTAETEERNFPHGNEHLLNWARKEYGAVTSFTELKIARNIYIKV GEDQVFPPKCNIGKNFLSLNYLAEYLQPKAAEGCVMSSQPQNEEVH IIELITPNSNPYSAFQVDITIDIRPSQEDLEVVKNLILILKCKKSVNWVI KSFDVKGSLKIIAPNSIGFGKESERSMTMTKSIRDDIPSTQGNLVKW ALDNGYSPITSYTMAPVANRFHLRLENNAEEMGDEEVHTIPPELRIL LDPGALPALQNPPIRGGEGQNGGLPFPFPDISRRVWNEEGEDGLPRP KDPVIPSIQLFPGLREPEEVQGSVDIALSVKCDNEKMIVAVEKDSFQ ASGYSGMDVTLLDPTCKAKMNGTHFVLESPLNGCGTRPRWSALDG VVYYNSIVIQVPALGDSSGWPDGYEDLESGDNGFPGDMDEGDASLF TRPEIVVFNCSLQQVRNPSSFQEQPHGNITFNMELYNTDLFLVPSQG VFSVPENGHVYVEVSVTKAEQELGFAIQTCFISPYSNPDRMSHYTIIE NICPKDESVKFYSPKRVHFPIPQADMDKKRFSFVFKPVFNTSLLFLQ CELTLCTKMEKHPQKLPKCVPPDEACTSLDASIIWAMMQNKKTFTK PLAVIHHEAESKEKGPSMKEPNPISPPIFHGLDTLTVMGIAFAAFVIG ALLTGALWYIYSHTGETAGRQQVPTSPPASENSSAAHSIGSTQSTPC SSSSTA |
| SEQ ID NO: 325 | Human TGFBR3 isoform 1 (Q03167-1) | GPEPGALCELSPVSASHPVQALMESFTVLSGCASRGTTGLPQEVHVL NLRTAGQGPGQLQREVTLHLNPISSVHIHHKSVVFLLNSPHPLVWH LKTERLATGVSRLFLVSEGSVVQFSSANFSLTAETEERNFPHGNEHL LNWARKEYGAVTSFTELKIARNIYIKVGEDQVFPPKCNIGKNFLSLN YLAEYLQPKAAEGCVMSSQPQNEEVHIIELITPNSNPYSAFQVDITID IRPSQEDLEVVKNLILILKCKKSVNWVIKSFDVKGSLKIIAPNSIGFGK ESERSMTMTKSIRDDIPSTQGNLVKWALDNGYSPITSYTMAPVANR FHLRLENNAEEMGDEEVHTIPPELRILLDPGALPALQNPPIRGGEGQ NGGLPFPFPDISRRVWNEEGEDGLPRPKDPVIPSIQLFPGLREPEEVQ GSVDIALSVKCDNEKMIVAVEKDSFQASGYSGMDVTLLDPTCKAK MNGTHFVLESPLNGCGTRPRWSALDGVVYYNSIVIQVPALGDSSG WPDGYEDLESGDNGFPGDMDEGDASLFTRPEIVVFNCSLQQVRNPS SFQEQPHGNITFNMELYNTDLFLVPSQGVFSVPENGHVYVEVSVTK AEQELGFAIQTCFISPYSNPDRMSHYTIIENICPKDESVKFYSPKRVHF PIPQADMDKKRFSFVFKPVFNTSLLFLQCELTLCTKMEKHPQKLPKC VPPDEACTSLDASIIWAMMQNKKTFTKPLAVIHHEAESKEKGPSMK EPNPISPPIFHGLDTLTVMGIAFAAFVIGALLTGALWYIYSHTGETAG RQQVPTSPPASENSSAAHSIGSTQSTPCSSSSTA |
| SEQ ID NO: 307 | Immature human TGFBR3 isoform 2 (Q03167-2) | MTSHYVIAIFALMSSCLATAGPEPGALCELSPVSASHPVQALMESFT VLSGCASRGTTGLPQEVHVLNLRTAGQGPGQLQREVTLHLNPISSV HIHHKSVVFLLNSPHPLVWHLKTERLATGVSRLFLVSEGSVVQFSSA NFSLTAETEERNFPHGNEHLLNWARKEYGAVTSFTELKIARNIYIKV GEDQVFPPKCNIGKNFLSLNYLAEYLQPKAAEGCVMSSQPQNEEVH IIELITPNSNPYSAFQVDITIDIRPSQEDLEVVKNLILILKCKKSVNWVI KSFDVKGSLKIIAPNSIGFGKESERSMTMTKSIRDDIPSTQGNLVKW ALDNGYSPITSYTMAPVANRFHLRLENNEEMGDEEVHTIPPELRLL DPGALPALQNPPIRGGEGQNGGLPFPFPDISRRVWNEEGEDGLPRPK DPVIPSIQLFPGLREPEEVQGSVDIALSVKCDNEKMIVAVEKDSFQAS GYSGMDVTLLDPTCKAKMNGTHFVLESPLNGCGTRPRWSALDGV VYYNSIVIQVPALGDSSGWPDGYEDLESGDNGFPGDMDEGDASLFT RPEIVVFNCSLQQVRNPSSFQEQPHGNITFNMELYNTDLFLVPSQGV FSVPENGHVYVEVSVTKAEQELGFAIQTCFISPYSNPDRMSHYTIIEN ICPKDESVKFYSPKRVHFPIPQADMDKKRFSFVFKPVFNTSLLFLQCE LTLCTKMEKHPQKLPKCVPPDEACTSLDASIIWAMMQNKKTFTKPL AVIHHEAESKEKGPSMKEPNPISPPIFHGLDTLTVMGIAFAAFVIGAL LTGALWYIYSHTGETAGRQQVPTSPPASENSSAAHSIGSTQSTPCSSS STA |
| SEQ ID NO: 326 | Human TGFBR3 isoform 2 (Q03167-2) | GPEPGALCELSPVSASHPVQALMESFTVLSGCASRGTTGLPQEVHVL NLRTAGQGPGQLQREVTLHLNPISSVHIHHKSVVFLLNSPHPLVWH LKTERLATGVSRLFLVSEGSVVQFSSANFSLTAETEERNFPHGNEHL LNWARKEYGAVTSFTELKIARNIYIKVGEDQVFPPKCNIGKNFLSLN YLAEYLQPKAAEGCVMSSQPQNEEVHIIELITPNSNPYSAFQVDITID IRPSQEDLEVVKNLILILKCKKSVNWVIKSFDVKGSLKIIAPNSIGFGK ESERSMTMTKSIRDDIPSTQGNLVKWALDNGYSPITSYTMAPVANR FHLRLENNEEMGDEEVHTIPPELRILLDPGALPALQNPPIRGGEGQN GGLPFPFPDISRRVWNEEGEDGLPRPKDPVIPSIQLFPGLREPEEVQG SVDIALSVKCDNEKMIVAVEKDSFQASGYSGMDVTLLDPTCKAKM NGTHFVLESPLNGCGTRPRWSALDGVVYYNSIVIQVPALGDSSGWP DGYEDLESGDNGFPGDMDEGDASLFTRPEIVVFNCSLQQVRNPSSF QEQPHGNITFNMELYNTDLFLVPSQGVFSVPENGHVYVEVSVTKAE QELGFAIQTCFISPYSNPDRMSHYTIIENICPKDESVKFYSPKRVHFPI |

TABLE 12-continued

Exemplary amino acid sequences of TGF-beta polypeptides or TGF-beta receptor polypeptides

| SEQ ID NO | Description | Amino acid sequence |
|---|---|---|
| | | PQADMDKKRFSFVFKPVFNTSLLFLQCELTLCTKMEKHPQKLPKCV PPDEACTSLDASIIWAMMQNKKTFTKPLAVIHHEAESKEKGPSMKE PNPISPPIFHGLDTLTVMGIAFAAFVIGALLTGALWYIYSHTGETAGR QQVPTSPPASENSSAAHSIGSTQSTPCSSSSTA |
| SEQ ID NO: 308 | Human TGFBR3 fragment 1 | GPEPGALCELSPVSASHPVQALMESFTVLSGCASRGTTGLPQEVHVL NLRTAGQGPGQLQREVTLHLNPISSSVHIHHKSVVFLLNSPHPLVWH LKTERLATGVSRLFLVSEGSVVQFSSANFSLTAETEERNFPHGNEHL LNWARKEYGAVTSFTELKIARNIYIKVGEDQVFPPKCNIGKNFLSLN YLAEYLQPKAAEGCVMSSQPQNEEVHIIELITPNSNPYSAFQVDITID IRPSQEDLEVVKNLILILKCKKSVNWVIKSFDVKGSLKIIAPNSIGFGK ESERSMTMTKSIRDDIPSTQGNLVKWALDNGYSPITSYTMAPVANR FHLRLENNAEEMGDEEVHTIPPELRILLDPGALPALQNPPIRGGEGQ NGGLPFPFPDISRRVWNEEGEDGLPRPKDPVIPSIQLFPGLREPEEVQ GSVDIALSVKCDNEKMIVAVEKDSFQASGYSGMDVTLLDPTCKAK MNGTHFVLESPLNGCGTRPRWSALDGVVYYNSIVIQVPALGDSSG WPDGYEDLESGDNGFPGDMDEGDASLFTRPEIVVFNCSLQQVRNPS SFQEQPHGNITFNMELYNTDLFLVPSQGVFSVPENGHVYVEVSVTK AEQELGFAIQTCFISPYSNPDRMSHYTIIENICPKDESVKFYSPKRVHF PIPQADMDKKRFSFVFKPVFNTSLLFLQCELTLCTKMEKHPQKLPKC VPPDEACTSLDASIIWAMMQNKKTFTKPLAVIHHEAESKEKGPSMK EPNPISPPIFHGLDTLTV |
| SEQ ID NO: 392 | hCH1-hFc_Hole-3x4GS-TGFbR2 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQVC TLPPSREEMTKNQVSLSCAVKGFYPSDIAVEWESNGQPENNYKTTP PVLDSDGSFFLVSKLTVDKSRWQQGNVFSCSVMHEALHNHYTQKS LSLSPGXGGGGSGGGGSGGGGSIPPHVQKSVNNDMIVTDNNGAVK FPQLCKFCDVRFSTCDNQKSCMSNCSITSICEKPQEVCVAVWRKND ENITLETVCHDPKLPYHDFILEDAASPKCIMKEKKKPGETFFMCSCS SDECNDNIIFSEEYNTSNPD, wherein X is K or absent |
| SEQ ID NO: 393 | hCH1-hFc_Knob-3x4GS-TGFbR2 | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEV TCVVVDVSHEDPEVKFNWYVDGVEVHNAKTKPREEQYNSTYRVV SVLTVLHQDWLNGKEYKCKVSNKALPAPIEKTISKAKGQPREPQVY TLPPCREEMTKNQVSLWCLVKGFYPSDIAVEWESNGQPENNYKTTP PVLDSDGSFFLYSKLTVDKSRWQQGNVFSCSVMHEALHNHYTQKS LSLSPGXGGGGSGGGGSGGGGSIPPHVQKSVNNDMIVTDNNGAVK FPQLCKFCDVRFSTCDNQKSCMSNCSITSICEKPQEVCVAVWRKND ENITLETVCHDPKLPYHDFILEDAASPKCIMKEKKKPGETFFMCSCS SDECNDNIIFSEEYNTSNPD, wherein X is K or absent |
| SEQ ID NO: 394 | hFc_Hole-3x4GS-TGFbR2 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVCTLPPSREE MTKNQVSLSCAVKGFYPSDIAVEWESNGQPENNYKTTPPVLDSDGS FFLVSKLTVDKSRWQQGNVFSCSVMHEALHNHYTQKSLSLSPGXG GGGSGGGGSGGGGSIPPHVQKSVNNDMIVTDNNGAVKFPQLCKFC DVRFSTCDNQKSCMSNCSITSICEKPQEVCVAVWRKNDENITLETV CHDPKLPYHDFILEDAASPKCIMKEKKKPGETFFMCSCSSDECNDNI IFSEEYNTSNPD, wherein X is K or absent |
| SEQ ID NO: 395 | hFc_Knob-3x4GS-TGFbR2 | DKTHTCPPCPAPELLGGPSVFLFPPKPKDTLMISRTPEVTCVVVDVS HEDPEVKFNWYVDGVEVHNAKTKPREEQYNSTYRVVSVLTVLHQ DWLNGKEYKCKVSNKALPAPIEKTISKAKGQPREPQVYTLPPCREE MTKNQVSLWCLVKGFYPSDIAVEWESNGQPENNYKTTPPVLDSDG SFFLYSKLTVDKSRWQQGNVFSCSVMHEALHNHYTQKSLSLSPGX GGGGSGGGGSGGGGSIPPHVQKSVNNDMIVTDNNGAVKFPQLCKF CDVRFSTCDNQKSCMSNCSITSICEKPQEVCVAVWRKNDENITLET VCHDPKLPYHDFILEDAASPKCIMKEKKKPGETFFMCSCSSDECND NIIFSEEYNTSNPD, wherein X is K or absent |
| SEQ ID NO: 396 | TGFbR2-3x4GS-hCH1-hFc_Hole | IPPHVQKSVNNDMIVTDNNGAVKFPQLCKFCDVRFSTCDNQKSCMS NCSITSICEKPQEVCVAVWRKNDENITLETVCHDPKLPYHDFILEDA ASPKCIMKEKKKPGETFFMCSCSSDECNDNIIFSEEYNTSNPDGGGG SGGGGSGGGGSASTKGPSVFPLAPSSKSTSGGTAALGCLVKDYFPEP VTVSWNSGALTSGVHTFPAVLQSSGLYSLSSVVTVPSSSLGTQTYIC NVNHKPSNTKVDKRVEPKSCDKTHTCPPCPAPELLGGPSVFLFPPKP KDTLMISRTPEVTCVVVDVSHEDPEVKFNWYVDGVEVHNAKTKPR |

TABLE 12-continued

Exemplary amino acid sequences of TGF-beta polypeptides or
TGF-beta receptor polypeptides

| SEQ ID NO | Description | Amino acid sequence |
|---|---|---|
| | | EEQYNSTYRVVSVLTVLHQDWLNGKEYKCKVSNKALPAPIEKTISK<br>AKGQPREPQVCTLPPSREEMTKNQVSLSCAVKGFYPSDIAVEWESN<br>GQPENNYKTTPPVLDSDGSFFLVSKLTVDKSRWQQGNVFSCSVMH<br>EALHNHYTQKSLSLSPGX, wherein X is K or absent |
| SEQ ID NO: 397 | TGFbR2-<br>3x4GS-<br>hCH1-<br>hFc_Knob | IPPHVQKSVNNDMIVTDNNGAVKFPQLCKFCDVRFSTCDNQKSCMS<br>NCSITSICEKPQEVCVAVWRKNDENITLETVCHDPKLPYHDFILEDA<br>ASPKCIMKEKKKPGETFFMCSCSSDECNDNIIFSEEYNTSNPDGGGG<br>SGGGGSGGGGSASTKGPSVFPLAPSSKSTSGGTAALGCLVKDYFPEP<br>VTVSWNSGALTSGVHTFPAVLQSSGLYSLSSVVTVPSSSLGTQTYIC<br>NVNHKPSNTKVDKRVEPKSCDKTHTCPPCPAPELLGGPSVFLFPPKP<br>KDTLMISRTPEVTCVVVDVSHEDPEVKFNWYVDGVEVHNAKTKPR<br>EEQYNSTYRVVSVLTVLHQDWLNGKEYKCKVSNKALPAPIEKTISK<br>AKGQPREPQVYTLPPCREEMTKNQVSLWCLVKGFYPSDIAVEWES<br>NGQPENNYKTTPPVLDSDGSFFLYSKLTVDKSRWQQGNVFSCSVM<br>HEALHNHYTQKSLSLSPGX, wherein X is K or absent |
| SEQ ID NO: 398 | TGFbR2-<br>3x4GS-<br>hCLIg_vl | IPPHVQKSVNNDMIVTDNNGAVKFPQLCKFCDVRFSTCDNQKSCMS<br>NCSITSICEKPQEVCVAVWRKNDENITLETVCHDPKLPYHDFILEDA<br>ASPKCIMKEKKKPGETFFMCSCSSDECNDNIIFSEEYNTSNPDGGGG<br>SGGGGSGGGGSGQPKANPTVTLFPPSSEELQANKATLVCLISDFYPG<br>AVTVAWKADGSPVKAGVETTKPSKQSNNKYAASSYLSLTPEQWKS<br>HRSYSCQVTHEGSTVEKTVAPTECS |
| SEQ ID NO: 399 | TGFβR2-<br>3x4GS-<br>hCLIg_vk | IPPHVQKSVNNDMIVTDNNGAVKFPQLCKFCDVRFSTCDNQKSCMS<br>NCSITSICEKPQEVCVAVWRKNDENITLETVCHDPKLPYHDFILEDA<br>ASPKCIMKEKKKPGETFFMCSCSSDECNDNIIFSEEYNTSNPDGGGG<br>SGGGGSGGGGSRTVAAPSVFIFPPSDEQLKSGTASVVCLLNNFYPRE<br>AKVQWKVDNALQSGNSQESVTEQDSKDSTYSLSSTLTLSKADYEK<br>HKVYACEVTHQGLSSPVTKSFNRGEC |

Cytokine Molecules

Cytokines are generally polypeptides that influence cellular activity, for example, through signal transduction pathways. Accordingly, a cytokine of the multispecific or multifunctional polypeptide is useful and can be associated with receptor-mediated signaling that transmits a signal from outside the cell membrane to modulate a response within the cell. Cytokines are proteinaceous signaling compounds that are mediators of the immune response. They control many different cellular functions including proliferation, differentiation and cell survival/apoptosis; cytokines are also involved in several pathophysiological processes including viral infections and autoimmune diseases. Cytokines are synthesized under various stimuli by a variety of cells of both the innate (monocytes, macrophages, dendritic cells) and adaptive (T- and B-cells) immune systems. Cytokines can be classified into two groups: pro- and anti-inflammatory. Pro-inflammatory cytokines, including IFNγ, IL-1, IL-6 and TNF-alpha, are predominantly derived from the innate immune cells and Th1 cells. Anti-inflammatory cytokines, including IL-10, IL-4, IL-13 and IL-5, are synthesized from Th2 immune cells.

The present disclosure provides, inter alia, multispecific (e.g., bi-, tri-, quad-specific) or multifunctional molecules, that include, e.g., are engineered to contain, one or more cytokine molecules, e.g., immunomodulatory (e.g., proinflammatory) cytokines and variants, e.g., functional variants, thereof. Accordingly, in some embodiments, the cytokine molecule is an interleukin or a variant, e.g., a functional variant thereof. In some embodiments the interleukin is a proinflammatory interleukin. In some embodiments the interleukin is chosen from interleukin-2 (IL-2), interleukin-12 (IL-12), interleukin-15 (IL-15), interleukin-18 (IL-18), interleukin-21 (IL-21), interleukin-7 (IL-7), or interferon gamma. In some embodiments, the cytokine molecule is a proinflammatory cytokine.

In certain embodiments, the cytokine is a single chain cytokine. In certain embodiments, the cytokine is a multichain cytokine (e.g., the cytokine comprises 2 or more (e.g., 2) polypeptide chains. An exemplary multichain cytokine is IL-12.

Examples of useful cytokines include, but are not limited to, GM-CSF, IL-1α, IL-10, IL-2, IL-3, IL-4, IL-5, IL-6, IL-7, IL-8, IL-10, IL-12, IL-21, IFN-α, IFN-β, IFN-γ, MIP-1α, MIP-1β, TGF-β, TNF-α, and TNFβ. In one embodiment the cytokine of the multispecific or multifunctional polypeptide is a cytokine selected from the group of GM-CSF, IL-2, IL-7, IL-8, IL-10, IL-12, IL-15, IL-21, IFN-α, IFN-γ, MIP-1α, MIP-1β and TGF-β. In one embodiment the cytokine of the i the multispecific or multifunctional polypeptide is a cytokine selected from the group of IL-2, IL-7, IL-10, IL-12, IL-15, IFN-α, and IFN-γ. In certain embodiments the cytokine is mutated to remove N- and/or O-glycosylation sites. Elimination of glycosylation increases homogeneity of the product obtainable in recombinant production.

In one embodiment, the cytokine of the multispecific or multifunctional polypeptide is IL-2. In a specific embodiment, the IL-2 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity. In another particular embodiment the IL-2 cytokine is a mutant IL-2 cytokine having reduced binding affinity to the .alpha.-subunit of the IL-2 receptor. Together with the .beta.- and .gamma.-subunits (also known as CD122 and CD132, respectively), the .alpha.-subunit (also known as CD25) forms the heterotrimeric high-affinity IL-2 receptor, while the dimeric receptor consisting only of the β- and γ-subunits is termed the intermediate-affinity IL-2 receptor. As described in PCT patent application number PCT/EP2012/051991, which is incorporated herein by reference in its entirety, a mutant IL-2 polypeptide with reduced binding to the .alpha.-subunit of the IL-2 receptor has a reduced ability to induce IL-2 signaling in regulatory T cells, induces less activation-induced cell death (AICD) in T cells, and has a reduced toxicity profile in vivo, compared to a wild-type IL-2 polypeptide. The use of such an cytokine with reduced toxicity is particularly advantageous in a multispecific or multifunctional polypeptide according to the invention, having a long serum half-life due to the presence of an Fc domain. In one embodiment, the mutant IL-2 cytokine of the multispecific or multifunctional polypeptide according to the invention comprises at least one amino acid mutation that reduces or abolishes the affinity of the mutant IL-2 cytokine to the .alpha.-subunit of the IL-2 receptor (CD25) but preserves the affinity of the mutant IL-2 cytokine to the intermediate-affinity IL-2 receptor (consisting of the R and 7 subunits of the IL-2 receptor), compared to the non-mutated IL-2 cytokine. In one embodiment the one or more amino acid mutations are amino acid substitutions. In a specific embodiment, the mutant IL-2 cytokine comprises one, two or three amino acid substitutions at one, two or three position(s) selected from the positions corresponding to residue 42, 45, and 72 of human IL-2. In a more specific embodiment, the mutant IL-2 cytokine comprises three amino acid substitutions at the positions corresponding to residue 42, 45 and 72 of human IL-2. In an even more specific embodiment, the mutant IL-2 cytokine is human IL-2 comprising the amino acid substitutions F42A, Y45A and L72G. In one embodiment the mutant IL-2 cytokine additionally comprises an amino acid mutation at a position corresponding to position 3 of human IL-2, which eliminates the O-glycosylation site of IL-2. Particularly, said additional amino acid mutation is an amino acid substitution replacing a threonine residue by an alanine residue. A particular mutant IL-2 cytokine useful in the invention comprises four amino acid substitutions at positions corresponding to residues 3, 42, 45 and 72 of human IL-2. Specific amino acid substitutions are T3A, F42A, Y45A and L72G. As demonstrated in PCT patent application number PCT/EP2012/051991 and in the appended Examples, said quadruple mutant IL-2 polypeptide (IL-2 qm) exhibits no detectable binding to CD25, reduced ability to induce apoptosis in T cells, reduced ability to induce IL-2 signaling in T.sub.reg cells, and a reduced toxicity profile in vivo. However, it retains ability to activate IL-2 signaling in effector cells, to induce proliferation of effector cells, and to generate IFN-γ as a secondary cytokine by NK cells.

The IL-2 or mutant IL-2 cytokine according to any of the above embodiments may comprise additional mutations that provide further advantages such as increased expression or stability. For example, the cysteine at position 125 may be replaced with a neutral amino acid such as alanine, to avoid the formation of disulfide-bridged IL-2 dimers. Thus, in certain embodiments the IL-2 or mutant IL-2 cytokine of the multispecific or multifunctional polypeptide according to the invention comprises an additional amino acid mutation at a position corresponding to residue 125 of human IL-2. In one embodiment said additional amino acid mutation is the amino acid substitution C125A.

In a specific embodiment the IL-2 cytokine of the multi-specific or multifunctional polypeptide comprises the polypeptide sequence of SEQ ID NO: 227 [APTSSSTKKTQLQLEHLLLDLQMILNGINN YKNPKLTRMLTFKFYMPK-KATELKHLQCLEEELKPLEEVLNLAQSKNFHL RPRDLISNINVIVLELKGSETTFMCEYADETATIVE-FLNRWITFAQSIISTLT]. In another specific embodiment the IL-2 cytokine of the multispecific or multifunctional polypeptide comprises the polypeptide sequence of SEQ ID NO: 228 [APASSSTKKTQLQLEHLLLD LQMILNGIN-NYKNPKLTRMLTAKFAMPKKATELKHLQCLE EELKPLEEVLNGAQSKNFHLRPRDLISNIN VIVLELKGSETTFMCEYADETATIVEFLNRWITFAQSI-ISTLT].

In another embodiment the cytokine of the multispecific or multifunctional polypeptide is IL-12. In a specific embodiment said IL-12 cytokine is a single chain IL-12 cytokine. In an even more specific embodiment the single chain IL-12 cytokine comprises the polypeptide sequence of SEQ ID NO: 229

[IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQK

EPKNKTFLRCEAKNYSGRFTCWWLTTISTDLTFSVKSSRGSSDPQGVTCG

AATLSAERVRGDNKEYEYSVECQEDSACPAAEESLPIEVMVDAVHKLKYE

NYTSSFFIRDIIKPDPPKNLQLKPLKNSRQVEVSWEYPDTWSTPHSYFSL

TFCVQVQGKSKREKKDRVFTDKTSATVICRKNASISVRAQDRYYSSSWSE

WASVPCSGGGGSGGGGSGGGGSRNLPVATPDPGMFPCLHHSQNLLRAVSN

MLQKARQTLEFYPCTSEEIDHEDITKDKTSTVEACLPLELTKNESCLNSR

ETSFITNGSCLASRKTSFMMALCLSSIYEDLKMYQVEFKTMNAKLLMDPK

RQIFLDQNMLAVIDELMQALNFNSETVPQKSSLEEPDFYKTKIKLCILLH

AFRIRAVTIDRVMSYLNAS].

In one embodiment, the IL-12 cytokine can elicit one or more of the cellular responses selected from the group consisting of: proliferation in a NK cell, differentiation in a NK cell, proliferation in a T cell, and differentiation in a T cell.

In another embodiment the cytokine of the multispecific or multifunctional polypeptide is IL-10. In a specific embodiment said IL-10 cytokine is a single chain IL-10 cytokine. In an even more specific embodiment the single chain IL-10 cytokine comprises the polypeptide sequence of SEQ ID NO: 230

[SPGQGTQSENSCTHFPGNLPNMLRDLRDAFSRVKTFFQMKDQLDNLLLK

ESLLEDFKGYLGCQALSEMIQFYLEEVMPQAENQDPDIKAHVNSLGENLK

TLRLRLRRCHRFLPCENKSKAVEQVKNAFNKLQEKGIYKAMSEFDIFINY

IEAYMTMKIRNGGGGSGGGGSGGGGSGGGGSSPGQGTQSENSCTHFPGNL

PNMLRDLRDAFSRVKTFFQMKDQLDNLLLKESLLEDFKGYLGCQALSEMI

QFYLEEVMPQAENQDPDIKAHVNSLGENLKTLRLRLRRCHRFLPCENKSK

AVEQVKNAFNKLQEKGIYKAMSEFDIFINYIEAYMTMKIRN].

In another specific embodiment the IL-10 cytokine is a monomeric IL-10 cytokine. In a more specific embodiment the monomeric IL-10 cytokine comprises the polypeptide sequence of SEQ ID NO: 231 [SPGQGTQSEN-SCTHFPGNLPNMLRDLRDAFSRVKTFFQMKDQLDNLLL5-KESLLEDFKG YLGCQALSEMIQFYLEEVMPQAE-NQDPDIKAHVNSLGENLKTLRLRLRRCHRFLPCENG GGSGGKSKAVEQVKNAFNKLQEKGIYKAMSEFDI-FINYIEAYMTMKIRN]. In one embodiment, the IL-10 cytokine can elicit one or more of the cellular responses selected from the group consisting of: inhibition of cytokine secretion, inhibition of antigen presentation by antigen presenting cells, reduction of oxygen radical release, and inhibition of T cell proliferation. A multispecific or multifunctional polypeptide according to the invention wherein the cytokine is IL-10 is particularly useful for downregulation of inflammation, e.g. in the treatment of an inflammatory disorder.

In another embodiment, the cytokine of the multispecific or multifunctional polypeptide is IL-15. In a specific embodiment said IL-15 cytokine is a mutant IL-15 cytokine having reduced binding affinity to the α-subunit of the IL-15 receptor. Without wishing to be bound by theory, a mutant IL-15 polypeptide with reduced binding to the .alpha.-subunit of the IL-15 receptor has a reduced ability to bind to fibroblasts throughout the body, resulting in improved pharmacokinetics and toxicity profile, compared to a wild-type IL-15 polypeptide. The use of an cytokine with reduced toxicity, such as the described mutant IL-2 and mutant IL-15 effector moieties, is particularly advantageous in a multispecific or multifunctional polypeptide according to the invention, having a long serum half-life due to the presence of an Fc domain. In one embodiment the mutant IL-15 cytokine of the multispecific or multifunctional polypeptide according to the invention comprises at least one amino acid mutation that reduces or abolishes the affinity of the mutant IL-15 cytokine to the .alpha.-subunit of the IL-15 receptor but preserves the affinity of the mutant IL-15 cytokine to the intermediate-affinity IL-15/IL-2 receptor (consisting of the .beta.- and .gamma.-subunits of the IL-15/IL-2 receptor), compared to the non-mutated IL-15 cytokine. In one embodiment the amino acid mutation is an amino acid substitution. In a specific embodiment, the mutant IL-15 cytokine comprises an amino acid substitution at the position corresponding to residue 53 of human IL-15. In a more specific embodiment, the mutant IL-15 cytokine is human IL-15 comprising the amino acid substitution E53A. In one embodiment the mutant IL-15 cytokine additionally comprises an amino acid mutation at a position corresponding to position 79 of human IL-15, which eliminates the N-glycosylation site of IL-15. Particularly, said additional amino acid mutation is an amino acid substitution replacing an asparagine residue by an alanine residue. In an even more specific embodiment the IL-15 cytokine comprises the polypeptide sequence of SEQ ID NO: 232 [NWVNVISDLK-KIEDLIQSMHIDATLYTESDVHPSCKVTAMKCFL-LELQVISLASGDASIH DTVENLIILANNSLSSNGAVTESGCKECEELEEKNI-KEFLQSFVHIVQMFINTS]. In one embodiment, the IL-15 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) anti-tumor cytotoxicity.

Mutant cytokine molecules useful as effector moieties in the multispecific or multifunctional polypeptide can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. Substitution or insertion may involve natural as well as non-natural amino acid residues. Amino acid modification includes well known methods of chemical modification such as the addition or removal of glycosylation sites or carbohydrate attachments, and the like.

In one embodiment, the cytokine, particularly a single-chain cytokine, of the multispecific or multifunctional polypeptide is GM-CSF. In a specific embodiment, the GM-CSF cytokine can elicit proliferation and/or differentiation in a granulocyte, a monocyte or a dendritic cell. In one embodiment, the cytokine, particularly a single-chain cytokine, of the multispecific or multifunctional polypeptide is IFN-α. In a specific embodiment, the IFN-α cytokine can elicit one or more of the cellular responses selected from the group consisting of: inhibiting viral replication in a virus-infected cell, and upregulating the expression of major histocompatibility complex I (MHC I). In another specific embodiment, the IFN-α cytokine can inhibit proliferation in a tumor cell. In one embodiment the cytokine, particularly a single-chain cytokine, of the multispecific or multifunctional polypeptide is IFNγ. In a specific embodiment, the IFN-γ cytokine can elicit one or more of the cellular responses selected from the group of: increased macrophage activity, increased expression of MHC molecules, and increased NK cell activity. In one embodiment the cytokine, particularly a single-chain cytokine, of the multispecific or multifunctional polypeptide is IL-7. In a specific embodiment, the IL-7 cytokine can elicit proliferation of T and/or B lymphocytes. In one embodiment, the cytokine, particularly a single-chain cytokine, of the multispecific or multifunctional polypeptide is IL-8. In a specific embodiment, the IL-8 cytokine can elicit chemotaxis in neutrophils. In one embodiment, the cytokine, particularly a single-chain cytokine, of the multispecific or multifunctional polypeptide, is MIP-1α. In a specific embodiment, the MIP-1α cytokine can elicit chemotaxis in monocytes and T lymphocyte cells. In one embodiment, the cytokine, particularly a single-chain cytokine, of the multispecific or multifunctional polypeptide is MIP-1β. In a specific embodiment, the MIP-1β cytokine can elicit chemotaxis in monocytes and T lymphocyte cells. In one embodiment, the cytokine, particularly a single-chain cytokine, of the multispecific or multifunctional polypeptide is TGF-β. In a specific embodiment, the TGF-β cytokine can elicit one or more of the cellular responses selected from the group consisting of: chemotaxis in monocytes, chemotaxis in macrophages, upregulation of IL-1 expression in activated macrophages, and upregulation of IgA expression in activated B cells.

In one embodiment, the multispecific or multifunctional polypeptide of the invention binds to an cytokine receptor with a dissociation constant ($K_D$) that is at least about 1, 1.5, 2, 2.5, 3, 3.5, 4, 4.5, 5, 5.5, 6, 6.5, 7, 7.5, 8, 8.5, 9, 9.5 or 10 times greater than that for a control cytokine. In another embodiment, the multispecific or multifunctional polypeptide binds to an cytokine receptor with a $K_D$ that is at least 2, 3, 4, 5, 6, 7, 8, 9, or 10 times greater than that for a corresponding multispecific or multifunctional polypeptide comprising two or more effector moieties. In another embodiment, the multispecific or multifunctional polypeptide binds to an cytokine receptor with a dissociation constant $K_D$ that is about 10 times greater than that for a corresponding the multispecific or multifunctional polypeptide comprising two or more cytokines.

In some embodiments, the multispecific molecules disclosed herein include a cytokine molecule. In embodiments, the cytokine molecule includes a full length, a fragment or a variant of a cytokine; a cytokine receptor domain, e.g., a cytokine receptor dimerizing domain; or an agonist of a cytokine receptor, e.g., an antibody molecule (e.g., an agonistic antibody) to a cytokine receptor.

In some embodiments the cytokine molecule is chosen from IL-2, IL-12, IL-15, IL-18, IL-7, IL-21, or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain.

In other embodiments, the cytokine molecule is an agonist of a cytokine receptor, e.g., an antibody molecule (e.g., an agonistic antibody) to a cytokine receptor chosen from an IL-15Ra or IL-21R.

In one embodiment, the cytokine molecule is IL-15, e.g., human IL-15 (e.g., comprising the amino acid sequence: NWVNVISDLKKIEDLIQSMHIDATLYTESDVHP- SCKVTAMKCFLLELQVISLESGDASIH DTVEN- LIILANNSLSSNGNVTESGCKECEELEEKNIKE- FLQSFVHIVQMFINTS (SEQ ID NO: 17), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 17.

In some embodiments, the cytokine molecule comprises a receptor dimerizing domain, e.g., an IL15Ralpha dimerizing domain. In one embodiment, the IL15Ralpha dimerizing domain comprises the amino acid sequence: MAPR- RARGCRTLGLPALLLLLLRPPATRGITCPPPMSVE- HADIWVKSYSLYSRERYICN SGFKRKAGTSSLTECVL (SEQ ID NO: 18), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 18. In some embodiments, the cytokine molecule (e.g., IL-15) and the receptor dimerizing domain (e.g., an IL15Ralpha dimerizing domain) of the multispecific molecule are covalently linked, e.g., via a linker (e.g., a Gly-Ser linker, e.g., a linker comprising the amino acid sequence SGGSGGGGSGGGSGGGGSLQ (SEQ ID NO: 19). In other embodiments, the cytokine molecule (e.g., IL-15) and the receptor dimerizing domain (e.g., an IL15Ralpha dimerizing domain) of the multispecific molecule are not covalently linked, e.g., are non-covalently associated.

In other embodiments, the cytokine molecule is IL-2, e.g., human IL-2 (e.g., comprising the amino acid sequence: APTSSSTKKTQLQLEHLLLDLQMILNGINNYKNPKL- TRMLTFKFYMPKKATELKHLQCL EEELKPLEEVLN- LAQSKNFHLRPRDLISNINVIVLELKGSETTFMCEYA- DETATIVEFLNR WITFCQSIISTLT (SEQ ID NO: 20), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO:20).

In other embodiments, the cytokine molecule is IL-18, e.g., human IL-18 (e.g., comprising the amino acid sequence: YFGKLESKL SVIRNLNDQVLFIDQGNR- PLFEDMTDSDCRDNAPRTIFIISMYKDSQPRGM AVTISVKCEKISTLSCENKIISFKEMNPPDNIKDTKS- DIIFFQRSVPGHDNKMQFESSSY EGYFLACEKER- DLFKLILKKEDELGDRSIMFTVQNED (SEQ ID NO: 21), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 21).

In other embodiments, the cytokine molecule is IL-21, e.g., human IL-21 (e.g., comprising the amino acid sequence: QGQDRHMIRMRQLIDI- VDQLKNYVNDLVPEFLPAPEDVETNCEWS- AFSCFQKAQLKSA NTGNNERIINVSIKKLKRKPPST- NAGRRQKHRLTCPSCDSYEKKPPKEFLERFKSLLQK MI HQHLSSRTHGSEDS (SEQ ID NO: 22), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 22).

In yet other embodiments, the cytokine molecule is interferon gamma, e.g., human interferon gamma (e.g., comprising the amino acid sequence: QDPYVKEAE- NLKKYFNAGHSDVADNGTLFLGILKNWKEESDRKI MQSQIVSFYFKLFK NFKDDQSIQKSVE- TIKEDMNVKFFNSNKKKRDDFEKLT- NYSVTDLNVQRKAIHELIQVM AELSPAAKTGKRKR- SQMLFRG (SEQ ID NO: 23), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 23).

Immune Cell Engagers

The immune cell engagers of the multispecific or multifunctional molecules disclosed herein can mediate binding to, and/or activation of, an immune cell, e.g., an immune effector cell. In some embodiments, the immune cell is chosen from a T cell, an NK cell, a B cell, a dendritic cell, or a macrophage cell engager, or a combination thereof. In some embodiments, the immune cell engager is chosen from one, two, three, or all of a T cell engager, NK cell engager, a B cell engager, a dendritic cell engager, or a macrophage cell engager, or a combination thereof. The immune cell engager can be an agonist of the immune system. In some embodiments, the immune cell engager can be an antibody molecule, a ligand molecule (e.g., a ligand that further comprises an immunoglobulin constant region, e.g., an Fc region), a small molecule, a nucleotide molecule.

Natural Killer Cell Engagers

Natural Killer (NK) cells recognize and destroy tumors and virus-infected cells in an antibody-independent manner. The regulation of NK cells is mediated by activating and inhibiting receptors on the NK cell surface. One family of activating receptors is the natural cytotoxicity receptors (NCRs) which include NKp30, NKp44 and NKp46. The NCRs initiate tumor targeting by recognition of heparan sulfate on cancer cells. NKG2D is a receptor that provides both stimulatory and costimulatory innate immune responses on activated killer (NK) cells, leading to cytotoxic activity. DNAM1 is a receptor involved in intercellular adhesion, lymphocyte signaling, cytotoxicity and lymphokine secretion mediated by cytotoxic T-lymphocyte (CTL) and NK cell. DAP10 (also known as HCST) is a transmembrane adapter protein which associates with KLRK1 to form an activation receptor KLRK1-HCST in lymphoid and myeloid cells; this receptor plays a major role in triggering cytotoxicity against target cells expressing cell surface ligands such as MHC class I chain-related MICA and MICB, and U (optionally L1)6-binding proteins (ULBPs); it KLRK1-HCST receptor plays a role in immune surveillance against tumors and is required for cytolysis of tumors cells; indeed, melanoma cells that do not express KLRK1 ligands escape from immune surveillance mediated by NK cells. CD16 is a receptor for the Fc region of IgG, which binds complexed or aggregated IgG and also monomeric IgG and thereby mediates antibody-dependent cellular cytotoxicity (ADCC) and other antibody-dependent responses, such as phagocytosis.

In some embodiments, the NK cell engager is a viral hemagglutinin (HA), HA is a glycoprotein found on the surface of influenza viruses. It is responsible for binding the virus to cells with sialic acid on the membranes, such as cells in the upper respiratory tract or erythrocytes. HA has at least 18 different antigens. These subtypes are named H1 through H18. NCRs can recognize viral proteins. NKp46 has been shown to be able to interact with the HA of influenza and the HA-NA of Paramyxovirus, including Sendai virus and Newcastle disease virus. Besides NKp46, NKp44 can also functionally interact with HA of different influenza subtypes.

The present disclosure provides, inter alia, multispecific (e.g., bi-, tri-, quad-specific) or multifunctional molecules, that are engineered to contain one or more NK cell engagers that mediate binding to and/or activation of an NK cell. Accordingly, in some embodiments, the NK cell engager is selected from an antigen binding domain or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80, CD244 (also known as SLAMF4 or 2B4), SLAMF6, SLAMF7, KIR2DS2, KIR2DS4, KIR3DS1, KIR2DS3, KIR2DS5, KIR2DS1, CD94, NKG2C, NKG2E, or CD160.

In one embodiment, the NK cell engager is a ligand of NKp30 is a B7-6, e.g., comprises the amino acid sequence of:

```
                                      (SEQ ID NO: 24)
DLKVEMMAGGTQITPLNDNVTIFCNIFYSQPLNITSMGITWFWKSLTFDK

EVKVFEFFGDHQEAFRPGAIVSPWRLKSGDASLRLPGIQLEEAGEYRCEV

VVTPLKAQGTVQLEVVASPASRLLLDQVGMKENEDKYMCESSGFYPEAIN

ITWEKQTQKFPHPIEISEDVITGPTIKNMDGTFNVTSCLKLNSSQEDPGT

VYQCVVRHASLHTPLRSNFTLTAARHSLSETEKTDNFS,
``` a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 24.

In other embodiments, the NK cell engager is a ligand of NKp44 or NKp46, which is a viral HA. Viral hemagglutinins (HA) are glyco proteins which are on the surface of viruses. HA proteins allow viruses to bind to the membrane of cells via sialic acid sugar moieties which contributes to the fusion of viral membranes with the cell membranes (see e.g., Eur J Immunol. 2001 September; 31(9):2680-9 "Recognition of viral hemagglutinins by NKp44 but not by NKp30"; and Nature. 2001 Feb. 22; 409(6823):1055-60 "Recognition of haemagglutinins on virus-infected cells by NKp46 activates lysis by human NK cells" the contents of each of which are incorporated by reference herein).

In other embodiments, the NK cell engager is a ligand of NKG2D chosen from MICA, MICB, or ULBP1, e.g., wherein:

(i) MICA comprises the amino acid sequence:

```
                                      (SEQ ID NO: 25)
EPHSLRYNLTVLSWDGSVQSGFLTEVHLDGQPFLRCDRQKCRAKPQGQWA

EDVLGNKTWDRETRDLTGNGKDLRMTLAHIKDQKEGLHSLQEIRVCEIHE

DNSTRSSQHFYYDGELFLSQNLETKEWTMPQSSRAQTLAMNVRNFLKEDA

MKTKTHYHAMHADCLQELRRYLKSGVVLRRTVPPMVNVTRSEASEGNITV

TCRASGFYPWNITLSWRQDGVSLSHDTQQWGDVLPDGNGTYQTWVATRIC

QGEEQRFTCYMEHSGNHSTHPVPSGKVLVLQSHW,
``` a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 25;

(ii) MICB comprises the amino acid sequence:

```
                                      (SEQ ID NO: 26)
AEPHSLRYNLMVLSQDESVQSGFLAEGHLDGQPFLRYDRQKRRAKPQGQW

AEDVLGAKTWDTETEDLTENGQDLRRTLTHIKDQKGGLHSLQEIRVCEIH

EDSSTRGSRHFYYDGELFLSQNLETQESTVPQSSRAQTLAMNVTNFWKED

AMKTKTHYRAMQADCLQKLQRYLKSGVAIRRTVPPMVNVTCSEVSEGNIT

VTCRASSFYPRNITLTWRQDGVSLSHNTQQWGDVLPDGNGTYQTWVATRI

RQGEEQRFTCYMEHSGNHGTHPVPSGKVLVLQSQRTD,
``` a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 26; or (iii) ULBP1 comprises the amino acid sequence:

```
                                      (SEQ ID NO: 27)
GWVDTHCLCYDFIITPKSRPEPQWCEVQGLVDERPFLHYDCVNHKAKAFA

SLGKKVNVTKTWEEQTETLRDVVDFLKGQLLDIQVENLIPIEPLTLQARM

SCEHEAHGHGRGSWQFLFNGQKFLLFDSNNRKWTALHPGAKKMTEKWEKN

RDVTMFFQKISLGDCKMWLEEFLMYWEQMLDPTKPPSLAPG,
``` a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 27.

In other embodiments, the NK cell engager is a ligand of DNAM1 chosen from NECTIN2 or NECL5, e.g., wherein:

(i) NECTIN2 comprises the amino acid sequence:

(SEQ ID NO: 28)
QDVRVQVLPEVRGQLGGTVELPCHLLPPVPGLYISLVTWQRPDAPANHQN

VAAFHPKMGPSFPSPKPGSERLSFVSAKQSTGQDTEAELQDATLALHGLT

VEDEGNYTCEFATFPKGSVRGMTWLRVIAKPKNQAEAQKVTFSQDPTTVA

LCISKEGRPPARISWLSSLDWEAKETQVSGTLAGTVTVTSRFTLVPSGRA

DGVTVTCKVEHESFEEPALIPVTLSVRYPPEVSISGYDDNWYLGRTDATL

SCDVRSNPEPTGYDWSTTSGTFPTSAVAQGSQLVIHAVDSLFNTTFVCTV

TNAVGMGRAEQVIFVRETPNTAGAGATGG, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 28; or (ii) NECL5 comprises the amino acid sequence:

(SEQ ID NO: 29)
WPPPGTGDVVVQAPTQVPGFLGDSVTLPCYLQVPNMEVTHVSQLTWARHG

ESGSMAVFHQTQGPSYSESKRLEFVAARLGAELRNASLRMFGLRVEDEGN

YTCLFVTFPQGSRSVDIWLRVLAKPQNTAEVQKVQLTGEPVPMARCVSTG

GRPPAQITWHSDLGGMPNTSQVPGFLSGTVTVTSLWILVPSSQVDGKNVT

CKVEHESFEKPQLLTVNLTVYYPPEVSISGYDNNWYLGQNEATLTCDARS

NPEPTGYNWSTTMGPLPPFAVAQGAQLLIRPVDKPINTTLICNVTNALGA

RQAELTVQVKEGPPSEHSGISRN, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 29.

In yet other embodiments, the NK cell engager is a ligand of DAP10, which is an adapter for NKG2D (see e.g., Proc Natl Acad Sci USA. 2005 May 24; 102(21): 7641-7646; and Blood, 15 Sep. 2011 Volume 118, Number 11, the full contents of each of which is incorporated by reference herein).

In other embodiments, the NK cell engager is a ligand of CD16, which is a CD16a/b ligand, e.g., a CD16a/b ligand further comprising an antibody Fc region (see e.g., Front Immunol. 2013; 4: 76 discusses how antibodies use the Fc to trigger NK cells through CD16,the full contents of which are incorporated herein).

In other embodiments, the NK cell engager is a ligand of CRTAM, which is NECL2, e.g., wherein NECL2 comprises the amino acid sequence:

(SEQ ID NO: 30)
QNLFTKDVTVIEGEVATISCQVNKSDDSVIQLLNPNRQTIYFRDFRPLKD

SRFQLLNFSSSELKVSLTNVSISDEGRYFCQLYTDPPQESYTTITVLVPP

RNLMIDIQKDTAVEGEEIEVNCTAMASKPATTIRWFKGNTELKGKSEVEE

WSDMYTVTSQLMLKVHKEDDGVPVICQVEHPAVTGNLQTQRYLEVQYKPQ

VHIQMTYPLQGLTREGDALELTCEAIGKPQPVMVTWVRVDDEMPQHAVLS

GPNLFINNLNKTDNGTYRCEASNIVGKAHSDYMLYVYDPPTTIPPPTTTT

TTTTTTTTILTIITDSRAGEEGSIRAVDH, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 30.

In other embodiments, the NK cell engager is a ligand of CD27, which is CD70, e.g., wherein CD70 comprises the amino acid sequence:

(SEQ ID NO: 31)
QRFAQAQQQLPLESLGWDVAELQLNHTGPQQDPRLYWQGGPALGRSFLHG

PELDKGQLRIHRDGIYMVHIQVTLAICSSTTASRHHPTTLAVGICSPASR

SISLLRLSFHQGCTIASQRLTPLARGDTLCTNLTGTLLPSRNTDETFFGV

QWVRP, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 31.

In other embodiments, the NK cell engager is a ligand of PSGL1, which is L-selectin (CD62L), e.g., wherein L-selectin comprises the amino acid sequence:

(SEQ ID NO: 32)
WTYHYSEKPMNWQRARRFCRDNYTDLVAIQNKAEIEYLEKTLPFSRSYYW

IGIRKIGGIWTWVGTNKSLTEEAENWGDGEPNNKKNKEDCVEIYIKRNKD

AGKWNDDACHKLKAALCYTASCQPWSCSGHGECVEIINNYTCNCDVGYYG

PQCQFVIQCEPLEAPELGTMDCTHPLGNFSFSSQCAFSCSEGTNLTGIEE

TTCGPFGNWSSPEPTCQVIQCEPLSAPDLGIMNCSHPLASFSFTSACTFI

CSEGTELIGKKKTICESSGIWSNPSPICQKLDKSFSMIKEGDYN, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 32.

In other embodiments, the NK cell engager is a ligand of CD96, which is NECL5, e.g., wherein NECL5 comprises the amino acid sequence:

(SEQ ID NO: 29)
WPPPGTGDVVVQAPTQVPGFLGDSVTLPCYLQVPNMEVTHVSQLTWARHG

ESGSMAVFHQTQGPSYSESKRLEFVAARLGAELRNASLRMFGLRVEDEGN

YTCLFVTFPQGSRSVDIWLRVLAKPQNTAEVQKVQLTGEPVPMARCVSTG

GRPPAQITWHSDLGGMPNTSQVPGFLSGTVTVTSLWILVPSSQVDGKNVT

CKVEHESFEKPQLLTVNLTVYYPPEVSISGYDNNWYLGQNEATLTCDARS

NPEPTGYNWSTTMGPLPPFAVAQGAQLLIRPVDKPINTTLICNVTNALGA

RQAELTVQVKEGPPSEHSGISRN, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 30.

In other embodiments, the NK cell engager is a ligand of CD100 (SEMA4D), which is CD72, e.g., wherein CD72 comprises the amino acid sequence:

(SEQ ID NO: 33)
RYLQVSQQLQQTNRVLEVINSSLRQQLRLKITQLGQSAEDLQGSRRELAQ

SQEALQVEQRAHQAAEGQLQACQADRQKTKETLQSEEQQRRALEQKLSNM

ENRLKPFFTCGSADTCCPSGWIMHQKSCFYISLTSKNWQESQKQCETLSS

KLATFSEIYPQSHSYYFLNSLLPNGGSGNSYWTGLSSNKDWKLTDDTQRT

RTYAQSSKCNKVHKTWSWWTLESESCRSSLPYICEMTAFRFPD, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 33.

In other embodiments, the NK cell engager is a ligand of NKp80, which is CLEC2B (AICL), e.g., wherein CLEC2B (AICL) comprises the amino acid sequence:

(SEQ ID NO: 34)
KLTRDSQSLCPYDWIGFQNKCYYFSKEEGDWNSSKYNCSTQHADLTIIDN

IEEMNFLRRYKCSSDHWIGLKMAKNRTGQWVDGATFTKSFGMRGSEGCAY

LSDDGAATARCYTERKWICRKRIH, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 34.

In other embodiments, the NK cell engager is a ligand of CD244, which is CD48, e.g., wherein CD48 comprises the amino acid sequence:

(SEQ ID NO: 35)
QGHLVHMTVVSGSNVTLNISESLPENYKQLTWFYTFDQKIVEWDSRKSKY

FESKFKGRVRLDPQSGALYISKVQKEDNSTYIMRVLKKTGNEQEWKIKLQ

VLDPVPKPVIKIEKIEDMDDNCYLKLSCVIPGESVNYTWYGDKRPFPKEL

QNSVLETTLMPHNYSRCYTCQVSNSVSSKNGTVCLSPPCTLARS, a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 35.

T Cell Engagers

The present disclosure provides, inter alia, multispecific (e.g., bi-, tri-, quad-specific) or multifunctional molecules, that are engineered to contain one or more T cell engager that mediate binding to and/or activation of a T cell. Accordingly, in some embodiments, the T cell engager is selected from an antigen binding domain or ligand that binds to (e.g., and in some embodiments activates) one or more of CD3, TCRα, TCRβ, TCRγ, TCRζ, ICOS, CD28, CD27, HVEM, LIGHT, CD40, 4-1BB, OX40, DR3, GITR, CD30, TIM1, SLAM, CD2, or CD226. In other embodiments, the T cell engager is selected from an antigen binding domain or ligand that binds to and does not activate one or more of CD3, TCRα, TCRβ, TCRγ, TCRζ, ICOS, CD28, CD27, HVEM, LIGHT, CD40, 4-1BB, OX40, DR3, GITR, CD30, TIM1, SLAM, CD2, or CD226. In some embodiments, the T cell engager binds to CD3.

B Cell, Macrophage & Dendritic Cell Engagers

Broadly, B cells, also known as B lymphocytes, are a type of white blood cell of the lymphocyte subtype. They function in the humoral immunity component of the adaptive immune system by secreting antibodies. Additionally, B cells present antigen (they are also classified as professional antigen-presenting cells (APCs)) and secrete cytokines. Macrophages are a type of white blood cell that engulfs and digests cellular debris, foreign substances, microbes, cancer cells via phagocytosis. Besides phagocytosis, they play important roles in nonspecific defense (innate immunity) and also help initiate specific defense mechanisms (adaptive immunity) by recruiting other immune cells such as lymphocytes. For example, they are important as antigen presenters to T cells. Beyond increasing inflammation and stimulating the immune system, macrophages also play an important anti-inflammatory role and can decrease immune reactions through the release of cytokines. Dendritic cells (DCs) are antigen-presenting cells that function in processing antigen material and present it on the cell surface to the T cells of the immune system.

The present disclosure provides, inter alia, multispecific (e.g., bi-, tri-, quad-specific) or multifunctional molecules, that include, e.g., are engineered to contain, one or more B cell, macrophage, and/or dendritic cell engager that mediate binding to and/or activation of a B cell, macrophage, and/or dendritic cell.

Accordingly, in some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); an agonist of a Toll-like receptor (e.g., as described herein, e.g., a TLR4, e.g., a constitutively active TLR4 (caTLR4), or a TLR9 agonists); a 41BB; a CD2; a CD47; or a STING agonist, or a combination thereof.

In some embodiments, the B cell engager is a CD40L, an OX40L, or a CD70 ligand, or an antibody molecule that binds to OX40, CD40 or CD70.

In some embodiments, the macrophage engager is a CD2 agonist. In some embodiments, the macrophage engager is an antigen binding domain that binds to: CD40L or antigen binding domain or ligand that binds CD40, a Toll like receptor (TLR) agonist (e.g., as described herein), e.g., a TLR9 or TLR4 (e.g., caTLR4 (constitutively active TLR4), CD47, or a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In some embodiments, the dendritic cell engager is a CD2 agonist. In some embodiments, the dendritic cell engager is a ligand, a receptor agonist, or an antibody molecule that binds to one or more of: OX40L, 41BB, a TLR agonist (e.g., as described herein) (e.g., TLR9 agonist, TLR4 (e.g., caTLR4 (constitutively active TLR4)), CD47, or and a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In other embodiments, the immune cell engager mediates binding to, or activation of, one or more of a B cell, a macrophage, and/or a dendritic cell. Exemplary B cell, macrophage, and/or dendritic cell engagers can be chosen from one or more of CD40 ligand (CD40L) or a CD70 ligand; an antibody molecule that binds to CD40 or CD70; an antibody molecule to OX40; an OX40 ligand (OX40L); a Toll-like receptor agonist (e.g., a TLR4, e.g., a constitutively active TLR4 (caTLR4) or a TLR9 agonist); a 41BB agonist; a CD2; a CD47; or a STING agonist, or a combination thereof.

In some embodiments, the B cell engager is chosen from one or more of a CD40L, an OX40L, or a CD70 ligand, or an antibody molecule that binds to OX40, CD40 or CD70.

In other embodiments, the macrophage cell engager is chosen from one or more of a CD2 agonist; a CD40L; an OX40L; an antibody molecule that binds to OX40, CD40 or CD70; a Toll-like receptor agonist or a fragment thereof (e.g., a TLR4, e.g., a constitutively active TLR4 (caTLR4)); a CD47 agonist; or a STING agonist.

In other embodiments, the dendritic cell engager is chosen from one or more of a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist.

In one embodiment, the OX40L comprises the amino acid sequence:

```
                                        (SEQ ID NO: 36)
QVSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKVY

LNVTTDNTSLDDFHVNGGELILIHQNPGEFCVL,
``` a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 36.

In another embodiment, the CD40L comprises the amino acid sequence:

```
                                        (SEQ ID NO: 37)
MQKGDQNPQIAAHVISEASSKTTSVLQWAEKGYYTMSNNLVTLENGKQLT

VKRQGLYYIYAQVTFCSNREASSQAPFIASLCLKSPGRFERILLRAANTH

SSAKPCGQQSIHLGGVFELQPGASVFVNVTDPSQVSHGTGFTSFGLLKL,
``` a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 37.

In yet other embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages.

In one embodiment, the immune cell engager includes 41BB ligand, e.g., comprising the amino acid sequence:

```
                                        (SEQ ID NO: 38)
ACPWAVSGARASPGSAASPRLREGPELSPDDPAGLLDLRQGMFAQLVAQN

VLLIDGPLSWYSDPGLAGVSLTGGLSYKEDTKELVVAKAGVYYVFFQLEL

RRVVAGEGSGSVSLALHLQPLRSAAGAAALALTVDLPPASSEARNSAFGF

QGRLLHLSAGQRLGVHLHTEARARHAWQLTQGATVLGLFRVTPEIPAGLP

SPRSE,
``` a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 38.

Toll-Like Receptors

Toll-Like Receptors (TLRs) are evolutionarily conserved receptors are homologues of the Drosophila Toll protein, and recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. PAMPs include various bacterial cell wall components such as lipopolysaccharide (LPS), peptidoglycan (PGN) and lipopeptides, as well as flagellin, bacterial DNA and viral double-stranded RNA. DAMPs include intracellular proteins such as heat shock proteins as well as protein fragments from the extracellular matrix. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses, including the production of interferons (IFNs), pro-inflammatory cytokines and effector cytokines that direct the adaptive immune response. TLRs are implicated in a number of inflammatory and immune disorders and play a role in cancer (Rakoff-Nahoum S. & Medzhitov R., 2009. Toll-like receptors and cancer. Nat Revs Cancer 9:57-63.)

TLRs are type I transmembrane proteins characterized by an extracellular domain containing leucine-rich repeats (LRRs) and a cytoplasmic tail that contains a conserved region called the Toll/IL-1 receptor (TTR) domain. Ten human and twelve murine TLRs have been characterized, TLR1 to TLR10 in humans, and TLR1 to TLR9, TLR11, TLR12 and TLR13 in mice, the homolog of TLR10 being a pseudogene. TLR2 is essential for the recognition of a variety of PAMPs from Gram-positive bacteria, including bacterial lipoproteins, lipomannans and lipoteichoic acids. TLR3 is implicated in virus-derived double-stranded RNA.

TLR4 is predominantly activated by lipopolysaccharide. TLR5 detects bacterial flagellin and TLR9 is required for response to unmethylated CpG DNA. Finally, TLR7 and TLR8 recognize small synthetic antiviral molecules, and single-stranded RNA was reported to be their natural ligand. TLR11 has been reported to recognize uropathogenic *E. coli* and a profilin-like protein from *Toxoplasma gondii*. The repertoire of specificities of the TLRs is apparently extended by the ability of TLRs to heterodimerize with one another. For example, dimers of TLR2 and TLR6 are required for responses to diacylated lipoproteins while TLR2 and TLR1 interact to recognize triacylated lipoproteins. Specificities of the TLRs are also influenced by various adapter and accessory molecules, such as MD-2 and CD14 that form a complex with TLR4 in response to LPS.

TLR signaling consists of at least two distinct pathways: a MyD88-dependent pathway that leads to the production of inflammatory cytokines, and a MyD88-independent pathway associated with the stimulation of IFN-β and the maturation of dendritic cells. The MyD88-dependent pathway is common to all TLRs, except TLR3 (Adachi O. et al., 1998. Targeted disruption of the MyD88 gene results in loss of IL-1- and IL-18-mediated function. Immunity. 9(1):143-50). Upon activation by PAMPs or DAMPs, TLRs hetero- or homodimerize inducing the recruitment of adaptor proteins via the cytoplasmic TTR domain. Individual TLRs induce different signaling responses by usage of the different adaptor molecules. TLR4 and TLR2 signaling requires the adaptor TIRAP/Mal, which is involved in the MyD88-dependent pathway. TLR3 triggers the production of IFN-β in response to double-stranded RNA, in a MyD88-independent manner, through the adaptor TRIF/TICAM-1. TRAM/TICAM-2 is another adaptor molecule involved in the MyD88-independent pathway which function is restricted to the TLR4 pathway.

TLR3, TLR7, TLR8 and TLR9 recognize viral nucleic acids and induce type I IFNs. The signaling mechanisms leading to the induction of type I IFNs differ depending on the TLR activated. They involve the interferon regulatory factors, IRFs, a family of transcription factors known to play a critical role in antiviral defense, cell growth and immune regulation. Three IRFs (IRF3, IRF5 and IRF7) function as direct transducers of virus-mediated TLR signaling. TLR3 and TLR4 activate IRF3 and IRF7, while TLR7 and TLR8 activate IRF5 and IRF7 (Doyle S. et al., 2002. IRF3 mediates a TLR3/TLR4-specific antiviral gene program. Immunity. 17(3):251-63). Furthermore, type I IFN production stimulated by TLR9 ligand CpG-A has been shown to be mediated by PI(3)K and mTOR (Costa-Mattioli M. & Sonenberg N. 2008. RAPping production of type I interferon in pDCs through mTOR. Nature Immunol. 9: 1097-1099).

TLR-9

TLR9 recognizes unmethylated CpG sequences in DNA molecules. CpG sites are relatively rare (~1%) on vertebrate genomes in comparison to bacterial genomes or viral DNA. TLR9 is expressed by numerous cells of the immune system such as B lymphocytes, monocytes, natural killer (NK) cells, and plasmacytoid dendritic cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I interferon and IL-12.

TLR Agonists

A TLR agonist can agonize one or more TLR, e.g., one or more of human TLR-1, 2, 3, 4, 5, 6, 7, 8, 9, or 10. In some embodiments, an adjunctive agent described herein is a TLR agonist. In some embodiments, the TLR agonist specifically agonizes human TLR-9. In some embodiments, the TLR-9 agonist is a CpG moiety. As used herein, a CpG moiety, is a linear dinucleotide having the sequence: 5'-C-phosphate-G-3', that is, cytosine and guanine separated by only one phosphate.

In some embodiments, the CpG moiety comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more CpG dinucleotides. In some embodiments, the CpG moiety consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 CpG dinucleotides. In some embodiments, the CpG moiety has 1-5, 1-10, 1-20, 1-30, 1-40, 1-50, 5-10, 5-20, 5-30, 10-20, 10-30, 10-40, or 10-50 CpG dinucleotides.

In some embodiments, the TLR-9 agonist is a synthetic ODN (oligodeoxynucleotides). CpG ODNs are short synthetic single-stranded DNA molecules containing unmethylated CpG dinucleotides in particular sequence contexts (CpG motifs). CpG ODNs possess a partially or completely phosphorothioated (PS) backbone, as opposed to the natural phosphodiester (PO) backbone found in genomic bacterial DNA. There are three major classes of CpG ODNs: classes A, B and C, which differ in their immunostimulatory activities. CpG-A ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g. IL-6) production. CpG-B ODNs contain a full PS backbone with one or more CpG dinucleotides. They strongly activate B cells and TLR9-dependent NF-κB signaling but weakly stimulate IFN-α secretion. CpG-C ODNs combine features of both classes A and B. They contain a complete PS backbone and a CpG-containing palindromic motif. C-Class CpG ODNs induce strong IFN-α production from pDC as well as B cell stimulation.

Stromal Modifying Moieties

Solid tumors have a distinct structure that mimics that of normal tissues and comprises two distinct but interdependent compartments: the parenchyma (neoplastic cells) and the stroma that the neoplastic cells induce and in which they are dispersed. All tumors have stroma and require stroma for nutritional support and for the removal of waste products. In the case of tumors which grow as cell suspensions (e.g., leukemias, ascites tumors), the blood plasma serves as stroma (Connolly J L et al. Tumor Structure and Tumor Stroma Generation. In: Kufe D W et al., editors. Holland-Frei Cancer Medicine. 6th edition. Hamilton: BC Decker; 2003). The stroma includes a variety of cell types, including fibroblasts/myofibroblasts, glial, epithelial, fat, vascular, smooth muscle, and immune cells along with extracellular matrix (ECM) and extracellular molecules (Li Hanchen et al. Tumor Microenvironment: The Role of the Tumor Stroma in Cancer. *J of Cellular Biochemistry* 101: 805-815 (2007)).

Stromal modifying moieties described herein include moieties (e.g., proteins, e.g., enzymes) capable of degrading a component of the stroma, e.g., an ECM component, e.g., a glycosaminoglycan, e.g., hyaluronan (also known as hyaluronic acid or HA), chondroitin sulfate, chondroitin, dermatan sulfate, heparin sulfate, heparin, entactin, tenascin, aggrecan and keratin sulfate; or an extracellular protein, e.g., collagen, laminin, elastin, fibrinogen, fibronectin, and vitronectin.

Stromal Modifying Enzymes

In some embodiments, the stromal modifying moiety is an enzyme. For example, the stromal modifying moiety can include, but is not limited to a hyaluronidase, a collagenase, a chondroitinase, a matrix metalloproteinase (e.g., macrophage metalloelastase).

Hyaluronidases

Hyaluronidases are a group of neutral- and acid-active enzymes found throughout the animal kingdom. Hyaluronidases vary with respect to substrate specificity, and mechanism of action. There are three general classes of hyaluronidases: (1) Mammalian-type hyaluronidases, (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates; (2) Bacterial hyaluronidases (EC 4.2.99.1) degrade hyaluronan and, and to various extents, chondroitin sulfate and dermatan sulfate. They are endo-beta-N-acetylhexosaminidases that operate by a beta elimination reaction that yields primarily disaccharide end products; (3) Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: (1) neutral active and (2) acid active enzymes. There are six hyaluronidase-like genes in the human genome, HYAL1, HYAL2, HYAL3 HYAL4 HYALPI and PH20/SPAM1. HYALPI is a pseudogene, and HYAL3 has not been shown to possess enzyme activity toward any known substrates. HYAL4 is a chondroitinase and lacks activity towards hyaluronan. HYAL1 is the prototypical acid-active enzyme and PH20 is the prototypical neutral-active enzyme. Acid active hyaluronidases, such as HYAL1 and HYAL2 lack catalytic activity at neutral pH. For example, HYAL1 has no catalytic activity in vitro over pH 4.5 (Frost and Stern, "A Microtiter-Based Assay for Hyaluronidase Activity Not Requiring Specialized Reagents", Analytical Biochemistry, vol. 251, pp. 263-269 (1997). HYAL2 is an acid active enzyme with a very low specific activity in vitro.

In some embodiments the hyaluronidase is a mammalian hyaluronidase. In some embodiments the hyaluronidase is a recombinant human hyaluronidase. In some embodiments, the hyaluronidase is a neutral active hyaluronidase. In some embodiments, the hyaluronidase is a neutral active soluble hyaluronidase. In some embodiments, the hyaluronidase is a recombinant PH20 neutral-active enzyme. In some embodiments, the hyaluronidase is a recombinant PH20 neutral-active soluble enzyme. In some embodiments the hyaluronidase is glycosylated. In some embodiments, the hyaluronidase possesses at least one N-linked glycan. A recombinant hyaluronidase can be produced using conventional methods known to those of skill in the art, e.g., U.S. Pat. No. 7,767,429, the entire contents of which are incorporated by reference herein.

In some embodiments the hyaluronidase is rHuPH20 (also referred to as Hylenex®; presently manufactured by Halozyme; approved by the FDA in 2005 (see e.g., Scodeller P (2014) Hyaluronidase and other Extracellular Matrix Degrading Enzymes for Cancer Therapy: New Uses and Nano-Formulations. *J Carcinog Mutage* 5:178; U.S. Pat. Nos. 7,767,429; 8,202,517; 7,431,380; 8,450,470; 8,772,246; 8,580,252, the entire contents of each of which is incorporated by reference herein). rHuPH20 is produced by genetically engineered CHO cells containing a DNA plasmid encoding for a soluble fragment of human hyaluronidase PH20. In some embodiments the hyaluronidase is glycosylated. In some embodiments, the hyaluronidase possesses at least one N-linked glycan. A recombinant hyaluronidase can be produced using conventional methods known to those of skill in the art, e.g., U.S. Pat. No. 7,767,429, the entire contents of which are incorporated by reference herein. In some embodiments, rHuPH20 has a sequence at least 95% (e.g., at least 96%, 97%, 98%, 99%, 100%) identical to the amino acid sequence of

```
                                              (SEQ ID NO: 39)
LNFRAPPVIPNVPFLWAWNAPSEFCLGKFDEPLDMSLFSFIGSPRINATG

QGVTIFYVDRLGYYPYIDSITGVTVNGGIPQKISLQDHLDKAKKDITFYM

PVDNLGMAVIDWEEWRPTWARNWKPKDVYKNRSIELVQQQNVQLSLTEAT

EKAKQEFEKAGKDFLVETIKLGKLLRPNHLWGYYLFPDCYNHHYKKPGYN

GSCFNVEIKRNDDLSWLWNESTALYPSIYLNTQQSPVAATLYVRNRVREA

IRVSKIPDAKSPLPVFAYTRIVFTDQVLKFLSQDELVYTFGETVALGASG

IVIWGTLSIMRSMKSCLLLDNYMETILNPYIINVTLAAKMCSQVLCQEQG

VCIRKNWNSSDYLHLNPDNFAIQLEKGGKFTVRGKPTLEDLEQFSEKFYC

SCYSTLSCKEKADVKDTDAVDVCIADGVCIDAFLKPPMETEEPQIFYNAS

PSTLS.
```

In any of the methods provided herein, the anti-hyaluronan agent can be an agent that degrades hyaluronan or can be an agent that inhibits the synthesis of hyaluronan. For example, the anti-hyaluronan agent can be a hyaluronan degrading enzyme. In another example, the anti-hyaluronan agent or is an agent that inhibits hyaluronan synthesis. For example, the anti-hyaluronan agent is an agent that inhibits hyaluronan synthesis such as a sense or antisense nucleic acid molecule against an HA synthase or is a small molecule drug. For example, an anti-hyaluronan agent is 4-methylumbelliferone (MU) or a derivative thereof, or leflunomide or a derivative thereof. Such derivatives include, for example, a derivative of 4-methylumbelliferone (MU) that is 6,7-dihydroxy-4-methyl coumarin or 5,7-dihydroxy-4-methyl coumarin.

In further examples of the methods provided herein, the hyaluronan degrading enzyme is a hyaluronidase. In some examples, the hyaluronan-degrading enzyme is a PH20 hyaluronidase or truncated form thereof to lacking a C-terminal glycosylphosphatidylinositol (GPI) attachment site or a portion of the GPI attachment site. In specific examples, the hyaluronidase is a PH20 selected from a human, monkey, bovine, ovine, rat, mouse or guinea pig PH20. For example, the hyaluronan-degrading enzyme is a human PH20 hyaluronidase that is neutral active and N-glycosylated and is selected from among (a) a hyaluronidase polypeptide that is a full-length PH20 or is a C-terminal truncated form of the PH20, wherein the truncated form includes at least amino acid residues 36-464 of SEQ ID NO: 39, such as 36-481, 36-482, 36-483, where the full-length PH20 has the sequence of amino acids set forth in SEQ ID NO: 39; or (b) a hyaluronidase polypeptide comprising a sequence of amino acids having at least 85%, 86%, 87%, 88%, 89%, 90%, 91%, 92%, 93%, 94%, 95%, 96%, 97%, 98%, 99% or more sequence identity with the polypeptide or truncated form of sequence of amino acids set forth in SEQ ID NO: 39; or (c) a hyaluronidase polypeptide of (a) or (b) comprising amino acid substitutions, whereby the hyaluronidase polypeptide has a sequence of amino acids having at least 85%, 86%, 87%, 88%, 89%, 90%, 91%, 92%, 93%, 94%, 95%, 96%, 97%, 98%, 99% or more sequence identity with the polypeptide set forth in SEQ ID NO: 39 or with the corresponding truncated forms thereof. In exemplary examples, the hyaluronan-degrading enzyme is a PH20 that comprises a composition designated rHuPH20.

In other examples, the anti-hyaluronan agent is a hyaluronan degrading enzyme that is modified by conjugation to a polymer. The polymer can be a PEG and the anti-hyaluronan agent a PEGylated hyaluronan degrading enzyme. Hence, in some examples of the methods provided herein the hyaluronan-degrading enzyme is modified by conjugation to a polymer. For example, the hyaluronan-degrading enzyme is conjugated to a PEG, thus the hyaluronan degrading enzyme is PEGylated. In an exemplary example, the hyaluronan-degrading enzyme is a PEGylated PH20 enzyme (PEGPH20). In the methods provided herein, the corticosteroid can be a glucocorticoid that is selected from among cortisones, dexamethasones, hydrocortisones, methylprednisolones, prednisolones and prednisones.

Chondroitinases

Chondroitinases are enzymes found throughout the animal kingdom which degrade glycosaminoglycans, specifically chondroitins and chondroitin sulfates, through an endoglycosidase reaction. In some embodiments the chondroitinase is a mammalian chondroitinase. In some embodiments the chondroitinase is a recombinant human chondroitinase. In some embodiments the chondroitinase is HYAL4. Other exemplary chondroitinases include chondroitinase ABC (derived from *Proteus vulgaris*; Japanese Patent Application Laid-open No 6-153947, T. Yamagata et al. J. Biol. Chem., 243, 1523 (1968), S. Suzuki et al, J. Biol. Chem., 243, 1543 (1968)), chondroitinase AC (derived from *Flavobacterium heparinum*; T. Yamagata et al., J. Biol. Chem., 243, 1523 (1968)), chondroitinase AC II (derived from *Arthrobacter aurescens*; K. Hiyama, and S. Okada, J. Biol. Chem., 250, 1824 (1975), K. Hiyama and S. Okada, J. Biochem. (Tokyo), 80, 1201 (1976)), Hyaluronidase ACIII (derived from *Flavobacterium* sp. Hp102; Hirofumi Miyazono et al., Seikagaku, 61, 1023 (1989)), chondroitinase B (derived from *Flavobacterium heparinum*; Y. M. Michelacci and C. P. Dietrich, Biochem. Biophys. Res. Commun., 56, 973 (1974), Y. M. Michelacci and C. P. Dietrich, Biochem. J., 151, 121 (1975), Kenichi Maeyama et al, Seikagaku, 57, 1189 (1985)), chondroitinase C (derived from *Flavobacterium* sp. Hp102; Hirofumi Miyazono et al, Seikagaku, 61, 1023 (1939)), and the like.

Matrix Metalloproteinases

Matrix metalloproteases (MMPs) are zinc-dependent endopeptidases that are the major proteases involved in extracellular matrix (ECM) degradation. MMPs are capable of degrading a wide range of extracellular molecules and a number of bioactive molecules. Twenty-four MMP genes have been identified in humans, which can be organized into six groups based on domain organization and substrate preference: Collagenases (MMP-1, -8 and -13), Gelatinases (MMP-2 and MMP-9), Stromelysins (MMP-3, -10 and -11), Matrilysin (MMP-7 and MMP-26), Membrane-type (MT)-MMPs (MMP-14, -15, -16, -17, -24 and -25) and others (MMP-12, -19, -20, -21, -23, -27 and -28). In some embodiments, the stromal modifying moiety is a human recombinant MMP (e.g., MMP-1, -2, -3, -4, -5, -6, -7, -8, -9, 10, -11, -12, -13, -14, 15, -15, -17, -18, -19, 20, -21, -22, -23, or -24).

Collagenases

The three mammalian collagenases (MMP-1, -8, and -13) are the principal secreted endopeptidases capable of cleaving collagenous extracellular matrix. In addition to fibrillar collagens, collagenases can cleave several other matrix and non-matrix proteins including growth factors. Collagenases are synthesized as inactive pro-forms, and once activated, their activity is inhibited by specific tissue inhibitors of metalloproteinases, TIMPs, as well as by non-specific proteinase inhibitors (Ala-aho R et al. Biochimie. Collagenases in cancer. 2005 March-April; 87(3-4):273-86). In some embodiments, the stromal modifying moiety is a collagenase. In some embodiments, the collagenase is a human recombinant collagenase. In some embodiments, the collagenase is MMP-1. In some embodiments, the collagenase is MMP-8. In some embodiments, the collagenase is MMP-13.

Macrophage Metalloelastase

Macrophage metalloelastase (MME), also known as MMP-12, is a member of the stromelysin subgroup of MMPs and catalyzes the hydrolysis of soluble and insoluble elastin and a broad selection of matrix and nonmatrix substrates including type IV collagen, fibronectin, laminin, vitronectin, entactin, heparan, and chondroitin sulfates (Erja Kerkela et al. Journal of Investigative Dermatology (2000) 114, 1113-1119; doi:10.1046/j.1523-1747.2000.00993). In some embodiments, the stromal modifying moiety is a MME. In some embodiments, the MME is a human recombinant MME. In some embodiments, the MME is MMP-12.

Additional Stromal Modifying Moieties

In some embodiments, the stromal modifying moiety causes one or more of: decreases the level or production of a stromal or extracellular matrix (ECM) component; decreases tumor fibrosis; increases interstitial tumor transport; improves tumor perfusion; expands the tumor microvasculature; decreases interstitial fluid pressure (IFP) in a tumor; or decreases or enhances penetration or diffusion of an agent, e.g., a cancer therapeutic or a cellular therapy, into a tumor or tumor vasculature.

In some embodiments, the stromal or ECM component decreased is chosen from a glycosaminoglycan or an extracellular protein, or a combination thereof. In some embodiments, the glycosaminoglycan is chosen from hyaluronan (also known as hyaluronic acid or HA), chondroitin sulfate, chondroitin, dermatan sulfate, heparin, heparin sulfate, entactin, tenascin, aggrecan and keratin sulfate. In some embodiments, the extracellular protein is chosen from collagen, laminin, elastin, fibrinogen, fibronectin, or vitronectin. In some embodiments, the stromal modifying moiety includes an enzyme molecule that degrades a tumor stroma or extracellular matrix (ECM). In some embodiments, the enzyme molecule is chosen from a hyaluronidase molecule, a collagenase molecule, a chondroitinase molecule, a matrix metalloproteinase molecule (e.g., macrophage metalloelastase), or a variant (e.g., a fragment) of any of the aforesaid. The term "enzyme molecule" includes a full length, a fragment or a variant of the enzyme, e.g., an enzyme variant that retains at least one functional property of the naturally-occurring enzyme.

In some embodiments, the stromal modifying moiety decreases the level or production of hyaluronic acid. In other embodiments, the stromal modifying moiety comprises a hyaluronan degrading enzyme, an agent that inhibits hyaluronan synthesis, or an antibody molecule against hyaluronic acid.

In some embodiments, the hyaluronan degrading enzyme is a hyaluronidase molecule, e.g., a full length or a variant (e.g., fragment thereof) thereof. In some embodiments, the hyaluronan degrading enzyme is active in neutral or acidic pH, e.g., pH of about 4-5. In some embodiments, the hyaluronidase molecule is a mammalian hyaluronidase molecule, e.g., a recombinant human hyaluronidase molecule, e.g., a full length or a variant (e.g., fragment thereof, e.g., a truncated form) thereof. In some embodiments, the hyaluronidase molecule is chosen from HYAL1, HYAL2, or PH-20/SPAM1, or a variant thereof (e.g., a truncated form thereof). In some embodiments, the truncated form lacks a C-terminal glycosylphosphatidylinositol (GPI) attachment site or a portion of the GPI attachment site. In some embodiments, the hyaluronidase molecule is glycosylated, e.g., comprises at least one N-linked glycan.

In some embodiments, the hyaluronidase molecule comprises the amino acid sequence:

(SEQ ID NO: 61)
LNFRAPPVIPNVPFLWAWNAPSEFCLGKFDEPLDMSLFSFIGSPRINATG

QGVTIFYVDRLGYYPYIDSITGVTVNGGIPQKISLQDHLDKAKKDITFYM

PVDNLGMAVIDWEEWRPTWARNWKPKDVYKNRSIELVQQQNVQLSLTEAT

EKAKQEFEKAGKDFLVETIKLGKLLRPNHLWGYYLFPDCYNHHYKKPGYN

GSCFNVEIKRNDDLSWLWNESTALYPSIYLNTQQSPVAATLYVRNRVREA

IRVSKIPDAKSPLPVFAYTRIVFTDQVLKFLSQDELVYTFGETVALGASG

IVIWGTLSIMRSMKSCLLLDNYMETILNPYIINVTLAAKMCSQVLCQEQG

VCIRKNWNSSDYLHLNPDNFAIQLEKGGKFTVRGKPTLEDLEQFSEKFYC

SCYSTLSCKEKADVKDTDAVDVCIADGVCIDAFLKPPMETEEPQIFYNAS

PSTLS, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 61.

In some embodiments, the hyaluronidase molecule comprises:
(i) the amino acid sequence of 36-464 of SEQ ID NO: 61;
(ii) the amino acid sequence of 36-481, 36-482, or 36-483 of PH20, wherein PH20 has the sequence of amino acids set forth in SEQ ID NO: 61; or
(iii) an amino acid sequence having at least 95% to 100% sequence identity to the polypeptide or truncated form of sequence of amino acids set forth in SEQ ID NO: 61; or
(iv) an amino acid sequence having 30, 20, 10, 5 or fewer amino acid substitutions to the amino acid sequence set forth in SEQ ID NO: 61. In some embodiments, the hyaluronidase molecule comprises an amino acid sequence at least 95% (e.g., at least 95%, 96%, 97%, 98%, 99%, 100%) identical to the amino acid sequence of SEQ ID NO: 61. In some embodiments, the hyaluronidase molecule is encoded by a nucleotide sequence at least 95% (e.g., at least 96%, 97%, 98%, 99%, 100%) identical to the nucleotide sequence of SEQ ID NO: 61.

In some embodiments, the hyaluronidase molecule is PH1120, e.g., r-HuPH120. In some embodiments, the hyaluronidase molecule is HYAL1 and comprises the amino acid sequence:

(SEQ ID NO: 62)
FRGPLLPNRPFTTVWNANTQWCLERHGVDVDVSVFDVVANPGQTFRGPDM

TIFYSSQGTYPYYTPTGEPVFGGLPQNASLIAHLARTFQDILAAIPAPDF

SGLAVIDWEAWRPRWAFNWDTKDIYRQRSRALVQAQHPDWPAPQVEAVAQ

DQFQGAARAWMAGTLQLGRALRPRGLWGFYGFPDCYNYDFLSPNYTGQCP

SGIRAQNDQLGWLWGQSRALYPSIYMPAVLEGTGKSQMYVQHRVAEAFRV

AVAAGDPNLPVLPYVQIFYDTTNHFLPLDELEHSLGESAAQGAAGVVLWV

SWENTRTKESCQAIKEYMDTTLGPFILNVTSGALLCSQALCSGHGRCVRR

TSHPKALLLLNPASFSIQLTPGGGPLSLRGALSLEDQAQMAVEFKCRCYP

GWQAPWCERKSMW, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 62.

In some embodiments, the hyaluronan degrading enzyme, e.g., the hyaluronidase molecule, further comprises a polymer, e.g., is conjugated to a polymer, e.g., PEG. In some embodiments, the hyaluronan-degrading enzyme is a PEGylated PH20 enzyme (PEGPH20). In some embodiments, the hyaluronan degrading enzyme, e.g., the hyaluronidase molecule, further comprises an immunoglobulin chain constant region (e.g., Fc region) chosen from, e.g., the heavy chain constant regions of IgG1, IgG2, IgG3, and IgG4, more particularly, the heavy chain constant region of human IgG1, IgG2, IgG3, or IgG4. In some embodiments, the immunoglobulin constant region (e.g., the Fc region) is linked, e.g., covalently linked to, the hyaluronan degrading enzyme, e.g., the hyaluronidase molecule. In some embodiments, the immunoglobulin chain constant region (e.g., Fc region) is altered, e.g., mutated, to increase or decrease one or more of: Fc receptor binding, antibody glycosylation, the number of cysteine residues, effector cell function, or complement function. In some embodiments, the hyaluronan degrading enzyme, e.g., the hyaluronidase molecule forms a dimer.

In some embodiments, the stromal modifying moiety comprises an inhibitor of the synthesis of hyaluronan, e.g., an HA synthase. In some embodiments, the inhibitor comprises a sense or an antisense nucleic acid molecule against an HA synthase or is a small molecule drug. In some embodiments, the inhibitor is 4-methylumbelliferone (MU) or a derivative thereof (e.g., 6,7-dihydroxy-4-methyl coumarin or 5,7-dihydroxy-4-methyl coumarin), or leflunomide or a derivative thereof.

In some embodiments, the stromal modifying moiety comprises antibody molecule against hyaluronic acid.

In some embodiments, the stromal modifying moiety comprises a collagenase molecule, e.g., a mammalian collagenase molecule, or a variant (e.g., fragment) thereof. In some embodiments, the collagenase molecule is collagenase molecule IV, e.g., comprising the amino acid sequence of:

(SEQ ID NO: 63)
YNFFPRKPKWDKNQITYRIIGYTPDLDPETVDDAFARAFQVWSDVTPLRF

SRIHDGEADIMINFGRWEHGDGYPFDGKDGLLAHAFAPGTGVGGDSHFDD

DELWTLGEGQVVRVKYGNADGEYCKFPPLFNGKEYNSCTDTGRSDGFLWC

STTYNFEKDGKYGFCPHEALFTMGGNAEGQPCKFPPFRFQGTSYDSCTTEG

RTDGYRWCGTTEDYDRDKKYGFCPETAMSTVGGNSEGAPCVFPFTFLGNK

-continued

YESCTSAGRSDGKMWCATTANYDDDRKWGFCPDQGYSLFLVAAHEFGHAM

GLEHSQDPGALMAPIYTYTKNFRLSQDDIKGIQELYGASPDIDLGTGPTP

TLGPVTPEICKQDIVFDGIAQIRGEIFFFKDRFIWRTVTPRDKPMGPLLV

ATFWPELPEKIDAVYEAPQEEKAVFFAGNEYWIYSASTLERGYPKPLTSL

GLPPDVQRVDAAFNWSKNKKTYIFAGDKFWRYNEVKKKMDPGFPKLIADA

WNAIPDNLDAVVDLQGGGHSYFFKGAYYLKLENQSLKSVKFGSIKSDWLG

C, or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 63.

Linkers

The multispecific or multifunctional molecule disclosed herein can further include a linker, e.g., a linker between one or more of: the antigen binding domain and the cytokine molecule (or the modulator of a cytokine molecule), the antigen binding domain and the immune cell engager, the antigen binding domain and the stromal modifying moiety, the cytokine molecule (or the modulator of a cytokine molecule) and the immune cell engager, the cytokine molecule (or the modulator of a cytokine molecule) and the stromal modifying moiety, the immune cell engager and the stromal modifying moiety, the antigen binding domain and the immunoglobulin chain constant region, the cytokine molecule (or the modulator of a cytokine molecule) and the immunoglobulin chain constant region, the immune cell engager and the immunoglobulin chain constant region, or the stromal modifying moiety and the immunoglobulin chain constant region. In embodiments, the linker is chosen from: a cleavable linker, a non-cleavable linker, a peptide linker, a flexible linker, a rigid linker, a helical linker, or a non-helical linker, or a combination thereof.

In one embodiment, the multispecific molecule can include one, two, three or four linkers, e.g., a peptide linker. In one embodiment, the peptide linker includes Gly and Ser. In some embodiments, the peptide linker is selected from GGGGS (SEQ ID NO: 42); GGGGSGGGGS (SEQ ID NO: 43); GGGGSGGGGSGGGGS (SEQ ID NO: 44); and DVPSGPGGGGSGGGGS (SEQ ID NO: 45). In some embodiments, the peptide linker is a A(EAAAK)nA family of linkers (e.g., as described in Protein Eng. (2001) 14 (8): 529-532). These are stiff helical linkers with n ranging from 2-5. In some embodiments, the peptide linker is selected from AEAAAKEAAAKAAA (SEQ ID NO: 75); AEAAAKEAAAKEAAAKAAA (SEQ ID NO: 76); AEAAAKEAAAKEAAAKEAAAKAAA (SEQ ID NO: 77); and AEAAAKEAAAKEAAAKEAAAKEAAAKAAA (SEQ ID NO: 78).

Nucleic Acids

Nucleic acids encoding the aforementioned multispecific or multifunctional molecules are also disclosed.

In certain embodiments, the invention features nucleic acids comprising nucleotide sequences that encode heavy and light chain variable regions and CDRs or hypervariable loops of the antibody molecules, as described herein. For example, the invention features a first and second nucleic acid encoding heavy and light chain variable regions, respectively, of an antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In certain embodiments, the nucleic acid can comprise a nucleotide sequence encoding a cytokine molecule (or the modulator of a cytokine molecule), an immune cell engager, or a stromal modifying moiety disclosed herein.

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising the nucleotide sequences encoding a multispecific or multifunctional molecule described herein. In one embodiment, the vectors comprise nucleotides encoding a multispecific or multifunctional molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity.

Methods and conditions for culturing the resulting transfected cells and for recovering the antibody molecule produced are known to those skilled in the art, and may be varied or optimized depending upon the specific expression vector and mammalian host cell employed, based upon the present description.

Cells

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Uses and Combination Therapies

Methods described herein include treating a cancer in a subject by using a multispecific or multifunctional molecule described herein, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sezary syndrome, Waldenstrom macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a myeloproliferative neoplasm, e.g., primary or idiopathic myelofibrosis (MF), essential thrombocytosis (ET), polycythemia vera (PV), or chronic myelogenous leukemia (CML). In embodiments, the cancer is myelofibrosis. In embodiments, the subject has myelofibrosis. In embodiments, the subject has a calreticulin mutation, e.g., a calreticulin mutation disclosed herein. In embodiments, the subject does not have the JAK2-V617F mutation. In embodiments, the subject has the JAK2-V617F mutation. In embodiments, the subject has a MPL mutation. In embodiments, the subject does not have a MPL mutation.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In embodiments, the multispecific or multifunctional molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or multispecific or multifunctional molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the multispecific or multifunctional molecules or pharmaceutical composition is administered to the subject parenterally. In embodiments, the cells are administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319:1676, 1988) or an intravenous push. In embodiments, the cells are administered as an injectable depot formulation. In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Combination Therapies

The multispecific or multifunctional molecules disclosed herein can be used in combination with a second therapeutic agent or procedure.

In embodiments, the multispecific or multifunctional molecule and the second therapeutic agent or procedure are administered/performed after a subject has been diagnosed with a cancer, e.g., before the cancer has been eliminated from the subject. In embodiments, the multispecific or multifunctional molecule and the second therapeutic agent or procedure are administered/performed simultaneously or concurrently. For example, the delivery of one treatment is still occurring when the delivery of the second commences, e.g., there is an overlap in administration of the treatments. In other embodiments, the multispecific or multifunctional molecule and the second therapeutic agent or procedure are administered/performed sequentially. For example, the delivery of one treatment ceases before the delivery of the other treatment begins.

In embodiments, combination therapy can lead to more effective treatment than monotherapy with either agent alone. In embodiments, the combination of the first and second treatment is more effective (e.g., leads to a greater reduction in symptoms and/or cancer cells) than the first or second treatment alone. In embodiments, the combination therapy permits use of a lower dose of the first or the second treatment compared to the dose of the first or second treatment normally required to achieve similar effects when administered as a monotherapy. In embodiments, the combination therapy has a partially additive effect, wholly additive effect, or greater than additive effect.

In one embodiment, the multispecific or multifunctional molecule is administered in combination with a therapy, e.g., a cancer therapy (e.g., one or more of anti-cancer agents, immunotherapy, photodynamic therapy (PDT), surgery and/or radiation). The terms "chemotherapeutic," "chemotherapeutic agent," and "anti-cancer agent" are used interchangeably herein. The administration of the multispecific or multifunctional molecule and the therapy, e.g., the cancer therapy, can be sequential (with or without overlap) or simultaneous. Administration of the multispecific or multifunctional molecule can be continuous or intermittent during the course of therapy (e.g., cancer therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) *CA Cancer J. Clin.* 61:250-281).

Anti-Cancer Therapies

In other embodiments, the multispecific or multifunctional molecule is administered in combination with a low or small molecular weight chemotherapeutic agent. Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-transretinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (*Erwinia* L-asparaginase, L-asparaginase, ELSPAR®, KIDROLASE®), BCNU (carmustine, BiCNU@), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the multispecific or multifunctional molecule is administered in conjunction with a biologic. Biologics useful in the treatment of cancers are known in the art and a binding molecule of the invention may be administered, for example, in conjunction with such known biologics. For example, the FDA has approved the following biologics for the treatment of breast cancer: HERCEPTIN® (trastuzumab, Genentech Inc., South San Francisco, Calif; a humanized monoclonal antibody that has anti-tumor activity in HER2-positive breast cancer); FASLODEX® (fulvestrant, AstraZeneca Pharmaceuticals, LP, Wilmington, Del.; an estrogen-receptor antagonist used to treat breast cancer); ARIMIDEX® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the binding molecules of the invention may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include VELCADE® Velcade (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), bavituximab, bectumomab (LYMPHOSCAN®), belimumab (BENLYSTA®, LYMPHOSTAT-B®), besilesomab (SCINTIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THERACIM®, THERALOC®), nofetumomab merpentan (VERLUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), tremelimumab, tucotuzumab celmoleukin, veltuzumab, volociximab, votumumab (HUMASPECT®), zalutumumab (HUMAX-EGFR®), and zanolimumab (HUMAX-CD4®).

In other embodiments, the multispecific or multifunctional molecule is administered in combination with a viral cancer therapeutic agent. Exemplary viral cancer therapeutic agents include, but not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/AS04 vaccine, MVA-EBNA1/LMP2 Inj. vaccine, quadrivalent HPV vaccine, quadrivalent human papillomavirus (types 6, 11, 16, 18) recombinant vaccine (GARDASIL®), recombinant fowlpox-CEA(6D)/TRICOM vaccine; recombinant vaccinia-CEA(6D)-TRICOM vaccine, recombinant modified vaccinia Ankara-5T4 vaccine, recombinant fowlpox-TRICOM vaccine, oncolytic herpes virus NV1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC(2) melanoma multi-antigen therapeutic vaccine, ALVAC-hB7.1, canarypox-hTL-12 melanoma vaccine, Ad-REIC/Dkk-3, rAd-IFN SCH 721015, TIL-Ad-INFg, Ad-ISF35, and coxsackievirus A21 (CVA21, CAVATAK®).

In other embodiments, the multispecific or multifunctional molecule is administered in combination with a nanopharmaceutical. Exemplary cancer nanopharmaceuticals include, but not limited to, ABRAXANE® (paclitaxel bound albumin nanoparticles), CRLX101 (CPT conjugated to a linear cyclodextrin-based polymer), CRLX288 (conjugating docetaxel to the biodegradable polymer poly (lactic-co-glycolic acid)), cytarabine liposomal (liposomal Ara-C, DEPOCYT™), daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the multispecific or multifunctional molecule is administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Other cancer therapeutic agents include, but not limited to, cytokines (e.g., aldesleukin (IL-2, Interleukin-2, PROLEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte-Colony Stimulating Factor, NEUPOGEN®), GM-CSF (Granulocyte Macrophage Colony Stimulating Factor, sargramostim, LEUKINE™), IL-11 (Interleukin-11, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METICORTEN®, ORASONE®)), and bisphosphonates (e.g., pamidronate (AREDIA®), and zoledronic acid (ZOMETA®))

In some embodiments, the multispecific or multifunctional molecule is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-8 inhibitor)), a RAF-1 inhibitor, a KIT inhibitor and a RET inhibitor. In some embodiments, the anti-cancer agent used in combination with the AHCM agent is selected from the group consisting of: axitinib (AG013736), bosutinib (SKI-606), cediranib (RECENTIN$^T$m, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TK1258, CHIR-258), BIBW 2992 (TOVOK$^T$m), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951(tivozanib), axitinib, BAY 73-4506 (regorafenib), brivanib alaninate (BMS-582664), brivanib (BMS-540215), cediranib (AZD2171), CHIR-258 (dovitinib), CP 673451, CYC116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68(SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In one embodiment, the multispecific or multifunctional molecule is administered in combination with one of more of: an anti-angiogenic agent, or a vascular targeting agent or a vascular disrupting agent. Exemplary anti-angiogenic agents include, but are not limited to, VEGF inhibitors (e.g., anti-VEGF antibodies (e.g., bevacizumab); VEGF receptor inhibitors (e.g., itraconazole); inhibitors of cell proliferatin and/or migration of endothelial cells (e.g., carboxyamidotriazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P. E. (2004) *Clin. Cancer Res.* Vol. 10:415-427). VTAs can be small-molecule. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

Immune Checkpoint Inhibitors

In other embodiments, methods described herein comprise use of an immune checkpoint inhibitor in combination with the multispecific or multifunctional molecule. The methods can be used in a therapeutic protocol in vivo.

In embodiments, an immune checkpoint inhibitor inhibits a checkpoint molecule. Exemplary checkpoint molecules include but are not limited to CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class II, GAL9, VISTA, BTLA, TIGIT, LAIR1, and A2aR. See, e.g., Pardoll. Nat. Rev. Cancer 12.4 (2012):252-64, incorporated herein by reference.

In embodiments, the immune checkpoint inhibitor is a PD-1 inhibitor, e.g., an anti-PD-1 antibody such as Nivolumab, Pembrolizumab or Pidilizumab. Nivolumab (also called MDX-1106, MDX-1106-04, ONO-4538, or BMS-936558) is a fully human IgG4 monoclonal antibody that specifically inhibits PD1. See, e.g., U.S. Pat. No. 8,008,449 and WO2006/121168. Pembrolizumab (also called Lambrolizumab, MK-3475, MK03475, SCH-900475 or KEYTRUDA®; Merck) is a humanized IgG4 monoclonal antibody that binds to PD-1. See, e.g., Hamid, O. et al. (2013) *New England Journal of Medicine* 369 (2): 134-44, U.S. Pat. No. 8,354,509 and WO2009/114335. Pidilizumab (also called CT-011 or Cure Tech) is a humanized IgG1k monoclonal antibody that binds to PD1. See, e.g., WO2009/101611. In one embodiment, the inhibitor of PD-1 is an antibody molecule having a sequence substantially identical or similar thereto, e.g., a sequence at least 85%, 90%, 95% identical or higher to the sequence of Nivolumab, Pembrolizumab or Pidilizumab. Additional anti-PD1 antibodies, e.g., AMP 514 (Amplimmune), are described, e.g., in U.S. Pat. No. 8,609,089, US 2010028330, and/or US 20120114649.

In some embodiments, the PD-1 inhibitor is an immunoadhesin, e.g., an immunoadhesin comprising an extracellular/PD-1 binding portion of a PD-1 ligand (e.g., PD-L1 or PD-L2) that is fused to a constant region (e.g., an Fc region of an immunoglobulin). In embodiments, the PD-1 inhibitor is AMP-224 (B7-DCIg, e.g., described in WO2011/066342 and WO2010/027827), a PD-L2 Fc fusion soluble receptor that blocks the interaction between B7-H1 and PD-1.

In embodiments, the immune checkpoint inhibitor is a PD-L1 inhibitor, e.g., an antibody molecule. In some embodiments, the PD-L1 inhibitor is YW243.55.S70, MPDL3280A, MEDI-4736, MSB-0010718C, or MDX-1105. In some embodiments, the anti-PD-L1 antibody is MSB0010718C (also called A09-246-2; Merck Serono), which is a monoclonal antibody that binds to PD-L1. Exemplary humanized anti-PD-L1 antibodies are described, e.g., in WO2013/079174. In one embodiment, the PD-L1 inhibitor is an anti-PD-L1 antibody, e.g., YW243.55.S70. The YW243.55.S70 antibody is described, e.g., in WO 2010/077634. In one embodiment, the PD-L1 inhibitor is MDX-1105 (also called BMS-936559), which is described, e.g., in WO2007/005874. In one embodiment, the PD-L1 inhibitor is MDPL3280A (Genentech /Roche), which is a human Fc-optimized IgG1 monoclonal antibody against PD-L1. See, e.g., U.S. Pat. No. 7,943,743 and U.S Publication No.: 20120039906. In one embodiment, the inhibitor of PD-L1 is an antibody molecule having a sequence substantially identical or similar thereto, e.g., a sequence at least 85%, 90%, 95% identical or higher to the sequence of YW243.55.S70, MPDL3280A, MEDI-4736, MSB-0010718C, or MDX-1i05.

In embodiments, the immune checkpoint inhibitor is a PD-L2 inhibitor, e.g., AMP-224 (which is a PD-L2 Fc fusion soluble receptor that blocks the interaction between PD1 and B7-H1. See, e.g., WO2010/027827 and WO2011/066342.

In one embodiment, the immune checkpoint inhibitor is a LAG-3 inhibitor, e.g., an anti LAG-3 antibody molecule. In embodiments, the anti-LAG-3 antibody is BMS-986016 (also called BMS986016; Bristol-Myers Squibb). BMS-986016 and other humanized anti-LAG-3 antibodies are described, e.g., in US 2011/0150892, WO2010/019570, and WO2014/008218.

In embodiments, the immune checkpoint inhibitor is a TIM-3 inhibitor, e.g., anti-TIM3 antibody molecule, e.g., described in U.S. Pat. No. 8,552,156, WO 2011/155607, EP 2581113 and U.S Publication No.: 2014/044728.

In embodiments, the immune checkpoint inhibitor is a CTLA-4 inhibitor, e.g., anti-CTLA-4 antibody molecule. Exemplary anti-CTLA4 antibodies include Tremelimumab (IgG2 monoclonal antibody from Pfizer, formerly known as ticilimumab, CP-675,206); and Ipilimumab (also called MDX-010, CAS No. 477202-00-9). Other exemplary anti-CTLA-4 antibodies are described, e.g., in U.S. Pat. No. 5,811,097.

EXAMPLES

The following examples are intended to be illustrative, and are not meant in any way to be limiting.

Example 1. Characterization of Anti-Calreticulin Antibodies

A murine anti-calreticulin antibody AbM-1 (also referred to as BIM0031) which comprises a VH of SEQ ID NO: 104 and a VL of SEQ ID NO: 106 was humanized. Five humanized VHs (SEQ ID NOs: 233-237 shown in Table 8) and five humanized VLs (SEQ ID NOs: 238-242 shown in Table 8) were generated. All the humanized VHs comprise a cysteine to alanine substitution in HCDR2. Antibodies BJM0040-BJM0064, as disclosed in Table 11, were synthesized and characterized for their biochemical and functional activities.

Briefly, expression level of purified proteins was measured after protein A elution. Proteins were analyzed by analytical SEC to assess aggregation and tested by differential scanning fluorimetry (DSF) to identify more stable candidates. Binding affinity of the candidates was measured in ELISA assay against mutant calreticulin C-terminal peptide fused to a human Fc. The results were summarized in Table 13. Humanized antibodies comprising the cysteine to alanine substitution in HCDR2 demonstrated reduced aggregation compared to the parental murine antibody.

TABLE 13

Summary of characterization of anti-calreticulin antibodies

|  | yield (mg/L) | % aggregation after ProA | Tm (C.) | ELISA IC50 |
|---|---|---|---|---|
| BJM0040 | 95.7 | 0 | 75 | 12.34 |
| BJM0041 | 193.6 | 5.3 | 75 | 18.79 |
| BJM0042 | 106.7 | 0 | 75 | 10.52 |
| BJM0043 | 181.5 | 3 | 75 | 8.279 |
| BJM0044 | 161.7 | 5.6 | 75 | 16.19 |
| BJM0045 | 42.9 | 8 | 73 | ~836101 |
| BJM0046 | 116.6 | 7.5 | 76 | ~362165 |
| BJM0047 | 93.5 | 7 | 76 | 802.9 |
| BJM0048 | 111.1 | 6 | 75 | 430.3 |
| BJM0049 | 103.4 | 6.8 | 76 | 943.6 |
| BJM0050 | 261.8 | 10.3 | — | 597627 |
| BJM0051 | 112.2 | 7.4 | 77 | 780.7 |
| BJM0052 | 123.2 | 12.4 | 77 | 776.2 |
| BJM0053 | 132 | 10.3 | 76 | 357.2 |
| BJM0054 | 128.7 | 12.3 | 77 | 657.2 |
| BJM0055 | 72.6 | 17.1 | 69 | 1E+06 |
| BJM0056 | 113.3 | 11.6 | 69 | 889.5 |
| BJM0057 | 67.1 | 12.1 | 69 | 4E+06 |
| BJM0058 | 92.4 | 9.1 | 69 | 498.4 |
| BJM0059 | 136.4 | 12 | 68 | 83.11 |
| BJM0060 | 134.2 | 7.5 | 72 | ~4347 |
| BJM0061 | 140.8 | 8.5 | 73 | 356 |
| BJM0062 | 91.3 | 8.5 | 73 | 351.8 |
| BJM0063 | 145.2 | 8.8 | 73 | 988.6 |
| BJM0064 | 139.7 | 10 | 73 | 637.4 |
| BIM0031 |  |  |  | 24.32 |

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A multifunctional molecule, comprising:
   (i) a first antigen binding domain that binds to a first calreticulin protein and
   (ii) one, two, or all of:
      (a) an immune cell engager chosen from a T cell engager, an NK cell engager, a B cell engager, a dendritic cell engager, or a macrophage cell engager;
      (b) a cytokine molecule or a modulator of a cytokine molecule; and
      (c) a stromal modifying moiety, wherein:
   the first antigen binding domain comprises a heavy chain variable region (VH) comprising a heavy chain complementarity determining region 1 (VHCDR1) amino acid sequence of SEQ ID NO: 107, a VHCDR2 amino acid sequence of SEQ ID NO: 243, and a VHCDR3 amino acid sequence of SEQ ID NO: 109, and a light chain variable region (VL) comprising a light chain complementarity determining region 1 (VLCDR1) amino acid sequence of SEQ ID NO: 113, a VLCDR2 amino acid sequence of SEQ ID NO: 114, and a VLCDR3 amino acid sequence of SEQ ID NO: 115.

2. The multifunctional molecule of claim 1, wherein the multifunctional molecule preferentially binds to a myeloproliferative neoplasm cell over a non-tumor cell, optionally wherein the binding between the multifunctional molecule and the myeloproliferative neoplasm cell is more than 10, 20, 30, 40, 50-fold greater than the binding between the multifunctional molecule and a non-tumor cell.

3. The multifunctional molecule of claim 2, wherein the myeloproliferative neoplasm cell is chosen from a myelofibrosis cell, an essential thrombocythemia cell, a polycythemia vera cell, or a chronic myeloid cancer cell, optionally wherein:
   the myeloproliferative neoplasm cell does not comprise a JAK2 V617F mutation, or the myeloproliferative neoplasm cell does not comprise a MPL mutation.

4. The multifunctional molecule of claim 1, wherein the first antigen binding domain comprises:
   (i) a VH comprising a heavy chain framework region 1 (VHFWR1) amino acid sequence of SEQ ID NO: 80, a VHFWR2 amino acid sequence of SEQ ID NO: 81, a VHFWR3 amino acid sequence of SEQ ID NO: 82, and/or a VHFWR4 amino acid sequence of SEQ ID NO: 83;
   (ii) a VH comprising a heavy chain framework region 1 (VHFWR1) amino acid sequence of SEQ ID NO: 84, a VHFWR2 amino acid sequence of SEQ ID NO: 85, a VHFWR3 amino acid sequence of SEQ ID NO: 86, and/or a VHFWR4 amino acid sequence of SEQ ID NO: 83; and/or
   (iii) a VL comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, and/or a VLFWR4 amino acid sequence of SEQ ID NO: 90.

5. The multifunctional molecule of claim 1, wherein the first antigen binding domain comprises:
   (i) a VH comprising an amino acid sequence having at least 80% sequence identity to SEQ ID NO: 233, and/or a VL comprising an amino acid sequence having at least 90% sequence identity to SEQ ID NO: 238;
   (ii) a VH comprising an amino acid sequence having at least 80% sequence identity to SEQ ID NO: 234, and/or a VL comprising an amino acid sequence having at least 90% sequence identity to SEQ ID NO: 238;
   (iii) a VH comprising an amino acid sequence having at least 80% sequence identity to SEQ ID NO: 235, and/or a VL comprising an amino acid sequence having at least 90% sequence identity to SEQ ID NO: 238;
   (iv) a VH comprising an amino acid sequence having at least 80% sequence identity to SEQ ID NO: 236, and/or a VL comprising an amino acid sequence having at least 90% sequence identity to SEQ ID NO: 238;
   (v) a VH comprising an amino acid sequence having at least 80% sequence identity to SEQ ID NO: 237, and/or a VL comprising an amino acid sequence having at least 90% sequence identity to SEQ ID NO: 238; or
   (vi) a VH comprising an amino acid sequence having at least 80% sequence identity to SEQ ID NO: 244, and/or a VL comprising an amino acid sequence having at least 90% sequence identity to SEQ ID NO: 245.

6. The multifunctional molecule of claim 5, wherein the first antigen binding domain comprises:
    (i) VH comprising the amino acid sequence of SEQ ID NO: 233, and/or a VL comprising the amino acid sequence of SEQ ID NO: 238;
    (ii) a VH comprising the amino acid sequence of SEQ ID NO: 234, and/or a VL comprising the amino acid sequence of SEQ ID NO: 238;
    (iii) a VH comprising the amino acid sequence of SEQ ID NO: 235, and/or a VL comprising the amino acid sequence of SEQ ID NO: 238;
    (iv) a VH comprising the amino acid sequence of SEQ ID NO: 236, and/or a VL comprising the amino acid sequence of SEQ ID NO: 238;
    (v) a VH comprising the amino acid sequence of SEQ ID NO: 237, and/or a VL comprising the amino acid sequence of SEQ ID NO: 238; or
    (vi) a VH comprising the amino acid sequence of SEQ ID NO: 244, and/or a VL comprising the amino acid sequence of SEQ ID NO: 245.

7. The multifunctional molecule of claim 1, wherein the multifunctional molecule further comprises a second antigen binding domain that binds to a second calreticulin protein, wherein the second antigen binding domain comprises:
    (i) a heavy chain variable region (VH) comprising a heavy chain complementarity determining region 1 (VHCDR1) amino acid sequence of SEQ ID NO: 107, a VHCDR2 amino acid sequence of SEQ ID NO: 243, and a VHCDR3 amino acid sequence of SEQ ID NO: 109, and a light chain variable region (VL) comprising a light chain complementarity determining region 1 (VLCDR1) amino acid sequence of SEQ ID NO: 113, a VLCDR2 amino acid sequence of SEQ ID NO: 114, and a VLCDR3 amino acid sequence of SEQ ID NO: 115;
    (ii) a VH comprising a VHCDR1 amino acid sequence of SEQ ID NO: 107, a VHCDR2 amino acid sequence of SEQ ID NO: 108, and a VHCDR3 amino acid sequence of SEQ ID NO: 109; and a VL comprising a VLCDR1 amino acid sequence of SEQ ID NO: 113, a VLCDR2 amino acid sequence of SEQ ID NO: 114, and a VLCDR3 amino acid sequence of SEQ ID NO: 115; or
    (iii) a VH comprising a VHCDR1 amino acid sequence of SEQ ID NO: 110, a VHCDR2 amino acid sequence of SEQ ID NO: 111, and a VHCDR3 amino acid sequence of SEQ ID NO: 112 or 116, and a VL comprising a VLCDR1 amino acid sequence of SEQ ID NO: 113, a VLCDR2 amino acid sequence of SEQ ID NO: 114, and a VLCDR3 amino acid sequence of SEQ ID NO: 115.

8. The multifunctional molecule of claim 1, wherein the multifunctional molecule further comprises a second antigen binding domain that binds to a second calreticulin protein wherein the second antigen binding domain comprises:
    (i) a heavy chain variable region (VH) comprising a heavy chain framework region 1 (VHFWRI) amino acid sequence of SEQ ID NO: 80, a VHFWR2 amino acid sequence of SEQ ID NO: 81, a VHFWR3 amino acid sequence of SEQ ID NO: 82, or a VHFWR4 amino acid sequence of SEQ ID NO: 83,
    (ii) a heavy chain variable region (VH) comprising a heavy chain framework region 1 (VHFWRI) amino acid sequence of SEQ ID NO: 84, a VHFWR2 amino acid sequence of SEQ ID NO: 85, a VHFWR3 amino acid sequence of SEQ ID NO: 86, or a VHFWR4 amino acid sequence of SEQ ID NO: 83, or
    (iii) a light chain variable region (VL) comprising a light chain framework region 1 (VLFWR1) amino acid sequence of SEQ ID NO: 87, a VLFWR2 amino acid sequence of SEQ ID NO: 88, a VLFWR3 amino acid sequence of SEQ ID NO: 89, or a VLFWR4 amino acid sequence of SEQ ID NO: 90.

9. The multifunctional molecule of claim 1, wherein the multifunctional molecule further comprises a second antigen binding domain that binds to a second calreticulin protein wherein the second antigen binding domain comprises:
    (i) a VH comprising an amino acid sequence having at least 80% sequence identity to SEQ ID NO: 233, and/or a VL comprising an amino acid sequence having at least 90% sequence identity to SEQ ID NO: 238;
    (ii) a VH comprising an amino acid sequence having at least 80% sequence identity to SEQ ID NO: 234, and/or a VL comprising an amino acid sequence having at least 90% sequence identity to SEQ ID NO: 238;
    (iii) a VH comprising an amino acid sequence having at least 80% sequence identity to SEQ ID NO: 235, and/or a VL comprising an amino acid sequence having at least 90% sequence identity to SEQ ID NO: 238;
    (iv) a VH comprising an amino acid sequence having at least 80% sequence identity to SEQ ID NO: 236, and/or a VL comprising an amino acid sequence having at least 90% sequence identity to SEQ ID NO: 238;
    (v) a VH comprising an amino acid sequence having at least 80% sequence identity to SEQ ID NO: 237, and/or a VL comprising an amino acid sequence having at least 90% sequence identity to SEQ ID NO: 238; or
    (vi) a VH comprising an amino acid sequence having at least 80% sequence identity to SEQ ID NO: 244, and/or a VL comprising an amino acid sequence having at least 90% sequence identity to SEQ ID NO: 245.

10. The multifunctional molecule of claim 1, wherein the multifunctional molecule further comprises a second antigen binding domain that binds to a second calreticulin protein wherein the second antigen binding domain comprises:
    (i) VH comprising the amino acid sequence of SEQ ID NO: 233, and/or a VL comprising the amino acid sequence of SEQ ID NO: 238;
    (ii) a VH comprising the amino acid sequence of SEQ ID NO: 234, and/or a VL comprising the amino acid sequence of SEQ ID NO: 238;
    (iii) a VH comprising the amino acid sequence of SEQ ID NO: 235, and/or a VL comprising the amino acid sequence of SEQ ID NO: 238;
    (iv) a VH comprising the amino acid sequence of SEQ ID NO: 236, and/or a VL comprising the amino acid sequence of SEQ ID NO: 238;
    (v) a VH comprising the amino acid sequence of SEQ ID NO: 237, and/or a VL comprising the amino acid sequence of SEQ ID NO: 238; or
    (vi) a VH comprising the amino acid sequence of SEQ ID NO: 244, and/or a VL comprising the amino acid sequence of SEQ ID NO: 245.

11. The multifunctional molecule of claim 1, wherein the multifunctional molecule comprises the cytokine molecule, wherein the cytokine molecule is chosen from interleukin-2 (IL-2) or a functional variant thereof, interleukin-7 (IL-7) or a functional variant thereof, interleukin-12 (IL-12) or a functional variant thereof, interleukin-15 (IL-15) or a functional variant thereof, interleukin-18 (IL-18) or a functional variant thereof, interleukin-21 (IL-21) or a functional variant thereof, interferon gamma or a functional variant thereof, and any combination thereof.

12. The multifunctional molecule of claim 11, wherein the interleukin-2 (IL-2) or a functional variant thereof comprises an amino acid sequence have at least 95% sequence identity of SEQ ID NO: 20, SEQ ID NO: 227 or SEQ ID NO: 228.

13. The multifunctional molecule of claim 1, wherein the multifunctional molecule comprises the following configuration:

A,B-[dimerization module]-C,-D, wherein:
(1) the dimerization module comprises an immunoglobulin constant domain, or a constant domain of an immunoglobulin variable region; and
(2) A, B, C, and D are independently absent; (i) an antigen binding domain that binds to a calreticulin protein; (ii) an immune cell engager chosen from a T cell engager, an NK cell engager, a B cell engager, a dendritic cell engager, or a macrophage cell engager;
(iii) a cytokine molecule or a modulator of a cytokine molecule; or (iv) a stromal modifying moiety, provided that:
at least one, two, or three of A, B, C, and D comprises an antigen binding domain that binds to a calreticulin protein, and
any of the remaining A, B, C, and D is absent or comprises one of an immune cell engager, a cytokine molecule or a modulator of a cytokine molecule, or a stromal modifying moiety.

14. The multifunctional molecule of claim 1, wherein the multifunctional molecule further comprises a dimerization module comprising a first immunoglobulin chain constant region and a second immunoglobulin chain constant region.

15. The multifunctional molecule of claim 14, wherein the first antigen binding domain is linked to the first immunoglobulin chain constant region.

16. The multifunctional molecule of claim 14, wherein the cytokine molecule or the modulator of a cytokine molecule is linked to the first immunoglobulin chain constant region, the second immunoglobulin chain constant region, or the first immunoglobulin chain constant region and the second immunoglobulin chain constant region.

17. The multifunctional molecule of claim 1, wherein the multifunctional molecule further comprises one or more of:
(i) a linker between the first antigen binding domain and the immune cell engager,
(ii) a linker between the first antigen binding domain and the cytokine molecule or the modulator of a cytokine molecule,
(iii) a linker between the first antigen binding domain and the stromal modifying moiety,
(iv) a linker between the immune cell engager and the cytokine molecule or the modulator of a cytokine molecule,
(v) a linker between the immune cell engager and the stromal modifying moiety, or
(vi) a linker between the cytokine molecule or the modulator of a cytokine molecule and the stromal modifying moiety, optionally, wherein the linker is chosen from: a cleavable linker, a non-cleavable linker, a peptide linker, a flexible linker, a rigid linker, a helical linker, and a non-helical linker.

18. The multifunctional molecule of claim 14, wherein the multifunctional molecule further comprises one or more of:
(i) a linker between the first antigen binding domain and the first immunoglobulin chain constant region,
(ii) a linker between the immune cell engager and the first immunoglobulin chain constant region, the second immunoglobulin chain constant region or the first immunoglobulin chain constant region and the second immunoglobulin chain constant region, or
(iii) a linker between the cytokine molecule or the modulator of a cytokine molecule and the first immunoglobulin chain constant region, the second immunoglobulin chain constant region or the first immunoglobulin chain constant region and the second immunoglobulin chain constant region, or a linker between or the stromal modifying moiety and the first immunoglobulin chain constant region, the second immunoglobulin chain constant region or the first immunoglobulin chain constant region and the second immunoglobulin chain constant region, optionally, wherein the linker is chosen from: a cleavable linker, a non-cleavable linker, a peptide linker, a flexible linker, a rigid linker, a helical linker, and a non-helical linker.

19. The multifunctional molecule of claim 7, wherein the multifunctional molecule further comprises one or more of:
(i) a linker between the second antigen binding domain and the immune cell engager,
(ii) a linker between the second antigen binding domain and the cytokine molecule or the modulator of a cytokine molecule, or
(iii) a linker between the second antigen binding domain and the stromal modifying moiety, optionally, wherein the linker is chosen from: a cleavable linker, a non-cleavable linker, a peptide linker, a flexible linker, a rigid linker, a helical linker, and a non-helical linker.

20. The multifunctional molecule of claim 7, wherein the multifunctional molecule further comprises a dimerization module comprising a first immunoglobulin chain constant region and a second immunoglobulin chain constant region, and wherein the multifunctional molecule further comprises one or more of a linker between the second antigen binding domain and the first immunoglobulin chain constant region, the second immunoglobulin chain constant region, or the first immunoglobulin chain constant region and the second immunoglobulin chain constant region,
optionally, wherein the linker is chosen from: a cleavable linker, a non-cleavable linker, a peptide linker, a flexible linker, a rigid linker, a helical linker, and a non-helical linker.

* * * * *